(12) United States Patent
Carroll et al.

(10) Patent No.: US 8,338,623 B2
(45) Date of Patent: Dec. 25, 2012

(54) COMPOUNDS AS CANNABINOID RECEPTOR LIGANDS

(75) Inventors: William A. Carroll, Evanston, IL (US); Michael J. Dart, Highland Park, IL (US); Arturo Perez-Medrano, Grayslake, IL (US); Derek W. Nelson, Highland Park, IL (US)

(73) Assignee: AbbVie Inc., North Chicago, IL (US)

( * ) Notice: Subject to any disclaimer, the term of this patent is extended or adjusted under 35 U.S.C. 154(b) by 836 days.

(21) Appl. No.: 12/169,418

(22) Filed: Jul. 8, 2008

(65) Prior Publication Data
US 2009/0018114 A1 Jan. 15, 2009

Related U.S. Application Data

(60) Provisional application No. 60/948,578, filed on Jul. 9, 2007.

(51) Int. Cl.
*C07D 205/04* (2006.01)
*C07D 333/50* (2006.01)
*A61K 31/381* (2006.01)

(52) U.S. Cl. .................. 548/953; 549/57; 514/210.18; 514/443

(58) Field of Classification Search ............... 548/953; 549/57; 514/210.18, 443
See application file for complete search history.

(56) References Cited

FOREIGN PATENT DOCUMENTS

| WO | WO-2005115972 A1 | 12/2005 |
| WO | WO-2005115986 A1 | 12/2005 |
| WO | WO-2007061360 A2 | 5/2007 |

OTHER PUBLICATIONS

Padgett (Life Sciences 77 (2005) 1767-1798).*
Kubinyi (3D QSAR in Drug Design: Ligand-Protein Interactions and Molecular Similarity, vol. 2-3, Springer, 1998, 800 pages). TOC and pp. 243-244 provided.*
Wermuth, The Practice of Medicinal Chemsitry, 2d ed. (2003), 768 pages. Chs 9-10 provided.*
"IUPAC Commission on Nomenclature of Organic Chemistry Rules for the Nomenclature of Organic Chemistry, Section E: Stereochemistry (Recommendations 1974)," Pure Appl Chem, 1976, 13-30, vol. 45.
Arevalo-Martin, A., et al., "Therapeutic Action of Cannabinoids in a Murine Model of Multiple Sclerosis," Journal of Neuroscience, 2003, 2511-2516, vol. 23, No. 7.
Bacon ER, "Synthesis of 7-Ethyl-4, 7-dihydro-4-oxo-2-(4-pyridinyl)thieno[2,3-b]pyridine-5-carboxylic Acid", J Heterocyclic Chem, 1991, 28, 1953-55.
Bartlett PA, "Chorismate Mutase Inhibitors: Synthesis and Evaluation of Some Potential Transition-State Analogues", J Org Chem, American Chemical Society, 1988, 53, 3195-3210.
Benito, C, et al., "A Glial Endogenous Cannabinoid System is Upregulated in the Brains of Macaques with Simian Immunodeficiency Virus-Induced Encephalitis," Journal of Neuroscience, 2005, 2530-2536, vol. 25—Issue 10.
Benito, C. et al., "Cannabinoid CB2 Receptors and Fatty Acid Amide Hydrolase Are Selectively Overexpressed in Neuritic Plaque-Associated Glia in Alzheimer's Disease Brains," Journal of Neuroscience, 2003, 11136-11141, vol. 23—Issue 35.
Berge, S.M. et al., "Journal of Pharmaceutical Sciences, Pharmaceutical Salts," J Pharmaceutical Sciences, 1977, 1-19, vol. 66.
Bouchard, J-F et al., "Contribution of endocannabinoids in the endothelial protection afforded by ischemic preconditioning in the isolated rat heart", Life Sciences, 2003, 1859-1870, vol. 72.
Boyle, W.J. et al., "Osteoclast differentiation and activation," (Binary/Image), 2003, 337-342, vol. 423.
Brennan, T.J. et al., "Characterization of a rat model of incisional pain," (Binary/Image), 1996, 493-501, vol. 64.
Buckley, N.E. et al., "Immunomodulation by cannabinoids is absent in mice deficient for the cannabinoid CB receptor," European Journal of Pharmacology, 2000, 141-149, vol. 396.
Carrier, E.J. et al., "Endocannabinoids in Neuroimmunology and Stress," Current Drug Targets CNS & Neurological Disorders, 2005, 657-665, vol. 4.
Casanova, M.L. et al., "Inhibition of skin tumor growth and angiogenesis in vivo by activation of cannabinoid receptors," Journal of Clinical Investigation, 2003, 43-50, vol. 111.
Chaplan, S.R. et al., "Quantitative assessment of tactile allodynia in the rat paw," Journal of Neuroscience Methods, 1994, 55-63, vol. 53.
Cichewicz, D.L. et al., "Synergistic interactions between cannabinoid and opioid analgesics," Life Sciences, 2004, 1317-1324, vol. 74.
Clayton, N. et al., "CB1 and CB2 cannabinoid receptors are implicated in inflammatory pain," (Binary/Image), 2002, 253-260, vol. 96.
Dixon, W.J. "Efficient analysis of experimental observations," Annual Review of Pharmacology and Toxicology, 1980, 441-462, vol. 20.
Filippo, C.D. et al., "Cannabinoid CB2 receptor activation reduces mouse myocardial ischemia-reperfusion injury: involvement of cytokine/chemokines and PMN," Journal of Leukocyte Biology, 2004, 453-459, vol. 75.

(Continued)

*Primary Examiner* — Robert Havlin
(74) *Attorney, Agent, or Firm* — Nancy J. Gettel; Sonali S. Srivastava

(57) ABSTRACT

The present application relates to cannabinoid receptor ligands containing compounds of formula (I)

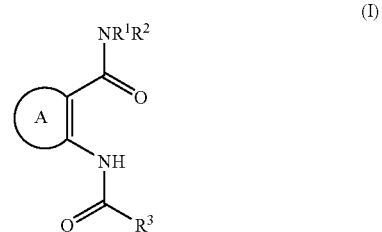

(I)

wherein A, $R^1$, $R^2$, and $R^3$ are as defined in the specification. The present application also relates to compositions comprising such compounds, and methods of treating conditions and disorders using such compounds and compositions.

13 Claims, No Drawings

OTHER PUBLICATIONS

Galiégue, et al., "Expression of central and peripheral cannabinoid receptors in human immune tissues and leukocyte subpopulations," European Journal of Biochemistry, 1995, 54-61, vol. 232.

Golech, S.A. et al., "Human brain endothelium: coexpression and function of vannilloid and endocannabinoid receptors," Molecular Brain Research, 2004, 87-92, vol. 132.

Greene, T.W. et al., "Protective Groups in Organic Synthesis", 1999, 3 rd Ed, 494-653.

Grotenhermen, F. et al., "IACM 2nd Conference on Cannabinoids in Medicine," Expert Opinion in Pharmacotherapy, 2003, 2367-2371, vol. 4—Issue 12.

Hanus, L. et al., "HU-308: A specific agonist for CB 2, a peripheral cannabinoid receptor," Proceedings of the National Academy of Science, 1999, 14228-14233, vol. 96.

Hohmann, A.G. et al., "Selective Activation of Cannabinoid CB2 Receptors Suppresses Hyperalgesia Evoked by Intradermal Capsaicin," Journal of Pharmacology and Experimental Therapeutics, 2004, 446-453, vol. 308.

Ibrahim, M.M. et al., "Activation of CB2 cannabinoid receptors by AM1241 inhibits experimental neuropathic pain: Pain inhibition by receptors not present in the CNS," Proceedings of the National Academy of Science, 2003, 10529-10533, vol. 100—Issue 18.

Ibrahim, M.M. et al., "CB2 cannabinoid receptor activation produces antinociception by stimulating peripheral release of endogenous opioids," Proceedings of the National Academy of Science, 2005, 3093-3098, vol. 102—Issue 8.

Ihenetu, K. et al., "Inhibition of interleukin-8 release in the human colonic epithelial cell line HT-29 by cannabinoids," European Journal of Pharmacology, 2003, 207-215, vol. 458.

International Search Report for application No. PCT/US08/069453, Mailed on Sep. 25, 2008, 2 pages.

Joshi S.K. et al., "Comparison of Antinociceptive Actoins of Standard Analgesics in Attenuating Capsaicin and Nerve-Injury-Induced Mechanical Hypersensitivty," Neurosci, 587-596, vol. 143.

Julien, B, et al., "Antifibrogenic Role of the Cannabinoid Receptor CB2 in the Liver," Gastroenterology, 2005, 742-755, vol. 128.

Karsak, M, et al., "Cannabinoid receptor type 2 gene is associated with human osteoporosis," Human Molecular Genetics, 2005, 3389-3396, vol. 14—Issue 22.

Khusnutdinov, R.I., Shchadneva, N.A., Baiguzina, A, "Chlorination of adamantane and its derivatives by carbon tetrachloride in the presence of manganese-, vanadium-, and molybdenum-containing catalysts", Neftekhimiya, 2004, 44/2, 148-155.

Kim, S.H. & Chung, J.M. "An experimental model for peripheral neuropathy produced by segmental spinal nerve ligation in the rat," (Binary/Image), 1992, 355-363, vol. 50—Issue 3.

Kreutzberg, G W "Microglia: a sensor for pathological events in the CNS," Trends in Neuroscience, 1996, 312-318, vol. 19.

Lepicier, P. et al., "Endocannabinoids protect the rat isolated heart against ischaemia," British Journal of Pharmacology, 2003, 805-815, vol. 139.

Lotersztajn, S. et al., "Hepatic Fibrosis: Molecular Mechanisms and Drug Targets," Annual Review of Pharmacology and Toxicology, 2005, 605-628, vol. 45.

Malan, T.P. et al., "CB2 cannabinoid receptor-mediated peripheral antinociception," (Binary/Image), 2001, 239-245, vol. 93.

Maresz, K, et al., "Modulation of the cannabinoid CB2 receptor in microglial cells in response to inflammatory stimuli," Journal of Neurochemistry, 2005, 437-445, vol. 95.

Mathison, R, et al., "Effects of cannabinoid receptor-2 activation on accelerated gastrointestinal transit in lipopolysaccharide-treated rats," British Journal of Pharmacology, 2004, 1247-1254, vol. 142.

McKallip, R.J. et al., "Targeting CB2 cannabinoid receptors as a novel therapy to treat malignant lymphoblastic disease," (Binary/Image), 2002, 627-634, vol. 15—Issue 2.

Molina-Holgado, F. et al., "Endogenous Interleukin-1 Receptor Antagonist Mediates Anti-Inflammatory and Neuroprotective Actions of Cannabinoids in Neurons and Glia," Journal of Neuroscience, 2003, 6470-6474, vol. 23—Issue 16.

Morii T, "A General Strategy to Determine a Target DNA Sequence of a Short Peptide: Application to a [D]-Peptide", J Am Chem Society, 2002, 124/2, 180-181.

Nackley, A.G. et al., "Selective activation of cannabinoid CB2 receptors suppresses spinal fos protein expression and pain behavior in a rat model of inflammation," Neuroscience, 2003, 747-757, vol. 119.

Ni, X. et al., "Win 55212-2, a cannabinoid receptor agonist, attenuates leukocyte/endothelial interactions in an experimental autoimmune encephalomyelitis model," Multiple Sclerosis, 2004, 158-164, vol. 10.

Nunez, E. et al., "Cannabinoid CB2 Receptors Are Expressed by Perivascular Microglial Cells in the Human Brain: An Immunohistochemical Study," Synapse, 2004, 208-213, vol. 53.

Partch, Ret al., "2-Oxaadamantane-1-N,N,N-trimethylmethanaminium Iodide:1 Synthesis and Potential for Muscarinic Activity," Croatia Chemical Acta, 1985, 661-669, vol. 58—Issue 4.

Patel, J.J. et al., "Inhibition of guinea-pig and human sensory nerve activity and the cough reflex in guinea-pigs by cannabinoid (CB2) receptor activation," British Journal of Pharmacology, 2003, 261-268, vol. 140.

Pertwee, R.G. "Cannabinoids and multiple sclerosis," Pharmacology & Therapeutics, 2002, 165-174, vol. 95.

Quartilho, A. et al., "Inhibition of Inflammatory Hyperalgesia by Activation of Peripheral CB2 Cannabinoid Receptors," Anesthesiology, 2003, 955-960, vol. 99.

Ralston, S.H. "Genetic determinants of susceptibility to osteoporosis," Current Opinion in Pharmacology, 2003, 286-290, vol. 3.

Ralston, S.H. "Regulation of bone mass, bone loss and osteoclast activity by cannabinoid receptors," Nature Medicine, 2005, 774-779, vol. 11.

Ramirez, B.G. et al., "Prevention of Alzheimer's Disease Pathology by Cannabinoids: Neuroprotection Mediated by Blockade of Microglial Activation," Journal of Neuroscience, 2005, 1904-1913, vol. 25—Issue 8.

Sanchez C. et al., "Inhibition of Glioma Growth in Vivo by Selective Activation of the CB2 Cannabinoid Receptor1," Cancer Research, 2001, 5784-5789, vol. 61.

Steffens S. et al., "Low dose oral cannabinoid therapy reduces progression of atherosclerosis in mice," (Binary/Image), 2005, 782-786, vol. 434.

Valenzano K.J. et al., "Pharmacological and pharmacokinetic characterization of the cannabinoid receptor 2 agonist, GW405833, utilizing rodent models of acute and chronic pain, anxiety, ataxia and catalepsy," Neuropharmacology, 2005, 658-672, vol. 48.

Walter L. et al., "Cannabinoids and neuroinflammation," Pharmacology, 2004, 775-785, vol. 141.

Warhurst A.C. et al., "Interferon ? induces differential upregulation of a and β chemokine secretion in colonic epithelial cell lines," (Binary/Image), 1998, 208-213, vol. 42.

Watkins L.R. et al, "Glial activation: a driving force for pathological pain," Trends in Neuroscience, 2001, 450-455, vol. 24—Issue 8.

Williams K. et al., "Central nervous system perivascular cells are immunoregulatory cells that connect the CNS with the peripheral immune system," (Binary/Image), 2001, 156-164, vol. 36.

Wright K. et al., "Differential Expression of Cannabinoid Receptors in the Human Colon: Cannabinoids Promote Epithelial Wound Healing," Gastroenterology, 2005, 437-453, vol. 129.

Yoshihara S. et al., "Cannabinoid Receptor Agonists Inhibit Sensory Nerve Activation in Guinea Pig Airways", American Journal of Respiratory and Critical Care Medicine, 2004, 941-946, vol. 170.

Yoshihara S. et al., "Endogenous Cannabinoid Receptor Agonists Inhibit Neurogenic Inflammations in Guinea Pig Airways" Allergy and Immunology, 2005, 80-87, vol. 138.

Yoshihara S. et al., "The Cannabinoid Receptor Agonist WIN 55212-2 Inhibits Neurogenic Inflammations in Airway Tissues," Journal of Pharmacological Sciences, 2005, 77-82, vol. 98—Issue 1.

Zimmer, A et al., "Increased mortality, hypoactivity, and hypoalgesia in cannabinoid CB1 receptor knockout mice," Proceedings of the National Academy of Science, 1999, 5780-5785, vol. 96.

* cited by examiner

COMPOUNDS AS CANNABINOID RECEPTOR LIGANDS

This application claims priority to U.S. Ser. No. 60/948,578, filed Jul. 9, 2007, and is incorporated herein by reference in its entirety.

TECHNICAL FIELD AND BACKGROUND

The present application relates to compounds that are cannabinoid receptor ligands, compositions comprising such compounds, and methods of treating conditions and disorders using such compounds and compositions.

(−)-$\Delta^9$-Tetrahydrocannabinol ($\Delta^9$-THC), the major psychoactive constituent of marijuana, exerts a broad range of effects through its interactions with two cannabinoid (CB) receptor subtypes, $CB_1$ and $CB_2$. $CB_1$ receptors are highly expressed in the central nervous system and to a lesser degree in the periphery in a variety of tissues of the cardiovascular and gastrointestinal systems. By contrast, $CB_2$ receptors are most abundantly expressed in multiple lymphoid organs and cells of the immune system, including spleen, thymus, tonsils, bone marrow, pancreas and mast cells.

The psychotropic effects caused by $\Delta^9$-THC and other nonselective CB agonists are mediated by $CB_1$ receptors. These $CB_1$ receptor-mediated effects, such as euphoria, sedation, hypothermia, catalepsy, and anxiety, have limited the development and clinical utility of nonselective CB agonists. Recent studies have demonstrated that $CB_2$ modulators are analgesic in pre-clinical models of nociceptive and neuropathic pain without causing the adverse side effects associated with $CB_1$ receptor activation. Therefore, compounds that selectively target $CB_2$ receptors are an attractive approach for the development of novel analgesics.

Pain is the most common symptom of disease and the most frequent complaint with which patients present to physicians. Pain is commonly segmented by duration (acute vs. chronic), intensity (mild, moderate, and severe), and type (nociceptive vs. neuropathic). Nociceptive pain is the most well known type of pain, and is caused by tissue injury detected by nociceptors at the site of injury. After the injury, the site becomes a source of ongoing pain and tenderness. This pain and tenderness are considered "acute" nociceptive pain. This pain and tenderness gradually diminish as healing progresses and disappear when healing is complete. Examples of acute nociceptive pain include surgical procedures (post-op pain) and bone fractures. Even though there may be no permanent nerve damage, "chronic" nociceptive pain results from some conditions when pain extends beyond six months. Examples of chronic nociceptive pain include osteoarthritis, rheumatoid arthritis, and musculoskeletal conditions (e.g., back pain), cancer pain, etc.

Neuropathic pain is defined as "pain initiated or caused by a primary lesion or dysfunction in the nervous system" by the International Association for the Study of Pain. Neuropathic pain is not associated with nociceptive stimulation, although the passage of nerve impulses that is ultimately perceived as pain by the brain is the same in both nociceptive and neuropathic pain. The term neuropathic pain encompasses a wide range of pain syndromes of diverse etiologies. The three most commonly diagnosed pain types of neuropathic nature are diabetic neuropathy, cancer neuropathy, and HIV pain. In addition, neuropathic pain is diagnosed in patients with a wide range of other disorders, including trigeminal neuralgia, post-herpetic neuralgia, traumatic neuralgia, phantom limb, as well as a number of other disorders of ill-defined or unknown origin.

Managing the spectrum of pain etiologies remains a major public health problem and both patients and clinicians are seeking improved strategies to effectively manage pain. No currently available therapies or drugs effectively treat all types of nociceptive and neuropathic pain states. The compounds of the present invention are novel $CB_2$ receptor modulators that have utility in treating pain, including nociceptive and neuropathic pain.

The location of $CB_2$ receptors on the surface of immune cells suggests a role for these receptors in immunomodulation and inflammation. Recent studies have demonstrated that $CB_2$ receptor ligands have immunomodulatory and anti-inflammatory properties. Therefore, compounds that interact with $CB_2$ receptors offer a unique pharmacotherapy for the treatment of immune and inflammatory disorders.

SUMMARY OF THE INVENTION

The invention is directed to compounds of formula (I)

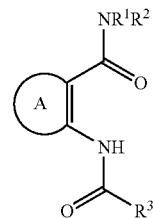

or a pharmaceutically acceptable salt thereof, wherein

A is formula (i), (ii), (iii), (iv), or (v)

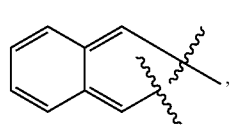

(i)

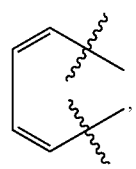

(ii)

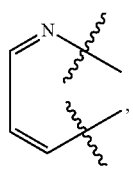

(iii)

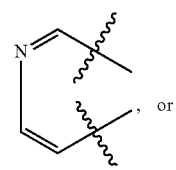

(iv)

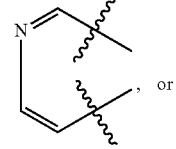

or (v)

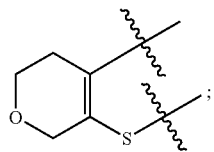

wherein each of the formulae (i)-(v) is independently unsubstituted or further substituted with 1, 2, 3, 4, or 5 substituents independently selected from the group consisting of alkyl, alkenyl, alkynyl, halogen, oxo, —CN, —NO$_2$, —OR$^a$, —S(R$^c$), —S(O)(R$^c$), —S(O)$_2$R$^c$, —S(O)$_2$N(R$^b$)$_2$, —C(O)R$^b$, —C(O)O(R$^b$), —C(O)N(R$^b$)$_2$, —N(R$^b$)$_2$, —N(R$^b$)C(O)R$^b$, —N(R$^b$)C(O)O(R$^b$), —N(R$^b$)S(O)$_2$R$^c$, haloalkyl, —(CR$^d$R$^e$)$_m$—OR$^c$, —(CR$^d$R$^e$)$_m$—S(R$^c$), —(CR$^d$R$^e$)$_m$—S(O)(R$^c$), —(CR$^d$R$^e$)$_m$—S(O)$_2$R$^c$, —(CR$^d$R$^e$)$_m$—S(O)$_2$N(R$^b$)$_2$, —(CR$^d$R$^e$)$_m$—C(O)R$^b$, —(CR$^d$R$^e$)$_m$—C(O)O(R$^b$), —(CR$^d$R$^e$)$_m$—C(O)N(R$^b$)$_2$, —(CR$^d$R$^e$)$_m$—N(R$^b$)$_2$, (CR$^d$R$^e$)$_m$—N(R$^b$)C(O)R$^b$, —(CR$^d$R$^e$)$_m$—N(R$^b$)C(O)O(R$^b$), and —(CR$^d$R$^e$)$_m$—N(R$^b$)S(O)$_2$R$^c$; two of the substituents on the same carbon atom of formula (v), together with the carbon atom to which they are attached, optionally form a 3-, 4-, 5- or 6-membered monocyclic cycloalkyl, wherein the monocyclic cycloalkyl is optionally substituted with 1, 2, 3, 4, 5, or 6 substituents selected from the group consisting of alkyl, haloalkyl and oxo;

R$^1$ is hydrogen, alkyl, or haloalkyl;

R$^2$ is alkyl, alkenyl, alkynyl, G$^1$, —N(R$^b$)(R$^f$), —(CR$^d$R$^e$)$_m$—CN, —(CR$^d$R$^e$)—OR$^f$, —(CR$^d$R$^e$)$_n$—S(R$^c$), —(CR$^d$R$^e$)$_m$—S(O)$_2$R$^c$, —(CR$^d$R$^e$)$_n$—N(R$^b$)(R$^f$), (CR$^d$R$^e$)$_m$—C(O)R$^b$, —(CR$^d$R$^e$)$_m$—C(O)O(R$^b$), —(CR$^d$R$^e$)$_m$-G$^1$, or haloalkyl; or R$^1$ and R$^2$, together with the nitrogen atom to which they are attached, form a 4- to 8-membered monocyclic heterocycle containing zero or one additional heteroatom selected from the group consisting of O, N, or S, and two non-adjacent atoms of said monocyclic heterocycle are optionally linked by an alkylene bridge of 1-4 carbon atoms, or linked by an alkenylene bridge of 2-4 carbon atoms, said monocyclic heterocycle is optionally substituted with 1, 2, 3, 4, 5, or 6 substituents independently selected from the group consisting of alkyl, halogen, oxo, —OR$^a$, G$^1$, haloalkyl, —(CR$^d$R$^e$)$_m$—OR$^a$, and —(CR$^d$R$^e$)$_m$-G$^1$;

G$^1$, at each occurrence, is independently aryl, heteroaryl, heterocycle, cycloalkyl, or cycloalkenyl; wherein each G$^1$ is independently unsubstituted or further substituted with 1, 2, 3, 4, 5, or 6 substituents independently selected from the group consisting of alkyl, alkenyl, alkynyl, halogen, oxo, —CN, —NO$_2$, —OR$^a$, —S(R$^c$), —S(O)(R$^c$), —S(O)$_2$R$^c$, —S(O)$_2$N(R$^b$)$_2$, C(O)R$^b$, —C(O)O(R$^b$), —C(O)N(R$^b$)$_2$, —N(R$^b$)$_2$, —N(R$^b$)C(O)R$^b$, —N(R$^b$)C(O)O(R$^b$), —N(R$^b$)S(O)$_2$R$^c$, haloalkyl, —(CR$^d$R$^e$)$_m$—OR$^a$, —(CR$^d$R$^e$)$_m$—S(R$^c$), —(CR$^d$R$^e$)$_m$—S(O)(R$^c$), —(CR$^d$R$^e$)$_m$—S(O)$_2$R$^c$, —(CR$^d$R$^e$)$_m$—S(O)$_2$N(R$^b$)$_2$, —(CR$^d$R$^e$)$_m$—C(O)R$^b$, —(CR$^d$R$^e$)$_m$—C(O)O(R$^b$), —(CR$^d$R$^e$)$_m$—C(O)N(R$^b$)$_2$, —(CR$^d$R$^e$)$_m$—N(R$^b$)$_2$, —(CR$^d$R$^e$)$_m$—N(R$^b$)C(O)R$^b$, —(CR$^d$R$^e$)$_m$—N(R$^b$)C(O)O(R$^b$), and —(CR$^d$R$^e$)$_m$—N(R$^b$)S(O)$_2$R$^c$;

R$^a$, at each occurrence, is independently hydrogen, alkyl, haloalkyl, or —(CR$^d$R$^e$)$_m$—O(alkyl), R$^b$, at each occurrence, is independently hydrogen, alkyl, or haloalkyl;

R$^c$, at each occurrence, is independently alkyl or haloalkyl;

R$^f$, at each occurrence, is independently hydrogen, alkyl, G$^1$, —(CR$^d$R$^e$)$_m$-G$^1$, or haloalkyl;

R$^d$ and R$^e$, at each occurrence, are each independently hydrogen, halogen, alkyl, or haloalkyl;

m, at each occurrence, is independently 1, 2, 3, 4, 5, or 6;

n, at each occurrence, is independently 2, 3, 4, 5, or 6;

R$^3$ is formula (a), (b), (c), or (d), (a)

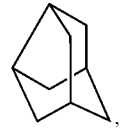

(b)

(c)

(d)

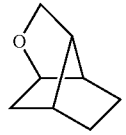

wherein each of the formulae (a)-(d) is independently unsubstituted or further substituted with 1, 2, 3, 4, or 5 substituents independently selected from the group consisting of alkyl, halogen, oxo, —CN, —O(alkyl), and haloalkyl.

Another aspect of the invention relates to pharmaceutical compositions comprising therapeutically effective amount of compound(s) of the invention or pharmaceutically acceptable salts thereof, in combination with one or more pharmaceutically acceptable carrier. Such compositions can be administered in accordance with a method of the invention, typically as part of a therapeutic regimen for treatment or prevention of conditions and disorders related to cannabinoid (CB) receptor subtype CB$_2$. More particularly, the method is useful for treating conditions related to neuropathic pain, nociceptive pain, inflammatory pain, inflammatory disorders, immune disorders, neurological disorders, cancers of the immune system, respiratory disorders, obesity, diabetes, cardiovascular disorders, or for providing neuroprotection.

Further, the present invention provides the use of compounds of the present invention or a pharmaceutically acceptable salt thereof, in the manufacture of a medicament for the treatment of the disease conditions described above, alone or in combination with one or more pharmaceutically acceptable carrier, particularly for the treatment of neuropathic pain, nociceptive pain, inflammatory pain, or combination thereof.

The compounds, compositions comprising the compounds, and methods for treating or preventing conditions and disorders by administering the compounds are further described herein.

These and other objects of the invention are described in the following paragraphs. These objects should not be deemed to narrow the scope of the invention.

DETAILED DESCRIPTION

Compounds of formula (I) are disclosed in this invention

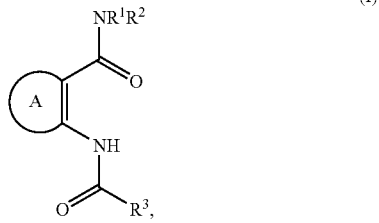

wherein A, $R^1$, $R^2$, and $R^3$ are as defined above in the Summary of the Invention and below in the Detailed Description. Compositions comprising such compounds and methods for treating conditions and disorders using such compounds and compositions are also disclosed.

In various embodiments, the present invention provides at least one variable that occurs more than one time in any substituent or in the compound of the invention or any other formulae herein. Definition of a variable on each occurrence is independent of its definition at another occurrence. Further, combinations of substituents are permissible only if such combinations result in stable compounds. Stable compounds are compounds, which can be isolated from a reaction mixture.

a. Definitions

As used in the specification and the appended claims, unless specified to the contrary, the following terms have the meaning indicated:

The term "alkenyl" as used herein, means a straight or branched hydrocarbon chain containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkenylene" denotes a divalent group derived from a straight or branched chain hydrocarbon of 2 to 4 carbon atoms and contains at least one carbon-carbon double. Representative examples of alkylene include, but are not limited to, —CH=CH— and —CH$_2$CH=CH—.

The term "alkyl" as used herein, means a straight or branched, saturated hydrocarbon chain containing from 1 to 10 carbon atoms. The term "lower alkyl" or "$C_{1-6}$ alkyl" means a straight or branched chain hydrocarbon containing 1 to 6 carbon atoms. The term "$C_{1-3}$ alkyl" means a straight or branched chain hydrocarbon containing 1 to 3 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkylene" denotes a divalent group derived from a straight or branched chain hydrocarbon 1 to 10 carbon atoms. Representative examples of alkylene include, but are not limited to, —CH$_2$—, —CH$_2$CH$_2$—, —CH$_2$CH$_2$CH$_2$—, —CH$_2$CH$_2$CH$_2$CH$_2$—, and —CH$_2$CH(CH$_3$)CH$_2$—.

The term "alkynyl" as used herein, means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "aryl" as used herein, means phenyl or a bicyclic aryl. The bicyclic aryl is naphthyl, or a phenyl fused to a monocyclic cycloalkyl, or a phenyl fused to a monocyclic cycloalkenyl. Representative examples of the aryl groups include, but are not limited to, dihydroindenyl, indenyl, naphthyl, dihydronaphthalenyl, and tetrahydronaphthalenyl. The bicyclic aryl is attached to the parent molecular moiety through any carbon atom contained within the bicyclic ring system. The aryl groups of the present invention can be unsubstituted or substituted.

The term "cycloalkyl" or "cycloalkane" as used herein, means a monocyclic, a bicyclic, or a tricyclic cycloalkyl. The monocyclic cycloalkyl is a carbocyclic ring system containing three to eight carbon atoms, zero heteroatoms and zero double bonds. Examples of monocyclic ring systems include cyclopropyl, cyclobutyl, cyclopentyl, cyclohexyl, cycloheptyl, and cyclooctyl. The bicyclic cycloalkyl is a monocyclic cycloalkyl fused to a monocyclic cycloalkyl ring, or a bridged monocyclic ring system in which two non-adjacent carbon atoms of the monocyclic ring are linked by an alkylene bridge containing one, two, three, or four carbon atoms. Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1] nonane, and bicyclo[4.2.1]nonane. Tricyclic cycloalkyls are exemplified by a bicyclic cycloalkyl fused to a monocyclic cycloalkyl, or a bicyclic cycloalkyl in which two non-adjacent carbon atoms of the ring systems are linked by an alkylene bridge of 1, 2, 3, or 4 carbon atoms. Representative examples of tricyclic-ring systems include, but are not limited to, tricyclo[3.3.1.0$^{3,7}$]nonane (octahydro-2,5-methanopentalene or noradamantane), and tricyclo[3.3.1.1$^{3,7}$]decane (adamantane). The monocyclic, bicyclic, and tricyclic cycloalkyls can be unsubstituted or substituted, and are attached to the parent molecular moiety through any substitutable atom contained within the ring system.

The term "cycloalkenyl" or "cycloalkene" as used herein, means a monocyclic or a bicyclic hydrocarbon ring system. The monocyclic cycloalkenyl has four-, five-, six-, seven- or eight carbon atoms and zero heteroatoms. The four-membered ring systems have one double bond, the five- or six-membered ring systems have one or two double bonds, and the seven- or eight-membered ring systems have one, two or three double bonds. Representative examples of monocyclic cycloalkenyl groups include, but are not limited to, cyclobutenyl, cyclopentenyl, cyclohexenyl, cycloheptenyl and cyclooctenyl. The bicyclic cycloalkenyl is a monocyclic cycloalkenyl fused to a monocyclic cycloalkyl group, or a monocyclic cycloalkenyl fused to a monocyclic cycloalkenyl group. The monocyclic or bicyclic cycloalkenyl ring may contain one or two alkylene bridges, each consisting of one, two or three carbon atoms, each linking two non-adjacent carbon atoms of the ring system. Representative examples of the bicyclic cycloalkenyl groups include, but are not limited to, 4,5,6,7-tetrahydro-3aH-indene, octahydronaphthalenyl and 1,6-dihydro-pentalene. The monocyclic and bicyclic cycloalkenyl can be attached to the parent molecular moiety through any substitutable atom contained within the ring systems, and can be unsubstituted or substituted.

The term "halo" or "halogen" as used herein, means Cl, Br, I, or F.

The term "haloalkyl" as used herein, means an alkyl group, as defined herein, in which one, two, three, four, five or six hydrogen atoms are replaced by halogen. Representative examples of haloalkyl include, but are not limited to, chloromethyl, 2-fluoroethyl, 2,2,2-trifluoroethyl, trifluoromethyl, difluoromethyl, pentafluoroethyl, 2-chloro-3-fluoropentyl, and trifluoropropyl such as 3,3,3-trifluoropropyl.

The term "heterocycle" or "heterocyclic" as used herein, means a monocyclic heterocycle, a bicyclic heterocycle, or a tricyclic heterocycle. The monocyclic heterocycle is a three-, four-, five-, six-, seven-, or eight-membered ring containing at least one heteroatom independently selected from the group consisting of O, N, and S. The three- or four-membered ring contains zero or one double bond, and one heteroatom selected from the group consisting of O, N, and S. The five-membered ring contains zero or one double bond and one, two or three heteroatoms selected from the group consisting of O, N and S. The six-membered ring contains zero, one or two double bonds and one, two, or three heteroatoms selected from the group consisting of O, N, and S. The seven- and eight-membered rings contains zero, one, two, or three double bonds and one, two, or three heteroatoms selected from the group consisting of O, N, and S. Representative examples of monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydropyranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to a phenyl group, or a monocyclic heterocycle fused to a monocyclic cycloalkyl, or a monocyclic heterocycle fused to a monocyclic cycloalkenyl, or a monocyclic heterocycle fused to a monocyclic heterocycle, or a bridged monocyclic heterocycle ring system in which two non adjacent atoms of the ring are linked by an alkylene bridge of 1, 2, 3, or 4 carbon atoms, or an alkenylene bridge of two, three, or four carbon atoms. Representative examples of bicyclic heterocycles include, but are not limited to, benzopyranyl, benzothiopyranyl, 2,3-dihydrobenzofuranyl, 2,3-dihydrobenzothienyl, azabicyclo[2.2.1]heptyl (including 2-azabicyclo[2.2.1]hept-2-yl), and 2,3-dihydro-1H-indolyl. Tricyclic heterocycles are exemplified by a bicyclic heterocycle fused to a phenyl group, or a bicyclic heterocycle fused to a monocyclic cycloalkyl, or a bicyclic heterocycle fused to a monocyclic cycloalkenyl, or a bicyclic heterocycle fused to a monocyclic heterocycle, or a bicyclic heterocycle in which two non adjacent atoms of the bicyclic ring are linked by an alkylene bridge of 1, 2, 3, or 4 carbon atoms, or an alkenylene bridge of two, three, or four carbon atoms. Examples of tricyclic heterocycles include, but not limited to, octahydro-2,5-epoxypentalene, hexahydro-2H-2,5-methanocyclopenta[b]furan, hexahydro-1H-1,4-methanocyclopenta[c]furan, aza-admantane (1-azatricyclo[3.3.1$^{3,7}$]decane), and oxa-adamantane (2-oxatricyclo[3.3.1.1$^{3,7}$]decane). The monocyclic, bicyclic, and tricyclic heterocycles are connected to the parent molecular moiety through any carbon atom or any nitrogen atom contained within the rings, and can be unsubstituted or substituted.

The term "heteroaryl" as used herein, means a monocyclic heteroaryl or a bicyclic heteroaryl. The monocyclic heteroaryl is a five- or six-membered ring. The five-membered ring contains two double bonds. The five membered ring may contain one heteroatom selected from O or S; or one, two, three, or four nitrogen atoms and optionally one oxygen or sulfur atom. The six-membered ring contains three double bonds and one, two, three or four nitrogen atoms. Representative examples of monocyclic heteroaryl include, but are not limited to, furanyl, imidazolyl, isoxazolyl, isothiazolyl, oxadiazolyl, 1,3-oxazolyl, pyridinyl, pyridazinyl, pyrimidinyl, pyrazinyl, pyrazolyl, pyrrolyl, tetrazolyl, thiadiazolyl, 1,3-thiazolyl, thienyl, triazolyl, and triazinyl. The bicyclic heteroaryl consists of a monocyclic heteroaryl fused to a phenyl, or a monocyclic heteroaryl fused to a monocyclic cycloalkyl, or a monocyclic heteroaryl fused to a monocyclic cycloalkenyl, or a monocyclic heteroaryl fused to a monocyclic heteroaryl, or a monocyclic heteroaryl fused to a monocyclic heterocycle. Representative examples of bicyclic heteroaryl groups include, but are not limited to, benzofuranyl, benzothienyl, benzoxazolyl, benzimidazolyl, benzoxadiazolyl, 6,7-dihydro-1,3-benzothiazolyl, imidazo[1,2-a]pyridinyl, indazolyl, indolyl, isoindolyl, isoquinolinyl, naphthyridinyl, pyridoimidazolyl, quinolinyl, thiazolo[5,4-b]pyridin-2-yl, thiazolo[5,4-d]pyrimidin-2-yl, and 5,6,7,8-tetrahydroquinolin-5-yl. The monocyclic and bicyclic heteroaryl groups of the present invention can be substituted or unsubstituted and are connected to the parent molecular moiety through any carbon atom or any nitrogen atom contained within the ring systems.

The term "heteroatom" as used herein, means a nitrogen, oxygen, or sulfur atom.

The term "oxo" as used herein, means a =O group.

b. Compounds

Compounds of the invention have the formula (I) as described above.

Particular values of variable groups in compounds of formula (I) are as follows. Such values may be used where appropriate with any of the other values, definitions, claims or embodiments defined hereinbefore or hereinafter.

As described generally above for compounds of formula (I), A is formula (i), (ii), (iii), (iv), or (v)

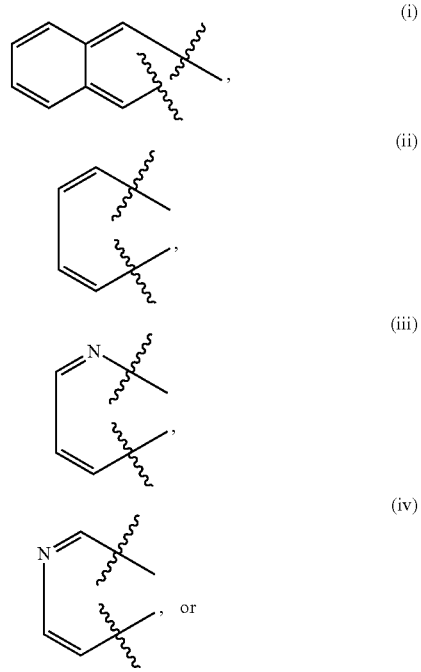

-continued

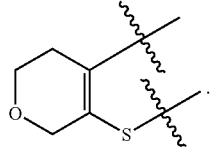
(v)

Compounds of formula (I) can include, but are not limited to, compounds wherein A is formula

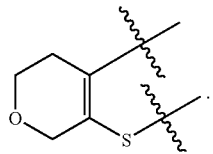
(v)

Thus, compounds within formula (I) include compounds of the following formula II and pharmaceutically acceptable salts thereof:

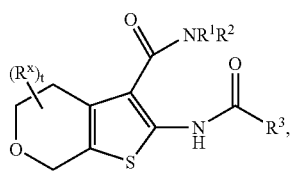
(II)

wherein $R^x$ is an optional substituent, and each $R^x$ is independently alkyl, alkenyl, alkynyl, halogen, oxo, —CN, —NO₂, —OR$^a$, —S(R$^c$), —S(O)(R$^c$), —S(O)₂R$^c$, —S(O)₂N(R$^b$)₂, —C(O)R$^b$, —C(O)O(R$^b$), —C(O)N(R$^b$)₂, —N(R$^b$)₂, —N(R$^b$)C(O)R$^b$, —N(R$^b$)C(O)O(R$^b$), —N(R$^b$)S(O)₂R$^c$, haloalkyl, —(CR$^d$R$^e$)$_m$—OR$^a$, —(CR$^d$R$^e$)$_m$—S(R$^c$), —(CR$^d$R$^e$)$_m$—S(O)(R$^c$), —(CR$^d$R$^e$)$_m$—S(O)₂R$^c$, —(CR$^d$R$^e$)$_m$—S(O)₂N(R$^b$)₂, —(CR$^d$R$^e$)$_m$—C(O)R$^b$, —(CR$^d$R$^e$)$_m$—C(O)O(R$^b$), —(CR$^d$R$^e$)$_m$—C(O)N(R$^b$)₂, —(CR$^d$R$^e$)$_m$—N(R$^b$)₂, —(CR$^d$R$^e$)$_m$—N(R$^b$)C(O)R$^b$, —(CR$^d$R$^e$)$_m$—N(R$^b$)C(O)O(R$^b$), or —(CR$^d$R$^e$)$_m$—N(R$^b$)S(O)₂R$^c$; two $R^x$ on the same carbon atom, together with the carbon atom to which they are attached, optionally form a 3-, 4-, 5- or 6-membered monocyclic cycloalkyl, wherein the monocyclic cycloalkyl is optionally substituted with 1, 2, 3, 4, 5, or 6 substituents selected from the group consisting of alkyl, haloalkyl and oxo;

t is 0, 1, 2, 3, 4, or 5; and $R^1$, $R^2$, $R^3$, $R^a$, $R^b$, $R^c$, $R^d$, $R^e$, and m are as disclosed in the Summary and the embodiments described herein.

Other compounds of the present invention include those in which A is

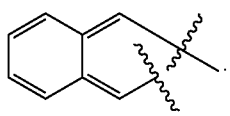
(i)

Thus, the present invention provides compounds of formula (III) and pharmaceutically acceptable salts thereof:

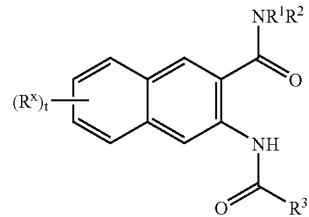
(III)

wherein $R^x$ is an optional substituent, and each $R^x$ is independently alkyl, alkenyl, alkynyl, halogen, —CN, —NO₂, —OR$^a$, —S(R$^c$), —S(O)(R$^c$), —S(O)₂R$^c$, —S(O)₂N(R$^b$)₂, —C(O)R$^b$, —C(O)O(R$^b$), —C(O)N(R$^b$)₂, —N(R$^b$)₂, —N(R$^b$)C(O)R$^b$, —N(R$^b$)C(O)O(R$^b$), —N(R$^b$)S(O)₂R$^c$, haloalkyl, —(CR$^d$R$^e$)$_m$—OR$^a$, —(CR$^d$R$^e$)$_m$—S(R$^c$), —(CR$^d$R$^e$)$_m$—S(O)(R$^c$), —(CR$^d$R$^e$)$_m$—S(O)₂R$^c$, —(CR$^d$R$^e$)$_m$—S(O)₂N(R$^b$)₂, —(CR$^d$R$^e$)$_m$—C(O)R$^b$, —(CR$^d$R$^e$)$_m$—C(O)O(R$^b$), —(CR$^d$R$^e$)$_m$—C(O)N(R$^b$)₂, —(CR$^d$R$^e$)$_m$—N(R$^b$)₂, —(CR$^d$R$^e$)$_m$—N(R$^b$)C(O)R$^b$, —(CR$^d$R$^e$)$_m$—N(R$^b$)C(O)O(R$^b$), or —(CR$^d$R$^e$)$_m$—N(R$^b$)S(O)₂R$^c$;

t is 0, 1, 2, 3, 4, or 5; and $R^1$, $R^2$, $R^3$, $R^a$, $R^b$, $R^c$, $R^d$, $R^e$, and m are as disclosed in the Summary and the embodiments described herein.

Yet other compounds of formula (I) include those wherein A is

(ii)

Thus, the present invention further provides compounds of formula (IV) or pharmaceutically acceptable salts thereof:

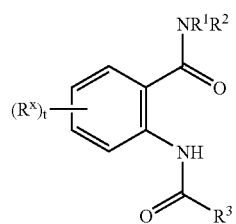
(IV)

wherein $R^x$ is an optional substituent, and each $R^x$ is independently alkyl, alkenyl, alkynyl, halogen, —CN, —NO₂— OR$^a$, —S(R$^c$), —S(O)(R$^c$), —S(O)₂R$^c$, —S(O)₂N(R$^b$)₂, —C(O)R$^b$, —C(O)O(R$^b$), —C(O)N(R$^b$)₂, —N(R$^b$)₂, —N(R$^b$)C(O)R$^b$, —N(R$^b$)C(O)O(R$^b$), —N(R$^b$)S(O)₂R$^c$, haloalkyl, —(CR$^d$R$^e$)$_m$—OR$^a$, —(CR$^d$R$^e$)$_m$—S(R$^c$), —(CR$^d$R$^e$)$_m$—S(O)(R$^c$), —(CR$^d$R$^e$)$_m$—S(O)₂R$^c$, —(CR$^d$R$^e$)$_m$—S(O)₂N(R$^b$)₂, —(CR$^d$R$^e$)$_m$—C(O)R$^b$, —(CR$^d$R$^e$)$_m$—C(O)O(R$^b$), —(CR$^d$R$^e$)$_m$—C(O)N(R$^b$)₂, —(CR$^d$R$^e$)$_m$—N(R$^b$)₂, —(CR$^d$R$^e$)$_m$—N(R$^b$)C(O)R$^b$, —(CR$^d$R$^e$)$_m$—N(R$^b$)C(O)O(R$^b$), or —(CR$^d$R$^e$)$_m$—N(R$^b$)S(O)₂R$^c$;

t is 0, 1, 2, 3, or 4; and $R^1$, $R^2$, $R^3$, $R^a$, $R^b$, $R^c$, $R^d$, $R^e$, and m are as disclosed in the Summary and the embodiments described herein.

Still other compounds of formula (I) include those in which A is formula

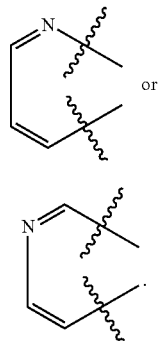

Thus, still other embodiments of the invention are related to compounds of formula (V) or (VI), or pharmaceutically acceptable salts thereof:

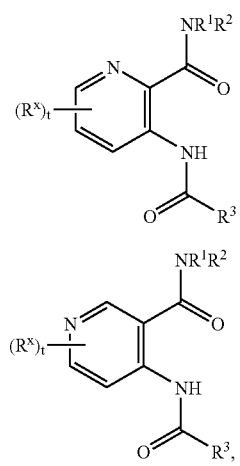

wherein $R^x$ is an optional substituent, and each $R^x$ is independently alkyl, alkenyl, alkynyl, halogen, —CN, —NO$_2$, —OR$^a$, —S(R$^c$), —S(O)(R$^c$), —S(O)$_2$R$^c$, —S(O)$_2$N(R$^b$)$_2$, —C(O)R$^b$, —C(O)O(R$^b$), —C(O)N(R$^b$)$_2$, —N(R$^b$)$_2$, —N(R$^b$)C(O)R$^b$, —N(R$^b$)C(O)O(R$^k$), —N(R$^b$)S(O)$_2$R$^c$, haloalkyl, —(CR$^d$R$^e$)$_m$—OR$^a$, —(CR$^d$R$^e$)$_m$—S(R$^c$), —(CR$^d$ R$^e$)$_m$—S(O)(R$^c$), —(CR$^d$R$^e$)$_m$—S(O)$_2$R$^c$, —(CR$^d$R$^e$)$_m$—S (O)$_2$N(R$^b$)$_2$, —(CR$^d$R$^e$)$_m$—C(O)R$^b$, —(CR$^d$R$^e$)$_m$—C(O)O (R$^b$), —(CR$^d$R$^e$)$_m$—C(O)N(R$^b$)$_2$, —(CR$^d$R$^e$)$_m$—N(R$^b$)$_2$, —(CR$^d$R$^e$)$_m$—N(R$^b$)C(O)R$^b$, —(CR$^d$R$^e$)$_m$—N(R$^b$)C(O)O (R$^b$), or —(CR$^d$R$^e$)$_m$—N(R$^b$)S(O)$_2$R$^c$; and t is 0, 1, 2, or 3; and $R^1$, $R^2$, $R^3$, $R^a$, $R^b$, $R^c$, $R^d$, $R^e$, and m are as disclosed in the Summary and the embodiments described herein.

For each substructure as defined by ring A, there exist the following embodiments which further define the scope of the compounds of the present invention. These further embodiments are contemplated to apply to each series of compounds of formula (I), (II), (III), (IV), (V), and (VI).

As described generally above for compounds of formula (I), (II), (III), (IV), (V), or (VI), $R^3$ is formula (a), (b), (c), or (d), wherein each of the formula (a)-(d) is independently unsubstituted or substituted.

Accordingly, one aspect of the invention is directed to a group of compounds of formula (I), (II), (III), (IV), (V), or (VI) wherein $R^3$ is formula (a):

Another aspect of the invention is related to a group of compounds of formula (I), (II), (III), (IV), (V), or (VI) wherein $R^3$ is formula (b) or (d):

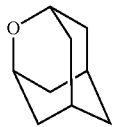

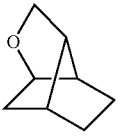

Within each group of the compounds of formula (I)-(VI) as described above, rings (a)-(d) are unsubstituted or substituted as described in the Summary. In certain embodiments, each of the rings (a)-(d) is unsubstituted. In certain embodiments, rings (a)-(d) may be substituted. Examples of the optional substituents include, but are not limited to, alkyl (e.g. methyl), halogen (e.g. F, Cl, Br, I), —S(O)$_2$(alkyl) (e.g. —S(O)$_2$(CH$_3$), and haloalkyl (e.g. trifluoromethyl).

For the each of the preceding groups of compounds of formula (I)-(VI), $R^1$ and $R^2$ have values as described in the Summary section.

For example, $R^1$ and $R^2$ together with the nitrogen atom to which they are attached form an optionally substituted 4- to 8-membered monocyclic heterocycle as described in the Summary. Examples of the monocyclic heterocycle include, but are not limited to, morpholine, piperidine, azetidine, pyrrolidine, and azabicyclo[2.2.1]hept-2-yl, each of which is optionally substituted. Examples of the optional substituents include, but are not limited to, alkyl (e.g. methyl), —OH, —O(alkyl) (e.g. —OCH$_3$), and halogen (e.g. fluoro).

Included among the preferred compounds are also the groups of compounds as described herein above in which $R^1$ is hydrogen and $R^2$ is alkyl (e.g. methyl, ethyl, n-propyl, n-butyl, isobutyl) alkynyl (e.g. prop-2-ynyl), or haloalkyl (e.g. 3,3,3-trifluoropropyl, 2,2,2-trifluoroethyl). Other compounds included in the present invention are those groups of compounds of formula (I)-(VI) described herein above wherein $R^1$ is hydrogen and $R^2$ is —(CR$^d$R$^e$)$_n$—OR$^f$, —(CR$^d$ R$^e$)$_m$—CN, —(CR$^d$R$^e$)$_n$—S(R$^c$), —(CR$^d$R$^e$)$_m$—S(O)$_2$R$^c$, or —N(R$^b$)(R$^f$), wherein all variables are as defined in the Summary. For example, $R^2$ is —(CR$^d$R$^e$)$_n$—OR$^f$ wherein R$^f$ is hydrogen or alkyl (e.g. methyl, ethyl), R$^d$, and R$^e$ are each independently hydrogen or alkyl (e.g. methyl, ethyl, isopropyl,), and n is 2 or 3; or $R^2$ is —CH$_2$—CN, —(CH$_2$)$_2$—CN, —(CH$_2$)$_3$—CN, —(CH$_2$)$_2$—S(CH$_3$), —(CH$_2$)$_2$—S(O)$_2$ (CH$_3$), or —N(R$^b$)(R$^f$) wherein R$^b$ is hydrogen and R$^f$ is G$^1$ (e.g. phenyl).

Other compounds comprised by the present invention are groups of compounds of formula (I)-(VI) as described above in which $R^1$ is hydrogen and $R^2$ is —$(CR^dR^e)_m$-$G^1$ wherein all variables are as disclosed in the Summary. Example of $R^d$ and $R^e$ include, but are not limited to, hydrogen and alkyl (e.g. methyl). m is, for example, 1, 2, or 3. Example of $G^1$ include, but are not limited to, aryl, (e.g. phenyl), heteroaryl (e.g. thienyl, pyridinyl), and heterocycle (e.g. tetrahydro-2H-pyranyl, tetrahydrofuranyl, tetrahydrothienyl), each of which is optionally substituted as described in the Summary. Examples of the optional substituents include, but are not limited to, alkyl (e.g. methyl), halogen (e.g. F), —$OR^a$ (e.g. —$OCH_3$, —OH), and —$N(R^b)_2$ (e.g. —$N(CH_3)_2$).

Other compounds comprised by the present invention are groups of compounds of formula (I)-(VI) as described above in which $R^1$ is hydrogen, $R^2$ is $G^1$ and $G^1$ is as described in the Summary. For example, $G^1$ is aryl (e.g. phenyl), cycloalkyl (e.g. cyclopropyl, cyclobutyl, cyclopentyl, cyclohexyl, bicyclo[3.1.1]heptyl, bicyclo[2.2.1]heptyl), or heterocycle (e.g. tetrahydrofuranyl), each of which is optionally substituted as described in the Summary. Examples of the optional substituents include, but are not limited to, alkyl (e.g methyl), haloalkyl (e.g. trifluoromethyl), —$OR^a$ (e.g. —OH, and —$OCH_3$), —$(CR^dR^e)_m$—$OR^a$ (e.g. —$CH_2OH$).

Specific embodiments of compounds contemplated as part of the invention include, but are not limited to:

N-{3-[(2,5-dimethylmorpholin-4-yl)carbonyl]-4,7-dihydro-5H-thieno[2,3-c]pyran-2-yl}hexahydro-2,5-methanopentalene-3a(1H)-carboxamide;

N-{3-[(4-hydroxypiperidin-1-yl)carbonyl]-4,7-dihydro-5H-thieno[2,3-c]pyran-2-yl}hexahydro-2,5-methanopentalene-3a(1H)-carboxamide;

2-[(hexahydro-2,5-methanopentalen-3a(1H)-ylcarbonyl)amino]-N-propyl-4,7-dihydro-5H-thieno[2,3-c]pyran-3-carboxamide;

N-[3-(morpholin-4-ylcarbonyl)-4,7-dihydro-5H-thieno[2,3-c]pyran-2-yl]hexahydro-2,5-methanopentalene-3a(1H)-carboxamide;

(1R,3aS,4R,6aR)-3a,6a-dimethyl-N-{3-[(propylamino)carbonyl]-4,7-dihydro-5H-thieno[2,3-c]pyran-2-yl}hexahydro-1H-1,4-methanocyclopenta[c]furan-1-carboxamide;

(1R,3aS,4R,6aR)-3a,6a-dimethyl-N-[3-(morpholin-4-ylcarbonyl)-4,7-dihydro-5H-thieno[2,3-c]pyran-2-yl]hexahydro-1H-1,4-methanocyclopenta[c]furan-1-carboxamide;

2-[(hexahydro-2,5-methanopentalen-3a(1H)-ylcarbonyl)amino]-N-(2-methoxyethyl)-4,7-dihydro-5H-thieno[2,3-c]pyran-3-carboxamide;

2-[(hexahydro-2,5-methanopentalen-3a(1H)-ylcarbonyl)amino]-N-(tetrahydro-2H-pyran-4-ylmethyl)-4,7-dihydro-5H-thieno[2,3-c]pyran-3-carboxamide;

2-[(hexahydro-2,5-methanopentalen-3a(1H)-ylcarbonyl)amino]-N-(3-hydroxypropyl)-4,7-dihydro-5H-thieno[2,3-c]pyran-3-carboxamide;

N-ethyl-2-[(hexahydro-2,5-methanopentalen-3a(1H)-ylcarbonyl)amino]-4,7-dihydro-5H-thieno[2,3-c]pyran-3-carboxamide;

2-[(hexahydro-2,5-methanopentalen-3a(1H)-ylcarbonyl)amino]-N-(2-phenylethyl)-4,7-dihydro-5H-thieno[2,3-c]pyran-3-carboxamide;

2-[(hexahydro-2,5-methanopentalen-3a(1H)-ylcarbonyl)amino]-N-(2-thien-2-ylethyl)-4,7-dihydro-5H-thieno[2,3-c]pyran-3-carboxamide;

N-[2-(2-fluorophenyl)ethyl]-2-[(hexahydro-2,5-methanopentalen-3a(1H)-ylcarbonyl)amino]-4,7-dihydro-5H-thieno[2,3-c]pyran-3-carboxamide;

2-[(hexahydro-2,5-methanopentalen-3a(1H)-ylcarbonyl)amino]-N-[2-(2-methoxyphenyl)ethyl]-4,7-dihydro-5H-thieno[2,3-c]pyran-3-carboxamide;

2-[(hexahydro-2,5-methanopentalen-3a(1H)-ylcarbonyl)amino]-N-(2-pyridin-2-ylethyl)-4,7-dihydro-5H-thieno[2,3-c]pyran-3-carboxamide;

N-(2-cyanoethyl)-2-[(hexahydro-2,5-methanopentalen-3a(1H)-ylcarbonyl)amino]-4,7-dihydro-5H-thieno[2,3-c]pyran-3-carboxamide;

N-{3-[(propylamino)carbonyl]-4,7-dihydro-5H-thieno[2,3-c]pyran-2-yl}-2-oxatricyclo[3.3.1.1$^{3,7}$]decane-1-carboxamide;

N-(2-ethoxyethyl)-2-[(hexahydro-2,5-methanopentalen-3a(1H)-ylcarbonyl)amino]-4,7-dihydro-5H-thieno[2,3-c]pyran-3-carboxamide;

2-[(hexahydro-2,5-methanopentalen-3a(1H)-ylcarbonyl)amino]-N-(3-hydroxybutyl)-4,7-dihydro-5H-thieno[2,3-c]pyran-3-carboxamide;

2-[(hexahydro-2,5-methanopentalen-3a(1H)-ylcarbonyl)amino]-N-[(1R)-1-(hydroxymethyl)-2-methylpropyl]-4,7-dihydro-5H-thieno[2,3-c]pyran-3-carboxamide;

2-[(hexahydro-2,5-methanopentalen-3a(1H)-ylcarbonyl)amino]-N-(1-methyl-3-phenylpropyl)-4,7-dihydro-5H-thieno[2,3-c]pyran-3-carboxamide;

2-[(hexahydro-2,5-methanopentalen-3a(1H)-ylcarbonyl)amino]-N-isobutyl-4,7-dihydro-5H-thieno[2,3-c]pyran-3-carboxamide;

2-[(hexahydro-2,5-methanopentalen-3a(1H)-ylcarbonyl)amino]-N-(2-methoxy-1-methylethyl)-4,7-dihydro-5H-thieno[2,3-c]pyran-3-carboxamide;

2-[(hexahydro-2,5-methanopentalen-3a(1H)-ylcarbonyl)amino]-N-[(2R)-tetrahydrofuran-2-ylmethyl]-4,7-dihydro-5H-thieno[2,3-c]pyran-3-carboxamide;

2-[(hexahydro-2,5-methanopentalen-3a(1H)-ylcarbonyl)amino]-N-[(2S)-tetrahydrofuran-2-ylmethyl]-4,7-dihydro-5H-thieno[2,3-c]pyran-3-carboxamide;

2-[(hexahydro-2,5-methanopentalen-3a(1H)-ylcarbonyl)amino]-N-(2-hydroxypropyl)-4,7-dihydro-5H-thieno[2,3-c]pyran-3-carboxamide;

2-[(hexahydro-2,5-methanopentalen-3a(1H)-ylcarbonyl)amino]-N-(2-hydroxybutyl)-4,7-dihydro-5H-thieno[2,3-c]pyran-3-carboxamide;

2-[(hexahydro-2,5-methanopentalen-3a(1H)-ylcarbonyl)amino]-N-[2-(methylthio)ethyl]-4,7-dihydro-5H-thieno[2,3-c]pyran-3-carboxamide;

2-[(hexahydro-2,5-methanopentalen-3a(1H)-ylcarbonyl)amino]-N-prop-2-ynyl-4,7-dihydro-5H-thieno[2,3-c]pyran-3-carboxamide;

N-(cyanomethyl)-2-[(hexahydro-2,5-methanopentalen-3a(1H)-ylcarbonyl)amino]-4,7-dihydro-5H-thieno[2,3-c]pyran-3-carboxamide;

Trans-2-[(hexahydro-2,5-methanopentalen-3a(1H)-ylcarbonyl)amino]-N-(2-hydroxycyclopentyl)-4,7-dihydro-5H-thieno[2,3-c]pyran-3-carboxamide;

N-hexahydro-2,5-methanopentalen-3a(1H)-yl-2-[(hexahydro-2,5-methanopentalen-3a(1H)-ylcarbonyl)amino]-4,7-dihydro-5H-thieno[2,3-c]pyran-3-carboxamide;

2-[(hexahydro-2,5-methanopentalen-3a(1H)-ylcarbonyl)amino]-N-(3-hydroxy-2,2-dimethylpropyl)-4,7-dihydro-5H-thieno[2,3-c]pyran-3-carb;

N-{3-[(2-phenylhydrazino)carbonyl]-4,7-dihydro-5H-thieno[2,3-c]pyran-2-yl}hexahydro-2,5-methanopentalene-3a(1H)-carboxamide;

2-[(hexahydro-2,5-methanopentalen-3a(1H)-ylcarbonyl)amino]-N-[2-(methylsulfonyl)ethyl]-4,7-dihydro-5H-thieno[2,3-c]pyran-3-carboxamide;

Trans-2-[(hexahydro-2,5-methanopentalen-3a(1H)-ylcarbonyl)amino]-N-(2-hydroxycyclohexyl)-4,7-dihydro-5H-thieno[2,3-c]pyran-3-carboxamide;

Cis-2-[(hexahydro-2,5-methanopentalen-3a(1H)-ylcarbonyl)amino]-N-(2-hydroxycyclohexyl)-4,7-dihydro-5H-thieno[2,3-c]pyran-3-carb;

2-[(hexahydro-2,5-methanopentalen-3a(1H)-ylcarbonyl)amino]-N-(3,3,3-trifluoropropyl)-4,7-dihydro-5H-thieno[2,3-c]pyran-3-carboxamide;

Trans-2-[(hexahydro-2,5-methanopentalen-3a(1H)-ylcarbonyl)amino]-N-(2-(hydroxymethyl)cyclohexyl)-4,7-dihydro-5H-thieno[2,3-c]pyran-3-carboxamide;

N-cyclobutyl-2-[(hexahydro-2,5-methanopentalen-3a(1H)-ylcarbonyl)amino]-4,7-dihydro-5H-thieno[2,3-c]pyran-3-carboxamide;

N-cyclopentyl-2-[(hexahydro-2,5-methanopentalen-3a(1H)-ylcarbonyl)amino]-4,7-dihydro-5H-thieno[2,3-c]pyran-3-carboxamide;

Cis-2-[(hexahydro-2,5-methanopentalen-3a(1H)-ylcarbonyl)amino]-N-(2-methylcyclohexyl)-4,7-dihydro-5H-thieno[2,3-c]pyran-3-carboxamide;

Trans-2-[(hexahydro-2,5-methanopentalen-3a(1H)-ylcarbonyl)amino]-N-(2-methylcyclohexyl)-4,7-dihydro-5H-thieno[2,3-c]pyran-3-carboxamide;

2-[(hexahydro-2,5-methanopentalen-3a(1H)-ylcarbonyl)amino]-N-(4-methylcyclohexyl)-4,7-dihydro-5H-thieno[2,3-c]pyran-3-carboxamide;

2-[(hexahydro-2,5-methanopentalen-3a(1H)-ylcarbonyl)amino]-N-[(1R,2S,3S,5S)-2,6,6-trimethylbicyclo[3.1.1]hept-3-yl]-4,7-dihydro-5H-thieno[2,3-c]pyran-3-carboxamide;

2-[(hexahydro-2,5-methanopentalen-3a(1H)-ylcarbonyl)amino]-N-[(1S,2R,3R,5R)-2,6,6-trimethylbicyclo[3.1.1]hept-3-yl]-4,7-dihydro-5H-thieno[2,3-c]pyran-3-carboxamide;

N-{[3-(dimethylamino)tetrahydrothien-3-yl]methyl}-2-[(hexahydro-2,5-methanopentalen-3a(1H)-ylcarbonyl)amino]-4,7-dihydro-5H-thieno[2,3-c]pyran-3-carboxamide;

N-benzyl-2-[(hexahydro-2,5-methanopentalen-3a(1H)-ylcarbonyl)amino]-4,7-dihydro-5H-thieno[2,3-c]pyran-3-carboxamide;

2-[(hexahydro-2,5-methanopentalen-3a(1H)-ylcarbonyl)amino]-N-[3-(methylthio)propyl]-4,7-dihydro-5H-thieno[2,3-c]pyran-3-carboxamide;

N-{3-[(3,3-difluoroazetidin-1-yl)carbonyl]-4,7-dihydro-5H-thieno[2,3-c]pyran-2-yl}hexahydro-2,5-methanopentalene-3a(1H)-carboxamide;

2-[(hexahydro-2,5-methanopentalen-3a(1H)-ylcarbonyl)amino]-N-phenyl-4,7-dihydro-5H-thieno[2,3-c]pyran-3-carboxamide;

exo-N-[bicyclo[2.2.1]hept-2-yl]-2-[(hexahydro-2,5-methanopentalen-3a(1H)-ylcarbonyl)amino]-4,7-dihydro-5H-thieno[2,3-c]pyran-3-carboxamide;

2-[(hexahydro-2,5-methanopentalen-3a(1H)-ylcarbonyl)amino]-N-(2,2,2-trifluoroethyl)-4,7-dihydro-5H-thieno[2,3-c]pyran-3-carboxamide;

N-{3-[2-azabicyclo[2.2.1]hept-2-ylcarbonyl]-4,7-dihydro-5H-thieno[2,3-c]pyran-2-yl}hexahydro-2,5-methanopentalene-3a(1H)-carboxamide;

N-{3-[(3-hydroxyazetidin-1-yl)carbonyl]-4,7-dihydro-5H-thieno[2,3-c]pyran-2-yl}hexahydro-2,5-methanopentalene-3a(1H)-carboxamide;

N-{3-[(3-methoxyazetidin-1-yl)carbonyl]-4,7-dihydro-5H-thieno[2,3-c]pyran-2-yl}hexahydro-2,5-methanopentalene-3a(1H)-carboxamide;

N-[3-(azetidin-1-ylcarbonyl)-4,7-dihydro-5H-thieno[2,3-c]pyran-2-yl]hexahydro-2,5-methanopentalene-3a(1H)-carboxamide;

N-{3-[(3,3-difluoropyrrolidin-1-yl)carbonyl]-4,7-dihydro-5H-thieno[2,3-c]pyran-2-yl}hexahydro-2,5-methanopentalene-3a(1H)-carboxamide;

2-[(hexahydro-2,5-methanopentalen-3a(1H)-ylcarbonyl)amino]-N-[(3R)-tetrahydrofuran-3-yl]-4,7-dihydro-5H-thieno[2,3-c]pyran-3-carboxamide;

N-{3-[(3,3-difluoroazetidin-1-yl)carbonyl]-4,7-dihydro-5H-thieno[2,3-c]pyran-2-yl}-2-oxatricyclo[3.3.1.1$^{3,7}$]decane-1-carboxamide;

N-cyclopropyl-2-[(hexahydro-2,5-methanopentalen-3a(1H)-ylcarbonyl)amino]-4,7-dihydro-5H-thieno[2,3-c]pyran-3-carboxamide;

N-{3-[(3,3-difluoroazetidin-1-yl)carbonyl]-2-naphthyl}hexahydro-2,5-methanopentalene-3a(1H)-carboxamide;

N-{4-bromo-2-[(3,3-difluoroazetidin-1-yl)carbonyl]phenyl}hexahydro-2,5-methanopentalene-3a(1H)-carboxamide;

N-{4-bromo-2-[(3,3-difluoroazetidin-1-yl)carbonyl]phenyl}hexahydro-2,5-methanopentalene-3a(1H)-carboxamide;

N-{2-[(3,3-difluoroazetidin-1-yl)carbonyl]-4-iodophenyl}hexahydro-2,5-methanopentalene-3a(1H)-carboxamide;

N-{2-[(3,3-difluoroazetidin-1-yl)carbonyl]-5-methylphenyl}hexahydro-2,5-methanopentalene-3a(1H)-carboxamide;

N-{2-[(3,3-difluoroazetidin-1-yl)carbonyl]-4,6-diiodophenyl}hexahydro-2,5-methanopentalene-3a(1H)-carboxamide;

N-{4-chloro-2-[(3,3-difluoroazetidin-1-yl)carbonyl]phenyl}hexahydro-2,5-methanopentalene-3a(1H)-carboxamide;

N-{2-[(3,3-difluoroazetidin-1-yl)carbonyl]-4,5-dimethoxyphenyl}hexahydro-2,5-methanopentalene-3a(1H)-carboxamide;

N-{5-chloro-2-[(3,3-difluoroazetidin-1-yl)carbonyl]phenyl}hexahydro-2,5-methanopentalene-3a(1H)-carboxamide;

N-[2-[(3,3-difluoroazetidin-1-yl)carbonyl]-5-(trifluoromethyl)phenyl]hexahydro-2,5-methanopentalene-3a(1H)-carboxamide;

N-{2-[(3,3-difluoroazetidin-1-yl)carbonyl]-5-fluorophenyl}hexahydro-2,5-methanopentalene-3a(1H)-carboxamide;

N-{2-[(3,3-difluoroazetidin-1-yl)carbonyl]-4-fluorophenyl}hexahydro-2,5-methanopentalene-3a(1H)-carboxamide;

N-{2-[(3,3-difluoroazetidin-1-yl)carbonyl]phenyl}hexahydro-2,5-methanopentalene-3a(1H)-carboxamide;

N-{2-[(3,3-difluoroazetidin-1-yl)carbonyl]-3-fluorophenyl}hexahydro-2,5-methanopentalene-3a(1H)-carboxamide;

N-{2-[(3,3-difluoroazetidin-1-yl)carbonyl]-5-nitrophenyl}hexahydro-2,5-methanopentalene-3a(1H)-carboxamide;

N-{2-[(3,3-difluoroazetidin-1-yl)carbonyl]-3-methylphenyl}hexahydro-2,5-methanopentalene-3a(1H)-carboxamide;

N-{3-chloro-2-[(3,3-difluoroazetidin-1-yl)carbonyl]phenyl}hexahydro-2,5-methanopentalene-3a(1H)-carboxamide;

N-[2-[(3,3-difluoroazetidin-1-yl)carbonyl]-5-(methylsulfonyl)phenyl]hexahydro-2,5-methanopentalene-3a(1H)-carboxamide;

N-{4,6-dibromo-3-chloro-2-[(3,3-difluoroazetidin-1-yl)carbonyl]phenyl}hexahydro-2,5-methanopentalene-3a(1H)-carboxamide;

N-{2-[(3,3-difluoroazetidin-1-yl)carbonyl]-4,5-difluorophenyl}hexahydro-2,5-methanopentalene-3a(1H)-carboxamide;

N-[2-[(3,3-difluoroazetidin-1-yl)carbonyl]-5-(methylsulfonyl)phenyl]-2-oxatricyclo[3.3.1.1$^{3,7}$]decane-1-carboxamide;

N-{2-[(3,3-difluoroazetidin-1-yl)carbonyl]-4,5-difluorophenyl}-2-oxatricyclo[3.3.1.1$^{3,7}$]decane-1-carboxamide;

N-{4-chloro-2-[(3,3-difluoroazetidin-1-yl)carbonyl]phenyl}-2-oxatricyclo[3.3.1.1$^{3,7}$]decane-1-carboxamide;

N-{2-[(3,3-difluoroazetidin-1-yl)carbonyl]-3-fluorophenyl}-2-oxatricyclo[3.3.1.1$^{3,7}$]decane-1-carboxamide;

N-{2-[(3,3-difluoroazetidin-1-yl)carbonyl]pyridin-3-yl}hexahydro-2,5-methanopentalene-3a(1H)-carboxamide; and N-{3-[(3,3-difluoroazetidin-1-yl)carbonyl]pyridin-4-yl}hexahydro-2,5-methanopentalene-3a(1H)-carboxamide.

Compounds of the present application may exist as stereoisomers wherein, asymmetric or chiral centers are present. These stereoisomers are "R" or "S" depending on the configuration of substituents around the chiral carbon atom. The terms "R" and "S" used herein are configurations as defined in IUPAC 1974 Recommendations for Section E, Fundamental Stereochemistry, Pure Appl. Chem., 1976, 45: 13-30.

The present application contemplates various stereoisomers and mixtures thereof and these are specifically included within the scope of this application. Stereoisomers include enantiomers and diastereomers, and mixtures of enantiomers or diastereomers. Individual stereoisomers of compounds of the present application may be prepared synthetically from commercially available starting materials which contain asymmetric or chiral centers or by preparation of racemic mixtures followed by resolution which is well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary or (2) direct separation of the mixture of optical enantiomers on chiral chromatographic columns.

Geometric isomers may exist in the present compounds. The invention contemplates the various geometric isomers and mixtures thereof resulting from the disposition of substituents around a carbon-carbon double bond, a carbon-nitrogen double bond, a cycloalkyl group, or a heterocycle group. Substituents around a carbon-carbon double bond or a carbon-nitrogen bond are designated as being of Z or E configuration and substituents around a cycloalkyl or a heterocycle are designated as being of cis or trans configuration.

Within the present invention it is to be understood that compounds disclosed herein may exhibit the phenomenon of tautomerism.

Thus, the formulae drawings within this specification can represent only one of the possible tautomeric or stereoisomeric forms. It is to be understood that the invention encompasses any tautomeric or stereoisomeric form, and mixtures thereof, and is not to be limited merely to any one tautomeric or stereoisomeric form utilized within the naming of the compounds or formulae drawings.

c. Biological Data (i) In Vitro Methods—$CB_2$ and $CB_1$ Radioligand Binding Assays:

The $CB_1$ and $CB_2$ radioligand binding assays described herein are utilized to ascertain the selectivity of compounds of the present application for binding to $CB_2$ relative to $CB_1$ receptors. limited merely to any one tautomeric or stereoisomeric form utilized within the naming of the compounds or formulae drawings.

HEK293 cells stably expressing human $CB_2$ receptors were grown until a confluent monolayer was formed. Briefly, the cells were harvested and homogenized in TE buffer (50 mM Tris-HCl, 1 mM $MgCl_2$, and 1 mM EDTA) using a polytron for 2×10 second bursts in the presence of protease inhibitors, followed by centrifugation at 45,000×g for 20 minutes. The final membrane pellet was re-homogenized in storage buffer (50 mM Tris-HCl, 1 mM $MgCl_2$, and 1 mM EDTA and 10% sucrose) and frozen at −78° C. until used. Saturation binding reactions were initiated by the addition of membrane preparation (protein concentration of 5 μg/well for human $CB_2$) into wells of a deep well plate containing [$^3$H]CP-55,940 (120 Ci/mmol, a nonselective CB agonist commercially available from Tocris) in assay buffer (50 mM Tris, 2.5 mM EDTA, 5 mM $MgCl_2$, and 0.5 mg/mL fatty acid free BSA, pH 7.4). After 90 min incubation at 30° C., binding reaction was terminated by the addition of 300 μl/well of cold assay buffer followed by rapid vacuum filtration through a UniFilter-96 GF/C filter plates (pre-soaked in 1 mg/mL BSA for 2 hours). The bound activity was counted in a TopCount using Microscint-20. Saturation experiments were conducted with twelve concentrations of [$^3$H]CP-55,940 ranging from 0.01 to 8 nM. Competition experiments were conducted with 0.5 nM [$^3$H]CP-55,940 and five concentrations (0.01 nM to 10 μM) of displacing ligands. The addition of 10 μM unlabeled CP-55,940 (Tocris, Ellisville, Mo.) was used to assess nonspecific binding.

The majority of the compounds of the present application bound to $CB_2$ receptors with $K_i$ of less than about 1,000 nM, preferably less than 400 nM, more preferably less than 200 nM, and most preferably lower than 100 nM.

HEK293 human $CB_1$ membranes were purchased from Perkin Elmer. Binding was initiated by the addition of membranes (8-12 μg per well) into wells (Scienceware 96-well DeepWell plate, VWR, West Chester, Pa.) containing [$^3$H]CP-55,940 (120 Ci/mmol, Perkin Elmer, Boston, Mass.) and a sufficient volume of assay buffer (50 mM Tris, 2.5 mM EDTA, 5 mM $MgCl_2$, and 0.5 mg/mL fatty acid free BSA, pH 7.4) to bring the total volume to 250 μL. After incubation (30° C. for 90 minutes), binding was terminated by the addition of 300 μL per well of cold assay buffer and rapid vacuum filtration (FilterMate Cell Harvester, Perkin Elmer, Boston, Mass.) through a UniFilter-96 GF/C filter plate (Perkin Elmer, Boston, Mass.) (pre-soaked in 0.3% PEI at least 3 hours), followed by five washes with cold assay buffer. The bound activity was counted in the TopCount using Microscint-20 (both from Perkin Elmer, Boston, Mass.). Competition experiments were conducted with 1 nM [$^3$H]CP-55,940 and five concentrations (1 nM to 10 μM) of displacing ligands. The addition of 10 μM unlabeled CP-55,940 (Tocris, Ellisville, Mo.) was used to assess nonspecific binding. The majority of the compounds of the present application tested for $CB_1$ binding, bound to $CB_1$ receptors with $K_i$ values 10×-1000× higher than the $K_i$ for $CB_2$. These results show that the compounds of the present application preferably bind to $CB_2$ receptors, therefore are selective ligands for the $CB_2$ receptor.

ii) In Vivo Data Animals

Adult male Sprague-Dawley rats (250-300 g body weight, Charles River Laboratories, Portage, Mich.) are used. Animal handling and experimental protocols are approved by the Institutional Animal Care and Use Committee (IACUC) at Abbott Laboratories. For all surgical procedures, animals are maintained under isoflurane anesthesia (4-5% to induce, 1-3% to maintain), and the incision sites are sterilized using a 10% povidone-iodine solution prior to and after surgeries.

Incision Model of Postoperative Pain

A skin incision model of postoperative pain was produced using the procedures previously described (Brennan et al., 1996, Pain, 64, 493). All rats were anesthetized with isofluorane delivered via a nose cone. Right hind paw incision was performed following sterilization procedures. The plantar aspect of the left hind paw was placed through a hole in a sterile plastic drape. A 1-cm longitudinal incision was made through the skin and fascia of the plantar aspect of the hind paw, starting 0.5 cm from the proximal edge of the heel and extending towards the toes, the plantar muscle was elevated and incised longitudinally leaving the muscle origin and insertion points intact. The skin was then closed with two mattress sutures (5-0 nylon). After surgery, animals were then allowed to recover for 2 hours, at which time tactile allodynia was assessed as described below. To evaluate the anti-nociceptive effects, animals were i.p. administered vehicle or test compound 90 minutes following skin incision and tactile allodynia was assessed 30 minutes after compound administration.

Tactile allodynia was measured using calibrated von Frey filaments (Stoelting, Wood Dale, Ill.) as described in Chaplan, S. R., F. W. Bach, J. M. Pogrel, J. M. Chung and T. L. Yaksh, 1994, Quantitative assessment of tactile allodynia in the rat paw, J. Neurosci. Methods, 53,55. Rats were placed into inverted individual plastic cage (20×12.5×20 cm) on top of a suspended wire mesh grid, and acclimated to the test chambers for 20 minutes. The von Frey filaments were applied perpendicularly from underneath the cage through openings in the wire mesh floor directly to an area within 1-3 mm (immediately adjacent) of the incision, and then held in this position for approximately 8 seconds with enough force to cause a slight bend in the filament. Positive responses included an abrupt withdrawal of the hind paw from the stimulus, or flinching behavior immediately following removal of the stimulus. A 50% withdrawal threshold was determined using an up-down procedure (Dixon, W. J., 1980, Efficient analysis of experimental observations, Ann. Rev. Pharmacol. Toxicol. 20, 441).

Representative compounds of the present application showed a statistically significant change in paw withdrawal latency versus a saline vehicle at less than about 300 micromoles/kg in the incision model of postoperative pain. In a more preferred embodiment, compounds of the present application showed efficacy at less than about 50 micromoles/kg in the incision model of postoperative pain.

Spinal Nerve Ligation Model of Neuropathic Pain

A model of spinal nerve ligation-induced (SNL model) neuropathic pain as originally described by Kim and Chung (Kim, S. H. and J. M. Chung, 1992, Pain 50, 355) was used to test the compounds of the present application The left L5 and L6 spinal nerves of the rat were isolated adjacent to the vertebral column and tightly ligated with a 5-0 silk suture distal to the DRG, and care was taken to avoid injury of the L4 spinal nerve. Sham rats underwent the same procedure, but without nerve ligation. All animals were allowed to recover for at least one week and not more than three weeks prior to assessment of tactile allodynia.

Tactile allodynia was measured using calibrated von Frey filaments (Stoelting, Wood Dale, Ill.) as described in Chaplan, S. R., F. W. Bach, J. M. Pogrel, J. M. Chung and T. L. Yaksh, 1994, Quantitative assessment of tactile allodynia in the rat paw, J. Neurosci. Methods, 53,55. Rats were placed into inverted individual plastic containers (20×12.5×20 cm) on top of a suspended wire mesh grid, and acclimated to the test chambers for 20 minutes. The von Frey filaments were presented perpendicularly to the plantar surface of the selected hind paw, and then held in this position for approximately 8 sec with enough force to cause a slight bend in the filament. Positive responses include an abrupt withdrawal of the hind paw from the stimulus, or flinching behavior immediately following removal of the stimulus. A 50% withdrawal threshold was determined using an up-down procedure (Dixon, W. J., 1980, Efficient analysis of experimental observations, Ann. Rev. Pharmacol. Toxicol., 20, 441. Only rats with a baseline threshold score of less that 4.25 g were used in this study, and animals demonstrating motor deficit are excluded. Tactile allodynia thresholds were also assessed in several control groups, including naive, sham-operated, and saline infused animals as well as in the contralateral paws of nerve-injured rats.

A representative compound of the present application showed a statistically significant change in paw withdrawal latency versus a saline vehicle at less than about 300 micromoles/kg in the spinal nerve ligation model of neuropathic pain.

Capsaicin-Induced Secondary Mechanical Hypersensitivity:

Rats are allowed to acclimate to the study room for 1 h. They are then briefly restrained, and capsaicin is administered at 10 µg in 10 µl of vehicle (10% ethanol and 2-hydroxypropyl cyclodextrin) by intraplantar injection into the center of the right hind paw. Secondary mechanical hyperalgesia is measured at the heel away from the site of injection at 180 min following capsaicin (Joshi et al 2006, Neuroscience 143, 587-596). Compounds are injected (i.p.) 30 min before testing (150 min post-capsaicin).

Tactile allodynia can be measured as described above.

d. Methods of Using the Compounds

One embodiment of the present invention provides a method for treating pain (for example, inflammatory pain, neuropathic pain or nociceptive pain) in a mammal (including human) in need of such treatment. The method comprises administering to the mammal a therapeutically effective amount of any of the compounds as described herein, or a pharmaceutically acceptable salt thereof. In certain embodiments, the method comprises administering to the mammal a therapeutically effective amount of any of the compounds as described herein, or a pharmaceutically acceptable salt thereof, in combination with one or more nonsteroidal anti-inflammatory drug (NSAID).

Yet another embodiment of the present invention relates to a method for providing neuroprotection in a mammal in need of such treatment. This method comprises administering to the mammal a therapeutically effective amount of a compound of the invention or a pharmaceutically acceptable salt thereof.

In addition to the data contained herein, several lines of evidence support the assertion that $CB_2$ receptors play a role in analgesia. For example, Zimmer et al. have reported that the nonselective cannabinoid agonist $\Delta^9$-THC retains some analgesic efficacy in $CB_1$ receptor knockout mice (Zimmer, A., et al., Proc. Nat. Acad. Sci., 1999, 96, 5780-5785).

HU-308 is one of the first highly selective $CB_2$ agonists identified that elicits an antinociceptive response in the rat formalin model of persistent pain (Hanus, L., et al., Proc. Nat. Acad. Sci., 1999, 96, 14228-14233). The $CB_2$-selective cannabinoid ligand AM-1241 exhibits robust analgesic efficacy in animal models of acute thermal pain (Malan, T. P., et al., Pain, 2001, 93, 239-245; Ibrahim, M. M., et al., Proc. Nat. Acad. Sci., 2005, 102(8), 3093-3098), persistent pain (Hohmann, A. G., et al., J. Pharmacol. Exp. Ther., 2004, 308, 446-453), inflammatory pain (Nackley, A. G., et al., Neuroscience, 2003, 119, 747-757; Quartilho, A. et al., Anesthesiology, 2003, 99, 955-60), and neuropathic pain (Ibrahim, M. M., et al., Proc. Nat. Acad. Sci., 2003, 100, 10529-10533). The $CB_2$-selective partial agonist GW405833, also known as L768242, is efficacious in rodent models of neuropathic, incisional, and both chronic and acute inflammatory pain (Valenzano, K. J., et al., Neuropharmacology, 2005, 48, 658-672 and Clayton, N., et al., Pain, 2002, 96, 253-260). The analgesic effects induced by these $CB_2$-selective ligands are blocked by $CB_2$ and not by $CB_1$ receptor antagonists. Furthermore, at fully efficacious doses, AM-1241 and GW405833 are devoid of typical $CB_1$ receptor-mediated CNS side effects, providing evidence that modulation of $CB_2$ receptors can produce broad-spectrum pain relief with reduced side-effect liability.

The potential exists for $CB_2$ modulators to have opioid sparing effects. A synergy between the analgesic effects of morphine and the nonselective CB agonist $\Delta^9$-THC has been documented (Cichewicz, D. L., Life Sci. 2004, 74, 1317-1324). Therefore, $CB_2$ ligands have additive or synergistic analgesic effects when used in combination with lower doses of morphine or other opioids, providing a strategy for reducing adverse opioid events, such as tolerance, constipation, and respiratory depression, without sacrificing analgesic efficacy.

$CB_2$ receptors are present in tissues and cell types associated with immune functions and $CB_2$ receptor mRNA is expressed by human B cells, natural killer cells, monocytes, neutrophils, and T cells (Galiegue et al., Eur. J. Biochem., 1995, 232, 54-61). Studies with $CB_2$ knockout mice have suggested a role for $CB_2$ receptors in modulating the immune system (Buckley, N. E., et al., Eur. J. Pharmacol. 2000, 396, 141-149). Although immune cell development and differentiation are similar in knockout and wild type animals, the immunosuppressive effects of $\Delta^9$-THC are absent in the $CB_2$ receptor knockout mice, providing evidence for the involvement of $CB_2$ receptors in immunomodulation. As such, selective $CB_2$ modulators are useful for the treatment of autoimmune diseases including but not limited to multiple sclerosis, rheumatoid arthritis, systemic lupus, myasthenia gravis, type I diabetes, irritable bowel syndrome, psoriasis, psoriatic arthritis, and hepatitis; and immune related disorders including but not limited to tissue rejection in organ transplants, gluten-sensitive enteropathy (Celiac disease), asthma, chronic obstructive pulmonary disease, emphysema, bronchitis, acute respiratory distress syndrome, allergies, allergic rhinitis, dermatitis, and Sjogren's syndrome.

Microglial cells are considered to be the immune cells of the central nervous system (CNS) where they regulate the initiation and progression of immune responses. They are quiescent and resting having a ramified morphology as long as the CNS is healthy. Microglia express a variety of receptors enabling them to survey the CNS and respond to pathological events. Insult or injury to the CNS leads to microglial cell activation, which is characterized by various morphological changes allowing response to the lesion. Ramifications are retracted and microglia are transformed into amoeboid-like cells with phagocytic function. They can proliferate, rapidly migrate to the site of injury, and produce and release cytokines, chemokines and complement components (Watkins L. R., et al., Trends in Neuroscience, 2001, 24(8), 450; Kreutzberg, G. W., Trends Neurosci., 1996, 19, 312-318). $CB_2$ receptor expression on microglia is dependent upon inflammatory state with higher levels of $CB_2$ found in primed, proliferating, and migrating microglia relative to resting or fully activated microglial (Carlisle, S. J., et al. Int. Immunopharmacol., 2002, 2, 69). Neuroinflammation induces many changes in microglia cell morphology and there is an upregulation of $CB_2$ receptors and other components of the endocannabinoid system. It is conceivable that $CB_2$ receptors may be more susceptible to pharmacological effects during neuroinflammation (Walter, L., Stella, N., Br. J. Pharmacol. 2004, 141, 775-785). Neuroinflammation occurs in several neurodegenerative diseases, and induction of microglial $CB_2$ receptors has been observed (Carrier, E. J., et al., Current Drug Targets —CNS & Neurological Disorders, 2005, 4, 657-665). Thus, $CB_2$ ligands may be clinically useful for the treatment of neuroinflammation.

$CB_2$ receptor expression has been detected in perivascular microglial cells within normal, healthy human cerebellum (Nunez, E., et al., Synapse, 2004, 58, 208-213). Perivascular cells are immunoregulatory cells located adjacent to CNS blood vessels and, along with parenchymal microglia and astrocytes; they play a pivotal role in maintaining CNS homeostasis and blood-brain barrier functionality (Williams, K., et al., Glia, 2001, 36, 156-164). $CB_2$ receptor expression has also been detected on cerebromicrovascular endothelial cells, which represent a main component of the blood-brain barrier (Golech, S. A., et al., Mol. Brain. Res., 2004, 132, 87-92). A recent report demonstrated that $CB_2$ receptor expression is up-regulated in the brains of macaques with simian immunodeficiency virus-induced encephalitis (Benito, C., et al., J. Neurosci. 2005, 25(10), 2530-2536). Thus, compounds that affect $CB_2$ signaling may protect the blood-brain barrier and be clinically useful in the treatment of neuroinflammation and a variety of neuroinflammatory disorders including retroviral encephalitis, which occurs with human immunodeficiency virus (HIV) infection in the CNS.

Multiple sclerosis is common immune-mediated disease of the CNS in which the ability of neurons to conduct impulses becomes impaired through demyelination and axonal damage. The demyelination occurs as a consequence of chronic inflammation and ultimately leads to a broad range of clinical symptoms that fluctuate unpredictably and generally worsen with age. These include painful muscle spasms, tremor, ataxia, motor weakness, sphincter dysfunction, and difficulty speaking (Pertwee, R. G., Pharmacol. Ther. 2002, 95, 165-174). The $CB_2$ receptor is up-regulated on activated microglial cells during experimental autoimmune encephalomyelitis (EAE) (Maresz, K., et al., J. Neurochem. 2005, 95, 437-445). $CB_2$ receptor activation prevents the recruitment of inflammatory cells such as leukocytes into the CNS (Ni, X., et al., Multiple Sclerosis, 2004, 10, 158-164) and plays a protective role in experimental, progressive demyelination (Arevalo-Martin, A.; et al., J. Neurosci., 2003, 23(7), 2511-2516), which are critical features in the development of multiple sclerosis. Thus, $CB_2$ receptor modulators provide a unique treatment for demyelinating pathologies.

Alzheimer's disease is a chronic neurodegenerative disorder accounting for the most common form of elderly dementia. Recent studies have revealed that $CB_2$ receptor expression is upregulated in neuritic plaque-associated microglia from brains of Alzheimer's disease patients (Benito, C., et al., J. Neurosci., 2003, 23(35), 11136-11141). In vitro, treatment with the $CB_2$ agonist JWH-133 abrogated β-amyloid-induced microglial activation and neurotoxicity, effects that can be blocked by the CB$_2$ antagonist SR144528 (Ramirez, B. G., et al., J. Neurosci. 2005, 25(8), 1904-1913). CB$_2$ modulators possess both anti-inflammatory and neuroprotective actions and thus have clinical utility in treating neuroinflammation and in providing neuroprotection associated with the development of Alzheimer's disease.

Increased levels of epithelial CB$_2$ receptor expression are observed in human inflammatory bowel disease tissue (Wright, K., et al., Gastroenterology, 2005, 129, 437-453). Activation of CB$_2$ receptors re-established normal gastrointestinal transit after endotoxic inflammation was induced in rats (Mathison, R., et al., Br. J. Pharmacol. 2004, 142, 1247-1254). CB$_2$ receptor activation in a human colonic epithelial cell line inhibited TNF-α-induced interleukin-8 (IL-8) release (Ihenetu, K. et al., Eur. J. Pharmacol. 2003, 458, 207-215). Chemokines released from the epithelium, such as the neutrophil chemoattractant IL-8, are upregulated in inflammatory bowel disease (Warhurst, A. C., et al., Gut, 1998, 42, 208-213). Thus, administration of CB$_2$ receptor modulators represents a novel approach for the treatment of inflammation and disorders of the gastrointestinal tract including but not limited to inflammatory bowel disease, irritable bowel syndrome, secretory diarrhea, ulcerative colitis, Crohn's disease and gastro-esophageal reflux disease (GERD).

Hepatic fibrosis occurs as a response to chronic liver injury and ultimately leads to cirrhosis, which is a major worldwide health issue due to the severe accompanying complications of portal hypertension, liver failure, and hepato-cellular carcinoma (Lotersztajn, S., et al., Annu. Rev. Pharmacol. Toxicol., 2005, 45, 605-628). Although CB$_2$ receptors were not detectable in normal human liver, CB$_2$ receptors were expressed liver biopsy specimens from patients with cirrhosis. Activation of CB$_2$ receptors in cultured hepatic myofibroblasts produced potent antifibrogenic effects (Julien, B., et al., Gastroenterology, 2005, 128, 742-755). In addition, CB$_2$ knockout mice developed enhanced liver fibrosis after chronic administration of carbon tetrachloride relative to wild-type mice. Administration of CB$_2$ receptor modulators represents a unique approach for the treatment of liver fibrosis.

CB$_2$ receptors are involved in the neuroprotective and anti-inflammatory mechanisms induced by the interleukin-1 receptor antagonist (IL-Ira) (Molina-Holgado, F., et al., J. Neurosci., 2003, 23(16), 6470-6474). IL-Ira is an important anti-inflammatory cytokine that protects against ischemic, excitotoxic, and traumatic brain insults. CB$_2$ receptors play a role in mediating these neuroprotective effects indicating that CB$_2$ ligands are useful in the treatment of traumatic brain injury, stroke, and in mitigating brain damage.

Cough is a dominant and persistent symptom of many inflammatory lung diseases, including asthma, chronic obstructive pulmonary disease, viral infections, and pulmonary fibrosis (Patel, H. J., et al., Brit. J. Pharmacol., 2003, 140, 261-268). Recent studies have provided evidence for the existence of neuronal CB$_2$ receptors in the airways, and have demonstrated a role for CB$_2$ receptor activation in cough suppression (Patel, H. J., et al., Brit. J. Pharmacol., 2003, 140, 261-268 and Yoshihara, S., et al., Am. J. Respir. Crit. Care Med., 2004, 170, 941-946). Both exogenous and endogenous cannabinoid ligands inhibit the activation of C-fibers via CB$_2$ receptors and reduce neurogenic inflammatory reactions in airway tissues (Yoshihara, S., et al., J. Pharmacol. Sci. 2005, 98(1), 77-82; Yoshihara, S., et al., Allergy and Immunology, 2005, 138, 80-87). Thus, CB$_2$-selective modulators have utility as antitussive agents for the treatment of pulmonary inflammation, chronic cough, and a variety of airway inflammatory diseases including but not limited to asthma, chronic obstructive pulmonary disease, and pulmonary fibrosis.

Osteoporosis is a disease characterized by reduced bone mass, which leads to deterioration of bone microstructure and increased susceptibility to fracture. Age is associated with bone loss and it is estimated that 50% of all Caucasian women will have osteoporosis by the age of 80 (Ralston, S. H., Curr. Opin. Pharmacol., 2003, 3, 286-290). There is a substantial genetic contribution to bone mass density and the CB$_2$ receptor gene is associated with human osteoporosis (Karsak, M., et al., Human Molecular Genetics, 2005, 14(22), 3389-3396). Osteoclasts and osteoblasts are largely responsible for maintaining bone structure and function through a process called remodeling, which involves resorption and synthesis of bone (Boyle, W. J., et al., Nature, 2003, 423, 337-342). CB$_2$ receptor expression has been detected on osteoclasts and osteoblasts precursor cells, and administration of a CB$_2$ agonist in mice caused a dose-dependent increase in bone formation (Grotenhermen, F. and Muller-Vahl, K., Expert Opin. Pharmacother., 2003, 4(12), 2367-2371). Cannabinoid inverse agonists, including the CB$_2$-selective inverse agonist SR144528, have been shown to inhibit osteoclast activity and reverse ovariectomy-induced bone loss in mice, which is a model for post-menopausal osteoporosis (Ralston, S. H., et al., Nature Medicine, 2005, 11, 774-779). Thus, CB$_2$ modulators are useful for the treatment and prevention of osteoporosis, osteoarthritis, and bone disorders.

Atherosclerosis is a chronic inflammatory disease and is a leading cause of heart disease and stroke. CB$_2$ receptors have been detected in both human and mouse atherosclerotic plaques. Administration of low doses of THC in apolipoprotein E knockout mice slowed the progression of atherosclerotic lesions, and these effects were inhibited by the CB$_2$-selective antagonist SR144528 (Steffens, S., et al., Nature, 2005, 434, 782-786). Thus, compounds with activity at the CB$_2$ receptor are clinically useful for the treatment of atherosclerosis.

CB$_2$ receptors are expressed on malignant cells of the immune system and targeting CB$_2$ receptors to induce apoptosis may constitute a novel approach to treating malignancies of the immune system. Selective CB$_2$ agonists induce regression of malignant gliomas (Sanchez, C., et al., Cancer Res., 2001, 61, 5784-5789), skin carcinomas (Casanova, M. L., et al., J. Clin. Invest., 2003, 111, 43-50), and lymphomas (McKallip, R. J., et al., Blood, 2002, 15(2), 637-634). Thus, CB$_2$ modulators have utility as anticancer agents against tumors of immune origin.

Recent studies indicate the presence of both cannabinoid CB$_1$ and CB$_2$ receptor immunoreactivity in rat pancreatic β- and non-β-cells, adding the endocrine pancreas to adipose tissue and the liver as potential sites for endocannabinoid regulation of glucose homeostasis, indicating that CB$_2$-selective modulators have utility in the treatment of diabetes and obesity (Bermudez-Silva et al., Eur. Journal of Pharmacology, 2007).

Activation of CB$_2$ receptors has been demonstrated to protect the heart against the deleterious effects of ischemia and reperfusion (Lepicier, P., et al., Brit. J. Pharm. 2003, 139, 805-815; Bouchard, J.-F., et al., Life Sci. 2003, 72, 1859-1870; Filippo, C. D., et al., J. Leukoc. Biol. 2004, 75, 453-459). Thus, CB$_2$ modulators have utility for the treatment or prophylaxis of cardiovascular disease and the development of myocardial infarction.

Actual dosage levels of active ingredients in the pharmaceutical compositions of this invention can be varied so as to obtain an amount of the active compound(s) that is effective to achieve the desired therapeutic response for a particular patient, compositions and mode of administration. The selected dosage level will depend upon the activity of the particular compound, the route of administration, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved.

Compounds of the invention can also be administered as a pharmaceutical composition comprising the compounds of interest in combination with one or more pharmaceutically acceptable carriers. The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of the invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well-known in the medical arts. For example, it is well within the skill of the art to start doses of the compound at levels lower than required to achieve the desired therapeutic effect and to gradually increase the dosage until the desired effect is achieved.

The total daily dose of the compounds of this invention administered to a human or other animal range from about 0.1 mg/kg body weight to about 100 mg/kg body weight. More preferable doses can be in the range of from about 0.3 mg/kg body weight to about 30 mg/kg body weight. If desired, the effective daily dose can be divided into multiple doses for purposes of administration. Consequently, single dose compositions may contain such amounts or submultiples thereof to make up the daily dose.

e. Pharmaceutical Compositions

The present invention further provides pharmaceutical compositions that comprise compounds of the present invention or a pharmaceutically acceptable salt or solvate thereof. The pharmaceutical compositions comprise compounds of the present invention that may be formulated together with one or more non-toxic pharmaceutically acceptable carriers.

Another aspect of the present invention is a pharmaceutical composition comprising compounds of the invention, or a pharmaceutically acceptable salt thereof, and one or more pharmaceutically acceptable carriers, alone or in combination with one or more nonsteroidal anti-inflammatory drug (NSAID).

The pharmaceutical compositions of this invention can be administered to humans and other mammals orally, rectally, parenterally, intracisternally, intravaginally, intraperitoneally, topically (as by powders, ointments or drops), bucally or as an oral or nasal spray. The term "parenterally" as used herein, refers to modes of administration which include intravenous, intramuscular, intraperitoneal, intrasternal, subcutaneous and intraarticular injection and infusion.

The term "pharmaceutically acceptable carrier" as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such a propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), vegetable oils (such as olive oil), injectable organic esters (such as ethyl oleate) and suitable mixtures thereof. Proper fluidity can be maintained, for example, by the use of coating materials such as lecithin, by the maintenance of the required particle size in the case of dispersions and by the use of surfactants.

These compositions may also contain adjuvants such as preservatives, wetting agents, emulsifying agents and dispersing agents. Prevention of the action of microorganisms can be ensured by the inclusion of various antibacterial and antifungal agents, for example, paraben, chlorobutanol, phenol sorbic acid and the like. It may also be desirable to include isotonic agents such as sugars, sodium chloride and the like. Prolonged absorption of the injectable pharmaceutical form can be brought about by the inclusion of agents which delay absorption such as aluminum monostearate and gelatin.

In some cases, in order to prolong the effect of the drug, it is desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders and granules. In such solid dosage forms, the active compound may be mixed with at least one inert, pharmaceutically acceptable excipient or carrier, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents.

Solid compositions of a similar type may also be employed as fillers in soft and hard-filled gelatin capsules using such carriers as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned carriers.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof.

Besides inert diluents, the oral compositions may also include adjuvants such as wetting agents, emulsifying and suspending agents, sweetening, flavoring and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, tragacanth and mixtures thereof.

Compositions for rectal or vaginal administration are preferably suppositories which can be prepared by mixing the compounds of this invention with suitable non-irritating carriers or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals which are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients and the like. The preferred lipids are natural and synthetic phospholipids and phosphatidyl cholines (lecithins) used separately or together.

Methods to form liposomes are known in the art. See, for example, Prescott, Ed., Methods in Cell Biology, Volume XIV, Academic Press, New York, N.Y. (1976), p. 33 et seq.

Dosage forms for topical administration of a compound of this invention include powders, sprays, ointments and inhalants. The active compound may be mixed under sterile conditions with a pharmaceutically acceptable carrier and any needed preservatives, buffers or propellants which may be required. Opthalmic formulations, eye ointments, powders and solutions are also contemplated as being within the scope of this invention.

The compounds of the present invention can be used in the form of pharmaceutically acceptable salts derived from inorganic or organic acids. The phrase "pharmaceutically acceptable salt" means those salts which are, within the scope of sound medical judgment, suitable for use in contact with the tissues of humans and lower animals without undue toxicity, irritation, allergic response and the like and are commensurate with a reasonable benefit/risk ratio.

Pharmaceutically acceptable salts are well known in the art. For example, S. M. Berge et al. describe pharmaceutically acceptable salts in detail in (J. Pharmaceutical Sciences, 1977, 66: 1 et seq). The salts can be prepared in situ during the final isolation and purification of the compounds of the invention or separately by reacting a free base function with a suitable organic acid. Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isothionate), lactate, malate, maleate, methanesulfonate, nicotinate, 2-naphthalenesulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as, but not limited to, methyl, ethyl, propyl, and butyl chlorides, bromides and iodides; dialkyl sulfates like dimethyl, diethyl, dibutyl and diamyl sulfates; long chain halides such as, but not limited to, decyl, lauryl, myristyl and stearyl chlorides, bromides and iodides; arylalkyl halides like benzyl and phenethyl bromides and others. Water or oil-soluble or dispersible products are thereby obtained. Examples of acids which can be employed to form pharmaceutically acceptable acid addition salts include such inorganic acids as hydrochloric acid, hydrobromic acid, sulfuric acid, and phosphoric acid and such organic acids as acetic acid, fumaric acid, maleic acid, 4-methylbenzenesulfonic acid, succinic acid and citric acid.

Basic addition salts can be prepared in situ during the final isolation and purification of compounds of this invention by reacting a carboxylic acid-containing moiety with a suitable base such as, but not limited to, the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as, but not limited to, lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, ethylamine and the like. Other representative organic amines useful for the formation of base addition salts include ethylenediamine, ethanolamine, diethanolamine, piperidine, piperazine and the like.

The term "pharmaceutically acceptable prodrug" or "prodrug" as used herein, represents those prodrugs of the compounds of the present invention which are, within the scope of sound medical judgment, suitable for use in contact with the tissues of humans and lower animals without undue toxicity, irritation, allergic response, and the like, commensurate with a reasonable benefit/risk ratio, and effective for their intended use.

The present invention contemplates compounds of the invention formed by synthetic means or formed by in vivo biotransformation of a prodrug.

The compounds of the invention can exist in unsolvated as well as solvated forms, including hydrated forms, such as hemi-hydrates. In general, the solvated forms, with pharmaceutically acceptable solvents such as water and ethanol among others are equivalent to the unsolvated forms for the purposes of the invention.

f. General Synthesis

This invention is intended to encompass compounds of the invention when prepared by synthetic processes or by metabolic processes. Preparation of the compounds by metabolic processes includes those occurring in the human or animal body (in vivo) or processes occurring in vitro.

The compounds of the invention may be prepared by a variety of processes well known for the preparation of compounds of this class. For example, the compounds of the invention wherein the groups $R^1$, $R^2$, and $R^3$, have the meanings as set forth in the summary section unless otherwise noted, can be synthesized as shown in Schemes 1-4.

Abbreviations which have been used in the descriptions of the Schemes and the Examples that follow are: DMAP for 4-(dimethylamino)pyridine, DMF for N,N-dimethylformamide, DMSO for dimethyl sulfoxide, EDCI for 1-(3-dimethylaminopropyl)-3-ethylcarbodiimide hydrochloride, EtOAc for ethyl acetate, $CHCl_3$ for chloroform, $CH_2Cl_2$ for dichloromethane, $CH_3CN$ for acetonitrile, HOBt for 1-hydroxybenzotriazole hydrate and THF for tetrahydrofuran.

Scheme 1

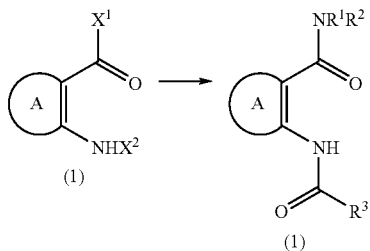

Compounds of formula (1) wherein $X^1$ is $NR^1R^2$ and $X^2$ is hydrogen can be converted to compounds of general formula (I) by treating with acids of formula $R^3COOH$ or acid chlorides of formula $R^3C(O)Cl$ using reaction conditions that are known in the art. For example, reaction of about equimolar quantities of compounds of formula (1) and compounds of formula $R^3C(O)Cl$, in a solvent such as chloroform, dichloromethane, tetrahydrofuran, or mixtures thereof, in the presence of a base such as but not limited to diisopropylethylamine, provides compounds of formula (I). Coupling reactions between compounds of formula (1) with an acid of formula $R^3COOH$ can be conducted in the presence of a coupling reagent, optionally in the presence of a coupling auxillary, and optionally in the presence of a base. Examples of coupling reagents include, but are not limited to, 1,1'-carbonyldiimidazole (CDI), bis(2-oxo-3-oxazolidinyl)phosphinic chloride (BOPCl), 1,3-dicyclohexylcarbodiimide (DCC), polymer supported 1,3-dicyclohexylcarbodiimide (PS-DCC), O-(7-azabenzotriazol-1-yl)-N,N,N',N'-tetramethyluronium hexafluorophosphate (HATU), and O-benzotriazol-1-yl-N,N,N',N'-tetramethyluronium tetrafluoroborate (TBTU). Examples of coupling auxiliaries include, but not limited to, 1-hydroxy-7-azabenzotriazole (HOAT) and 1-hydroxybenzotriazole hydrate (HOBT). Examples of suitable bases include, but are not limited to, N-methyl morpholine and diisopropylethylamine. The reaction is generally conducted in a solvent such as, but not limited to, tetrahydrofuran, N,N-dimethylacetamide, N,N-dimethylformamide, pyridine, dichloromethane, ethyl acetate, and mixtures thereof. Typical reactions can be carried out at a temperature between about 0° C. to about 65° C., and optionally conducted in a microwave reactor to facilitate the coupling.

Likewise, compounds of general formula (I) can also be prepared from (1) wherein $X^1$ is Cl or OH and $X^2$ is $C(O)R^3$ by treating with amines of formula $NHR^1R^2$, using similar reaction conditions as described above.

Acids of formula $R^3COOH$ are commercially available (for example, 3a,6a-dimethylhexahydro-1H-1,4-methanocyclopenta[c]furan-1-carboxylic acid), or prepared from corresponding commercially available esters. Some acids can be prepared using general procedures such as those illustrated in Schemes 2-4.

Scheme 2

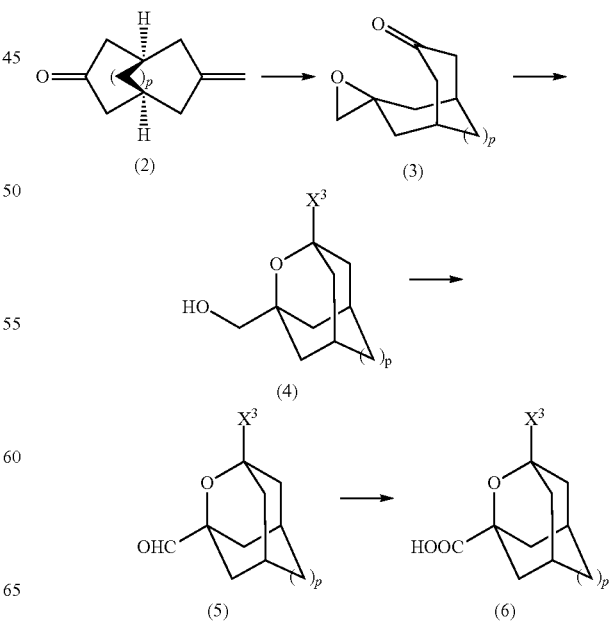

Synthesis of the compound of formula (2) when p is 0 reported by Harrowven, David C.; Lucas, Matthew C.; Howes, and Peter D. in *Tetrahedron*, 2001, 57, 9157-9162. The compound of formula (2) wherein p is 1 is commercially available. Treatment of compounds of formula (2) wherein p is 0 or 1 with m-chloroperbenzoic acid in a solvent such as, but not limited to, dichloromethane, at about ambient temperature (for example, 20-25° C.) provides compounds of formula (3). Reduction of (3) with a reducing agent such as sodium borohydride in a solvent such as, but not limited to, methanol, provides alcohols of formula (4) wherein $X^3$ is hydrogen. Treatment of (3) with methyl lithium in a solvent such as, but not limited to, tetrahydrofuran, provides alcohols of formula (4) wherein $X^3$ is methyl. Alcohols of formula (4) wherein $X^3$ is hydrogen or methyl can be converted to aldehydes of formula (5) under oxidation conditions such as Swern oxidation. The resulting aldehydes can be further treated with an oxidizing agent such as an aqueous solution or an alcoholic solution containing sodium chlorite and optionally a co-solvent such as 2-methylbut-2-ene to provide acids of formula (6). Acids of formula (6) wherein $X^3$ is hydrogen can also be obtained from hydrolysis of the corresponding methyl ester (Partch R., Brewster W., and Stoke B., *Croatia Chemical Acta*, 1969, 58(4), 661-669), for example, by treatment with sodium hydroxide in a mixture of alcohol (for example, methanol) and water, at a temperature from about room temperature to about reflux temperature of the solvent system employed.

Scheme 3

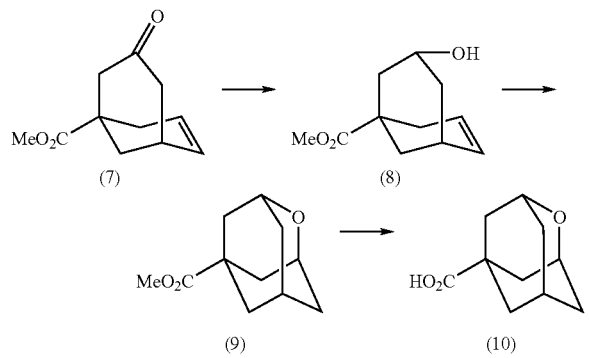

(7) (8) (9) (10)

The ketone of formula (7) (Bartlett, P. A., Nakagawa, Y., Johnson, C. R., Reich, S. H., Luis, A., *J. Org. Chem.*, 1988, 53, 3195-3210) can be selectively reduced to the alcohol of formula (8), utilizing a mild reducing agent such as, but not limited to, sodium borohydride, at about room temperature. In the presence of an acid such as, but not limited to, hydrochloric acid, p-toluenesulfonic acid, or trifluoroacetic acid, the alcohol of formula (8) can be converted to the compound of formula (9). Hydrolyzing the compound of formula (9) using methodologies known to one skilled in the art provides the acid of formula (10). For example, (9) can be converted to (10) in the presence of a base such as, but not limited to, a solution of sodium hydroxide in a mixture of water and alcohol (for example, methanol), at about room temperature.

Scheme 4

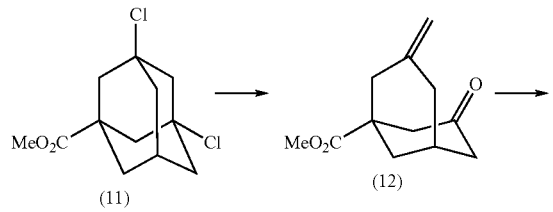

(11) (12)

-continued

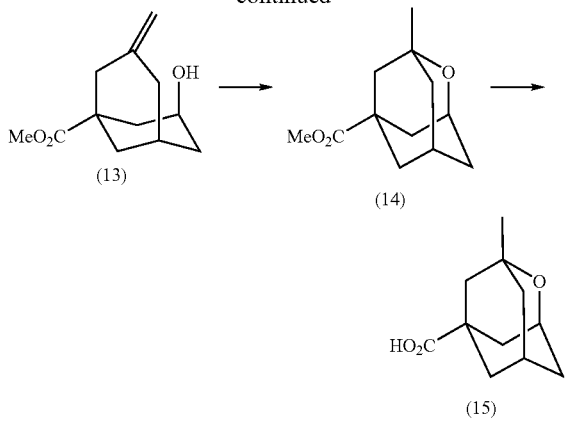

(13) (14)

(15)

Synthesis of the compound of formula (11) has been referred to in Khusnutdinov, R. I., Shchadneva, N. A., Baiguzina, A. R., Lavrent'eva, Y. Y., Burangulova, R. Y., Dzhemelev, U. M., *Neftekhimiya*, 2004, 44, 148-155. The compound of formula (11) can be converted to the compound of formula (12) by treatment with a base such as potassium carbonate, in a solvent such as an alcohol (for example, methanol), water, or mixture thereof, at a temperature from about room temperature to about the reflux temperature of the solvent employed. The resulting compound can be reduced to the corresponding alcohol (13) with a mild reducing agent known to those skilled in the art, such as, but not limited to, treatment with sodium borohydride in an alcoholic solvent such as methanol, at about ambient temperature (20-25° C.). Treatment of the alcohol with an acid such as, but not limited to, p-toluenesulfonic acid, hydrochloric acid, or trifluoroacetic acid, in a solvent such as tetrahydrofuran, at about ambient temperature (20-25° C.), affords the compound of formula (14). The ester of formula (14) can be converted to the acid of formula (15) by hydrolyzing the ester according to methods known to those skilled in the art, such as by base-catalysed hydrolysis.

It will be appreciated that the synthetic schemes and specific examples as illustrated in the Examples section are illustrative and are not to be read as limiting the scope of the invention as it is defined in the appended claims. All alternatives, modifications, and equivalents of the synthetic methods and specific examples are included within the scope of the claims.

Optimum reaction conditions and reaction times for each individual step may vary depending on the particular reactants employed and substituents present in the reactants used. Unless otherwise specified, solvents, temperatures and other reaction conditions may be readily selected by one of ordinary skill in the art. Specific procedures are provided in the Examples section. Reactions may be worked up in the conventional manner, e.g. by eliminating the solvent from the residue and further purified according to methodologies generally known in the art such as, but not limited to, crystallization, distillation, extraction, trituration and chromatography. Unless otherwise described, the starting materials and reagents are either commercially available or may be prepared by one skilled in the art from commercially available materials using methods described in the chemical literature.

Routine experimentations, including appropriate manipulation of the reaction conditions, reagents and sequence of the synthetic route, protection of any chemical functionality that may not be compatible with the reaction conditions, and deprotection at a suitable point in the reaction sequence of the method are included in the scope of the invention. Suitable protecting groups and the methods for protecting and deprotecting different substituents using such suitable protecting groups are well known to those skilled in the art; examples of which may be found in T. Greene and P. Wuts, Protecting Groups in Chemical Synthesis (3$^{rd}$ ed.), John Wiley & Sons, NY (1999), which is incorporated herein by reference in its entirety. Synthesis of the compounds of the invention may be accomplished by methods analogous to those described in the synthetic schemes described hereinabove and in specific examples.

Starting materials, if not commercially available, may be prepared by procedures selected from standard organic chemical techniques, techniques that are analogous to the synthesis of known, structurally similar compounds, or techniques that are analogous to the above described schemes or the procedures described in the synthetic examples section.

When an optically active form of a compound of the invention is required, it may be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound of the invention is required, it may be obtained by carrying out one of the above procedures using a pure geometric isomer as a starting material, or by resolution of a mixture of the geometric isomers of the compound or intermediates using a standard procedure such as chromatographic separation.

g. Examples

The compounds and processes of the present application will be better understood by reference to the following Examples, which are intended as an illustration of and not a limitation upon the scope of the application. Compounds of the application were named by ACD/ChemSketch version 5.01 (developed by Advanced Chemistry Development, Inc., Toronto, ON, Canada) or were given names consistent with ACD nomenclature.

Example 1 ethyl 2-{[(2,2,3,3-tetramethylcyclopropyl)carbonyl]amino}-1-benzothiophene-3-carboxylate To Example 12 (1.4 g, 4.0 mmol) in 40 mL benzene was added 2,3-dichloro-5,6-dicyano-1,4-benzoquinone (DDQ, 1.8 g, 8.0 mmol). The mixture was warmed to reflux and stirred for 2 hours. The material was then cooled to ambient temperature and filtered through Celite® and silica gel with ethyl acetate. The filtrate was concentrated under reduced pressure and the residue was purified by column chromatography ($SiO_2$, 75% hexanes:ethyl acetate) to afford the title compound. $^1$H NMR (300 MHz, $CDCl_3$) δ ppm 1.26 (s, 6H), 1.36 (s, 6H), 1.52 (t, J=7.1 Hz, 3H), 1.54 (s, 1H), 4.50 (q, J=7.1 Hz, 2H), 7.27 (ddd, J=8.1, 1.4 Hz, 1H), 7.40 (ddd, J=8.1, 7.1, 1.0 Hz, 1H), 7.71 (ddd, J=8.1, 1.4, 0.7 Hz, 1H), 8.27 (ddd, J=8.1, 0.7 Hz, 1H), 11.79 (s, 1H); MS ($DCI/NH_3$) m/z 346 (M+H)$^+$; anal. calculated for $C_{19}H_{23}NO_3S$: C, 66.06; H, 6.71; N, 4.05. Found: C, 65.93; H, 6.49; N, 3.92.

Example 2

N-ethyl-2-{[(2,2,3,3-tetramethylcyclopropyl)carbonyl]amino}-1-benzothiophene-3-carboxamide The title compound was prepared as described in Example 1, substituting Example 29B for Example 12. $^1$H NMR (300 MHz, $CDCl_3$) δ ppm 1.24 (s, 6H), 1.35 (t, J=7.1 Hz, 3H), 1.35 (s, 6H), 1.54 (s, 1H), 3.58 (m, 2H), 6.21 (s, 1H), 7.26 (m, 1H), 7.41 (ddd, J=7.7, 0.8 Hz, 1H), 7.76 (m, 2H), 12.04 (s, 1H); MS ($DCI/NH_3$) m/z 345 (M+H)$^+$; anal. calculated for $C_{19}H_{24}N_2O_2S.0.2CH_3OH$: C, 66.56; H, 6.77; N, 7.84. Found: C, 66.86; H, 7.08; N, 8.01.

Example 3

N-isopropyl-2-{[(2,2,3,3-tetramethylcyclopropyl)carbonyl]amino}-1-benzothiophene-3-carboxamide The title compound was prepared as described in Example 1, substituting Example 30 for Example 12. $^1$H NMR (300 MHz, $CDCl_3$) δ ppm 1.24 (s, 6H), 1.35 (s, 3H), 1.35 (s, 6H), 1.37 (s, 3H), 1.55 (s, 1H), 4.36 (m, 1H), 6.06 (m, 1H), 7.27 (ddd, J=8.1, 7.2, 1.0 Hz, 1H), 7.42 (ddd, J=8.2, 7.2, 1.2 Hz, 1H), 7.73 (d, J=8.1 Hz, 1H), 7.77 (m, 1H), 12.03 (s, 1H); MS ($DCI/NH_3$) m/z 359 (M+H)$^+$; anal. calculated for $C_{20}H_{26}N_2O_2S$: C, 67.01; H, 7.31; N, 7.81. Found: C, 66.81; H, 7.69; N, 7.74.

Example 4

6-tert-butyl 3-ethyl 2-{[(2,2,3,3-tetramethylcyclopropyl)carbonyl]amino}-4,7-dihydrothieno[2,3-c]pyridine-3,6(5H)-dicarboxylate Example 4A 2-Amino-4,7-dihydro-5H-thieno[2,3-c]pyridine-3,6-dicarboxylic acid 6-tert-butyl ester 3-ethyl ester To a solution of t-butyl-4-oxo-1-piperidinecarboxylate (25.1 g, 0.13 mol), ethyl cyanoacetate (14.8 mL, 0.14 mol) and sulfur (4.4 g, 0.14 mol) in 200 mL ethanol was added morpholine (30.8 mL, 0.35 mol). The mixture was warmed to 50° C. and stirred for 3 hours. The reaction mixture was then cooled to ambient temperature, diluted with diethyl ether and filtered. The residue was washed with $H_2O$ and diethyl ether. The filtrate was concentrated under reduced pressure and purified via column chromatography ($SiO_2$, 70% hexanes:ethyl acetate). The resulting material was combined with the filtration residue to afford the title compound. MS ($DCI/NH_3$) m/z 327 (M+H)$^+$.

Example 4B 6-tert-butyl 3-ethyl 2-{[(2,2,3,3-tetramethylcyclopropyl)carbonyl]amino}-4,7-dihydrothieno[2,3-c]pyridine-3,6(5H)-dicarboxylate Example 4A was reacted with 2,2,3,3-tetramethylcyclopropanecarbonyl chloride as described in Example 12 to afford the title compound. $^1$H NMR (300 MHz, $CDCl_3$) δ ppm 1.23 (s, 6H), 1.32 (s, 6H), 1.39 (t, J=7.1 Hz, 3H), 1.48 (s, 10H), 2.87 (m, 2H), 3.64 (t, J=5.8 Hz, 2H), 4.34 (q, J=7.1 Hz, 2H), 4.47 (s, 2H), 11.27 (s, 1H); MS ($DCI/NH_3$) m/z 451

(M+H)+; anal. calculated for $C_{23}H_{34}N_2O_5S\cdot 0.5H_2O$: C, 60.11; H, 7.68; N, 6.10. Found: C, 60.09; H, 7.59; N, 5.84.

Example 5 ethyl 2-{[(2,2,3,3-tetramethylcyclopropyl)carbonyl] amino}-4,5,6,7-tetrahydrothieno[2,3-c]pyridine-3-carboxylate Example 5A 2-[(2,2,3,3-Tetramethyl-cyclopropanecarbonyl)-amino]-4,5,6,7-tetrahydro-thieno[2,3-c]pyridine-3-carboxylic acid ethyl ester To Example 4B (0.5 g, 1.1 mol) in 4 mL $CH_2Cl_2$ at 0° C. was added trifluoroacetic acid. The mixture was allowed to warm to ambient temperature and was stirred for 2 hours. The material was concentrated under reduced pressure and purified via column chromatography ($SiO_2$, 9:1:0.1 $CH_2Cl_2$: $CH_3OH:NH_4OH$) to afford the title compound. MS (DCI/$NH_3$) m/z 351 (M+H)+.

Example 5B ethyl 2-{[(2,2,3,3-tetramethylcyclopropyl)carbonyl] amino}-4,5,6,7-tetrahydrothieno[2,3-c]pyridine-3-carboxylate To Example 5A (0.19 g, 0.53 mmol) in 5 mL of 10% $CH_3OH$ in ethyl acetate was added p-toluenesulfonic acid monohydrate (0.1 g, 0.53 mmol) in 2 mL ethyl acetate. The resulting precipitate was isolated via filtration to afford the title compound as the p-toluenesulfonic acid salt. $^1H$ NMR (300 MHz, $CDCl_3$) δ ppm 0.92 (t, J=7.5 Hz, 3H), 1.31 (s, 12H), 1.68 (dd, J=11.2, 5.1 Hz, 2H), 2.31-2.36 (m, 1H), 3.50 (s, 3H), 4.17-4.26 (m, 4H), 4.34 (q, J=7.0 Hz, 2H), 7.50-7.57 (m, 2H), 7.67-7.74 (m, 2H), 9.41-9.62 (m, 1H), 11.30 (s, 1H); MS (DCI/$NH_3$) m/z 351 (M+H)+; anal. calculated for $C_{18}H_{26}N_2O_3S\cdot C_7H_8O_3S\cdot 1.6H_2O$: C, 54.45; H, 6.80; N, 5.08. Found: C, 54.21; H, 6.53; N, 4.84.

Example 6 ethyl 6-methyl-2-{[(2,2,3,3-tetramethylcyclopropyl) carbonyl]amino}-4,5,6,7-tetrahydrothieno[2,3-c] pyridine-3-carboxylate To a solution of Example 5A (0.20 g, 0.58 mmol) in 5 mL formaldehyde (36% aqueous solution) was added sodium triacetoxyborohydride (0.19 g, 0.87 mmol). The mixture stirred at ambient temperature for 18 hours and was quenched with 5 mL saturated aqueous $NaHCO_3$ and diluted with 5 mL $CH_2Cl_2$. The layers were separated and the organic layer was dried over $Na_2SO_4$, filtered, concentrated under reduced pressure, and purified via column chromatography ($SiO_2$, 9:1:0.1 $CH_2Cl_2:CH_3OH:NH_4OH$) to afford the free base of the title compound. The free base was then converted to the corresponding p-toluenesulfonic acid salt as described in Example 5B to afford the title compound. $^1H$ NMR (300 MHz, $CDCl_3$) δ ppm 1.16 (s, 1H), 1.24 (s, 3H), 1.26 (s, 3H), 1.32 (s, 3H), 1.34 (s, 3H), 1.38 (t, J=7.1 Hz, 3H), 2.33 (s, 3H), 3.03 (d, J=4.8 Hz, 3H), 3.18-3.40 (m, 2H), 3.69-3.79 (m, 1H), 3.96 (dd, J=15.1, 5.9 Hz, 1H), 4.33 (q, J=7.1 Hz, 2H), 4.52-4.62 (m, 1H), 7.10 (d, J=7.8 Hz, 2H), 7.66 (d, J=8.1 Hz, 2H), 11.28 (s, 1H), 11.80 (s, 1H); MS (DCI/$NH_3$) m/z 365 (M+H)+; anal. calculated for $C_{19}H_{28}N_2O_3S\cdot 1.25C_7H_8O_3S$: C, 57.49; H, 6.61; N, 4.83. Found: C, 57.20; H, 6.50; N, 4.96.

Example 7 ethyl 2-{[(2,2,3,3-tetramethylcyclopropyl)carbonyl] amino}thieno[2,3-c]pyridine-3-carboxylate The title compound was prepared as described in Example 1, substituting Example 5A for Example 12. $^1H$ NMR (300 MHz, $CDCl_3$) δ ppm 1.26 (s, 1H), 1.29 (s, 6H), 1.37 (s, 6H), 1.53 (t, J=7.1 Hz, 3H), 4.52 (q, J=7.1 Hz, 2H), 8.11 (d, J=5.4 Hz, 1H), 8.51 (d, J=5.4 Hz, 1H), 8.94 (s, 1H), 11.89 (s, 1H); MS (DCI/$NH_3$) m/z 347 (M+H)+; anal. calculated for $C_{18}H_{22}N_2O_3S$: C, 62.40; H, 6.40; N, 8.09. Found: C, 62.44; H, 6.37; N, 8.07.

Example 8

N-(2-methoxyethyl)-6-methyl-2-{[(2,2,3,3-tetramethylcyclopropyl)carbonyl]amino}-4,5,6,7-tetrahydrothieno[2,3-c]pyridine-3-carboxamide Example 8A 3-(2-Methoxy-ethylcarbamoyl)-2-[(2,2,3,3-tetramethyl-cyclopropanecarbonyl)-amino]-4,7-dihydro-5H-thieno[2,3-c]pyridine-6-carboxylic acid tert-butyl ester The product of Example 4B and 2-methoxyethylamine were processed as in Examples 29A and 29B to afford the title compound. MS (DCI/$NH_3$) m/z 480 (M+H)+.

Example 8B

2-[(2,2,3,3-Tetramethyl-cyclopropanecarbonyl)-amino]-4,5,6,7-tetrahydro-thieno[2,3-c]pyridine-3-carboxylic acid (2-methoxy-ethyl)-amide The title compound was prepared as described in Example 5A, substituting Example 8A for Example 4B. MS (DCI/$NH_3$) m/z 380 (M+H)+.

Example 8C

N-(2-methoxyethyl)-6-methyl-2-{[(2,2,3,3-tetramethylcyclopropyl)carbonyl]amino}-4,5,6,7-tetrahydrothieno[2,3-c]pyridine-3-carboxamide The title compound was prepared as the p-toluenesulfonic acid salt as described in Example 6, substituting Example 8B for Example 5A. $^1H$ NMR (300 MHz, $CD_3OD$) δ ppm 1.25 (s, 6H), 1.30 (s, 6H), 1.32 (s, 1H), 2.36 (s, 3H), 3.06 (s, 3H), 3.09-3.16 (m, 2H), 3.29-3.35 (m, 1H), 3.39 (s, 3H), 3.41-3.48 (m, 1H), 3.55-3.62 (m, 4H), 4.22-4.32 (m, 1H), 4.50-4.59 (m, 1H), 7.18-7.25 (m, 2H), 7.66-7.71 (m, 2H); MS (DCI/$NH_3$) m/z 394 (M+H)+; anal. calculated for $C_{20}H_{31}N_3O_3S\cdot C_7H_8O_3S\cdot 1.5H_2O$: C, 54.71; H, 7.14; N, 7.09. Found: C, 54.69; H, 7.29; N, 7.10.

Example 9

4,5-dimethyl-2-{[(2,2,3,3-tetramethylcyclopropyl)carbonyl]amino}thiophene-3-carboxamide

Example 9A 4,5-Dimethyl-2-[(2,2,3,3-tetramethyl-cyclopropanecarbonyl)-amino]-thiophene-3-carboxylic acid ethyl ester The title compound was prepared as described in Example 12, substituting ethyl-2-amino-4,5-dimethylthiophene-3-carboxylate (Maybridge) for 2-amino-4,5,6,7-tetrahydrobenzo[b]thiophene-3-carboxylic acid ethyl ester. MS (DCI/NH$_3$) m/z 324 (M+H)$^+$.

Example 9B 4,5-Dimethyl-2-[(2,2,3,3-tetramethyl-cyclopropanecarbonyl)-amino]-thiophene-3-carboxylic acid The title compound was prepared as described in Example 29A, substituting Example 9A for Example 12. MS (DCI/NH$_3$) m/z 296 (M+H)$^+$.

Example 9C 4,5-dimethyl-2-{[(2,2,3,3-tetramethylcyclopropyl)carbonyl]amino}thiophene-3-carboxamide To a solution of Example 9B (0.30 g, 1.0 mmol) and N,N-diisopropylethylamine (0.21 mL, 1.2 mmol) in 5 mL tetrahydrofuran was added o-(7-azabenzotriazol-1-yl)-N,N,N',N'-tetramethyluronium hexafluorophosphate (HATU, 0.41 g, 1.1 mmol). The mixture stirred for 2 hours at ambient temperature, and 5 mL of NH$_4$OH was added and the reaction mixture stirred for an additional 1 hour. The mixture was concentrated under reduced pressure and the residue was dissolved in 10 mL CH$_2$Cl$_2$. NH$_4$Cl (5 mL) was added, the layers were separated and the aqueous layer was extracted 2×5 mL CH$_2$Cl$_2$. The combined organics were dried over anhydrous Na$_2$SO$_4$, filtered, concentrated, and purified via column chromatography (SiO$_2$, 50% hexanes:ethyl acetate) to afford the title compound. $^1$H NMR (300 MHz, CDCl$_3$) δ ppm 1.15 (s, 1H), 1.21 (s, 6H), 1.32 (s, 6H), 2.26 (s, 3H), 2.30 (s, 3H), 5.60-5.84 (m, 2H), 11.88 (s, 1H); MS (DCI/NH$_3$) m/z 295 (M+H)$^+$; anal. calculated for C$_{15}$H$_{22}$N$_2$O$_2$S: C, 61.19; H, 7.53; N, 9.52. Found: C, 61.28; H, 7.74; N, 9.44.

Example 10 ethyl 2-{[(2,2,3,3-tetramethylcyclopropyl)carbonyl]amino}-4,7-dihydro-5H-thieno[2,3-c]pyran-3-carboxylate

Example 10A

2-Amino-4,7-dihydro-5H-thieno[2,3-c]pyran-3-carboxylic acid ethyl ester

To a solution of tetrahydro-4H-pyran-4-one (5 g, 49.9 mmol), ethyl cyanoacetate (5.9 mL, 54.9 mmol) and sulfur (1.8 g, 54.9 mmol) in 80 mL ethanol was added morpholine (12.2 mL, 0.14 mol). The mixture was warmed to 50° C., stirred for 3 hours and cooled to ambient temperature and concentrated under reduced pressure. The residue was dissolved in 20 mL CH$_2$Cl$_2$ and washed with 10 mL NH$_4$Cl. The layers were separated and the aqueous layer was extracted with 2×5 mL CH$_2$Cl$_2$. The combined organics were dried over anhydrous Na$_2$SO$_4$, filtered, concentrated under reduced pressure and purified via column chromatography (SiO$_2$, 50% hexanes:ethyl acetate) to afford the title compound. MS (DCI/NH$_3$) m/z 228 (M+H)$^+$.

Example 10B ethyl 2-{[(2,2,3,3-tetramethylcyclopropyl)carbonyl]amino}-4,7-dihydro-5H-thieno[2,3-c]pyran-3-carboxylate The title compound was prepared as described in Example 12, substituting Example 10A for 2-amino-4,5,6,7-tetrahydro-benzo[b]thiophene-3-carboxylic acid ethyl ester. $^1$H NMR (300 MHz, CDCl$_3$) δ ppm 1.15 (s, 1H), 1.23 (s, 6H), 1.32 (s, 6H), 1.39 (t, J=7.1 Hz, 3H), 2.83-2.93 (m, 2H), 3.93 (t, J=5.6 Hz, 2H), 4.34 (q, J=7.1 Hz, 2H), 4.67 (t, J=1.9 Hz, 2H), 11.26 (s, 1H); MS (DCI/NH$_3$) m/z 352 (M+H)$^+$; anal. calculated for C$_{18}$H$_{25}$NO$_4$S: C, 61.51; H, 7.17; N, 3.99. Found: C, 61.19; H, 6.99; N, 3.72.

Example 11

N-ethyl-2-{[(2,2,3,3-tetramethylcyclopropyl)carbonyl]amino}-4,7-dihydro-5H-thieno[2,3-c]pyran-3-carboxamide The product of Example 10B and ethylamine were processed as in Examples 29A and Example 29B to afford the title compound. $^1$H NMR (300 MHz, CDCl$_3$) δ ppm 1.18 (s, 1H), 1.21 (s, 6H), 1.26 (t, J=7.3 Hz, 3H), 1.32 (s, 6H), 2.77-2.83 (m, 2H), 3.41-3.55 (m, 2H), 3.98 (t, J=5.3 Hz, 2H), 4.71 (t, J=1.7 Hz, 2H), 5.70-5.82 (m, 1H), 12.02 (s, 1H); MS (DCI/NH$_3$) m/z 352 (M+H)$^+$; anal. calculated for C$_{18}$H$_{26}$N$_2$O$_3$S: C, 61.69; H, 7.48; N, 7.99. Found: C, 61.58; H, 7.39; N, 7.94.

Example 12 ethyl 2-{[(2,2,3,3-tetramethylcyclopropyl)carbonyl]amino}-4,5,6,7-tetrahydro-1-benzothiophene-3-carboxylate Step One A solution of 2,2,3,3-tetramethylcyclopropanecarboxylic acid (Aldrich, 1.0 g, 7.0 mmol) in 10 mL SOCl$_2$ was warmed to reflux and allowed to stir for 1 hour. The mixture was cooled to ambient temperature and concentrated under reduced pressure. This material was dissolved in 10 mL benzene and concentrated under reduced pressure. This dilution and concentration was repeated two additional times. The crude acid chloride was used without further purification or characterization.

Step Two

To a solution of 2-amino-4,5,6,7-tetrahydro-benzo[b]thiophene-3-carboxylic acid ethyl ester (Aldrich) (1.2 g, 5.3 mmol) and pyridine (0.51 mL, 6.3 mmol) in 40 mL CH$_3$CN at 0° C. was added the product of step one in 5 mL CH$_3$CN via cannula. The ice bath was removed after the addition was complete and the reaction mixture was warmed to reflux at and stirred for 3 hours. The mixture was cooled to ambient temperature, diluted with 20 mL CH$_2$Cl$_2$, and washed with 10 mL NH$_4$Cl. The layers were separated and the aqueous layer was extracted with 2×5 mL CH$_2$Cl$_2$. The combined organics were dried over Na$_2$SO$_4$, filtered, concentrated under reduced pressure, and purified via column chromatography (SiO$_2$, 10% ethyl acetate/hexanes) to afford the title compound. $^1$H NMR (300 MHz, CD$_3$OD) δ ppm 1.26 (s, 6H), 1.27 (s, 1H), 1.29 (s, 6H), 1.37 (t, J=7.1 Hz, 3H), 1.74-1.85 (m, 4H), 2.59-2.66 (m, 2H), 2.73-2.81 (m, 2H), 4.34 (q, J=7.1 Hz, 2H); MS (DCI/NH$_3$) m/z 350 (M+H)$^+$; anal. calculated for C$_{19}$H$_{27}$NO$_3$S: C, 65.30; H, 7.79; N, 4.01. Found: C, 65.29; H, 7.66; N, 4.06.

Example 13 ethyl 2-[(cyclohexylcarbonyl)amino]-4,5,6,7-tetrahydro-1-benzothiophene-3-carboxylate The title compound was prepared as described in Example 12, substituting cyclohexanecarboxylic acid for 2,2,3,3-tetramethylcyclopropanecarboxylic acid. $^1$H NMR (300 MHz, CD$_3$OD) δ ppm 1.24-1.58 (m, 5H), 1.38 (t, J=7.1 Hz, 3H), 1.68-1.88 (m, 7H), 1.95-2.05 (m, 2H), 2.37-2.51 (m, 1H), 2.60-2.67 (m, 2H), 2.72-2.83 (m, 2H), 4.34 (q, J=7.1 Hz, 2H); MS (DCI/NH$_3$) m/z 336 (M+H)$^+$; anal. calculated for C$_{18}$H$_{25}$NO$_3$S: C, 64.45; H, 7.51; N, 4.18. Found: C, 64.53; H, 7.66; N, 4.06.

Example 14 ethyl 2-[(2-ethylbutanoyl)amino]-4,5,6,7-tetrahydro-1-benzothiophene-3-carboxylate The title compound was prepared as described in Example 12, substituting 2-ethylbutyric acid for 2,2,3,3-tetramethylcyclopropanecarboxylic acid. $^1$H NMR (300 MHz, CD$_3$OD) δ ppm 0.93 (t, J=7.5 Hz, 6H), 1.38 (t, J=7.1 Hz, 3H), 1.56-1.74 (m, 4H), 1.75-1.86 (m, 4H), 2.22-2.34 (m, 1H), 2.61-2.68 (m, 2H), 2.74-2.84 (m, 2H), 4.35 (q, J=7.2 Hz, 2H); MS (DCI/NH$_3$) m/z 324 (M+H)$^+$; anal. calculated for C$_{17}$H$_{25}$NO$_3$S: C, 63.13; H, 7.79; N, 4.33. Found: C, 63.08; H, 8.08; N, 4.18.

Example 15

2-[(cyclohexylcarbonyl)amino]-N-methyl-4,5,6,7-tetrahydro-1-benzothiophene-3-carboxamide The product of Example 13 and methylamine were processed as in Examples 29A and 29B to afford the title compound. $^1$H NMR (300 MHz, CDCl$_3$) δ ppm 1.20-1.40 (m, 3H), 1.45-1.61 (m, 2H), 1.65-1.73 (m, 1H), 1.78-1.89 (m, 6H), 1.97-2.06 (m, 2H), 2.37 (tt, J=11.6, 3.7, 3.6 Hz, 1H), 2.64-2.73 (m, 4H), 2.98 (d, J=5.1 Hz, 3H), 5.94 (s, 1H), 12.17 (s, 1H); MS (DCI/NH$_3$) m/z 321 (M+H)$^+$; anal. calculated for C$_{17}$H$_{24}$N$_2$O$_2$S: C, 63.72; H, 7.55; N, 8.74. Found: C, 63.47; H, 7.45; N, 8.55.

Example 16

N-benzyl-2-[(cyclohexylcarbonyl)amino]-4,5,6,7-tetrahydro-1-benzothiophene-3-carboxamide The product of Example 13 and benzylamine were processed as in Examples 29A and 29B to afford the title compound. $^1$H NMR (300 MHz, CDCl$_3$) δ ppm 1.19-1.41 (m, 3H), 1.45-1.62 (m, 2H), 1.64-1.73 (m, 1H), 1.76-1.88 (m, 6H), 1.96-2.06 (m, 2H), 2.38 (tt, J=11.5, 3.6 Hz, 1H), 2.61-2.72 (m, 4H), 4.63 (d, J=5.4 Hz, 2H), 6.18-6.26 (m, 1H), 7.27-7.42 (m, 5H), 12.15 (s, 1H); MS (DCI/NH$_3$) m/z 397 (M+H)$^+$; anal. calculated for C$_{23}$H$_{28}$N$_2$O$_2$S: C, 69.66; H, 7.12; N, 7.06. Found: C, 69.62; H, 7.07; N, 6.88.

Example 17

N-methyl-2-{[(2,2,3,3-tetramethylcyclopropyl)carbonyl]amino}-4,5,6,7-tetrahydro-1-benzothiophene-3-carboxamide The product of Example 12 and methylamine were processed as in Examples 29A and 29B to afford the title compound. $^1$H NMR (300 MHz, CDCl$_3$) δ ppm 1.17 (s, 1H), 1.20 (s, 6H), 1.32 (s, 6H), 1.76-1.91 (m, 4H), 2.62-2.73 (m, 4H), 2.98 (d, J=4.8 Hz, 3H), 5.85-5.97 (m, 1H), 12.07 (s, 1H); MS (DCI/NH$_3$) m/z 335 (M+H)$^+$; anal. calculated for C$_{18}$H$_{26}$N$_2$O$_2$S: C, 64.64; H, 7.83; N, 8.38. Found: C, 64.21; H, 8.01; N, 8.25.

Example 18

N-benzyl-2-{[(2,2,3,3-tetramethylcyclopropyl)carbonyl]amino}-4,5,6,7-tetrahydro-1-benzothiophene-3-carboxamide The product of Example 12 and benzylamine were processed as in Examples 29A and 29B to afford the title compound. $^1$H NMR (300 MHz, CDCl$_3$) δ ppm 1.17 (s, 1H), 1.21 (s, 6H), 1.32 (s, 6H), 1.73-1.87 (m, 4H), 2.60-2.70 (m, 4H), 4.63 (d, J=5.4 Hz, 2H), 6.17-6.28 (m, 1H), 7.28-7.42 (m, 5H), 12.06 (s, 1H); MS (DCI/NH$_3$) m/z 411 (M+H)$^+$; anal. calculated for C$_{24}$H$_{30}$N$_2$O$_2$S: C, 70.21; H, 7.36; N, 6.82. Found: C, 70.06; H, 7.51; N, 6.80.

Example 19

N,N-dimethyl-2-{[(2,2,3,3-tetramethylcyclopropyl)carbonyl]amino}-4,5,6,7-tetrahydro-1-benzothiophene-3-carboxamide The product of Example 12 and dimethylamine were processed as in Examples 29A and 29B to afford the title compound. $^1$H NMR (300 MHz, CDCl$_3$) δ ppm 1.02 (s, 1H), 1.19 (s, 6H), 1.30 (s, 6H), 1.69-1.88 (m, 4H), 2.44 (t, J=5.9 Hz, 2H), 2.66 (t, J=6.3 Hz, 2H), 3.04 (s, 6H), 8.95 (s, 1H); MS (DCI/NH$_3$) m/z 349 (M+H)$^+$; anal. calculated for C$_{19}$H$_{28}$N$_2$O$_2$S: C, 65.48; H, 8.10; N, 8.04. Found: C, 65.19; H, 8.22; N, 7.94.

Example 20

N-benzyl-2-[(2-ethylbutanoyl)amino]-4,5,6,7-tetrahydro-1-benzothiophene-3-carboxamide The product of Example 14 and benzylamine were processed as in Examples 29A and 29B to afford the title compound. $^1$H NMR (300 MHz, CD$_3$OD) δ ppm 0.91 (t, J=7.5 Hz, 6H), 1.52-1.71 (m, 4H), 1.77-1.89 (m, 4H), 2.16-2.29 (m, 1H), 2.64-2.75 (m, 4H), 4.56 (s, 2H), 7.21-7.29 (m, 1H), 7.31-7.37 (m, 4H); MS (DCI/NH$_3$) m/z 385 (M+H)$^+$; anal. calculated for C$_{22}$H$_{28}$N$_2$O$_2$S: C, 68.72; H, 7.34; N, 7.28. Found: C, 68.45; H, 7.49; N, 7.17.

Example 21

N-[2-(dimethylamino)ethyl]-2-[(2-ethylbutanoyl)amino]-4,5,6,7-tetrahydro-1-benzothiophene-3-carboxamide The product of Example 14 and N,N-dimethylethylenediamine were processed as in Examples 29A, 29B and 5B to afford the title compound. $^1$H NMR (300 MHz, CD$_3$OD) δ ppm 0.92 (t, J=7.5 Hz, 6H), 1.54-1.72 (m, 4H), 1.80-1.89 (m, 4H), 2.19-2.30 (m, 1H), 2.36 (s, 3H), 2.64-2.78 (m, 4H), 3.00 (s, 6H), 3.38 (t, J=5.9 Hz, 2H), 3.75 (t, J=5.8 Hz, 2H), 7.21 (d, J=7.8 Hz, 2H), 7.65-7.72 (m, 2H); MS (DCI/NH$_3$) m/z 366 (M+H)$^+$; anal. calculated for C$_{19}$H$_{31}$N$_3$O$_2$S.C$_7$H$_8$O$_3$S—H$_2$O: C, 56.19; H, 7.44; N, 7.56. Found: C, 56.43; H, 7.61; N, 7.61.

Example 22

2-[(cyclohexylcarbonyl)amino]-N-[2-(dimethylamino)ethyl]-4,5,6,7-tetrahydro-1-benzothiophene-3-carboxamide The product of Example 13 and N,N-dimethylethylenediamine were processed as in Examples 29A, 29B and 5B to afford the title compound. $^1$H NMR (300 MHz, CD$_3$OD) δ ppm 1.16-1.57 (m, 5H), 1.68-1.77 (m, 1H), 1.78-1.89 (m, 6H), 1.90-2.00 (m, 2H), 2.34-2.45 (m, 1H), 2.36 (s, 3H), 2.61-2.79 (m, 4H), 3.00 (s, 6H), 3.38 (t, J=5.9 Hz, 2H), 3.75 (t, J=5.9 Hz, 2H), 7.22 (d, J=8.1 Hz, 2H), 7.66-7.72 (m, 2H); MS (DCI/NH$_3$) m/z 378 (M+H)$^+$; anal. calculated for C$_{20}$H$_{31}$N$_3$O$_2$S.C$_7$H$_8$O$_3$S.1.2H$_2$O: C, 56.76; H, 7.30; N, 7.35. Found: C, 56.86; H, 7.45; N, 7.05.

Example 23

N-[2-(dimethylamino)ethyl]-2-{[(2,2,3,3-tetramethylcyclopropyl)carbonyl]amino}-4,5,6,7-tetrahydro-1-benzothiophene-3-carboxamide The product of Example 12 and N,N-dimethylethylenediamine were processed as in Examples 29A, 29B and 5B to afford the title compound. $^1$H NMR (300 MHz, CD$_3$OD) δ ppm 1.24 (s, 1H), 1.25 (s, 6H), 1.29 (s, 6H), 1.79-1.88 (m, 4H), 2.36 (s, 3H), 2.61-2.78 (m, 4H), 3.00 (s, 6H), 3.37 (t, J=5.9 Hz, 2H), 3.74 (t, J=5.9 Hz, 2H), 7.19-7.24 (m, 2H), 7.66-7.71 (m, 2H); MS (DCI/NH$_3$) m/z 392 (M+H)$^+$; anal. calculated for C$_{21}$H$_{33}$N$_3$O$_2$S.C$_7$H$_8$O$_3$S.0.5H$_2$O: C, 58.71; H, 7.39; N, 7.34. Found: C, 58.62; H, 7.63; N, 7.13.

Example 24

2-[(1-adamantylcarbonyl)amino]-N-methyl-4,5,6,7-tetrahydro-1-benzothiophene-3-carboxamide The product of Example 31 and methylamine were processed as in Examples 29A and 29B to afford the title compound. $^1$H NMR (300 MHz, CDCl$_3$) δ ppm 1.76 (t, J=3.1 Hz, 6H), 1.80-1.91 (m, 4H), 2.00 (d, J=3.1 Hz, 6H), 2.05-2.14 (m, 3H), 2.65-2.73 (m, 4H), 2.99 (d, J=4.8 Hz, 3H), 5.90-5.98 (m, 1H), 12.36 (s, 1H); MS (DCI/NH$_3$) m/z 373 (M+H)$^+$; anal. calculated for C$_{21}$H$_{28}$N$_2$O$_2$S.0.5H$_2$O: C, 66.11; H, 7.66; N, 7.34. Found: C, 66.04; H, 7.31; N, 7.25.

Example 25

2-[(1-adamantylcarbonyl)amino]-N,N-dimethyl-4,5,6,7-tetrahydro-1-benzothiophene-3-carboxamide The product of Example 31 and dimethylamine were processed as in Examples 29A and 29B to afford the title compound. $^1$H NMR (300 MHz, CDCl$_3$) δ ppm 1.74 (s, 8H), 1.79-1.88 (m, 2H), 1.93 (d, J=2.7 Hz, 6H), 2.04-2.11 (m, 3H), 2.43-2.52 (m, 2H), 2.66-2.74 (m, 2H), 3.03 (s, 6H), 9.44 (s, 1H); MS (DCI/NH$_3$) m/z 387 (M+H)$^+$; anal. calculated for C$_{22}$H$_{30}$N$_2$O$_2$S—H$_2$O: C, 65.31; H, 7.97; N, 6.92. Found: C, 65.02; H, 7.41; N, 6.71.

Example 26

2-[(1-adamantylcarbonyl)amino]-N-(2-morpholin-4-ylethyl)-4,5,6,7-tetrahydro-1-benzothiophene-3-carboxamide The product of Example 31 and 4-(2-aminoethyl)morpholine were processed as in Examples 29A and 29B to afford the title compound. $^1$H NMR (300 MHz, CDCl$_3$) δ ppm 1.75 (t, J=3.1 Hz, 6H), 1.80-1.93 (m, 4H), 1.99 (d, J=3.1 Hz, 6H), 2.04-2.13 (m, 3H), 2.48-2.56 (m, 4H), 2.60 (t, J=5.9 Hz, 2H), 2.69 (t, J=4.8 Hz, 2H), 2.78 (t, J=4.6 Hz, 2H), 3.47-3.57 (m, 2H), 3.68-3.77 (m, 4H), 6.86 (s, 1H), 12.42 (s, 1H); MS (DCI/NH$_3$) m/z 472 (M+H)$^+$; anal. calculated for C$_{26}$H$_{37}$N$_3$O$_3$S.1.1H$_2$O: C, 63.54; H, 8.04; N, 8.55. Found: C, 63.83; H, 7.70; N, 8.11.

Example 27

2-[(1-adamantylcarbonyl)amino]-N-[2-(dimethylamino)ethyl]-4,5,6,7-tetrahydro-1-benzothiophene-3-carboxamide The product of Example 31 and N,N-dimethylethylenediamine were processed as in Examples 29A and 29B to afford the title compound. $^1$H NMR (300 MHz, CDCl$_3$) δ ppm 1.75 (t, J=3.1 Hz, 6H), 1.80-1.86 (m, 4H), 1.99 (d, J=3.1 Hz, 6H), 2.05-2.12 (m, 3H), 2.28 (s, 6H), 2.47-2.57 (m, 2H), 2.64-2.74 (m, 4H), 3.45-3.53 (m, 2H), 6.77-6.84 (m, 1H), 12.39 (s, 1H); MS (DCI/NH$_3$) m/z 430 (M+H)$^+$; anal. calculated for C$_{24}$H$_{35}$N$_3$O$_2$S.0.1H$_2$O: C, 66.82; H, 8.22; N, 9.74. Found: C, 66.60; H, 8.40; N, 9.74.

Example 28

2-[(1-adamantylcarbonyl)amino]-N-(3-morpholin-4-ylpropyl)-4,5,6,7-tetrahydro-1-benzothiophene-3-carboxamide The product of Example 31 and 4-(3-aminopropyl)morpholine were processed as in Examples 29A and 29B to afford the title compound. $^1$H NMR (300 MHz, CDCl$_3$) δ ppm 1.75 (t, J=3.1 Hz, 6H), 1.79-1.90 (m, 6H), 1.99 (d, J=2.7 Hz, 6H), 2.05-2.13 (m, 3H), 2.40-2.51 (m, 6H), 2.65-2.78 (m, 4H), 3.53 (q, J=6.4 Hz, 2H), 3.64-3.74 (m, 4H), 6.37-6.47 (m, 1H), 12.26 (s, 1H); MS (DCI/NH$_3$) m/z 486 (M+H)$^+$; anal. calculated for C$_{27}$H$_{39}$N$_3$O$_3$S.0.2NH$_4$OH: C, 65.82; H, 8.18; N, 9.10. Found: C, 65.63; H, 7.85; N, 9.15.

Example 29

N-ethyl-2-{[(2,2,3,3-tetramethylcyclopropyl)carbonyl]amino}-4,5,6,7-tetrahydro-1-benzothiophene-3-carboxamide Example 29A 2-[(2,2,3,3-Tetramethyl-cyclopropanecarbonyl)-amino]-4,5,6,7-tetrahydro-benzo[b]thiophene-3-carboxylic acid To Example 12 (6.2 g, 17.8 mmol) in 120 mL ethanol was added 40 mL of 10% aqueous KOH. This mixture was warmed to reflux and stirred for 4 hours. The material was then cooled to 0° C., quenched with 1 N HCl and diluted with 20 mL $CH_2Cl_2$. The layers were separated and the aqueous layer was extracted with 2×10 mL $CH_2Cl_2$. The combined organics were dried over anhydrous $Na_2SO_4$, filtered, concentrated under reduced pressure, and purified via column chromatography ($SiO_2$, 10% $CH_3OH$:ethyl acetate) to afford the title compound. MS ($DCI/NH_3$) m/z 322 $(M+H)^+$.

Example 29B

N-ethyl-2-{[(2,2,3,3-tetramethylcyclopropyl)carbonyl]amino}-4,5,6,7-tetrahydro-1-benzothiophene-3-carboxamide To a solution of Example 29A (2.33 g, 7.3 mmol), ethylamine (4.4 mL, 8.7 mmol) and N,N-diisopropylethylamine (1.5 mL, 8.7 mmol) in 50 mL tetrahydrofuran was added o-(7-azabenzotriazol-1-yl)-N,N,N'-tetramethyluronium hexafluorophosphate (HATU, 2.9 g, 7.6 mmol). This mixture stirred at ambient temperature for 18 hours and was quenched with 15 mL $H_2O$ and diluted with 15 mL ethyl acetate. The layers were separated and the organic layer was washed with 10 mL $NaHCO_3$. The combined aqueous layers were extracted with 2×10 mL ethyl acetate and the combined organic layers were dried over $Na_2SO_4$, filtered, concentrated under reduced pressure and purified via column chromatography ($SiO_2$, 70% hexanes:ethyl acetate) to afford the title compound. $^1$H NMR (300 MHz, $CDCl_3$) δ ppm 1.16 (s, 1H), 1.20 (s, 6H), 1.25 (t, J=7.3 Hz, 3H), 1.32 (s, 6H), 1.75-1.91 (m, 4H), 2.61-2.73 (m, 4H), 3.40-3.51 (m, 2H), 5.83-5.93 (m, 1H), 12.06 (s, 1H); MS ($DCI/NH_3$) m/z 349 $(M+H)^+$; anal. calculated for $C_{19}H_{28}N_2O_2S$: C, 65.48; H, 8.10; N, 8.04. Found: C, 65.52; H, 8.26; N, 8.02.

Example 30

N-isopropyl-2-{[(2,2,3,3-tetramethylcyclopropyl)carbonyl]amino}-4,5,6,7-tetrahydro-1-benzothiophene-3-carboxamide The product of Example 12 and isopropylamine were processed as in Examples 29A and 29B to afford the title compound. $^1$H NMR (300 MHz, $CD_3OD$) δ ppm 1.23 (s, 3H), 1.24 (s, 7H), 1.25 (s, 3H), 1.29 (s, 6H), 1.76-1.91 (m, 4H), 2.62-2.71 (m, 4H), 4.09-4.22 (m, 1H); MS ($DCI/NH_3$) m/z 363 $(M+H)^+$; anal. calculated for $C_{20}H_{30}N_2O_2S$: C, 66.26; H, 8.34; N, 7.73. Found: C, 66.35; H, 8.44; N, 7.73.

Example 31 ethyl 2-[(1-adamantylcarbonyl)amino]-4,5,6,7-tetrahydro-1-benzothiophene-3-carboxylate The title compound was prepared as described in Example 12, substituting 1-adamantanecarboxylic acid for 2,2,3,3-tetramethylcyclopropanecarboxylic acid. $^1$H NMR (300 MHz, $CDCl_3$) δ ppm 1.39 (t, J=7.1 Hz, 3H), 1.70-1.83 (m, 10H), 1.99 (d, J=3.1 Hz, 6H), 2.07-2.15 (m, 3H), 2.60-2.68 (m, 2H), 2.73-2.81 (m, 2H), 4.34 (q, J=7.1 Hz, 2H), 11.54 (s, 1H); MS ($DCI/NH_3$) m/z 388 $(M+H)^+$; anal. calculated for $C_{22}H_{29}NO_3S-H_2O$: C, 65.16; H, 7.70; N, 3.45. Found: C, 64.76; H, 7.49; N, 3.10.

Example 32 ethyl 2-(heptanoylamino)-4,5,6,7-tetrahydro-1-benzothiophene-3-carboxylate

The title compound was prepared as described in Example 12, substituting heptanoic acid for 2,2,3,3-tetramethylcyclopropanecarboxylic acid. $^1$H NMR (300 MHz, $CDCl_3$) δ ppm 0.84-0.93 (m, 3H), 1.27-1.41 (m, 6H), 1.38 (t, J=7.1 Hz, 3H), 1.67-1.85 (m, 6H), 2.46 (t, J=7.6 Hz, 2H), 2.61-2.68 (m, 2H), 2.73-2.81 (m, 2H), 4.33 (q, J=7.1 Hz, 2H), 11.28 (s, 1H); MS ($DCI/NH_3$) m/z 338 $(M+H)^+$; anal. calculated for $C_{18}H_{27}NO_3S$: C, 64.06; H, 8.06; N, 4.15. Found: C, 63.95; H, 7.92; N, 4.12.

Example 33 ethyl 2-(hexanoylamino)-4,5,6,7-tetrahydro-1-benzothiophene-3-carboxylate

The title compound was prepared as described in Example 12, substituting hexanoic acid for 2,2,3,3-tetramethylcyclopropanecarboxylic acid. $^1$H NMR (300 MHz, $CDCl_3$) δ ppm 0.87-0.94 (m, 3H), 1.31-1.38 (m, 4H), 1.38 (t, J=7.1 Hz, 3H), 1.69-1.84 (m, 6H), 2.45 (t, J=7.5 Hz, 2H), 2.60-2.68 (m, 2H), 2.73-2.81 (m, 2H), 4.33 (q, J=7.1 Hz, 2H), 11.27 (s, 1H); MS ($DCI/NH_3$) m/z 324 $(M+H)^+$; anal. calculated for $C_{17}H_{25}NO_3S$: C, 63.13; H, 7.79; N, 4.33. Found: C, 63.07; H, 7.73; N, 4.10.

Example 34 ethyl 2-[(2-butyloctanoyl)amino]-4,5,6,7-tetrahydro-1-benzothiophene-3-carboxylate The title compound was prepared as described in Example 12, substituting 2-butyloctanoic acid for 2,2,3,3-tetramethylcyclopropanecarboxylic acid. $^1$H NMR (300 MHz, $CDCl_3$) δ ppm 0.81-0.90 (m, 6H), 1.20-1.34 (m, 14H), 1.38 (t, J=7.1 Hz, 3H), 1.63-1.75 (m, 2H), 1.75-1.83 (m, 4H), 2.27-2.39 (m, 1H), 2.60-2.68 (m, 2H), 2.74-2.81 (m, 2H), 4.33 (q, J=7.1 Hz, 2H), 11.29 (s, 1H); MS ($DCI/NH_3$) m/z 408 $(M+H)^+$; anal. calculated for $C_{23}H_{37}NO_3S$: C, 67.77; H, 9.15; N, 3.44. Found: C, 67.82; H, 9.40; N, 3.38.

Example 35 ethyl 2-[(2-bromo-5-nitrobenzoyl)amino]-4,5,6,7-tetrahydro-1-benzothiophene-3-carboxylate The title compound was prepared as described in Example 12, substituting 2-bromo-5-nitrobenzoic acid for 2,2,3,3-tetramethylcyclopropanecarboxylic acid. $^1$H NMR (300 MHz, $CDCl_3$) δ ppm 1.37 (t, J=7.1 Hz, 3H), 1.74-1.90 (m, 4H), 2.68-2.75 (m, 2H), 2.78-2.85 (m, 2H), 4.33 (q, J=7.1 Hz, 2H), 7.86 (d, J=8.8 Hz, 1H), 8.18 (dd, J=8.8, 2.7 Hz, 1H), 8.49 (d, J=2.7 Hz, 1H), 11.94 (s, 1H); MS ($DCI/NH_3$) m/z 453 $(M+H)^+$; anal. calculated for $C_{18}H_{17}BrN_2O_5S$: C, 47.69; H, 3.78; N, 6.18. Found: C, 47.52; H, 3.63; N, 6.07.

Example 36

2-(hexanoylamino)-N,N-dimethyl-4,5,6,7-tetrahydro-1-benzothiophene-3-carboxamide The product of Example 33 and dimethylamine were processed as in Examples 29A and 29B to afford the title compound. $^1$H NMR (300 MHz, CDCl$_3$) δ ppm 0.88-0.96 (m, 4H), 1.29-1.41 (m, 4H), 1.54-1.72 (m, 3H), 1.73-1.91 (m, 3H), 2.33-2.42 (m, 4H), 2.63-2.71 (m, 2H), 2.92 (s, 3H), 3.05 (s, 3H); MS (DCI/NH$_3$) m/z 323 (M+H)$^+$; anal. calculated for C$_{17}$H$_{26}$N$_2$O$_2$S.0.75C$_8$H$_{17}$NO.0.3H$_2$O: C, 63.46; H, 9.11; N, 8.85. Found: C, 63.15; H, 9.46; N, 8.66.

Example 37

N-propyl-2-{[(2,2,3,3-tetramethylcyclopropyl)carbonyl]amino}-4,5,6,7-tetrahydro-1-benzothiophene-3-carboxamide The product of Example 12 and propylamine were processed as in Examples 29A and 29B to afford the title compound. $^1$H NMR (300 MHz, CDCl$_3$) δ ppm 1.00 (t, J=7.5 Hz, 3H), 1.16 (s, 1H), 1.20 (s, 6H), 1.31 (s, 6H), 1.59-1.71 (m, 2H), 1.77-1.90 (m, 4H), 2.62-2.74 (m, 4H), 3.34-3.43 (m, 2H), 5.89-5.97 (m, 1H), 12.06 (s, 1H); MS (DCI/NH$_3$) m/z 363 (M+H)$^+$; anal. calculated for C$_{20}$H$_{30}$N$_2$O$_2$S—H$_2$O: C, 63.12; H, 8.48; N, 7.36. Found: C, 63.46; H, 8.52; N, 7.00.

Example 38

N-(1,2-dimethylpropyl)-2-{[(2,2,3,3-tetramethylcyclopropyl)carbonyl]amino}-4,5,6,7-tetrahydro-1-benzothiophene-3-carboxamide The product of Example 12 and 1,2-dimethylpropylamine were processed as in Examples 29A and 29B to afford the title compound. $^1$H NMR (300 MHz, CDCl$_3$) δ ppm 0.96 (d, J=6.8 Hz, 3H), 0.98 (d, J=6.8 Hz, 3H), 1.17 (d, J=6.8 Hz, 3H), 1.17 (s, 1H), 1.20 (s, 6H), 1.31 (s, 6H), 1.76-1.91 (m, 5H), 2.62-2.74 (m, 4H), 4.00-4.11 (m, 1H), 5.75-5.82 (m, 1H), 12.08 (s, 1H); MS (DCI/NH$_3$) m/z 391 (M+H)$^+$; anal. calculated for C$_{22}$H$_{34}$N$_2$O$_2$S.0.5H$_2$O: C, 66.13; H, 8.83; N, 7.01. Found: C, 66.26; H, 8.85; N, 6.67.

Example 39

N-isobutyl-2-{[(2,2,3,3-tetramethylcyclopropyl)carbonyl]amino}-4,5,6,7-tetrahydro-1-benzothiophene-3-carboxamide The product of Example 12 and isobutylamine were processed as in Examples 29A and 29B to afford the title compound. $^1$H NMR (300 MHz, CDCl$_3$) δ ppm 0.99 (d, J=6.8 Hz, 6H), 1.16 (s, 1H), 1.20 (s, 6H), 1.31 (s, 6H), 1.77-1.95 (m, 5H), 2.63-2.73 (m, 4H), 3.23-3.29 (m, 2H), 5.92-6.01 (m, 1H), 12.07 (s, 1H); MS (DCI/NH$_3$) m/z 377 (M+H)$^+$; anal. calculated for C$_{21}$H$_{32}$N$_2$O$_2$S: C, 66.98; H, 8.57; N, 7.44. Found: C, 67.05; H, 8.59; N, 7.30.

Example 40

N-(3-methylbutyl)-2-{[(2,2,3,3-tetramethylcyclopropyl)carbonyl]amino}-4,5,6,7-tetrahydro-1-benzothiophene-3-carboxamide The product of Example 12 and isoamylamine were processed as in Examples 29A and 29B to afford the title compound. $^1$H NMR (300 MHz, CDCl$_3$) δ ppm 0.96 (d, J=6.4 Hz, 6H), 1.17 (s, 1H), 1.20 (s, 6H), 1.31 (s, 6H), 1.46-1.53 (m, 2H), 1.62-1.73 (m, 1H), 1.77-1.91 (m, 4H), 2.62-2.71 (m, 4H), 3.39-3.48 (m, 2H), 5.81-5.91 (m, 1H), 12.06 (s, 1H); MS (DCI/NH$_3$) m/z 391 (M+H)$^+$; anal. calculated for C$_{22}$H$_{34}$N$_2$O$_2$S: C, 67.65; H, 8.77; N, 7.17. Found: C, 67.33; H, 8.87; N, 7.08.

Example 41

N-butyl-2-{[(2,2,3,3-tetramethylcyclopropyl)carbonyl]amino}-4,5,6,7-tetrahydro-1-benzothiophene-3-carboxamide The product of Example 12 and butylamine were processed as in Examples 29A and 29B to afford the title compound. $^1$H NMR (300 MHz, CDCl$_3$) δ ppm 0.97 (t, J=7.3 Hz, 3H), 1.16 (s, 1H), 1.20 (s, 6H), 1.31 (s, 6H), 1.36-1.48 (m, 2H), 1.55-1.65 (m, 2H), 1.77-1.91 (m, 4H), 2.62-2.72 (m, 4H), 3.38-3.46 (m, 2H), 5.86-5.94 (m, 1H), 12.06 (s, 1H); MS (DCI/NH$_3$) m/z 377 (M+H)$^+$; anal. calculated for C$_{21}$H$_{32}$N$_2$O$_2$S: C, 66.98; H, 8.57; N, 7.44. Found: C, 66.71; H, 8.71; N, 7.30.

Example 42

N-heptyl-2-{[(2,2,3,3-tetramethylcyclopropyl)carbonyl]amino}-4,5,6,7-tetrahydro-1-benzothiophene-3-carboxamide The product of Example 12 and heptylamine were processed as in Examples 29A and 29B to afford the title compound. $^1$H NMR (300 MHz, CDCl$_3$) δ ppm 0.85-0.93 (m, 3H), 1.16 (s, 1H), 1.20 (s, 6H), 1.31 (s, 6H), 1.32-1.41 (m, 8H), 1.57-1.65 (m, 2H), 1.78-1.91 (m, 4H), 2.61-2.74 (m, 4H), 3.36-3.45 (m, 2H), 5.85-5.95 (m, 1H), 12.06 (s, 1H); MS (DCI/NH$_3$) m/z 377 (M+H)$^+$; anal. calculated for C$_{24}$H$_{38}$N$_2$O$_2$S: C, 68.86; H, 9.15; N, 6.69. Found: C, 68.71; H, 9.02; N, 6.44.

Example 43

N-propyl-2-{[(2,2,3,3-tetramethylcyclopropyl)carbonyl]amino}-1-benzothiophene-3-carboxamide The title compound was prepared as described in Example 1, substituting Example 37 for Example 12. $^1$H NMR (300 MHz, CDCl$_3$) δ ppm 1.06 (t, J=7.5 Hz, 3H), 1.24 (s, 7H), 1.35 (s, 6H), 1.67-1.80 (m, 2H), 3.46-3.55 (m, 2H), 6.22-6.31 (m, 1H), 7.27 (dt, J=7.5, 1.19 Hz, 1H), 7.42 (dt, J=7.6, 1.0 Hz, 1H), 7.72-7.80 (m, 2H), 12.04 (s, 1H); MS (DCI/NH$_3$) m/z 359 (M+H)$^+$; anal. calculated for C$_{20}$H$_{26}$N$_2$O$_2$S: C, 67.01; H, 7.31; N, 7.81. Found: C, 67.17; H, 7.28; N, 7.67.

Example 44

N-(1,2-dimethylpropyl)-2-{[(2,2,3,3-tetramethylcyclopropyl)carbonyl]amino}-1-benzothiophene-3-carboxamide The title compound was prepared as described in Example 1, substituting Example 38 for Example 12. $^1$H NMR (300 MHz, CDCl$_3$) δ ppm 1.05 (t, J=6.8 Hz, 6H), 1.24 (s, 6H), 1.25 (s, 1H), 1.27 (s, 3H), 1.35 (s, 6H), 1.86-1.98 (m, 1H), 4.11-4.24 (m, 1H), 6.06-6.13 (m, 1H), 7.25-7.31 (m, 1H), 7.42 (dt, J=7.6, 1.4 Hz, 1H), 7.76 (dd, J=14.4, 8.0 Hz, 2H), 12.08 (s, 1H); MS (DCI/NH$_3$) m/z 387 (M+H)$^+$; anal. calculated for C$_{22}$H$_{30}$N$_2$O$_2$S.0.3CH$_2$Cl$_2$: C, 65.00; H, 7.49; N, 6.80. Found: C, 65.27; H, 7.88; N, 6.35.

Example 45

N-(tert-butyl)-2-{[(2,2,3,3-tetramethylcyclopropyl)carbonyl]amino}-4,5,6,7-tetrahydro-1-benzothiophene-3-carboxamide The product of Example 12 and tertbutylamine were processed as in Examples 29A and 29B to afford the title compound. $^1$H NMR (300 MHz, CDCl$_3$) δ ppm 1.18 (s, 1H), 1.21 (s, 6H), 1.32 (s, 6H), 1.46 (s, 9H), 1.77-1.89 (m, 4H), 2.62-2.69 (m, 4H), 5.78 (s, 1H), 11.95 (s, 1H); MS (DCI/NH$_3$) m/z 377 (M+H)$^+$; anal. calculated for C$_{21}$H$_{32}$N$_2$O$_2$S: C, 66.98; H, 8.57; N, 7.44. Found: C, 66.64; H, 8.23; N, 7.22.

Example 46

N-butyl-2-{[(2,2,3,3-tetramethylcyclopropyl)carbonyl]amino}-1-benzothiophene-3-carboxamide The title compound was prepared as described in Example 1, substituting Example 41 for Example 12. $^1$H NMR (300 MHz, CDCl$_3$) δ ppm 1.01 (t, J=7.3 Hz, 3H), 1.24 (s, 7H), 1.35 (s, 6H), 1.42-1.53 (m, 3H), 1.64-1.75 (m, 2H), 3.50-3.58 (m, 2H), 7.27 (dt, J=8.1, 1.0 Hz, 1H), 7.42 (dt, J=7.7, 1.2 Hz, 1H), 7.72-7.80 (m, 2H), 12.05 (s, 1H); MS (DCI/NH$_3$) m/z 373 (M+H)$^+$; anal. calculated for C$_{21}$H$_{28}$N$_2$O$_2$S: C, 67.71; H, 7.58; N, 7.52. Found: C, 67.86; H, 7.60; N, 7.31.

Example 47

N-isobutyl-2-{[(2,2,3,3-tetramethylcyclopropyl)carbonyl]amino}-1-benzothiophene-3-carboxamide The title compound was prepared as described in Example 1, substituting Example 39 for Example 12. $^1$H NMR (300 MHz, CDCl$_3$) δ ppm 1.06 (d, J=6.8 Hz, 6H), 1.24 (s, 7H), 1.35 (s, 6H), 1.93-2.08 (m, 1H), 3.38 (dd, J=6.8, 6.10 Hz, 2H), 6.27-6.35 (m, 1H), 7.28 (ddd, J=8.1, 7.1, 1.0 Hz, 1H), 7.42 (ddd, J=8.2, 7.0, 1.4 Hz, 1H), 7.73-7.81 (m, 2H), 12.05 (s, 1H); MS (DCI/NH$_3$) m/z 373 (M+H)$^+$; anal. calculated for C$_{21}$H$_{28}$N$_2$O$_2$S: C, 67.71; H, 7.58; N, 7.52. Found: C, 67.77; H, 7.46; N, 7.43.

Example 48

N-(3-methylbutyl)-2-{[(2,2,3,3-tetramethylcyclopropyl)carbonyl]amino}-1-benzothiophene-3-carboxamide The title compound was prepared as described in Example 1, substituting Example 40 for Example 12. $^1$H NMR (300 MHz, CDCl$_3$) δ ppm 1.01 (d, J=6.8 Hz, 6H), 1.24 (s, 7H), 1.35 (s, 6H), 1.55-1.65 (m, 2H), 1.68-1.84 (m, 1H), 3.51-3.60 (m, 2H), 6.14-6.25 (m, 1H), 7.23-7.31 (m, 1H), 7.42 (dt, J=7.7, 1.2 Hz, 1H), 7.75 (dd, J=13.1, 8.0 Hz, 2H), 12.05 (s, 1H); MS (DCI/NH$_3$) m/z 387 (M+H)$^+$; anal. calculated for C$_{22}$H$_{30}$N$_2$O$_2$S: C, 68.36; H, 7.82; N, 7.25. Found: C, 68.26; H, 7.78; N, 6.91.

Example 49

N-(2-methoxyethyl)-2-{[(2,2,3,3-tetramethylcyclopropyl)carbonyl]amino}-4,5,6,7-tetrahydro-1-benzothiophene-3-carboxamide The product of Example 12 and 2-methoxyethylamine were processed as in Examples 29A and 29B to afford the title compound. $^1$H NMR (300 MHz, CDCl$_3$) δ ppm 1.15 (s, 1H), 1.20 (s, 6H), 1.32 (s, 6H), 1.76-1.90 (m, 4H), 2.62-2.73 (m, 4H), 3.40 (s, 3H), 3.51-3.58 (m, 2H), 3.58-3.65 (m, 2H), 6.27-6.38 (m, 1H), 12.04 (s, 1H); MS (DCI/NH$_3$) m/z 379 (M+H)$^+$; anal. calculated for C$_{20}$H$_{30}$N$_2$O$_3$S: C, 63.46; H, 7.99; N, 7.40. Found: C, 63.31; H, 7.72; N, 7.24.

Example 50

N-(3-methoxypropyl)-2-{[(2,2,3,3-tetramethylcyclopropyl)carbonyl]amino}-4,5,6,7-tetrahydro-1-benzothiophene-3-carboxamide The product of Example 12 and 3-methoxypropylamine were processed as in Examples 29A and 29B to afford the title compound. $^1$H NMR (300 MHz, CDCl$_3$) δ ppm 1.16 (s, 1H), 1.20 (s, 6H), 1.31 (s, 6H), 1.77-1.95 (m, 6H), 2.60-2.75 (m, 4H), 3.36 (s, 3H), 3.49-3.60 (m, 4H), 6.63-6.72 (m, 1H), 12.16 (s, 1H); MS (DCI/NH$_3$) m/z 393 (M+H)$^+$; anal. calculated for C$_{21}$H$_{32}$N$_2$O$_3$S: C, 64.25; H, 8.22; N, 7.14. Found: C, 64.37; H, 8.27; N, 7.14.

Example 51

N-(4-hydroxybutyl)-2-{[(2,2,3,3-tetramethylcyclopropyl)carbonyl]amino}-4,5,6,7-tetrahydro-1-benzothiophene-3-carboxamide The product of Example 12 and 4-amino-1-butanol were processed as in Examples 29A and 29B to afford the title compound. $^1$H NMR (300 MHz, CDCl$_3$) δ ppm 1.16 (s, 1H), 1.20 (s, 6H), 1.32 (s, 6H), 1.63-1.77 (m, 4H), 1.78-1.90 (m, 4H), 2.63-2.72 (m, 4H), 3.48 (q, J=6.50 Hz, 2H), 3.73 (t, J=5.9 Hz, 2H), 5.99-6.08 (m, 1H), 12.03 (s, 1H); MS (DCI/NH$_3$) m/z 393 (M+H)$^+$; anal. calculated for C$_{21}$H$_{32}$N$_2$O$_3$S: C, 64.25; H, 8.22; N, 7.14. Found: C, 64.04; H, 8.50; N, 7.02.

Example 52

N-(5-hydroxypentyl)-2-{[(2,2,3,3-tetramethylcyclopropyl)carbonyl]amino}-4,5,6,7-tetrahydro-1-benzothiophene-3-carboxamide The product of Example 12 and 5-amino-1-pentanol were processed as in Examples 29A and 29B to afford the title compound. $^1$H NMR (300 MHz, CDCl$_3$) δ ppm 1.16 (s, 1H), 1.20 (s, 6H), 1.32 (s, 6H), 1.43-1.52 (m, 3H), 1.59-1.72 (m, 4H), 1.76-1.91 (m, 4H), 2.62-2.72 (m, 4H), 3.38-3.48 (m, 2H), 3.68 (t, J=6.3 Hz, 2H), 5.89-5.98 (m, 1H), 12.03 (s, 1H); MS (DCI/NH$_3$) m/z 407 (M+H)$^+$; anal. calculated for C$_{22}$H$_{34}$N$_2$O$_3$S: C, 64.99; H, 8.43; N, 6.89. Found: C, 64.80; H, 8.45; N, 6.79.

Example 53

N-(2-methoxyethyl)-2-{[(2,2,3,3-tetramethylcyclopropyl)carbonyl]amino}-1-benzothiophene-3-carboxamide The title compound was prepared as described in Example 1, substituting Example 49 for Example 12. $^1$H NMR (300 MHz, CDCl$_3$) δ ppm 1.23 (s, 1H), 1.24 (s, 6H), 1.35 (s, 6H), 3.44 (s, 3H), 3.61-3.67 (m, 2H), 3.69-3.77 (m, 2H), 6.62-6.73 (m, 1H), 7.28 (ddd, J=8.0, 7.1, 0.9 Hz, 1H), 7.42 (ddd, J=8.2, 7.2, 1.2 Hz, 1H), 7.74-7.82 (m, 2H), 12.04 (s, 1H); MS (DCI/

NH$_3$) m/z 375 (M+H)$^+$; anal. calculated for C$_{20}$H$_{26}$N$_2$O$_3$S: C, 64.14; H, 7.48; N, 7.14. Found: C, 64.32; H, 6.73; N, 7.60.

Example 54

N-(3-methoxypropyl)-2-{[(2,2,3,3-tetramethylcyclopropyl)carbonyl]amino}-1-benzothiophene-3-carboxamide The title compound was prepared as described in Example 1, substituting Example 50 for Example 12. $^1$H NMR (300 MHz, CDCl$_3$) δ ppm 1.24 (s, 7H), 1.35 (s, 6H), 1.93-2.03 (m, 2H), 3.39 (s, 3H), 3.60-3.72 (m, 4H), 7.22-7.30 (m, 2H), 7.40 (ddd, J=8.2, 7.0, 1.4 Hz, 1H), 7.76 (d, J=7.8 Hz, 1H), 7.86 (d, J=8.1 Hz, 1H), 12.28 (s, 1H); MS (DCI/NH$_3$) m/z 389 (M+H)$^+$; anal. calculated for C$_{21}$H$_{28}$N$_2$O$_3$S: C, 64.92; H, 7.26; N, 7.21. Found: C, 64.69; H, 7.42; N, 7.07.

Example 55 ethyl 2-[(2,2-dimethylbutanoyl)amino]-4,5,6,7-tetrahydro-1-benzothiophene-3-carboxylate The title compound was prepared as described in step two of Example 12, substituting 2,2,2-dimethylbutyryl chloride for the product of step one. $^1$H NMR (300 MHz, CDCl$_3$) δ ppm 0.87 (t, J=7.5 Hz, 3H), 1.29 (s, 6H), 1.38 (t, J=7.1 Hz, 3H), 1.68 (q, J=7.6 Hz, 2H), 1.74-1.86 (m, 4H), 2.60-2.69 (m, 2H), 2.74-2.82 (m, 2H), 4.34 (q, J=7.1 Hz, 2H), 11.60 (s, 1H); MS (DCI/NH$_3$) m/z 323 (M+H)$^+$; anal. calculated for C$_{17}$H$_{25}$NO$_3$S: C, 63.13; H, 7.79; N, 4.33. Found: C, 63.11; H, 7.96; N, 4.33.

Example 56

N-(5-hydroxypentyl)-2-{[(2,2,3,3-tetramethylcyclopropyl)carbonyl]amino}-1-benzothiophene-3-carboxamide The title compound was prepared as described in Example 1, substituting Example 52 for Example 12. $^1$H NMR (300 MHz, CDCl$_3$) δ ppm 1.20 (s, 1H), 1.24 (s, 6H), 1.32 (s, 1H), 1.35 (s, 6H), 1.61-1.86 (m, 6H), 3.51-3.60 (m, 2H), 3.70 (t, J=6.3 Hz, 2H), 6.25-6.32 (m, 1H), 7.23-7.31 (m, 1H), 7.42 (ddd, J=8.2, 7.2, 1.2 Hz, 1H), 7.70-7.80 (m, 2H), 12.03 (s, 1H); MS (DCI/NH$_3$) m/z 403 (M+H); anal. calculated for C$_{22}$H$_{30}$N$_2$O$_3$S.0.8H$_2$O: C, 63.37; H, 7.64; N, 6.72. Found: C, 63.11; H, 7.27; N, 6.55.

Example 57

N-(2-ethoxyethyl)-2-{[(2,2,3,3-tetramethylcyclopropyl)carbonyl]amino}-4,5,6,7-tetrahydro-1-benzothiophene-3-carboxamide The product of Example 12 and 2-ethoxyethylamine were processed as in Examples 29A and 29B to afford the title compound. $^1$H NMR (300 MHz, CDCl$_3$) δ ppm 1.15 (s, 1H), 1.20 (s, 6H), 1.23 (t, J=6.8 Hz, 3H), 1.32 (s, 6H), 1.83 (q, 4H), 2.68 (q, 4H), 3.55 (q, J=7.0 Hz, 2H), 3.59-3.65 (m, 4H), 6.36-6.46 (m, 1H), 12.05 (s, 1H); MS (DCI/NH$_3$) m/z 393 (M+H)$^+$; anal. calculated for C$_{21}$H$_{32}$N$_2$O$_3$S: C, 64.25; H, 8.22; N, 7.14. Found: C, 63.97; H, 8.34; N, 7.05.

Example 58

N-(2-hydroxyethyl)-2-{[(2,2,3,3-tetramethylcyclopropyl)carbonyl]amino}-4,5,6,7-tetrahydro-1-benzothiophene-3-carboxamide The product of Example 12 and ethanolamine were processed as in Examples 29A and 29B to afford the title compound. $^1$H NMR (300 MHz, CDCl$_3$) δ ppm 1.15 (s, 1H), 1.21 (s, 6H), 1.32 (s, 6H), 1.77-1.91 (m, 5H), 2.62-2.76 (m, 4H), 3.57-3.65 (m, 2H), 3.80-3.86 (m, 2H), 6.34-6.45 (m, 1H), 11.98 (s, 1H); MS (DCI/NH$_3$) m/z 365 (M+H)$^+$; anal. calculated for C$_{19}$H$_{28}$N$_2$O$_3$S.0.5H$_2$O: C, 61.10; H, 7.83; N, 7.50. Found: C, 61.42; H, 7.91; N, 7.05.

Example 59

N-(2-ethoxyethyl)-2-{[(2,2,3,3-tetramethylcyclopropyl)carbonyl]amino}-1-benzothiophene-3-carboxamide The title compound was prepared as described in Example 1, substituting Example 57 for Example 12. $^1$H NMR (300 MHz, CDCl$_3$) δ ppm 1.24 (s, 1H), 1.24 (s, 6H), 1.28 (t, J=7.1 Hz, 3H), 1.35 (s, 6H), 3.60 (q, J=7.0 Hz, 2H), 3.65-3.77 (m, 4H), 6.71-6.79 (m, 1H), 7.25-7.31 (m, 1H), 7.42 (ddd, J=7.7, 1.2 Hz, 1H), 7.76-7.80 (m, 1H), 7.82 (d, J=8.1 Hz, 1H), 12.05 (s, 1H); MS (DCI/NH$_3$) m/z 389 (M+H)$^+$; anal. calculated for C$_{21}$H$_{28}$N$_2$O$_3$S: C, 64.92; H, 7.26; N, 7.21. Found: C, 64.73; H, 7.50; N, 7.06.

Example 60

2,2,3,3-tetramethyl-N-[3-(morpholin-4-ylcarbonyl)-4,5,6,7-tetrahydro-1-benzothien-2-yl]cyclopropanecarboxamide The product of Example 12 and morpholine were processed as in Examples 29A and 29B to afford the title compound. $^1$H NMR (300 MHz, CDCl$_3$) δ ppm 1.03 (s, 1H), 1.20 (s, 6H), 1.31 (s, 6H), 1.68-1.89 (m, 4H), 2.43 (t, J=5.9 Hz, 2H), 2.66 (t, J=6.3 Hz, 2H), 3.45-3.80 (m, 8H), 8.99 (s, 1H); MS (DCI/NH$_3$) m/z 391 (M+H)$^+$; anal. calculated for C$_{21}$H$_{30}$N$_2$O$_3$S: C, 64.58; H, 7.74; N, 7.17. Found: C, 64.61; H, 7.84; N, 7.00.

Example 61

N-(2-hydroxyethyl)-2-{[(2,2,3,3-tetramethylcyclopropyl)carbonyl]amino}-1-benzothiophene-3-carboxamide The title compound was prepared as described in Example 1, substituting Example 58 for Example 12. $^1$H NMR (300 MHz, CDCl$_3$) δ ppm 1.23 (s, 1H), 1.25 (s, 6H), 1.36 (s, 6H), 3.69-3.77 (m, 2H), 3.93 (t, J=4.7 Hz, 2H), 6.68-6.78 (m, 1H), 7.25-7.32 (m, 1H), 7.42 (ddd, J=8.2, 7.2, 1.2 Hz, 1H), 7.79 (t, J=8.3 Hz, 2H), 12.01 (s, 1H); MS (DCI/NH$_3$) m/z 361 (M+H)$^+$; anal. calculated for C$_{19}$H$_{24}$N$_2$O$_3$S.0.5CH$_3$OH: C, 62.21; H, 6.96; N, 7.44. Found: C, 61.92; H, 6.58; N, 7.10.

Example 62

2,2,3,3-tetramethyl-N-[3-(morpholin-4-ylcarbonyl)-1-benzothien-2-yl]cyclopropanecarboxamide The title compound was prepared as described in Example 1, substituting Example 60 for Example 12. $^1$H NMR (300

MHz, CDCl$_3$) δ ppm 1.16 (s, 1H), 1.25 (s, 6H), 1.36 (s, 6H), 3.58-3.75 (m, 6H), 3.77-3.87 (m, 2H), 7.25 (ddd, J=8.1, 7.0, 1.2 Hz, 1H), 7.38 (ddd, J=8.1, 7.1, 1.0 Hz, 1H), 7.53 (d, J=8.1 Hz, 1H), 7.74 (d, J=7.8 Hz, 1H), 10.10 (s, 1H); MS (DCI/NH$_3$) m/z 387 (M+H)$^+$; anal. calculated for C$_{21}$H$_{26}$N$_2$O$_3$S.0.75H$_2$O: C, 63.05; H, 6.93; N, 7.00. Found: C, 63.33; H, 6.97; N, 6.62.

Example 63 ethyl 6-benzyl-2-{[(2,2,3,3-tetramethylcyclopropyl)carbonyl]amino}-4,5,6,7-tetrahydrothieno[2,3-c]pyridine-3-carboxylate The title compound was prepared as described in Example 6, substituting benzaldehyde for formaldehyde. $^1$H NMR (300 MHz, CD$_3$OD) δ ppm 1.27 (s, 6H), 1.29 (s, 6H), 1.35 (s, 1H), 1.38 (t, J=7.1 Hz, 3H), 2.36 (s, 3H), 3.30 (s, 2H), 3.31-3.34 (m, 2H), 4.31-4.33 (m, 2H), 4.37 (q, J=7.1 Hz, 2H), 4.46-4.52 (m, 2H), 7.18-7.23 (m, 2H), 7.49-7.59 (m, 5H), 7.65-7.71 (m, 2H), 11.28 (s, 1H); MS (DCI/NH$_3$) m/z 441 (M+H)$^+$; anal. calculated for C$_{25}$H$_{32}$N$_2$O$_3$S.C$_7$H$_8$O$_3$S: C, 62.72; H, 6.58; N, 4.57. Found: C, 62.50; H, 6.69; N, 4.46.

Example 64 ethyl 6-[(5-methyl-2-furyl)methyl]-2-{[(2,2,3,3-tetramethylcyclopropyl)carbonyl]amino}-4,5,6,7-tetrahydrothieno[2,3-c]pyridine-3-carboxylate The title compound was prepared as described in Example 6, substituting 5-methylfurfural for formaldehyde. $^1$H NMR (300 MHz, CD$_3$OD) δ ppm 1.27 (s, 6H), 1.30 (s, 6H), 1.36 (s, 1H), 1.39 (t, J=7.1 Hz, 3H), 2.34 (s, 3H), 2.36 (s, 3H), 3.20-3.34 (m, 4H), 4.32-4.34 (m, 2H), 4.38 (q, J=7.1 Hz, 2H), 4.49 (s, 2H), 6.13-6.16 (m, 1H), 6.63 (d, J=3.4 Hz, 1H), 7.18-7.25 (m, 2H), 7.67-7.72 (m, 2H), 11.29 (s, 1H); MS (DCI/NH$_3$) m/z 445 (M+H)$^+$; anal. calculated for C$_{24}$H$_{32}$N$_2$O$_4$S.C$_7$H$_8$O$_3$S.0.3H$_2$O: C, 59.84; H, 6.58; N, 4.50. Found: C, 59.87; H, 6.31; N, 4.27.

Example 65 ethyl 6-propyl-2-{[(2,2,3,3-tetramethylcyclopropyl)carbonyl]amino}-4,5,6,7-tetrahydrothieno[2,3-c]pyridine-3-carboxylate The title compound was prepared as described in Example 6, substituting propionaldehyde for formaldehyde. $^1$H NMR (300 MHz, CD$_3$OD) δ ppm 1.06 (t, J=7.3 Hz, 3H), 1.27 (s, 6H), 1.30 (s, 6H), 1.36 (s, 1H), 1.39 (t, J=7.1 Hz, 3H), 1.77-1.91 (m, 2H), 2.36 (s, 3H), 3.19-3.28 (m, 4H), 3.49-3.68 (m, 2H), 4.38 (q, J=7.1 Hz, 2H), 4.38-4.45 (m, 2H), 7.19-7.24 (m, 2H), 7.65-7.72 (m, 2H); MS (DCI/NH$_3$) m/z 393 (M+H)$^+$; anal. calculated for C$_{21}$H$_{32}$N$_2$O$_3$S.C$_7$H$_8$O$_3$S: C, 59.55; H, 7.14; N, 4.96. Found: C, 59.48; H, 7.27; N, 4.66.

Example 66 ethyl 6-butyl-2-{[(2,2,3,3-tetramethylcyclopropyl)carbonyl]amino}-4,5,6,7-tetrahydrothieno[2,3-c]pyridine-3-carboxylate The title compound was prepared as described in Example 6, substituting butyraldehyde for formaldehyde. $^1$H NMR (300 MHz, CD$_3$OD) δ ppm 1.02 (t, J=7.5 Hz, 3H), 1.27 (s, 6H), 1.30 (s, 6H), 1.36 (s, 1H), 1.39 (t, J=7.1 Hz, 3H), 1.42-1.52 (m, 2H), 1.74-1.87 (m, 2H), 2.36 (s, 3H), 3.20-3.33 (m, 4H), 3.49-3.66 (m, 2H), 4.38 (q, J=7.1 Hz, 2H), 4.40-4.45 (m, 2H), 7.18-7.24 (m, 2H), 7.65-7.71 (m, 2H); MS (DCI/NH$_3$) m/z 407 (M+H)$^+$; anal. calculated for C$_{22}$H$_{34}$N$_2$O$_3$S.C$_7$H$_8$O$_3$S: C, 60.18; H, 7.31; N, 4.84. Found: C, 59.95; H, 7.14; N, 4.48.

Example 67 ethyl 6-(1-benzofuran-2-ylmethyl)-2-{[(2,2,3,3-tetramethylcyclopropyl)carbonyl]amino}-4,5,6,7-tetrahydrothieno[2,3-c]pyridine-3-carboxylate The title compound was prepared as described in Example 6, substituting 2-benzofurancarboxaldehyde for formaldehyde. $^1$H NMR (300 MHz, CD$_3$OD) δ ppm 1.27 (s, 6H), 1.29 (s, 6H), 1.36 (s, 1H), 1.39 (t, J=7.1 Hz, 3H), 2.36 (s, 3H), 3.23-3.30 (m, 4H), 4.38 (q, J=7.2 Hz, 2H), 4.43-4.49 (m, 2H), 4.75 (s, 2H), 7.18-7.24 (m, 3H), 7.28-7.35 (m, 1H), 7.38-7.46 (m, 1H), 7.56-7.61 (m, 1H), 7.66-7.72 (m, 3H), 11.29 (s, 1H); MS (DCI/NH$_3$) m/z 481 (M+H)$^+$; anal. calculated for C$_{27}$H$_{32}$N$_2$O$_4$S.C$_7$H$_8$O$_3$S: C, 62.55; H, 6.18; N, 4.29. Found: C, 62.24; H, 6.10; N, 3.92.

Example 68 ethyl 6-ethyl-2-{[(2,2,3,3-tetramethylcyclopropyl)carbonyl]amino}-4,5,6,7-tetrahydrothieno[2,3-c]pyridine-3-carboxylate The title compound was prepared as described in Example 6, substituting acetaldehyde for formaldehyde. $^1$H NMR (300 MHz, CD$_3$OD) δ ppm 1.27 (s, 6H), 1.30 (s, 6H), 1.36 (s, 1H), 1.40 (t, J=7.1 Hz, 3H), 1.42 (t, J=7.3 Hz, 3H), 2.36 (s, 3H), 3.18-3.27 (m, 2H), 3.37 (q, J=7.1 Hz, 2H), 3.46-3.66 (m, 2H), 4.38 (q, J=7.1 Hz, 2H), 4.39-4.44 (m, 2H), 7.18-7.24 (m, 2H), 7.65-7.71 (m, 2H); MS (DCI/NH$_3$) m/z 379 (M+H)$^+$; anal. calculated for C$_{20}$H$_{30}$N$_2$O$_3$S.C$_7$H$_8$O$_3$S: C, 58.88; H, 6.95; N, 5.09. Found: C, 59.00; H, 7.04; N, 5.02.

Example 69 ethyl 6-(cyclopropylmethyl)-2-{[(2,2,3,3-tetramethylcyclopropyl)carbonyl]amino}-4,5,6,7-tetrahydrothieno[2,3-c]pyridine-3-carboxylate The title compound was prepared as described in Example 6, substituting cyclopropane carboxaldehyde for formaldehyde. $^1$H NMR (300 MHz, CD$_3$OD) δ ppm 0.44-0.52 (m, 2H), 0.75-0.88 (m, 2H), 1.15-1.24 (m, 1H), 1.25-1.29 (m, 6H), 1.30 (s, 6H), 1.36 (s, 1H), 1.40 (t, J=7.1 Hz, 3H), 2.36 (s, 3H), 3.16-3.27 (m, 4H), 3.51-3.71 (m, 2H), 4.39 (q, J=7.2 Hz, 2H), 4.41-4.50 (m, 2H), 7.17-7.26 (m, 2H), 7.64-7.72 (m, 2H); MS (DCI/NH$_3$) m/z 405 (M+H)$^+$; anal. calculated for C$_{22}$H$_{32}$N$_2$O$_3$S.C$_7$H$_8$O$_3$S: C, 60.39; H, 6.99; N, 4.86. Found: C, 60.30; H, 6.79; N, 4.72.

Example 70 ethyl 6-(2-methylbutyl)-2-{[(2,2,3,3-tetramethylcyclopropyl)carbonyl]amino}-4,5,6,7-tetrahydrothieno[2,3-c]pyridine-3-carboxylate The title compound was prepared as described in Example 6, substituting 2-methylbutyraldehyde for formaldehyde. $^1$H NMR (300 MHz, CD$_3$OD) δ ppm 0.99 (t, J=7.5 Hz, 3H), 1.08 (d, J=6.8 Hz, 3H), 1.27 (s, 6H), 1.30 (s, 6H), 1.36 (s, 1H), 1.40

(t, J=7.1 Hz, 3H), 1.47-1.58 (m, 1H), 1.95-2.09 (m, 1H), 2.36 (s, 3H), 3.04-3.15 (m, 2H), 3.16-3.27 (m, 4H), 3.37-3.58 (m, 1H), 4.19-4.33 (m, 1H), 4.39 (q, J=7.1 Hz, 2H), 4.47-4.63 (m, 1H), 7.18-7.25 (m, 2H), 7.66-7.71 (m, 2H); MS (DCI/NH$_3$) m/z 421 (M+H)$^+$; anal. calculated for C$_{23}$H$_{36}$N$_2$O$_3$S.C$_7$H$_8$O$_3$S: C, 60.78; H, 7.48; N, 4.73. Found: C, 60.72; H, 7.32; N, 4.62.

Example 71

N-ethyl-4,5-dimethyl-2-{[(2,2,3,3-tetramethylcyclopropyl)carbonyl]amino}thiophene-3-carboxamide Example 9B (18 mg, 0.060 mmol), two equivalents of polymer bound dicyclohexylcarbodidiimide (PS-DCC, commercially available from Argonaut Technologies), 1-hydroxybenzotriazole (HOBT, 8.9 mg, 0.066 mmol), N,N-diisopropylethylamine (7.8 mg, 0.060 mmol), and ethylamine (2.7 mg, 0.060 mmol) were combined in dimethylacetamide (3 mL) and heated in a microwave (Personal Chemistry Ermy's Optimizer) to 100° C. for 300 seconds. The mixture was filtered through Si-Carbonate (6 mL-1 g cartridge from Silicycle Chemical Division) and then concentrated to dryness. The residue was dissolved in 1:1 dimethylsulfoxide/methanol and purified by reverse phase HPLC to afford the title compound. $^1$H NMR (500 MHz, dimethylsulfoxide-d$_6$) δ ppm 1.09-1.14 (m, 3H) 1.18 (s, 6H) 1.21 (s, 6H) 1.40 (s, 1H) 2.12 (s, 3H) 2.19 (s, 3H) 3.23-3.28 (m, 2H) 7.64 (s, 1H) 10.85 (s, 1H); MS (ESI) m/z 323 (M+H)$^+$.

Example 72

4,5-dimethyl-N-propyl-2-{[(2,2,3,3-tetramethylcyclopropyl)carbonyl]amino}thiophene-3-carboxamide Example 9B (18 mg, 0.060 mmol), two equivalents of polymer bound dicyclohexylcarbodidiimide (PS-DCC, commercially available from Argonaut Technologies), 1-hydroxybenzotriazole (HOBT, 8.9 mg, 0.066 mmol), N,N-diisopropylethylamine (7.8 mg, 0.060 mmol), and propylamine (3.5 mg, 0.060 mmol) were combined in dimethylacetamide (3 mL) and heated in a Personal Chemistry Ermy's optimizer microwave to 100° C. for 300 seconds. The mixture was filtered through Si-Carbonate (6 mL-1 g cartridge from Silicycle Chemical Division) and then concentrated to dryness. The residue was dissolved in 1:1 dimethylsulfoxide/methanol and purified by reverse phase HPLC to afford the title compound. $^1$H NMR (500 MHz, dimethylsulfoxide-d$_6$) δ ppm 0.88-0.92 (m, 3H) 1.17 (s, 6H) 1.21 (s, 6H) 1.41 (s, 1H) 1.48-1.57 (m, 2H) 2.12 (s, 3H) 2.19 (s, 3H) 3.17-3.25 (m, 2H) 7.64 (s, 1H) 10.80 (s, 1H); MS (ESI) m/z 337 (M+H)$^+$.

Example 73

N-isopropyl-4,5-dimethyl-2-{[(2,2,3,3-tetramethylcyclopropyl)carbonyl]amino}thiophene-3-carboxamide Example 9B (18 mg, 0.060 mmol), two equivalents of polymer bound dicyclohexylcarbodidiimide (PS-DCC, commercially available from Argonaut Technologies), 1-hydroxybenzotriazole (HOBT, 8.9 mg, 0.066 mmol), N,N-diisopropylethylamine (7.8 mg, 0.060 mmol), and isopropylamine (3.5 mg, 0.060 mmol) were combined in dimethylacetamide (3 mL) and heated in a Personal Chemistry Ermy's optimizer microwave to 100° C. for 300 seconds. The mixture was filtered through Si-Carbonate (6 mL-1 g cartridge from Silicycle Chemical Division) and then concentrated to dryness. The residue was dissolved in 1:1 dimethylsulfoxide/methanol and purified by reverse phase HPLC to afford the title compound. $^1$H NMR (500 MHz, dimethylsulfoxide-d$_6$) δ ppm 0.88-0.92 (m, 3H) 1.17 (s, 6H) 1.21 (s, 6H) 1.41 (s, 1H) 1.48-1.57 (m, 2H) 2.12 (s, 3H) 2.19 (s, 3H) 3.17-3.25 (m, 2H) 7.64 (s, 1H) 10.80 (s, 1H); MS (ESI) m/z 337 (M+H)$^+$.

Example 74

N-butyl-4,5-dimethyl-2-{[(2,2,3,3-tetramethylcyclopropyl)carbonyl]amino}thiophene-3-carboxamide Example 9B (18 mg, 0.060 mmol), two equivalents of polymer bound dicyclohexylcarbodidiimide (PS-DCC, commercially available from Argonaut Technologies), 1-hydroxybenzotriazole (HOBT, 8.9 mg, 0.066 mmol), N,N-diisopropylethylamine (7.8 mg, 0.060 mmol), and butylamine (4.4 mg, 0.060 mmol) were combined in dimethylacetamide (3 mL) and heated in a Personal Chemistry Ermy's optimizer microwave to 100° C. for 300 seconds. The mixture was filtered through Si-Carbonate (6 mL-1 g cartridge from Silicycle Chemical Division) and then concentrated to dryness. The residue was dissolved in 1:1 dimethylsulfoxide/methanol and purified by reverse phase HPLC to afford the title compound. $^1$H NMR (500 MHz, dimethylsulfoxide-d$_6$) δ ppm 0.87-0.93 (m, 3H) 1.17 (s, 6H) 1.21 (s, 6H) 1.29-1.37 (m, 2H) 1.40 (s, 1H) 1.45-1.54 (m, 2H) 2.12 (s, 3H) 2.19 (s, 3H) 3.20-3.27 (m, 2H) 7.59-7.67 (m, 1H) 10.80 (s, 1H); MS (ESI) m/z 351 (M+H)$^+$.

Example 75

N-(sec-butyl)-4,5-dimethyl-2-{[(2,2,3,3-tetramethylcyclopropyl)carbonyl]amino}thiophene-3-carboxamide Example 9B (18 mg, 0.060 mmol), two equivalents of polymer bound dicyclohexylcarbodidiimide (PS-DCC, commercially available from Argonaut Technologies), 1-hydroxybenzotriazole (HOBT, 8.9 mg, 0.066 mmol), N,N-diisopropylethylamine (7.8 mg, 0.060 mmol), and sec-butylamine (4.4 mg, 0.060 mmol) were combined in dimethylacetamide (3 mL) and heated in a Personal Chemistry Ermy's optimizer microwave to 100° C. for 300 seconds. The mixture was filtered through Si-Carbonate (6 mL-1 g cartridge from Silicycle Chemical Division) and then concentrated to dryness. The residue was dissolved in 1:1 dimethylsulfoxide/methanol and purified by reverse phase HPLC to afford the title compound. $^1$H NMR (500 MHz, dimethylsulfoxide-d$_6$) δ ppm 0.86-0.91 (m, 3H) 1.11-1.15 (m, 3H) 1.17 (s, 6H) 1.21 (s, 6H) 1.39 (s, 1H) 1.45-1.54 (m, 2H) 2.11 (s, 3H) 2.19 (s, 3H) 3.85-3.93 (m, 1H) 7.38-7.47 (m, 1H) 10.57 (s, 1H); MS (ESI) m/z 351 (M+H)$^+$.

Example 76

N-isobutyl-4,5-dimethyl-2-{[(2,2,3,3-tetramethylcyclopropyl)carbonyl]amino}thiophene-3-carboxamide Example 9B (18 mg, 0.060 mmol), two equivalents of polymer bound dicyclohexylcarbodidiimide (PS-DCC, commercially available from Argonaut Technologies), 1-hydroxybenzotriazole (HOBT, 8.9 mg, 0.066 mmol), N,N-diisopropylethylamine (7.8 mg, 0.060 mmol), and isobutylamine (4.4 mg, 0.060 mmol) were combined in dimethylacetamide (3 mL) and heated in a Personal Chemistry Ermy's optimizer microwave to 100° C. for 300 seconds. The mixture was filtered through Si-Carbonate (6 mL-1 g cartridge from Silicycle Chemical Division) and then concentrated to dryness. The residue was dissolved in 1:1 dimethylsulfoxide/methanol and purified by reverse phase HPLC to afford the title compound. $^1$H NMR (500 MHz, dimethylsulfoxide-$d_6$) δ ppm 0.88-0.92 (m, 6H) 1.17 (s, 6H) 1.21 (s, 6H) 1.38 (s, 1H) 1.79-1.88 (m, 1H) 2.14 (s, 3H) 2.19 (s, 3H) 3.04-3.12 (m, 2H) 7.63-7.70 (m, 1H) 10.76 (s, 1H); MS (ESI) m/z 351 (M+H)$^+$.

Example 77

4,5-dimethyl-N-pentyl-2-{[(2,2,3,3-tetramethylcyclopropyl)carbonyl]amino}thiophene-3-carboxamide Example 9B (18 mg, 0.060 mmol), two equivalents of polymer bound dicyclohexylcarbodidiimide (PS-DCC, commercially available from Argonaut Technologies), 1-hydroxybenzotriazole (HOBT, 8.9 mg, 0.066 mmol), N,N-diisopropylethylamine (7.8 mg, 0.060 mmol), and pentylamine (5.2 mg, 0.060 mmol) were combined in dimethylacetamide (3 mL) and heated in a Personal Chemistry Ermy's optimizer microwave to 100° C. for 300 seconds. The mixture was filtered through Si-Carbonate (6 mL-1 g cartridge from Silicycle Chemical Division) and then concentrated to dryness. The residue was dissolved in 1:1 dimethylsulfoxide/methanol and purified by reverse phase HPLC to afford the title compound. $^1$H NMR (500 MHz, dimethylsulfoxide-$d_6$) δ ppm 0.83-0.91 (m, 3H) 1.17 (s, 6 H) 1.21 (s, 7H) 1.27-1.34 (m, 4H) 1.48-1.56 (m, 2H) 2.11 (s, 3H) 2.19 (s, 3H) 3.19-3.28 (m, 2H) 7.59-7.67 (m, 1H) 10.80 (s, 1H); MS (ESI) m/z 365 (M+H)$^+$.

Example 78

N-(1,2-dimethylpropyl)-4,5-dimethyl-2-{[(2,2,3,3-tetramethylcyclopropyl)carbonyl]amino}thiophene-3-carboxamide Example 9B (18 mg, 0.060 mmol), two equivalents of polymer bound dicyclohexylcarbodidiimide (PS-DCC, commercially available from Argonaut Technologies), 1-hydroxybenzotriazole (HOBT, 8.9 mg, 0.066 mmol), N,N-diisopropylethylamine (7.8 mg, 0.060 mmol), and 1,2-dimethylpropylamine (5.2 mg, 0.060 mmol) were combined in dimethylacetamide (3 mL) and heated in a Personal Chemistry Ermy's optimizer microwave to 100° C. for 300 seconds. The mixture was filtered through Si-Carbonate (6 mL-1 g cartridge from Silicycle Chemical Division) and then concentrated to dryness. The residue was dissolved in 1:1 dimethylsulfoxide/methanol and purified by reverse phase HPLC to afford the title compound. $^1$H NMR (500 MHz, dimethylsulfoxide-$d_6$) δ ppm 0.86-0.92 (m, 5H) 1.07-1.12 (m, 3H) 1.16-1.18 (m, 5H) 1.19-1.23 (m, 9H) 1.38 (s, 1H) 1.71-1.79 (m, 1H) 2.12 (s, 2H) 2.20 (s, 3H) 3.83 (s, 1H) 7.37-7.44 (m, 1H) 10.54 (s, 1H); MS (ESI) m/z 365 (M+H)$^+$.

Example 79

4,5-dimethyl-N-neopentyl-2-{[(2,2,3,3-tetramethylcyclopropyl)carbonyl]amino}thiophene-3-carboxamide Example 9B (18 mg, 0.060 mmol), two equivalents of polymer bound dicyclohexylcarbodidiimide (PS-DCC, commercially available from Argonaut Technologies), 1-hydroxybenzotriazole (HOBT, 8.9 mg, 0.066 mmol), N,N-diisopropylethylamine (7.8 mg, 0.060 mmol), and 2,2-dimethylpropylamine (5.2 mg, 0.060 mmol) were combined in dimethylacetamide (3 mL) and heated in a Personal Chemistry Ermy's optimizer microwave to 100° C. for 300 seconds. The mixture was filtered through Si-Carbonate (6 mL-1 g cartridge from Silicycle Chemical Division) and then concentrated to dryness. The residue was dissolved in 1:1 dimethylsulfoxide/methanol and purified by reverse phase HPLC to afford the title compound. $^1$H NMR (500 MHz, dimethylsulfoxide-$d_6$) δ ppm 0.90 (s, 6H) 1.17 (s, 4H) 1.19-1.23 (m, 7H) 1.23-1.26 (m, 3H) 2.14-2.22 (m, 6H) 2.31 (s, 1H) 2.36 (s, 1H) 3.05-3.13 (m, 1H) 3.83 (s, 1H) 7.59-7.67 (m, 1H) 10.74 (s, 1H); MS (ESI) m/z 365 (M+H)$^+$.

Example 80

N-(1-ethylpropyl)-4,5-dimethyl-2-{[(2,2,3,3-tetramethylcyclopropyl)carbonyl]amino}thiophene-3-carboxamide Example 9B (18 mg, 0.060 mmol), two equivalents of polymer bound dicyclohexylcarbodidiimide (PS-DCC, commercially available from Argonaut Technologies), 1-hydroxybenzotriazole (HOBT, 8.9 mg, 0.066 mmol), N,N-diisopropylethylamine (7.8 mg, 0.060 mmol), and 1-ethylpropylamine (5.2 mg, 0.060 mmol) were combined in dimethylacetamide (3 mL) and heated in a Personal Chemistry Ermy's optimizer microwave to 100° C. for 300 seconds. The mixture was filtered through Si-Carbonate (6 mL-1 g cartridge from Silicycle Chemical Division) and then concentrated to dryness. The residue was dissolved in 1:1 dimethylsulfoxide/methanol and purified by reverse phase HPLC to afford the title compound. $^1$H NMR (500 MHz, dimethylsulfoxide-$d_6$) δ ppm 0.83-0.91 (m, 6H) 1.18 (s, 12H) 1.36 (s, 1H) 1.43-1.48 (m, 2H) 1.50-1.55 (m, 2H) 2.12 (s, 3H) 2.19 (s, 3H) 3.72-3.80 (m, 1H) 7.29-7.36 (m, 1H) 10.50 (s, 1H); MS (ESI) m/z 365 (M+H)$^+$.

Example 81

N-(3,3-dimethylbutyl)-4,5-dimethyl-2-{[(2,2,3,3-tetramethylcyclopropyl)carbonyl]amino}thiophene-3-carboxamide Example 9B (18 mg, 0.060 mmol), two equivalents of polymer bound dicyclohexylcarbodidiimide (PS-DCC, commercially available from Argonaut Technologies), 1-hydroxybenzotriazole (HOBT, 8.9 mg, 0.066 mmol), N,N-diisopropylethylamine (7.8 mg, 0.060 mmol), and 3,3-dimethylbutylamine (6.1 mg, 0.060 mmol) were combined in dimethylacetamide (3 mL) and heated in a Personal Chemistry Ermy's optimizer microwave to 100° C. for 300 seconds. The mixture was filtered through Si-Carbonate (6 mL-1 g cartridge from Silicycle Chemical Division) and then concentrated to dryness. The residue was dissolved in 1:1 dimethylsulfoxide/methanol and purified by reverse phase HPLC to afford the title compound. $^1$H NMR (500 MHz, dimethylsulfoxide-$d_6$) δ ppm 0.92 (s, 9H) 1.16 (s, 6H) 1.21 (s, 6H) 1.39 (s, 1H) 1.41-1.48 (m, 2H) 2.12 (s, 3H) 2.18 (s, 3H) 3.22-3.31 (m, 2H) 7.54-7.61 (m, 1H) 10.85 (s, 1H); MS (ESI) m/z 379 (M+H)$^+$.

Example 82

N-(2-methoxyethyl)-4,5-dimethyl-2-{[(2,2,3,3-tetramethylcyclopropyl)carbonyl]amino}thiophene-3-carboxamide Example 9B (18 mg, 0.060 mmol), two equivalents of polymer bound dicyclohexylcarbodidiimide (PS-DCC, commercially available from Argonaut Technologies), 1-hydroxybenzotriazole (HOBT, 8.9 mg, 0.066 mmol), N,N-diisopropylethylamine (7.8 mg, 0.060 mmol), and 2-methoxyethylamine (4.5 mg, 0.060 mmol) were combined in dimethylacetamide (3 mL) and heated in a Personal Chemistry Ermy's optimizer microwave to 100° C. for 300 seconds. The mixture was filtered through Si-Carbonate (6 mL-1 g cartridge from Silicycle Chemical Division) and then concentrated to dryness. The residue was dissolved in 1:1 dimethylsulfoxide/methanol and purified by reverse phase HPLC to afford the title compound. $^1$H NMR (500 MHz, dimethylsulfoxide-$d_6$) δ ppm 0.92 (s, 9H) 1.18 (s, 6H) 1.21 (s, 5H) 1.37 (s, 1H) 2.10 (s, 3H) 2.17 (s, 3H) 3.28 (s, 3H) 3.29 (s, 3H) 3.39-3.43 (m, 2H) 7.64-7.72 (m, 1H) 10.72 (s, 1H); MS (ESI) m/z 352 (M+H)$^+$.

Example 83

N-(2-methoxy-1-methylethyl)-4,5-dimethyl-2-{[(2,2,3,3-tetramethylcyclopropyl)carbonyl]amino}thiophene-3-carboxamide Example 9B (18 mg, 0.060 mmol), two equivalents of polymer bound dicyclohexylcarbodidiimide (PS-DCC, commercially available from Argonaut Technologies), 1-hydroxybenzotriazole (HOBT, 8.9 mg, 0.066 mmol), N,N-diisopropylethylamine (7.8 mg, 0.060 mmol), and 2-methoxy-1-methylethylamine (5.3 mg, 0.060 mmol) were combined in dimethylacetamide (3 mL) and heated in a Personal Chemistry Ermy's optimizer microwave to 100° C. for 300 seconds. The mixture was filtered through Si-Carbonate (6 mL-1 g cartridge from Silicycle Chemical Division) and then concentrated to dryness. The residue was dissolved in 1:1 dimethylsulfoxide/methanol and purified by reverse phase HPLC to afford the title compound. $^1$H NMR (500 MHz, dimethylsulfoxide-$d_6$) δ ppm 0.92 (s, 9H) 1.10-1.15 (m, 3H) 1.17 (s, 6H) 1.22 (s, 6H) 1.38 (s, 1H) 2.09 (s, 3H) 2.18 (s, 3H) 3.28 (s, 3H) 3.36-3.44 (m, 2H) 4.17 (s, 1H) 7.50-7.56 (m, 1H) 10.50 (s, 1H); MS (ESI) m/z 367 (M+H)$^+$.

Example 84

4,5-dimethyl-N-[2-(methylthio)ethyl]-2-{[(2,2,3,3-tetramethylcyclopropyl)carbonyl]amino}thiophene-3-carboxamide Example 9B (18 mg, 0.060 mmol), two equivalents of polymer bound dicyclohexylcarbodidiimide (PS-DCC, commercially available from Argonaut Technologies), 1-hydroxybenzotriazole (HOBT, 8.9 mg, 0.066 mmol), N,N-diisopropylethylamine (7.8 mg, 0.060 mmol), and 2-methylsulfanylethylamine (5.5 mg, 0.060 mmol) were combined in dimethylacetamide (3 mL) and heated in a Personal Chemistry Ermy's optimizer microwave to 100° C. for 300 seconds. The mixture was filtered through Si-Carbonate (6 mL-1 g cartridge from Silicycle Chemical Division) and then concentrated to dryness. The residue was dissolved in 1:1 dimethylsulfoxide/methanol and purified by reverse phase HPLC to afford the title compound. $^1$H NMR (500 MHz, dimethylsulfoxide-$d_6$) δ ppm 1.17 (s, 6H) 1.21 (s, 5H) 1.39 (s, 1H) 2.09 (s, 3H) 2.13 (s, 3H) 2.19 (s, 3H) 2.62-2.70 (m, 2H) 3.26-3.31 (m, 3H) 7.75-7.83 (m, 1H) 10.75 (s, 1H); MS (ESI) m/z 369 (M+H)$^+$.

Example 85

N-(2-ethoxyethyl)-4,5-dimethyl-2-{[(2,2,3,3-tetramethylcyclopropyl)carbonyl]amino}thiophene-3-carboxamide Example 9B (18 mg, 0.060 mmol), two equivalents of polymer bound dicyclohexylcarbodidiimide (PS-DCC, commercially available from Argonaut Technologies), 1-hydroxybenzotriazole (HOBT, 8.9 mg, 0.066 mmol), N,N-diisopropylethylamine (7.8 mg, 0.060 mmol), and 2-ethoxyethylamine (5.3 mg, 0.060 mmol) were combined in dimethylacetamide (3 mL) and heated in a Personal Chemistry Ermy's optimizer microwave to 100° C. for 300 seconds. The mixture was filtered through Si-Carbonate (6 mL-1 g cartridge from Silicycle Chemical Division) and then concentrated to dryness. The residue was dissolved in 1:1 dimethylsulfoxide/methanol and purified by reverse phase HPLC to afford the title compound. $^1$H NMR (500 MHz, dimethylsulfoxide-$d_6$) δ ppm 1.07-1.12 (m, 3H) 1.16 (s, 6H) 1.19 (s, 6H) 1.29-1.36 (m, 1H) 2.09 (s, 3H) 2.16 (s, 3H) 7.58-7.65 (m, 1H) 10.73 (s, 1H); MS (ESI) m/z 367 (M+H)$^+$.

Example 86

N-(2-isopropoxyethyl)-4,5-dimethyl-2-{[(2,2,3,3-tetramethylcyclopropyl)carbonyl]amino}thiophene-3-carboxamide Example 9B (18 mg, 0.060 mmol), two equivalents of polymer bound dicyclohexylcarbodidiimide (PS-DCC, commercially available from Argonaut Technologies), 1-hydroxybenzotriazole (HOBT, 8.9 mg, 0.066 mmol), N,N-diisopropylethylamine (7.8 mg, 0.060 mmol), and 2-isopropoxyethylamine (6.2 mg, 0.060 mmol) were combined in dimethylacetamide (3 mL) and heated in a Personal Chemistry Ermy's optimizer microwave to 100° C. for 300 seconds. The mixture was filtered through Si-Carbonate (6 mL-1 g cartridge from Silicycle Chemical Division) and then concentrated to dryness. The residue was dissolved in 1:1 dimethylsulfoxide/methanol and purified by reverse phase HPLC to afford the title compound. $^1$H NMR (500 MHz, dimethylsulfoxide-$d_6$) δ ppm 1.07-1.11 (m, 6H) 1.18 (s, 6H) 1.21 (s, 6H) 1.38 (s, 1H) 2.13 (s, 3H) 2.20 (s, 3H) 3.34-3.42 (m, 2H) 3.46-3.52 (m, 2H) 3.54-3.62 (m, 1H) 7.54-7.62 (m, 1H) 10.84 (s, 1H); MS (ESI) m/z 381 (M+H)$^+$.

Example 87

4,5-dimethyl-N-(3-propoxypropyl)-2-{[(2,2,3,3-tetramethylcyclopropyl)carbonyl]amino}thiophene-3-carboxamide Example 9B (18 mg, 0.060 mmol), two equivalents of polymer bound dicyclohexylcarbodidiimide (PS-DCC, commercially available from Argonaut Technologies), 1-hydroxybenzotriazole (HOBT, 8.9 mg, 0.066 mmol), N,N-diisopropylethylamine (7.8 mg, 0.060 mmol), and 3-propoxypropylamine (7.0 mg, 0.060 mmol) were combined in dimethylacetamide (3 mL) and heated in a Personal Chemistry Ermy's optimizer microwave to 100° C. for 300 seconds. The mixture was filtered through Si-Carbonate (6 mL-1 g cartridge from Silicycle Chemical Division) and then concentrated to dryness. The residue was dissolved in 1:1 dimethylsulfoxide/methanol and purified by reverse phase HPLC to afford the title compound. $^1$H NMR (500 MHz, dimethylsulfoxide-$d_6$) δ ppm 0.83-0.88 (m, 3H) 1.17 (s, 6H) 1.21 (s, 6H) 1.38 (s, 1H) 1.46-1.54 (m, 2H) 1.71-1.79 (m, 2H) 2.12 (s, 3H) 2.19 (s, 3H) 3.30-3.34 (m, 4H) 3.40-3.45 (m, 2H) 7.59-7.67 (m, 1H) 10.84 (s, 1H); MS (ESI) m/z 395 (M+H)$^+$.

Example 88

N-(3-methoxypropyl)-4,5-dimethyl-2-{[(2,2,3,3-tetramethylcyclopropyl)carbonyl]amino}thiophene-3-carboxamide Example 9B (18 mg, 0.060 mmol), two equivalents of polymer bound dicyclohexylcarbodidiimide (PS-DCC, commercially available from Argonaut Technologies), 1-hydroxybenzotriazole (HOBT, 8.9 mg, 0.066 mmol), N,N-diisopropylethylamine (7.8 mg, 0.060 mmol), and 3-methoxypropylamine (5.3 mg, 0.060 mmol) were combined in dimethylacetamide (3 mL) and heated in a Personal Chemistry Ermy's optimizer microwave to 100° C. for 300 seconds. The mixture was filtered through Si-Carbonate (6 mL-1 g cartridge from Silicycle Chemical Division) and then concentrated to dryness. The residue was dissolved in 1:1 dimethylsulfoxide/methanol and purified by reverse phase HPLC to afford the title compound. $^1$H NMR (500 MHz, dimethylsulfoxide-$d_6$) δ ppm 1.17 (s, 6H) 1.21 (s, 6H) 1.37 (s, 1H) 1.71-1.79 (m, 2H) 2.12 (s, 3H) 2.19 (s, 3H) 3.27-3.35 (m, 5H) 3.35-3.43 (m, 2H) 7.60-7.68 (m, 1H) 10.86 (s, 1H); MS (ESI) m/z 367 (M+H)$^+$.

Example 89

4,5-dimethyl-N-(tetrahydrofuran-2-ylmethyl)-2-{[(2,2,3,3-tetramethylcyclopropyl)carbonyl]amino}thiophene-3-carboxamide Example 9B (18 mg, 0.060 mmol), two equivalents of polymer bound dicyclohexylcarbodidiimide (PS-DCC, commercially available from Argonaut Technologies), 1-hydroxybenzotriazole (HOBT, 8.9 mg, 0.066 mmol), N,N-diisopropylethylamine (7.8 mg, 0.060 mmol), and (S)-(+)-tetrahydrofurfurylamine (6.1 mg, 0.060 mmol) were combined in dimethylacetamide (3 mL) and heated in a Personal Chemistry Ermy's optimizer microwave to 100° C. for 300 seconds. The mixture was filtered through Si-Carbonate (6 mL-1 g cartridge from Silicycle Chemical Division) and then concentrated to dryness. The residue was dissolved in 1:1 dimethylsulfoxide/methanol and purified by reverse phase HPLC to afford the title compound. $^1$H NMR (500 MHz, dimethylsulfoxide-$d_6$) δ ppm 1.17 (s, 6H) 1.22 (s, 6H) 1.36 (s, 1H) 1.54-1.63 (m, 1H) 1.78-1.87 (m, 2H) 1.87-1.96 (m, 1H) 2.10 (s, 3H) 2.17 (s, 3H) 3.22-3.29 (m, 2H) 3.60-3.68 (m, 1H) 3.73-3.81 (m, 1H) 3.95-4.04 (m, 1H) 7.70-7.78 (m, 1H) 10.65 (s, 1H); MS (ESI) m/z 379 (M+H)$^+$.

Example 90

4,5-dimethyl-N-(tetrahydrofuran-3-ylmethyl)-2-{[(2,2,3,3-tetramethylcyclopropyl)carbonyl]amino}thiophene-3-carboxamide Example 9B (18 mg, 0.060 mmol), two equivalents of polymer bound dicyclohexylcarbodidiimide (PS-DCC, commercially available from Argonaut Technologies), 1-hydroxybenzotriazole (HOBT, 8.9 mg, 0.066 mmol), N,N-diisopropylethylamine (7.8 mg, 0.060 mmol), and tetrahydrofuran-3-ylmethylamine (6.1 mg, 0.060 mmol) were combined in dimethylacetamide (3 mL) and heated in a Personal Chemistry Ermy's optimizer microwave to 100° C. for 300 seconds. The mixture was filtered through Si-Carbonate (6 mL-1 g cartridge from Silicycle Chemical Division) and then concentrated to dryness. The residue was dissolved in 1:1 dimethylsulfoxide/methanol and purified by reverse phase HPLC to afford the title compound. $^1$H NMR (500 MHz, dimethylsulfoxide-$d_6$) δ ppm 1.15 (s, 6H) 1.22 (s, 6H) 1.39 (s, 1H) 1.56-1.64 (m, 1H) 1.91-1.99 (m, 1H) 2.10 (s, 3H) 2.19 (s, 3H) 2.39-2.49 (m, 1H) 3.19-3.27 (m, 2H) 3.45-3.53 (m, 1H) 3.58-3.66 (m, 1H) 3.67-3.77 (m, 2H) 7.78-7.86 (m, 1H) 10.69 (s, 1H); MS (ESI) m/z 379 (M+H)$^+$.

Example 91

N-cyclopropyl-4,5-dimethyl-2-{[(2,2,3,3-tetramethylcyclopropyl)carbonyl]amino}thiophene-3-carboxamide Example 9B (18 mg, 0.060 mmol), two equivalents of polymer bound dicyclohexylcarbodidiimide (PS-DCC, commercially available from Argonaut Technologies), 1-hydroxybenzotriazole (HOBT, 8.9 mg, 0.066 mmol), N,N-diisopropylethylamine (7.8 mg, 0.060 mmol), and cyclopropylamine (3.4 mg, 0.060 mmol) were combined in dimethylacetamide (3 mL) and heated in a Personal Chemistry Ermy's optimizer microwave to 100° C. for 300 seconds. The mixture was filtered through Si-Carbonate (6 mL-1 g cartridge from Silicycle Chemical Division) and then concentrated to dryness. The residue was dissolved in 1:1 dimethylsulfoxide/methanol and purified by reverse phase HPLC to afford the title compound. $^1$H NMR (500 MHz, dimethylsulfoxide-$d_6$) δ ppm 0.51-0.59 (m, 2H) 0.63-0.71 (m, 2H) 1.18 (s, 6H) 1.21 (s, 6H) 1.43 (s, 1H) 2.05 (s, 3H) 2.17 (s, 3H) 2.77-2.85 (m, 1H) 7.70-7.78 (m, 1H) 10.69 (s, 1H); MS (ESI) m/z 335 (M+H)$^+$.

Example 92

N-(cyclopropylmethyl)-4,5-dimethyl-2-{[(2,2,3,3-tetramethylcyclopropyl)carbonyl]amino}thiophene-3-carboxamide Example 9B (18 mg, 0.060 mmol), two equivalents of polymer bound dicyclohexylcarbodidiimide (PS-DCC, commercially available from Argonaut Technologies), 1-hydroxybenzotriazole (HOBT, 8.9 mg, 0.066 mmol), N,N-diisopropylethylamine (7.8 mg, 0.060 mmol), and cyclopropylmethylamine (4.3 mg, 0.060 mmol) were combined in dimethylacetamide (3 mL) and heated in a Personal Chemistry Ermy's optimizer microwave to 100° C. for 300 seconds. The mixture was filtered through Si-Carbonate (6 mL-1 g cartridge from Silicycle Chemical Division) and then concentrated to dryness. The residue was dissolved in 1:1 dimethylsulfoxide/methanol and purified by reverse phase HPLC to afford the title compound. $^1$H NMR (500 MHz, dimethylsulfoxide-$d_6$) δ ppm 1.17 (s, 6H) 1.21 (s, 6H) 1.39 (s, 1H) 1.61-1.70 (m, 2H) 1.98-2.07 (m, 2H) 2.12 (s, 3H) 2.16-2.25 (m, 5H) 4.35-4.44 (m, 1H) 7.82-7.90 (m, 1H) 10.66 (s, 1H); MS (ESI) m/z 349 (M+H)$^+$.

Example 93

N-cyclobutyl-4,5-dimethyl-2-{[(2,2,3,3-tetramethylcyclopropyl)carbonyl]amino}thiophene-3-carboxamide Example 9B (18 mg, 0.060 mmol), two equivalents of polymer bound dicyclohexylcarbodidiimide (PS-DCC, commercially available from Argonaut Technologies), 1-hydroxybenzotriazole (HOBT, 8.9 mg, 0.066 mmol), N,N-diisopropylethylamine (7.8 mg, 0.060 mmol), and cyclobutylamine (4.3 mg, 0.060 mmol) were combined in dimethylacetamide (3 mL) and heated in a Personal Chemistry Ermy's optimizer microwave to 100° C. for 300 seconds. The mixture was filtered through Si-Carbonate (6 mL-1 g cartridge from Silicycle Chemical Division) and then concentrated to dryness. The residue was dissolved in 1:1 dimethylsulfoxide/methanol and purified by reverse phase HPLC to afford the title compound. $^1$H NMR (500 MHz, dimethylsul-

Example 94

N-cyclopentyl-4,5-dimethyl-2-{[(2,2,3,3-tetramethylcyclopropyl)carbonyl]amino}thiophene-3-carboxamide Example 9B (18 mg, 0.060 mmol), two equivalents of polymer bound dicyclohexylcarbodidiimide (PS-DCC, commercially available from Argonaut Technologies), 1-hydroxybenzotriazole (HOBT, 8.9 mg, 0.066 mmol), N,N-diisopropylethylamine (7.8 mg, 0.060 mmol), and cyclopentylamine (5.1 mg, 0.060 mmol) were combined in dimethylacetamide (3 mL) and heated in a Personal Chemistry Ermy's optimizer microwave to 100° C. for 300 seconds. The mixture was filtered through Si-Carbonate (6 mL-1 g cartridge from Silicycle Chemical Division) and then concentrated to dryness. The residue was dissolved in 1:1 dimethylsulfoxide/methanol and purified by reverse phase HPLC to afford the title compound. $^1$H NMR (500 MHz, dimethylsulfoxide-$d_6$) δ ppm 1.17 (s, 6H) 1.21 (s, 6H) 1.40 (s, 1H) 1.48-1.57 (m, 4H) 1.62-1.70 (m, 2H) 1.82-1.90 (m, 2H) 2.09 (s, 3H) 2.18 (s, 3H) 4.16-4.25 (m, 1H) 7.53-7.61 (m, 1H) 10.59 (s, 1H); MS (ESI) m/z 363 (M+H)$^+$.

Example 95

N-cycloheptyl-4,5-dimethyl-2-{[(2,2,3,3-tetramethylcyclopropyl)carbonyl]amino}thiophene-3-carboxamide Example 9B (18 mg, 0.060 mmol), two equivalents of polymer bound dicyclohexylcarbodidiimide (PS-DCC, commercially available from Argonaut Technologies), 1-hydroxybenzotriazole (HOBT, 8.9 mg, 0.066 mmol), N,N-diisopropylethylamine (7.8 mg, 0.060 mmol), and cycloheptylamine (6.8 mg, 0.060 mmol) were combined in dimethylacetamide (3 mL) and heated in a Personal Chemistry Ermy's optimizer microwave to 100° C. for 300 seconds. The mixture was filtered through Si-Carbonate (6 mL-1 g cartridge from Silicycle Chemical Division) and then concentrated to dryness. The residue was dissolved in 1:1 dimethylsulfoxide/methanol and purified by reverse phase HPLC to afford the title compound. $^1$H NMR (500 MHz, dimethylsulfoxide-$d_6$) δ ppm 1.15 (s, 6H) 1.19 (s, 6H) 1.36-1.65 (m, 11H) 1.81-1.89 (m, 2H) 2.07 (s, 3H) 2.16 (s, 3H) 3.86-3.94 (m, 1H) 7.47-7.54 (m, 1H) 10.54 (s, 1H); MS (ESI) m/z 391 (M+H)$^+$.

Example 96

N-1-adamantyl-4,5-dimethyl-2-{[(2,2,3,3-tetramethylcyclopropyl)carbonyl]amino}thiophene-3-carboxamide Example 9B (18 mg, 0.060 mmol), two equivalents of polymer bound dicyclohexylcarbodidiimide (PS-DCC, commercially available from Argonaut Technologies), 1-hydroxybenzotriazole (HOBT, 8.9 mg, 0.066 mmol), N,N-diisopropylethylamine (7.8 mg, 0.060 mmol), and adamantan-1-ylamine (9.1 mg, 0.060 mmol) were combined in dimethylacetamide (3 mL) and heated in a Personal Chemistry Ermy's optimizer microwave to 100° C. for 300 seconds. The mixture was filtered through Si-Carbonate (6 mL-1 g cartridge from Silicycle Chemical Division) and then concentrated to dryness. The residue was dissolved in 1:1 dimethylsulfoxide/methanol and purified by reverse phase HPLC to afford the title compound. $^1$H NMR (500 MHz, dimethylsulfoxide-$d_6$) δ ppm 1.15 (s, 6H) 1.19 (s, 6H) 1.36-1.65 (m, 11H) 1.81-1.89 (m, 2H) 2.07 (s, 3H) 2.16 (s, 3H) 3.86-3.94 (m, 1H) 7.47-7.54 (m, 1H) 10.54 (s, 1H); MS (ESI) m/z 391 (M+H)$^+$.

Example 97

N-(2-cyclohex-1-en-1-ylethyl)-4,5-dimethyl-2-{[(2,2,3,3-tetramethylcyclopropyl)carbonyl]amino}thiophene-3-carboxamide Example 9B (18 mg, 0.060 mmol), two equivalents of polymer bound dicyclohexylcarbodidiimide (PS-DCC, commercially available from Argonaut Technologies), 1-hydroxybenzotriazole (HOBT, 8.9 mg, 0.066 mmol), N,N-diisopropylethylamine (7.8 mg, 0.060 mmol), and 2-cyclohex-1-enyl-ethylamine (7.5 mg, 0.060 mmol) were combined in dimethylacetamide (3 mL) and heated in a Personal Chemistry Ermy's optimizer microwave to 100° C. for 300 seconds. The mixture was filtered through Si-Carbonate (6 mL-1 g cartridge from Silicycle Chemical Division) and then concentrated to dryness. The residue was dissolved in 1:1 dimethylsulfoxide/methanol and purified by reverse phase HPLC to afford the title compound. $^1$H NMR (500 MHz, dimethylsulfoxide-$d_6$) δ ppm 1.11-1.29 (m, 12H) 1.34-1.42 (m, 1H) 1.44-1.66 (m, 3H) 1.89-1.98 (m, 3H) 2.08-2.23 (m, 7H) 3.32-3.39 (m, 2H) 3.77-3.88 (m, 1H) 5.37-5.48 (m, 1H) 7.28-7.76 (m, 1H) 10.77-10.96 (m, 1H); MS (ESI) m/z 403 (M+H)$^+$.

Example 98

N-(3-hydroxypropyl)-4,5-dimethyl-2-{[(2,2,3,3-tetramethylcyclopropyl)carbonyl]amino}thiophene-3-carboxamide Example 9B (18 mg, 0.060 mmol), two equivalents of polymer bound dicyclohexylcarbodidiimide (PS-DCC, commercially available from Argonaut Technologies), 1-hydroxybenzotriazole (HOBT, 8.9 mg, 0.066 mmol), N,N-diisopropylethylamine (7.8 mg, 0.060 mmol), and 3-hydroxypropylamine (4.5 mg, 0.060 mmol) were combined in dimethylacetamide (3 mL) and heated in a Personal Chemistry Ermy's optimizer microwave to 100° C. for 300 seconds. The mixture was filtered through Si-Carbonate (6 mL-1 g cartridge from Silicycle Chemical Division) and then concentrated to dryness. The residue was dissolved in 1:1 dimethylsulfoxide/methanol and purified by reverse phase HPLC to afford the title compound. $^1$H NMR (500 MHz, dimethylsulfoxide-$d_6$) δ ppm 1.18 (d, 12H) 1.34-1.42 (m, 1H) 1.58-1.74 (m, 2H) 2.05-2.14 (m, 3H) 2.14-2.25 (m, 3H) 3.44-3.58 (m, 2H) 7.57-7.73 (m, 1H) 10.83-10.93 (m, 1H); MS (ESI) m/z 353 (M+H)$^+$.

Example 99

N-(4-hydroxybutyl)-4,5-dimethyl-2-{[(2,2,3,3-tetramethylcyclopropyl)carbonyl]amino}thiophene-3-carboxamide Example 9B (18 mg, 0.060 mmol), two equivalents of polymer bound dicyclohexylcarbodidiimide (PS-DCC, commercially available from Argonaut Technologies), 1-hydroxybenzotriazole (HOBT, 8.9 mg, 0.066 mmol), N,N-diisopropylethylamine (7.8 mg, 0.060 mmol), and 3-hydroxypropylamine (5.3 mg, 0.060 mmol) were combined in dimethylacetamide (3 mL) and heated in a Personal Chemistry Ermy's optimizer microwave to 100° C. for 300 seconds. The mixture was filtered through Si-Carbonate (6 mL-1 g cartridge from Silicycle Chemical Division) and then concentrated to dryness. The residue was dissolved in 1:1 dimethylsulfoxide/methanol and purified by reverse phase HPLC to afford the title compound. $^1$H NMR (500 MHz, dimethylsulfoxide-$d_6$) δ ppm 1.19 (d, 12H) 1.34-1.41 (m, 1H) 1.41-1.52 (m, 2H) 1.50-1.62 (m, 2H) 2.09-2.16 (m, 3H) 2.15-2.24 (m, 3H) 3.18-3.27 (m, 2H) 3.39-3.47 (m, 2H) 7.53-7.75 (m, 1H) 10.75-10.91 (m, 1H); MS (ESI) m/z 367 (M+H)$^+$.

Example 100

N-[(1S)-1-(hydroxymethyl)-3-methylbutyl]-4,5-dimethyl-2-{[(2,2,3,3-tetramethylcyclopropyl)carbonyl]amino}thiophene-3-carboxamide Example 9B (18 mg, 0.060 mmol), two equivalents of polymer bound dicyclohexylcarbodidiimide (PS-DCC, commercially available from Argonaut Technologies), 1-hydroxybenzotriazole (HOBT, 8.9 mg, 0.066 mmol), N,N-diisopropylethylamine (7.8 mg, 0.060 mmol), and (S)-1-hydroxymethyl-3-methylbutylamine (7.0 mg, 0.060 mmol) were combined in dimethylacetamide (3 mL) and heated in a Personal Chemistry Ermy's optimizer microwave to 100° C. for 300 seconds. The mixture was filtered through Si-Carbonate (6 mL-1 g cartridge from Silicycle Chemical Division) and then concentrated to dryness. The residue was dissolved in 1:1 dimethylsulfoxide/methanol and purified by reverse phase HPLC to afford the title compound. $^1$H NMR (500 MHz, dimethylsulfoxide-$d_6$) δ ppm 0.80-0.99 (m, 6H) 1.12-1.24 (m, 12H) 1.33-1.37 (m, 1H) 1.59-1.70 (m, 1H) 2.03-2.12 (m, 3H) 2.14-2.23 (m, 4H) 3.34-3.52 (m, 2H) 3.97-4.12 (m, 1H) 7.43-7.52 (m, 1H) 10.47-10.52 (m, 1H); MS (ESI) m/z 395 (M+H)$^+$.

Example 101

4,5-dimethyl-N-(2-propoxyethyl)-2-{[(2,2,3,3-tetramethylcyclopropyl)carbonyl]amino}thiophene-3-carboxamide Example 9B (18 mg, 0.060 mmol), two equivalents of polymer bound dicyclohexylcarbodidiimide (PS-DCC, commercially available from Argonaut Technologies), 1-hydroxybenzotriazole (HOBT, 8.9 mg, 0.066 mmol), N,N-diisopropylethylamine (7.8 mg, 0.060 mmol), and 2-propoxyethylamine (6.2 mg, 0.060 mmol) were combined in dimethylacetamide (3 mL) and heated in a Personal Chemistry Ermy's optimizer microwave to 100° C. for 300 seconds. The mixture was filtered through Si-Carbonate (6 mL-1 g cartridge from Silicycle Chemical Division) and then concentrated to dryness. The residue was dissolved in 1:1 dimethylsulfoxide/methanol and purified by reverse phase HPLC to afford the title compound. $^1$H NMR (500 MHz, dimethylsulfoxide-$d_6$) δ ppm 0.75-0.95 (m, 3H) 1.07-1.29 (m, 12H) 1.33-1.42 (m, 1H) 1.44-1.64 (m, 2H) 2.00-2.27 (m, 6H) 3.39-3.46 (m, 2H) 3.47-3.59 (m, 2H) 3.69-4.03 (m, 1H) 7.40-7.78 (m, 1H) 10.67-10.92 (m, 1H); MS (ESI) m/z 381 (M+H)$^+$.

Example 102

N-(3-ethoxypropyl)-4,5-dimethyl-2-{[(2,2,3,3-tetramethylcyclopropyl)carbonyl]amino}thiophene-3-carboxamide Example 9B (18 mg, 0.060 mmol), two equivalents of polymer bound dicyclohexylcarbodidiimide (PS-DCC, commercially available from Argonaut Technologies), 1-hydroxybenzotriazole (HOBT, 8.9 mg, 0.066 mmol), N,N-diisopropylethylamine (7.8 mg, 0.060 mmol), and 3-ethoxypropylamine (6.2 mg, 0.060 mmol) were combined in dimethylacetamide (3 mL) and heated in a Personal Chemistry Ermy's optimizer microwave to 100° C. for 300 seconds. The mixture was filtered through Si-Carbonate (6 mL-1 g cartridge from Silicycle Chemical Division) and then concentrated to dryness. The residue was dissolved in 1:1 dimethylsulfoxide/methanol and purified by reverse phase HPLC to afford the title compound. $^1$H NMR (500 MHz, dimethylsulfoxide-$d_6$) δ ppm 1.06-1.13 (m, 3H) 1.14-1.26 (m, 12H) 1.34-1.47 (m, 1H) 1.67-1.85 (m, 2H) 2.08-2.15 (m, 3H) 2.14-2.25 (m, 3H) 3.37-3.55 (m, 4H) 7.51-7.76 (m, 1H) 10.69-11.02 (m, 1H); MS (ESI) m/z 381 (M+H)$^+$.

Example 103

N-(3-butoxypropyl)-4,5-dimethyl-2-{[(2,2,3,3-tetramethylcyclopropyl)carbonyl]amino}thiophene-3-carboxamide Example 9B (18 mg, 0.060 mmol), two equivalents of polymer bound dicyclohexylcarbodidiimide (PS-DCC, commercially available from Argonaut Technologies), 1-hydroxybenzotriazole (HOBT, 8.9 mg, 0.066 mmol), N,N-diisopropylethylamine (7.8 mg, 0.060 mmol), and 3-butoxypropylamine (7.9 mg, 0.060 mmol) were combined in dimethylacetamide (3 mL) and heated in a Personal Chemistry Ermy's optimizer microwave to 100° C. for 300 seconds. The mixture was filtered through Si-Carbonate (6 mL-1 g cartridge from Silicycle Chemical Division) and then concentrated to dryness. The residue was dissolved in 1:1 dimethylsulfoxide/methanol and purified by reverse phase HPLC to afford the title compound. $^1$H NMR (500 MHz, dimethylsulfoxide-$d_6$) δ ppm 0.86 (t, 3H) 1.09-1.26 (m, 13H) 1.26-1.57 (m, 4H) 1.67-1.83 (m, 2H) 2.05-2.27 (m, 6H) 3.24-3.45 (m, 5H) 3.78-3.87 (m, 1H) 7.54-7.71 (m, 1H) 10.79-10.91 (m, 1H); MS (ESI) m/z 409 (M+H)$^+$.

Example 104

N-(3-isopropoxypropyl)-4,5-dimethyl-2-{[(2,2,3,3-tetramethylcyclopropyl)carbonyl]amino}thiophene-3-carboxamide Example 9B (18 mg, 0.060 mmol), two equivalents of polymer bound dicyclohexylcarbodidiimide (PS-DCC, commercially available from Argonaut Technologies), 1-hydroxybenzotriazole (HOBT, 8.9 mg, 0.066 mmol), N,N-diisopropylethylamine (7.8 mg, 0.060 mmol), and 3-isopropoxypropylamine (7.0 mg, 0.060 mmol) were combined in dimethylacetamide (3 mL) and heated in a Personal Chemistry Ermy's optimizer microwave to 100° C. for 300 seconds. The mixture was filtered through Si-Carbonate (6 mL-1 g cartridge from Silicycle Chemical Division) and then concentrated to dryness. The residue was dissolved in 1:1 dimethylsulfoxide/methanol and purified by reverse phase HPLC to afford the title compound. $^1$H NMR (500 MHz, dimethylsulfoxide-$d_6$) δ ppm 0.94-1.31 (m, 14H) 1.34-1.44 (m, 1H) 1.64-1.80 (m, 1H) 2.01-2.25 (m, 5H) 3.24-3.38 (m, 6H) 3.39-3.47 (m, 2H) 3.47-3.60 (m, 1H) 7.32-7.87 (m, 1H) 10.68-10.99 (m, 1H); MS (ESI) m/z 395 (M+H)$^+$.

Example 105

4,5-dimethyl-N-[3-(methylthio)propyl]-2-{[(2,2,3,3-tetramethylcyclopropyl)carbonyl]amino}thiophene-3-carboxamide Example 9B (18 mg, 0.060 mmol), two equivalents of polymer bound dicyclohexylcarbodidiimide (PS-DCC, commercially available from Argonaut Technologies), 1-hydroxybenzotriazole (HOBT, 8.9 mg, 0.066 mmol), N,N-diisopropylethylamine (7.8 mg, 0.060 mmol), and 3-methylsulfanyl-propylamine (6.3 mg, 0.060 mmol) were combined in dimethylacetamide (3 mL) and heated in a Personal Chemistry Ermy's optimizer microwave to 100° C. for 300 seconds. The mixture was filtered through Si-Carbonate (6 mL-1 g cartridge from Silicycle Chemical Division) and then concentrated to dryness. The residue was dissolved in 1:1 dimethylsulfoxide/methanol and purified by reverse phase HPLC to afford the title compound. $^1$H NMR (500 MHz, dimethylsulfoxide-d$_6$) δ ppm 1.00-1.51 (m, 13H) 1.67-1.88 (m, 2H) 1.90-2.38 (m, 9H) 3.31-3.43 (m, 2H) 7.36-7.86 (m, 1H) 10.51-10.99 (m, 1H); MS (ESI) m/z 383 (M+H)$^+$.

Example 106

4,5-dimethyl-N-(3-phenylpropyl)-2-{[(2,2,3,3-tetramethylcyclopropyl)carbonyl]amino}thiophene-3-carboxamide Example 9B (18 mg, 0.060 mmol), two equivalents of polymer bound dicyclohexylcarbodidiimide (PS-DCC, commercially available from Argonaut Technologies), 1-hydroxybenzotriazole (HOBT, 8.9 mg, 0.066 mmol), N,N-diisopropylethylamine (7.8 mg, 0.060 mmol), and 3-phenylpropylamine (8.1 mg, 0.060 mmol) were combined in dimethylacetamide (3 mL) and heated in a Personal Chemistry Ermy's optimizer microwave to 100° C. for 300 seconds. The mixture was filtered through Si-Carbonate (6 mL-1 g cartridge from Silicycle Chemical Division) and then concentrated to dryness. The residue was dissolved in 1:1 dimethylsulfoxide/methanol and purified by reverse phase HPLC to afford the title compound. $^1$H NMR (500 MHz, dimethylsulfoxide-d$_6$) δ ppm 0.71-1.50 (m, 13H) 1.69-1.93 (m, 2H) 1.99-2.38 (m, 6H) 2.59-2.79 (m, 2H) 3.09-3.37 (m, 2H) 3.75-3.97 (m, 1H) 6.20-8.21 (m, 5H) 10.30-10.95 (m, 1H); MS (ESI) m/z 413 (M+H)$^+$.

Example 107

4,5-dimethyl-N-(2-phenoxyethyl)-2-{[(2,2,3,3-tetramethylcyclopropyl)carbonyl]amino}thiophene-3-carboxamide Example 9B (18 mg, 0.060 mmol), two equivalents of polymer bound dicyclohexylcarbodidiimide (PS-DCC, commercially available from Argonaut Technologies), 1-hydroxybenzotriazole (HOBT, 8.9 mg, 0.066 mmol), N,N-diisopropylethylamine (7.8 mg, 0.060 mmol), and 2-phenoxyethylamine (8.2 mg, 0.060 mmol) were combined in dimethylacetamide (3 mL) and heated in a Personal Chemistry Ermy's optimizer microwave to 100° C. for 300 seconds. The mixture was filtered through Si-Carbonate (6 mL-1 g cartridge from Silicycle Chemical Division) and then concentrated to dryness. The residue was dissolved in 1:1 dimethylsulfoxide/methanol and purified by reverse phase HPLC to afford the title compound. $^1$H NMR (500 MHz, dimethylsulfoxide-d$_6$) δ ppm 0.99-1.44 (m, 13H) 1.96-2.31 (m, 6H) 3.53-3.71 (m, 2H) 3.77-3.89 (m, 1H) 3.99-4.28 (m, 2H) 6.71-7.07 (m, 2H) 7.13-7.40 (m, 2H) 7.67-7.96 (m, 1H) 10.64-10.81 (m, 1H); MS (ESI) m/z 415 (M+H)$^+$.

Example 108

4,5-dimethyl-N-(1-methyl-3-phenylpropyl)-2-{[(2,2,3,3-tetramethylcyclopropyl)carbonyl]amino}thiophene-3-carboxamide Example 9B (18 mg, 0.060 mmol), two equivalents of polymer bound dicyclohexylcarbodidiimide (PS-DCC, commercially available from Argonaut Technologies), 1-hydroxybenzotriazole (HOBT, 8.9 mg, 0.066 mmol), N,N-diisopropylethylamine (7.8 mg, 0.060 mmol), and 1-methyl-3-phenyl-propylamine (9.0 mg, 0.060 mmol) were combined in dimethylacetamide (3 mL) and heated in a Personal Chemistry Ermy's optimizer microwave to 100° C. for 300 seconds. The mixture was filtered through Si-Carbonate (6 mL-1 g cartridge from Silicycle Chemical Division) and then concentrated to dryness. The residue was dissolved in 1:1 dimethylsulfoxide/methanol and purified by reverse phase HPLC to afford the title compound. $^1$H NMR (500 MHz, dimethylsulfoxide-d$_6$) δ ppm 0.93-1.45 (m, 16H) 1.63-1.92 (m, 2H) 2.03-2.31 (m, 6H) 2.53-2.70 (m, 2H) 3.70-3.87 (m, 1H) 3.86-4.19 (m, 1H) 6.97-7.95 (m, 5H) 10.27-10.68 (m, 1H); MS (ESI) m/z 427 (M+H)$^+$.

Example 109

4,5-dimethyl-2-{[(2,2,3,3-tetramethylcyclopropyl)carbonyl]amino}-N-(2-thien-2-ylethyl)thiophene-3-carboxamide Example 9B (18 mg, 0.060 mmol), two equivalents of polymer bound dicyclohexylcarbodidiimide (PS-DCC, commercially available from Argonaut Technologies), 1-hydroxybenzotriazole (HOBT, 8.9 mg, 0.066 mmol), N,N-diisopropylethylamine (7.8 mg, 0.060 mmol), and 2-thiophen-2-yl-ethylamine (7.6 mg, 0.060 mmol) were combined in dimethylacetamide (3 mL) and heated in a Personal Chemistry Ermy's optimizer microwave to 100° C. for 300 seconds. The mixture was filtered through Si-Carbonate (6 mL-1 g cartridge from Silicycle Chemical Division) and then concentrated to dryness. The residue was dissolved in 1:1 dimethylsulfoxide/methanol and purified by reverse phase HPLC to afford the title compound. $^1$H NMR (500 MHz, dimethylsulfoxide-d$_6$) δ ppm 0.83-1.46 (m, 13H) 1.87-2.36 (m, 6H) 2.86-3.15 (m, 2H) 3.45-3.65 (m, 2H) 3.68-3.95 (m, 1H) 6.49-7.46 (m, 2H) 7.52-7.97 (m, 1H) 10.61-10.93 (m, 1H); MS (ESI) m/z 405 (M+H)$^+$.

Example 110

N-(2,2-diphenylethyl)-4,5-dimethyl-2-{[(2,2,3,3-tetramethylcyclopropyl)carbonyl]amino}thiophene-3-carboxamide Example 9B (18 mg, 0.060 mmol), two equivalents of polymer bound dicyclohexylcarbodidiimide (PS-DCC, commercially available from Argonaut Technologies), 1-hydroxybenzotriazole (HOBT, 8.9 mg, 0.066 mmol), N,N-diisopropylethylamine (7.8 mg, 0.060 mmol), and 2,2-diphenyl-ethylamine (12 mg, 0.060 mmol) were combined in dimethylacetamide (3 mL) and heated in a Personal Chemistry Ermy's optimizer microwave to 100° C. for 300 seconds. The mixture was filtered through Si-Carbonate (6 mL-1 g cartridge from Silicycle Chemical Division) and then concentrated to dryness. The residue was dissolved in 1:1 dimethylsulfoxide/methanol and purified by reverse phase HPLC to afford the title compound. $^1$H NMR (500 MHz, dimethylsulfoxide-d$_6$) δ ppm 0.90-1.47 (m, 13H) 1.58-1.90 (m, 3H) 1.96-2.37 (m, 3H) 3.71-4.17 (m, 2H) 4.19-4.61 (m, 1H) 6.88-7.51 (m, 10H) 7.47-7.67 (m, 1H) 10.35-10.95 (m, 1H); MS (ESI) m/z 475 (M+H)$^+$.

Example 111

N-(3-iodobenzyl)-4,5-dimethyl-2-{[(2,2,3,3-tetramethylcyclopropyl)carbonyl]amino}thiophene-3-carboxamide Example 9B (18 mg, 0.060 mmol), two equivalents of polymer bound dicyclohexylcarbodidiimide (PS-DCC, commercially available from Argonaut Technologies), 1-hydroxybenzotriazole (HOBT, 8.9 mg, 0.066 mmol), N,N-diisopropylethylamine (7.8 mg, 0.060 mmol), and 3-iodobenzylamine (14 mg, 0.060 mmol) were combined in dimethylacetamide (3 mL) and heated in a Personal Chemistry Ermy's optimizer microwave to 100° C. for 300 seconds. The mixture was filtered through Si-Carbonate (6 mL-1 g cartridge from Silicycle Chemical Division) and then concentrated to dryness. The residue was dissolved in 1:1 dimethylsulfoxide/methanol and purified by reverse phase HPLC to afford the title compound. $^1$H NMR (500 MHz, dimethylsulfoxide-$d_6$) δ ppm 1.01-1.46 (m, 13H) 1.96-2.36 (m, 6H) 3.69-3.92 (m, 1H) 4.20-4.60 (m, 2H) 6.88-7.96 (m, 3H) 8.02-8.37 (m, 1H) 10.53-10.99 (m, 1H); MS (ESI) m/z 511 (M+H)$^+$.

Example 112

N-ethyl-N,4,5-trimethyl-2-{[(2,2,3,3-tetramethylcyclopropyl)carbonyl]amino}thiophene-3-carboxamide Example 9B (18 mg, 0.060 mmol), two equivalents of polymer bound dicyclohexylcarbodidiimide (PS-DCC, commercially available from Argonaut Technologies), 1-hydroxybenzotriazole (HOBT, 8.9 mg, 0.066 mmol), N,N-diisopropylethylamine (7.8 mg, 0.060 mmol), and ethylmethyl-amine (3.5 mg, 0.060 mmol) were combined in dimethylacetamide (3 mL) and heated in a Personal Chemistry Ermy's optimizer microwave to 100° C. for 300 seconds. The mixture was filtered through Si-Carbonate (6 mL-1 g cartridge from Silicycle Chemical Division) and then concentrated to dryness. The residue was dissolved in 1:1 dimethylsulfoxide/methanol and purified by reverse phase HPLC to afford the title compound. $^1$H NMR (500 MHz, dimethylsulfoxide-$d_6$) δ ppm 0.85-1.47 (m, 16H) 1.78-2.00 (m, 3H) 2.11-2.28 (m, 3H) 2.62-3.19 (m, 3H) 9.96-10.39 (m, 1H); MS (ESI) m/z 337 (M+H)$^+$.

Example 113

N,4,5-trimethyl-N-propyl-2-{[(2,2,3,3-tetramethylcyclopropyl)carbonyl]amino}thiophene-3-carboxamide Example 9B (18 mg, 0.060 mmol), two equivalents of polymer bound dicyclohexylcarbodidiimide (PS-DCC, commercially available from Argonaut Technologies), 1-hydroxybenzotriazole (HOBT, 8.9 mg, 0.066 mmol), N,N-diisopropylethylamine (7.8 mg, 0.060 mmol), and methylpropyl-amine (4.4 mg, 0.060 mmol) were combined in dimethylacetamide (3 mL) and heated in a Personal Chemistry Ermy's optimizer microwave to 100° C. for 300 seconds. The mixture was filtered through Si-Carbonate (6 mL-1 g cartridge from Silicycle Chemical Division) and then concentrated to dryness. The residue was dissolved in 1:1 dimethylsulfoxide/methanol and purified by reverse phase HPLC to afford the title compound. $^1$H NMR (500 MHz, dimethylsulfoxide-$d_6$) δ ppm 0.57-1.37 (m, 16H) 1.41-1.63 (m, 2H) 1.76-1.96 (m, 2H) 2.04-2.36 (m, 4H) 2.59-3.13 (m, 3H) 9.71-10.37 (m, 1H); MS (ESI) m/z 351 (M+H)$^+$.

Example 114

N-butyl-N,4,5-trimethyl-2-{[(2,2,3,3-tetramethylcyclopropyl)carbonyl]amino}thiophene-3-carboxamide Example 9B (18 mg, 0.060 mmol), two equivalents of polymer bound dicyclohexylcarbodidiimide (PS-DCC, commercially available from Argonaut Technologies), 1-hydroxybenzotriazole (HOBT, 8.9 mg, 0.066 mmol), N,N-diisopropylethylamine (7.8 mg, 0.060 mmol), and butylmethyl-amine (5.2 mg, 0.060 mmol) were combined in dimethylacetamide (3 mL) and heated in a Personal Chemistry Ermy's optimizer microwave to 100° C. for 300 seconds. The mixture was filtered through Si-Carbonate (6 mL-1 g cartridge from Silicycle Chemical Division) and then concentrated to dryness. The residue was dissolved in 1:1 dimethylsulfoxide/methanol and purified by reverse phase HPLC to afford the title compound. $^1$H NMR (500 MHz, dimethylsulfoxide-$d_6$) δ ppm 0.55-1.38 (m, 15H) 1.30-1.73 (m, 3H) 1.77-1.98 (m, 3H) 2.07-2.30 (m, 3H) 2.54-3.20 (m, 4H) 9.75-10.42 (m, 1H); MS (ESI) m/z 365 (M+H)$^+$.

Example 115

N-[3-(azetidin-1-ylcarbonyl)-4,5-dimethylthien-2-yl]-2,2,3,3-tetramethylcyclopropanecarboxamide Example 9B (18 mg, 0.060 mmol), two equivalents of polymer bound dicyclohexylcarbodidiimide (PS-DCC, commercially available from Argonaut Technologies), 1-hydroxybenzotriazole (HOBT, 8.9 mg, 0.066 mmol), N,N-diisopropylethylamine (7.8 mg, 0.060 mmol), and azetidine (3.4 mg, 0.060 mmol) were combined in dimethylacetamide (3 mL) and heated in a Personal Chemistry Ermy's optimizer microwave to 100° C. for 300 seconds. The mixture was filtered through Si-Carbonate (6 mL-1 g cartridge from Silicycle Chemical Division) and then concentrated to dryness. The residue was dissolved in 1:1 dimethylsulfoxide/methanol and purified by reverse phase HPLC to afford the title compound. $^1$H NMR (500 MHz, dimethylsulfoxide-$d_6$) δ ppm 0.91-1.38 (m, 14H) 1.83-2.00 (m, 2H) 2.07-2.33 (m, 5H) 3.66-4.20 (m, 4H) 9.87-10.56 (m, 1H), MS (ESI) m/z 335 (M+H)$^+$.

Example 116

N-[4,5-dimethyl-3-(pyrrolidin-1-ylcarbonyl)thien-2-yl]-2,2,3,3-tetramethylcyclopropanecarboxamide Example 9B (18 mg, 0.060 mmol), two equivalents of polymer bound dicyclohexylcarbodidiimide (PS-DCC, commercially available from Argonaut Technologies), 1-hydroxybenzotriazole (HOBT, 8.9 mg, 0.066 mmol), N,N-diisopropylethylamine (7.8 mg, 0.060 mmol), and pyrrolidine (4.3 mg, 0.060 mmol) were combined in dimethylacetamide (3 mL) and heated in a Personal Chemistry Ermy's optimizer microwave to 100° C. for 300 seconds. The mixture was filtered through Si-Carbonate (6 mL-1 g cartridge from Silicycle Chemical Division) and then concentrated to dryness. The residue was dissolved in 1:1 dimethylsulfoxide/methanol and purified by reverse phase HPLC to afford the title compound. $^1$H NMR (500 MHz, dimethylsulfoxide-$d_6$) δ ppm 1.02-1.35 (m, 13H) 1.71-1.89 (m, 4H) 1.88-1.98 (m, 3H) 2.07-2.38 (m, 3H) 2.93-3.20 (m, 2H) 3.38-3.65 (m, 2H) 9.97-10.46 (m, 1H); MS (ESI) m/z 349 (M+H)$^+$.

Example 117

N-{4,5-dimethyl-3-[(2-methylpyrrolidin-1-yl)carbonyl]thien-2-yl}-2,2,3,3-tetramethylcyclopropanecarboxamide Example 9B (18 mg, 0.060 mmol), two equivalents of polymer bound dicyclohexylcarbodidiimide (PS-DCC, commercially available from Argonaut Technologies), 1-hydroxybenzotriazole (HOBT, 8.9 mg, 0.066 mmol), N,N-diisopropylethylamine (7.8 mg, 0.060 mmol), and 2-methylpyrrolidine (5.1 mg, 0.060 mmol) were combined in dimethylacetamide (3 mL) and heated in a Personal Chemistry Ermy's optimizer microwave to 100° C. for 300 seconds. The mixture was filtered through Si-Carbonate (6 mL-1 g cartridge from Silicycle Chemical Division) and then concentrated to dryness. The residue was dissolved in 1:1 dimethylsulfoxide/methanol and purified by reverse phase HPLC to afford the title compound. $^1$H NMR (500 MHz, dimethylsulfoxide-$d_6$) δ ppm 0.74-1.35 (m, 16H) 1.44-1.65 (m, 1H) 1.64-2.10 (m, 6H) 2.07-2.33 (m, 4H) 2.90-3.22 (m, 1H) 3.38-4.53 (m, 2H); MS (ESI) m/z 363 (M+H)$^+$.

Example 118

N-[4,5-dimethyl-3-(piperidin-1-ylcarbonyl)thien-2-yl]-2,2,3,3-tetramethylcyclopropanecarboxamide Example 9B (18 mg, 0.060 mmol), two equivalents of polymer bound dicyclohexylcarbodidiimide (PS-DCC, commercially available from Argonaut Technologies), 1-hydroxybenzotriazole (HOBT, 8.9 mg, 0.066 mmol), N,N-diisopropylethylamine (7.8 mg, 0.060 mmol), and piperidine (5.1 mg, 0.060 mmol) were combined in dimethylacetamide (3 mL) and heated in a Personal Chemistry Ermy's optimizer microwave to 100° C. for 300 seconds. The mixture was filtered through Si-Carbonate (6 mL-1 g cartridge from Silicycle Chemical Division) and then concentrated to dryness. The residue was dissolved in 1:1 dimethylsulfoxide/methanol and purified by reverse phase HPLC to afford the title compound. $^1$H NMR (500 MHz, dimethylsulfoxide-$d_6$) δ ppm 1.02-1.30 (m, 13H) 1.32-1.50 (m, 2H) 1.53-1.76 (m, 3H) 1.80-1.95 (m, 3H) 2.07-2.34 (m, 3H) 3.05-3.26 (m, 3H) 3.33-3.50 (m, 2H) 9.91-10.32 (m, 1H); MS (ESI) m/z 363 (M+H)$^+$.

Example 119

N-{4,5-dimethyl-3-[(3-methylpiperidin-1-yl)carbonyl]thien-2-yl}-2,2,3,3-tetramethylcyclopropanecarboxamide Example 9B (18 mg, 0.060 mmol), two equivalents of polymer bound dicyclohexylcarbodidiimide (PS-DCC, commercially available from Argonaut Technologies), 1-hydroxybenzotriazole (HOBT, 8.9 mg, 0.066 mmol), N,N-diisopropylethylamine (7.8 mg, 0.060 mmol), and 3-methylpiperidine (6.0 mg, 0.060 mmol) were combined in dimethylacetamide (3 mL) and heated in a Personal Chemistry Ermy's optimizer microwave to 100° C. for 300 seconds. The mixture was filtered through Si-Carbonate (6 mL-1 g cartridge from Silicycle Chemical Division) and then concentrated to dryness. The residue was dissolved in 1:1 dimethylsulfoxide/methanol and purified by reverse phase HPLC to afford the title compound. $^1$H NMR (500 MHz, dimethylsulfoxide-$d_6$) δ ppm 0.77-1.36 (m, 16H) 1.34-1.51 (m, 1H) 1.56-1.80 (m, 2H) 1.81-1.98 (m, 3H) 2.08-2.28 (m, 3H) 2.71-3.03 (m, 1H) 3.15-3.29 (m, 2H) 9.93-10.30 (m, 1H); MS (ESI) m/z 377 (M+H)$^+$.

Example 120

N-{4,5-dimethyl-3-[(4-methylpiperidin-1-yl)carbonyl]thien-2-yl}-2,2,3,3-tetramethylcyclopropanecarboxamide Example 9B (18 mg, 0.060 mmol), two equivalents of polymer bound dicyclohexylcarbodidiimide (PS-DCC, commercially available from Argonaut Technologies), 1-hydroxybenzotriazole (HOBT, 8.9 mg, 0.066 mmol), N,N-diisopropylethylamine (7.8 mg, 0.060 mmol), and 4-methylpiperidine (6.0 mg, 0.060 mmol) were combined in dimethylacetamide (3 mL) and heated in a Personal Chemistry Ermy's optimizer microwave to 100° C. for 300 seconds. The mixture was filtered through Si-Carbonate (6 mL-1 g cartridge from Silicycle Chemical Division) and then concentrated to dryness. The residue was dissolved in 1:1 dimethylsulfoxide/methanol and purified by reverse phase HPLC to afford the title compound. $^1$H NMR (500 MHz, dimethylsulfoxide-$d_6$) δ ppm 0.75-1.36 (m, 16H) 1.53-1.67 (m, 2H) 1.79-1.97 (m, 3H) 2.09-2.31 (m, 3H) 2.60-2.95 (m, 2H) 3.17-3.28 (m, 2H) 9.94-10.28 (m, 1H); MS (ESI) m/z 377 (M+H)$^+$.

Example 121

N-[4,5-dimethyl-3-(morpholin-4-ylcarbonyl)thien-2-yl]-2,2,3,3-tetramethylcyclopropanecarboxamide Example 9B (18 mg, 0.060 mmol), two equivalents of polymer bound dicyclohexylcarbodidiimide (PS-DCC, commercially available from Argonaut Technologies), 1-hydroxybenzotriazole (HOBT, 8.9 mg, 0.066 mmol), N,N-diisopropylethylamine (7.8 mg, 0.060 mmol), and morpholine (5.3 mg, 0.060 mmol) were combined in dimethylacetamide (3 mL) and heated in a Personal Chemistry Ermy's optimizer microwave to 100° C. for 300 seconds. The mixture was filtered through Si-Carbonate (6 mL-1 g cartridge from Silicycle Chemical Division) and then concentrated to dryness. The residue was dissolved in 1:1 dimethylsulfoxide/methanol and purified by reverse phase HPLC to afford the title compound. $^1$H NMR (500 MHz, dimethylsulfoxide-$d_6$) δ ppm 0.94-1.39 (m, 13H) 1.83-1.97 (m, 3H) 2.08-2.26 (m, 3H) 2.71-3.06 (m, 2H) 3.34-3.88 (m, 6H) 10.09-10.38 (m, 1H); MS (ESI) m/z 365 (M+H)$^+$.

Example 122

N-[4,5-dimethyl-3-(thiomorpholin-4-ylcarbonyl)thien-2-yl]-2,2,3,3-tetramethylcyclopropanecarboxamide Example 9B (18 mg, 0.060 mmol), two equivalents of polymer bound dicyclohexylcarbodidiimide (PS-DCC, commercially available from Argonaut Technologies), 1-hydroxybenzotriazole (HOBT, 8.9 mg, 0.066 mmol), N,N-diisopropylethylamine (7.8 mg, 0.060 mmol), and thiomorpholine (6.2 mg, 0.060 mmol) were combined in dimethylacetamide (3 mL) and heated in a Personal Chemistry Ermy's optimizer microwave to 100° C. for 300 seconds. The mixture was filtered through Si-Carbonate (6 mL-1 g cartridge from Silicycle Chemical Division) and then concentrated to dryness. The residue was dissolved in 1:1 dimethylsulfoxide/methanol and purified by reverse phase HPLC to afford the title compound. $^1$H NMR (500 MHz, dimethylsulfoxide-$d_6$) δ ppm 1.10-1.33 (m, 13H) 1.50-1.55 (m, 1H) 1.84-1.96 (m, 2H) 2.08-2.34 (m, 4H) 2.58-3.07 (m, 2H) 3.40-3.91 (m, 2H) 10.06-10.31 (m, 1H); MS (ESI) m/z 381 (M+H)$^+$.

Example 123

N-{4,5-dimethyl-3-[(1,3,3-trimethyl-6-azabicyclo[3.2.1]oct-6-yl)carbonyl]thien-2-yl}-2,2,3,3-tetramethylcyclopropanecarboxamide Example 9B (18 mg, 0.060 mmol), two equivalents of polymer bound dicyclohexylcarbodidiimide (PS-DCC, commercially available from Argonaut Technologies), 1-hydroxybenzotriazole (HOBT, 8.9 mg, 0.066 mmol), N,N-diisopropylethylamine (7.8 mg, 0.060 mmol), and 1,3,3-trimethyl-6-azabicyclo[3.2.1]octane (9.2 mg, 0.060 mmol) were combined in dimethylacetamide (3 mL) and heated in a Personal Chemistry Ermy's optimizer microwave to 100° C. for 300 seconds. The mixture was filtered through Si-Carbonate (6 mL-1 g cartridge from Silicycle Chemical Division) and then concentrated to dryness. The residue was dissolved in 1:1 dimethylsulfoxide/methanol and purified by reverse phase HPLC to afford the title compound. $^1$H NMR (500 MHz, dimethylsulfoxide-$d_6$) δ ppm 0.40-2.07 (m, 27H) 2.08-2.26 (m, 2H) 2.25-2.44 (m, 3H) 2.90-3.19 (m, 1H) 3.39-3.96 (m, 1H); MS (ESI) m/z 431 (M+H)$^+$.

Example 124

N-[3-[(4-benzylpiperidin-1-yl)carbonyl]-4,5-dimethylthien-2-yl]-2,2,3,3-tetramethylcyclopropanecarboxamide Example 9B (18 mg, 0.060 mmol), two equivalents of polymer bound dicyclohexylcarbodidiimide (PS-DCC, commercially available from Argonaut Technologies), 1-hydroxybenzotriazole (HOBT, 8.9 mg, 0.066 mmol), N,N-diisopropylethylamine (7.8 mg, 0.060 mmol), and 4-benzyl-piperidine (11 mg, 0.060 mmol) were combined in dimethylacetamide (3 mL) and heated in a Personal Chemistry Ermy's optimizer microwave to 100° C. for 300 seconds. The mixture was filtered through Si-Carbonate (6 mL-1 g cartridge from Silicycle Chemical Division) and then concentrated to dryness. The residue was dissolved in 1:1 dimethylsulfoxide/methanol and purified by reverse phase HPLC to afford the title compound. $^1$H NMR (500 MHz, dimethylsulfoxide-$d_6$) δ ppm 1.05-1.32 (m, 18H) 1.46-1.64 (m, 3H) 1.80-1.95 (m, 2H) 2.11-2.29 (m, 6H) 3.66-4.06 (m, 2H) 6.85-7.50 (m, 4H) 9.97-10.44 (m, 1H); MS (ESI) m/z 454 (M+H)$^+$.

Example 125

N-(3-{[4-(2-ethoxyphenyl)piperazin-1-yl]carbonyl}-4,5-dimethylthien-2-yl)-2,2,3,3-tetramethylcyclopropanecarboxamide Example 9B (18 mg, 0.060 mmol), two equivalents of polymer bound dicyclohexylcarbodidiimide (PS-DCC, commercially available from Argonaut Technologies), 1-hydroxybenzotriazole (HOBT, 8.9 mg, 0.066 mmol), N,N-diisopropylethylamine (7.8 mg, 0.060 mmol), and 1-(2-ethoxyphenyl)-piperazine (12 mg, 0.060 mmol) were combined in dimethylacetamide (3 mL) and heated in a Personal Chemistry Ermy's optimizer microwave to 100° C. for 300 seconds. The mixture was filtered through Si-Carbonate (6 mL-1 g cartridge from Silicycle Chemical Division) and then concentrated to dryness. The residue was dissolved in 1:1 dimethylsulfoxide/methanol and purified by reverse phase HPLC to afford the title compound. $^1$H NMR (500 MHz, dimethylsulfoxide-$d_6$) δ ppm 0.86-1.47 (m, 16H) 1.75-2.00 (m, 3H) 2.01-2.33 (m, 3H) 2.71-3.43 (m, 7H) 3.90-4.11 (m, 2H) 6.19-7.02 (m, 4H) 9.80-10.66 (m, 1H); MS (ESI) m/z 483 (M+H)$^+$.

Example 126

N-(2-furylmethyl)-4,5-dimethyl-2-{[(2,2,3,3-tetramethylcyclopropyl)carbonyl]amino}thiophene-3-carboxamide Example 9B (18 mg, 0.060 mmol), two equivalents of polymer bound dicyclohexylcarbodidiimide (PS-DCC, commercially available from Argonaut Technologies), 1-hydroxybenzotriazole (HOBT, 8.9 mg, 0.066 mmol), N,N-diisopropylethylamine (7.8 mg, 0.060 mmol), and furan-2-ylmethyl amine (5.8 mg, 0.060 mmol) were combined in dimethylacetamide (3 mL) and heated in a Personal Chemistry Ermy's optimizer microwave to 100° C. for 300 seconds. The mixture was filtered through Si-Carbonate (6 mL-1 g cartridge from Silicycle Chemical Division) and then concentrated to dryness. The residue was dissolved in 1:1 dimethylsulfoxide/methanol and purified by reverse phase HPLC to afford the title compound. MS (ESI) m/z 375 (M+H)$^+$.

Example 127

N-(3-furylmethyl)-4,5-dimethyl-2-{[(2,2,3,3-tetramethylcyclopropyl)carbonyl]amino}thiophene-3-carboxamide Example 9B (18 mg, 0.060 mmol), two equivalents of polymer bound dicyclohexylcarbodidiimide (PS-DCC, commercially available from Argonaut Technologies), 1-hydroxybenzotriazole (HOBT, 8.9 mg, 0.066 mmol), N,N-diisopropylethylamine (7.8 mg, 0.060 mmol), and furan-3-ylmethyl amine (5.8 mg, 0.060 mmol) were combined in dimethylacetamide (3 mL) and heated in a Personal Chemistry Ermy's optimizer microwave to 100° C. for 300 seconds. The mixture was filtered through Si-Carbonate (6 mL-1 g cartridge from Silicycle Chemical Division) and then concentrated to dryness. The residue was dissolved in 1:1 dimethylsulfoxide/methanol and purified by reverse phase HPLC to afford the title compound. MS (ESI) m/z 375 (M+H)$^+$.

Example 128

N-propyl-2-{[(2,2,3,3-tetramethylcyclopropyl)carbonyl]amino}-4,7-dihydro-5H-thieno[2,3-c]pyran-3-carboxamide Example 128A 2-[(2,2,3,3-Tetramethyl-cyclopropanecarbonyl)-amino]-4,7-dihydro-5H-thieno[2,3-c]pyran-3-carboxylic acid The title compound was prepared as described in Example 166B, substituting Example 10B for Example 166A. The crude product was used for the next step without further purification. MS (ESI+) m/z 324 (M+H)$^+$ Example 128B N-propyl-2-{[(2,2,3,3-tetramethylcyclopropyl)carbonyl]amino}-4,7-dihydro-5H-thieno[2,3-c]pyran-3-carboxamide The title compound was prepared as described in Example 166C, substituting Example 128A for Example 166B. $^1$H NMR (500 MHz, dimethylsulfoxide-$d_6$) δ ppm 0.78-1.00 (m, 3H) 1.09-1.29 (m, J=8.81 Hz, 12H) 1.42 (s, 1H) 1.47-1.65 (m, 2H) 2.77 (t, J=5.26 Hz, 2H) 3.10-3.26 (m, 2H) 3.83 (t, J=5.42 Hz, 2H) 4.62 (s, 2H) 7.45 (t, J=5.42 Hz, 1H) 11.31 (s, 1H). MS (ESI+) m/z 365.1 (M+H)$^+$

Example 129

N-propyl-2-{[(2,2,3,3-tetramethylcyclopropyl)carbonyl]amino}-5,6-dihydro-4H-cyclopenta[b]thiophene-3-carboxamide

Example 129A

2-[(2,2,3,3-Tetramethyl-cyclopropanecarbonyl)-amino]-5,6-dihydro-4H-cyclopenta[b]thiophene-3-carboxylic acid ethyl ester The title compound was prepared as described in Example 12 substituting 2-amino-5,6-dihydro-4H-cyclopenta[b]thiophene-3-carboxylic acid ethyl ester (ACROS) for 2-amino-4,5,6,7-tetrahydro-benzo[b]thiophene-3-carboxylic acid ethyl ester. MS (ESI+) m/z 336.0 (M+H)$^+$

Example 129B

2-[(2,2,3,3-Tetramethyl-cyclopropanecarbonyl)-amino]-5,6-dihydro-4H-cyclopenta[b]thiophene-3-carboxylic acid The title compound was prepared as described in Example 166B, substituting 129A for Example 166A. The crude product was used for the next step without further purification. MS (ESI+) m/z 308.0 (M+H)$^+$

Example 129C

N-propyl-2-{[(2,2,3,3-tetramethylcyclopropyl)carbonyl]amino}-5,6-dihydro-4H-cyclopenta[b]thiophene-3-carboxamide The title compound was prepared as described in Example 166C, substituting 129B for Example 166B. $^1$H NMR (500 MHz, dimethylsulfoxide-d$_6$) δ ppm 0.88 (t, J=7.46 Hz, 3H) 1.08-1.29 (m, 12H) 1.35 (s, 1H) 1.41-1.70 (m, 2H) 2.24-2.45 (m, 2H) 2.77 (t, J=7.29 Hz, 2H) 2.91 (t, J=7.12 Hz, 2H) 3.13-3.28 (m, 2H) 7.07 (t, J=5.76 Hz, 1H) 11.85 (s, 1H). MS (ESI+) m/z 347.2 (M+H)$^+$. Anal. calcd. for C19H27N2O2S: C, 65.67; H, 7.83; N, 8.06. Found: C, 65.59; H, 8.25; N, 7.96.

Example 130

N-propyl-2-{[(2,2,3,3-tetramethylcyclopropyl)carbonyl]amino}thiophene-3-carboxamide

Example 130A

2-[(2,2,3,3-Tetramethyl-cyclopropanecarbonyl)-amino]-thiophene-3-carboxylic acid ethyl ester The title compound was prepared as described in Example 12, substituting 2-amino-thiophene-3-carboxylic acid ethyl ester (OAKWOOD) for 2-amino-4,5,6,7-tetrahydro-benzo[b]thiophene-3-carboxylic acid ethyl ester. MS (ESI+) m/z 296 (M+H)$^+$

Example 130B

2-[(2,2,3,3-Tetramethyl-cyclopropanecarbonyl)-amino]-thiophene-3-carboxylic acid The title compound was prepared as described in Example 166B, substituting Example 130A for Example 166A. The crude product was used for the next step without further purification. MS (ESI+) m/z 267.0 (M+H)$^+$

Example 130C

N-propyl-2-{[(2,2,3,3-tetramethylcyclopropyl)carbonyl]amino}thiophene-3-carboxamide The title compound was prepared as described in Example 166C, substituting Example 130B for Example 166B. $^1$H NMR (500 MHz, dimethylsulfoxide-d$_6$) δ ppm 0.81-0.97 (m, 3H) 1.12-1.31 (m, 12H) 1.30-1.47 (m, 1H) 1.44-1.63 (m, 2H) 3.06-3.31 (m, 2H) 6.90 (d, J=5.76 Hz, 1H) 7.40 (d, J=5.76 Hz, 1H) 8.35 (t, J=5.76 Hz, 1H) 12.22 (s, 1H). MS (ESI+) m/z 309.1 (M+H)$^+$ Anal. calcd. for C16H24N2O2S: C, 62.30; H, 7.84; N, 9.08. Found: C, 62.26; H, 8.09; N, 8.25.

Example 131

5-phenyl-N-propyl-2-{[(2,2,3,3-tetramethylcyclopropyl)carbonyl]amino}thiophene-3-carboxamide

Example 131A

5-Phenyl-2-[(2,2,3,3-tetramethyl-cyclopropanecarbonyl)-amino]-thiophene-3-carboxylic acid ethyl ester The title compound was prepared as described in Example 12, substituting 2-amino-5-phenyl-thiophene-3-carboxylic acid ethyl ester (FLUOROCHEM) for 2-amino-4,5,6,7-tetrahydro-benzo[b]thiophene-3-carboxylic acid ethyl ester. MS (ESI+) m/z 372 (M+H)$^+$

Example 131B

5-Phenyl-2-[(2,2,3,3-tetramethyl-cyclopropanecarbonyl)-amino]-thiophene-3-carboxylic acid The title compound was prepared as described in Example 166B, substituting Example 131A for Example 166A. The crude product was used for the next step without further purification. MS (ESI+) m/z 343.0 (M+H)$^+$

Example 131C 5-phenyl-N-propyl-2-{[(2,2,3,3-tetramethylcyclopropyl)carbonyl]amino}thiophene-3-carboxamide The title compound was prepared as described in Example 166C, substituting Example 131B for Example 166B. $^1$H NMR (500 MHz, dimethylsulfoxide-d$_6$) δ ppm 0.91 (t, J=7.46 Hz, 3H) 1.13-1.33 (m, 12H) 1.35-1.50 (m, 1H) 1.47-1.71 (m, 2H) 3.12-3.36 (m, 2H) 7.28 (t, J=7.29 Hz, 1H) 7.42 (t, J=7.63 Hz, 2H) 7.57 (d, J=7.12 Hz, 2H) 7.87 (s, 1H) 8.38 (t, J=5.59 Hz, 1H) 12.23 (s, 1H). MS (ESI+) m/z 385.2 (M+H)$^+$. Anal. calcd. for C22H28N2O2S: C, 68.72; H, 7.34; N, 7.29. Found: C, 68.31; H, 7.45; N, 7.00.

Example 132

4-methyl-N-propyl-2-{[(2,2,3,3-tetramethylcyclopropyl)carbonyl]amino}thiophene-3-carboxamide

Example 132A

4-Methyl-2-[(2,2,3,3-tetramethyl-cyclopropanecarbonyl)-amino]-thiophene-3-carboxylic acid ethyl ester The title compound was prepared as described in Example 12, substituting 2-amino-4-methyl-thiophene-3-carboxylic acid ethyl ester (ACROS) for 2-amino-4,5,6,7-tetrahydro-benzo[b]thiophene-3-carboxylic acid ethyl ester. MS (ESI+) m/z 310 (M+H)$^+$.

Example 132B

4-Methyl-2-[(2,2,3,3-tetramethyl-cyclopropanecarbonyl)-amino]-thiophene-3-carboxylic acid The title compound was prepared as described in Example 166B, substituting Example 132A for Example 166A. The crude product was used for the next step without further purification. MS (ESI+) m/z 281.0 (M+H)$^+$.

Example 132C 4-methyl-N-propyl-2-{[(2,2,3,3-tetramethylcyclopropyl)carbonyl]amino}thiophene-3-carboxamide The title compound was prepared as described in Example 166C, substituting Example 132B for Example 166B. $^1$H NMR (500 MHz, dimethylsulfoxide-d$_6$) δ ppm 0.90 (t, J=7.46 Hz, 3H) 1.10-1.28 (m, 12H) 1.42 (s, 1H) 1.46-1.67 (m, 2H) 2.18-2.36 (m, 3H) 3.11-3.28 (m, 2H) 6.56 (s, 1H) 7.63 (s, 1H) 11.12 (s, 1H). MS (ESI+) m/z 323.1 (M+H)$^+$. Anal. calcd. for C17H25N2O2S: C, 63.52; H, 7.84; N, 8.71. Found: C, 63.14; H, 8.38; N, 8.42.

Example 133

N-propyl-2-{[(2,2,3,3-tetramethylcyclopropyl)carbonyl]amino}-4,7-dihydro-5H-thieno[2,3-c]thiopyran-3-carboxamide

Example 133A

2-Amino-4,7-dihydro-5H-thieno[2,3-c]thiopyran-3-carboxylic acid ethyl ester

The title compound was prepared as described in Example 10A, substituting tetrahydro-thiopyran-4-one for tetrahydro-4H-pyran-4-one. MS (ESI+) m/z 243 (M+H)$^+$

Example 133B

2-[(2,2,3,3-Tetramethyl-cyclopropanecarbonyl)-amino]-4,7-dihydro-5H-thieno[2,3-c]thiopyran-3-carboxylic acid ethyl ester The title compound was prepared as described in Example 12, substituting Example 133A for 2-amino-4,5,6,7-tetrahydro-benzo[b]thiophene-3-carboxylic acid ethyl ester. MS (ESI+) m/z 368 (M)$^+$

Example 133C

2-[(2,2,3,3-Tetramethyl-cyclopropanecarbonyl)-amino]-4,7-dihydro-5H-thieno[2,3-c]thiopyran-3-carboxylic acid The title compound was prepared as described in Example 166B, substituting Example 133B for Example 166A. The crude product was used for the next step without further purification. MS (ESI+) m/z 339.0 (M)$^+$

Example 133D

N-propyl-2-{[(2,2,3,3-tetramethylcyclopropyl)carbonyl]amino}-4,7-dihydro-5H-thieno[2,3-c]thiopyran-3-carboxamide The title compound was prepared as described in Example 166C, substituting Example 133C for Example 166B. $^1$H NMR (500 MHz, dimethylsulfoxide-d$_6$) δ ppm 0.89 (t, J=7.46 Hz, 3H) 1.11-1.25 (m, 12H) 1.39-1.47 (m, 1H) 1.47-1.59 (m, 2H) 2.70-3.02 (m, 4H) 3.06-3.31 (m, 2H) 3.72 (s, 2H) 7.69 (t, J=5.43 Hz, 1H) 10.90 (s, 1H). MS (ESI+) m/z 381.3 (M+H)$^+$.

Example 134

N-propyl-2-{[(2,2,3,3-tetramethylcyclopropyl)carbonyl]amino}-4,7-dihydro-5H-thieno[2,3-c]thiopyran-3-carboxamide 6,6-dioxide To a solution of Example 133D (0.16 g, 0.41 mmol) in 40 mL acetone was added OXONE® (1 g, 1.29 mmol) in one portion. The resulting suspension was allowed to stir at room temperature for 16 hours. The reaction was diluted with ethyl acetate and washed with water (2×), brine (1×), dried (MgSO$_4$), filtered and concentrated. The crude material was chromatographed (15% ethyl acetate/hexanes) to afford the title compound. $^1$H NMR (500 MHz, dimethylsulfoxide-d$_6$) δ ppm 0.81-0.97 (m, 3H) 1.10-1.30 (m, 12H) 1.39-1.66 (m, 3H) 3.09-3.25 (m, 4H) 3.36 (t, J=6.10 Hz, 2H) 4.41 (s, 2H) 7.93 (t, J=5.49 Hz, 1H) 10.83 (s, 1H). MS (ESI+) m/z 413.1 (M+H)$^+$. Anal. calcd. for C19H28N2O4S2: C, 55.31; H, 6.84; N, 6.79. Found: C, 55.31; H, 7.13; N, 6.54.

Example 135

N-(tetrahydro-2H-pyran-4-ylmethyl)-2-{[(2,2,3,3-tetramethylcyclopropyl)carbonyl]amino}-4,7-dihydro-5H-thieno[2,3-c]pyran-3-carboxamide The title compound was prepared as described in Example 166C, substituting Example 128A for Example 166B, and C-(tetrahydro-pyran-4-yl)-methylamine for propylamine. $^1$H NMR (500 MHz, dimethylsulfoxide-d$_6$) δ ppm 1.08-1.28 (m, 14H) 1.41 (s, 1H) 1.51-1.65 (m, 2H) 1.70-1.89 (m, 1H) 2.77 (t, J=5.26 Hz, 2H) 3.16 (t, J=6.44 Hz, 2H) 3.20-3.31 (m, 2H) 3.68-4.06 (m, 4H) 4.62 (s, 2H) 7.19-7.80 (m, 1H) 11.30 (s, 1H). MS (ESI+) m/z 419.1 (M+H)$^+$. Anal. calcd. for C22H32N2O4S: C, 62.83; H, 7.67; N, 6.66. Found: C, 62.49; H, 7.50; N, 6.44.

Example 136

N-(3-hydroxypropyl)-2-{[(2,2,3,3-tetramethylcyclopropyl)carbonyl]amino}-4,7-dihydro-5H-thieno[2,3-c]pyran-3-carboxamide The title compound was prepared as described in Example 166C, substituting Example 128A for Example 166B and 3-amino-propan-1-ol for propylamine. $^1$H NMR (500 MHz, dimethylsulfoxide-d$_6$) δ ppm 1.20 (d, J=8.48 Hz, 12H) 1.41 (s, 1H) 1.56-1.82 (m, 2H) 2.62-2.86 (m, 2H) 3.24-3.40 (m, 2H) 3.42-3.56 (m, 2H) 3.83 (t, J=5.42 Hz, 2H) 4.28-4.93 (m, 3H) 7.46 (t, J=5.42 Hz, 1H) 11.40 (s, 1H). MS (ESI+) m/z 379.1 (M+H)⁺. Anal. calcd. for C19H28N2O4S: C, 59.97; H, 7.42; N, 7.36. Found: C, 59.45; H, 7.50; N, 7.20.

Example 137

N-(2-hydroxyethyl)-2-{[(2,2,3,3-tetramethylcyclopropyl)carbonyl]amino}-4,7-dihydro-5H-thieno[2,3-c]pyran-3-carboxamide The title compound was prepared as described in Example 166C, substituting Example 128A for Example 166B and 2-aminoethanol for propylamine. ¹H NMR (500 MHz, dimethylsulfoxide-d₆) δ ppm 1.20 (d, J=9.15 Hz, 12H) 1.41 (s, 1H) 2.77 (t, J=5.26 Hz, 2H) 3.22-3.41 (m, 2H) 3.52 (q, J=5.88 Hz, 2H) 3.83 (t, J=5.42 Hz, 2H) 4.62 (s, 2H) 4.70-4.89 (m, 1H) 7.37 (t, J=5.59 Hz, 1H) 11.34 (s, 1H). MS (ESI+) m/z 389.1 (M+Na)⁺. Anal. calcd. for C₁₈H₂₆N₂O₄S: C, 58.99; H, 7.15; N, 7.64. Found: C, 59.05; H, 7.12; N, 7.46.

Example 138

N-(2-methoxyethyl)-2-{[(2,2,3,3-tetramethylcyclopropyl)carbonyl]amino}-4,7-dihydro-5H-thieno[2,3-c]pyran-3-carboxamide The title compound was prepared as described in Example 166C, substituting Example 128A for Example 166B and 2-methoxy-ethylamine for propylamine. ¹H NMR (500 MHz, dimethylsulfoxide-d₆) δ ppm 1.20 (d, J=8.48 Hz, 12H) 1.41 (s, 1H) 2.75 (t, J=5.26 Hz, 2H) 3.31 (s, 3H) 3.37-3.53 (m, 4H) 3.83 (t, J=5.42 Hz, 2H) 4.62 (s, 2H) 7.14-7.80 (m, 1H) 11.27 (s, 1H). MS (ESI+) m/z 381.1 (M+H)⁺. Anal. calcd. for C19H28N2O4S: C, 59.97; H, 7.42; N, 7.36. Found: C, 59.77; H, 7.38; N, 7.18.

Example 139

N-(2-morpholin-4-ylethyl)-2-{[(2,2,3,3-tetramethylcyclopropyl)carbonyl]amino}-4,7-dihydro-5H-thieno[2,3-c]pyran-3-carboxamide The title compound was prepared as described in Example 166C, substituting Example 128A for Example 166B and 2-morpholin-4-yl-ethylamine for propylamine. ¹H NMR (500 MHz, dimethylsulfoxide-d₆) δ ppm 1.20 (d, J=8.48 Hz, 12H) 1.40 (s, 1H) 2.38-2.44 (m, 2H) 2.45-2.59 (m, 4H) 2.80 (t, J=5.09 Hz, 2H) 3.33-3.44 (m, 2H) 3.49-3.64 (m, 4H) 3.86 (t, J=5.43 Hz, 2H) 4.63 (s, 2H) 7.31 (t, J=5.26 Hz, 1H) 11.47 (s, 1H). MS (ESI+) m/z 436.2 (M+H)⁺. Anal. calcd. for C22H33N3O4S: C, 60.66; H, 7.64; N, 9.65. Found: C, 60.53; H, 7.61; N, 9.50.

Example 140

N-(pyridin-2-ylmethyl)-2-{[(2,2,3,3-tetramethylcyclopropyl)carbonyl]amino}-4,7-dihydro-5H-thieno[2,3-c]pyran-3-carboxamide The title compound was prepared as described in Example 166C, substituting Example 128A for Example 166B and C-pyridin-2-yl-methylamine for propylamine. ¹H NMR (500 MHz, dimethylsulfoxide-d₆) δ ppm 0.92-1.35 (m, 12H) 1.28-1.60 (m, 1H) 2.66-3.02 (m, 2H) 3.86 (t, J=5.42 Hz, 2H) 4.45-4.81 (m, 4H) 6.99-7.56 (m, 2H) 7.60-7.93 (m, 1H) 7.96-8.33 (m, 1H) 8.51 (d, J=5.76 Hz, 1H) 11.48 (s, 1H). MS (ESI+) m/z 414.2 (M+H)⁺. Anal. calcd. for C22H27N3O3S: C, 63.90; H, 6.58; N, 10.16. Found: C, 63.55; H, 6.73; N, 9.71.

Example 141

N-(pyridin-3-ylmethyl)-2-{[(2,2,3,3-tetramethylcyclopropyl)carbonyl]amino}-4,7-dihydro-5H-thieno[2,3-c]pyran-3-carboxamide The title compound was prepared as described in Example 166C, substituting Example 128A for Example 166B and C-pyridin-3-yl-methylamine for propylamine. ¹H NMR (500 MHz, dimethylsulfoxide-d₆) δ ppm 1.20 (d, J=8.48 Hz, 12H) 1.42 (s, 1H) 2.80 (t, J=5.26 Hz, 2H) 3.84 (t, J=5.42 Hz, 2H) 4.49 (d, J=6.10 Hz, 2H) 4.62 (s, 2H) 7.36 (dd, J=7.46, 4.41 Hz, 1H) 7.65-7.82 (m, 1H) 8.05 (t, J=5.76 Hz, 1H) 8.46 (dd, J=4.92, 1.53 Hz, 1H) 8.56 (d, J=1.36 Hz, 1H) 11.32 (s, 1H). MS (ESI+) m/z 414.2 (M+H)⁺. Anal. calcd. for C22H27N3O3S*0.7CH2Cl2: C, 63.19; H, 6.52; N, 10.02. Found: C, 63.60; H, 6.81; N, 9.56.

Example 142

N-(pyridin-4-ylmethyl)-2-{[(2,2,3,3-tetramethylcyclopropyl)carbonyl]amino}-4,7-dihydro-5H-thieno[2,3-c]pyran-3-carboxamide The title compound was prepared as described in Example 166C, substituting Example 128A for Example 166B and C-pyridin-4-yl-methylamine for propylamine. ¹H NMR (500 MHz, dimethylsulfoxide-d₆) δ ppm 1.19 (d, J=11.19 Hz, 12H) 1.41 (s, 1H) 2.75-2.98 (m, 2H) 3.86 (t, J=5.26 Hz, 2H) 4.49 (d, J=5.76 Hz, 2H) 4.64 (s, 2H) 7.32 (d, J=6.10 Hz, 2H) 7.87-8.22 (m, 1H) 8.29-8.71 (m, 2H) 11.35 (s, 1H). MS (ESI+) m/z 414.2 (M+H)⁺. Anal. calcd. for C22H27N3O3S*0.2CH2Cl2; C, 61.93; H, 6.41; N, 9.76. Found: C, 62.19; H, 6.78; N, 9.62.

Example 143

N-allyl-2-{[(2,2,3,3-tetramethylcyclopropyl)carbonyl]amino}-4,5,6,7-tetrahydro-1-benzothiophene-3-carboxamide The title compound was prepared as described in Example 166C, substituting Example 29A for Example 166B and allylamine for propylamine. ¹H NMR (300 MHz, dimethylsulfoxide-d₆) δ ppm 1.20 (d, J=9.15 Hz, 12H) 1.38 (s, 1H) 1.61-1.79 (m, 4H) 2.54-2.71 (m, 4H) 3.61-4.17 (m, 2H) 4.85-5.28 (m, 2H) 5.54-6.15 (m, 1H) 7.58 (t, J=5.59 Hz, 1H) 11.21 (s, 1H). MS (ESI+) m/z 361.3 (M+H)⁺

Example 144

N-propyl-2-{[(2,2,3,3-tetramethylcyclopropyl)carbonyl]amino}-4,7-dihydro-5H-spiro[1-benzothiophene-6,2'-[1,3]dioxolane]-3-carboxamide Example 144A ethyl 2-amino-5,7-dihydro-4H-spiro[benzo[b]thiophene-6,2'-[1,3]dioxolane]-3-carboxylate The title compound was prepared as described in Example 10A, substituting 1,4-dioxospiro[4.5]decan-8-one for tetrahydro-4H-pyran-4-one. MS (ESI+) m/z 284 (M+H)⁺

Example 144B ethyl 2-(2,2,3,3-tetramethylcyclopropanecarboxamido)-5,7-dihydro-4H-spiro[benzo[b]thiophene-6,2'-[1,3]dioxolane]-3-carboxylate The title compound was prepared as described in Example 10B, substituting Example 144A for Example 10A. MS (ESI+) m/z 408.0 (M+H)$^+$

Example 144C 2-(2,2,3,3-tetramethylcyclopropanecarboxamido)-5,7-dihydro-4H-spiro[benzo[b]thiophene-6,2'-[131]dioxolane]-3-carboxylic acid The title compound was prepared as described in Example 166B, substituting Example 144B for Example 166A. The crude product was used for the next step without further purification. MS (ESI+) m/z 380.0 (M+H)$^+$

Example 144D

N-propyl-2-{[(2,2,3,3-tetramethylcyclopropyl)carbonyl]amino}-4,7-dihydro-5H-spiro[1-benzothiophene-6,2'-[1,3]dioxolane]-3-carboxamide The title compound was prepared as described in Example 166C, substituting Example 144C for Example 166B. $^1$H NMR (300 MHz, dimethylsulfoxide-d$_6$) δ ppm 0.88 (t, J=7.29 Hz, 3H) 1.05-1.31 (m, 12H) 1.33-1.48 (m, 1H) 1.44-1.61 (m, 2H) 1.83 (t, J=5.93 Hz, 2H) 2.63-2.95 (m, 4H) 3.09-3.26 (m, 2H) 3.82-4.04 (m, 4H) 7.50 (t, J=5.26 Hz, 1H) 11.19 (s, 1H). MS (ESI+) m/z 419.2 (M+H)$^+$

Example 145

2-[(hexahydro-2,5-methanopentalen-3a(1H)-ylcarbonyl)amino]-4-phenyl-N-propylthiophene-3-carboxamide

Example 145A

2-[(Hexahydro-2,5-methano-pentalene-3a-carbonyl)-amino]-4-phenyl-thiophene-3-carboxylic acid ethyl ester The title compound was prepared as described in Example 167A, substituting 2-amino-4-phenyl-thiophene-3-carboxylic acid ethyl ester (MAYBRIDGE) for Example 10A. MS (ESI+) m/z 397 (M+H)$^+$

Example 145B

2-[(Hexahydro-2,5-methano-pentalene-3a-carbonyl)-amino]-4-phenyl-thiophene-3-carboxylic acid The title compound was prepared as described in Example 166B, substituting Example 145A for Example 166A. The crude product was used for the next step without further purification. MS (ESI+) m/z 368 (M+H)$^+$

Example 145C

2-[(hexahydro-2,5-methanopentalen-3a(1H)-ylcarbonyl)amino]-4-phenyl-N-propylthiophene-3-carboxamide The title compound was prepared as described in Example 166C, substituting Example 145B for Example 166B. $^1$H NMR (300 MHz, dimethylsulfoxide-d$_6$) δ ppm 0.65 (t, J=7.46 Hz, 3H) 1.10-1.31 (m, 2H) 1.57-1.71 (m, 3H) 1.74-1.93 (m, 3H) 2.01 (s, 2H) 2.25-2.40 (m, 2H) 2.34 (s, 2H) 2.64 (s, 1H) 2.88-3.16 (m, 2H) 6.27-6.45 (m, 1H) 6.93 (s, 1H) 7.13-7.82 (m, 5H) 11.80 (s, 1H). MS (ESI+) m/z 409.1 (M+H)$^+$

Example 146

2-[(hexahydro-2,5-methanopentalen-3a(1H)-ylcarbonyl)amino]-5-phenyl-N-propylthiophene-3-carboxamide

Example 146A

2-[(Hexahydro-2,5-methano-pentalene-3a-carbonyl)-amino]-5-phenyl-thiophene-3-carboxylic acid ethyl ester The title compound was prepared as described in Example 167A, substituting 2-amino-5-phenyl-thiophene-3-carboxylic acid ethyl ester (FLUOROCHEM) for Example 10A. MS (ESI+) m/z 397 (M+H)$^+$

Example 146B

2-[(Hexahydro-2,5-methano-pentalene-3a-carbonyl)-amino]-5-phenyl-thiophene-3-carboxylic acid The title compound was prepared as described in Example 166B, substituting Example 146A for Example 166A. The crude product was used for the next step without further purification. MS (ESI+) m/z 368 (M+H)$^+$

Example 146C

2-[(hexahydro-2,5-methanopentalen-3a(1H)-ylcarbonyl)amino]-5-phenyl-N-propylthiophene-3-carboxamide The title compound was prepared as described in Example 166C, substituting Example 146B for Example 166B. $^1$H NMR (300 MHz, dimethylsulfoxide-d$_6$) δ ppm 0.75-1.02 (m, 3H) 1.40-1.75 (m, 6H) 1.71-1.97 (m, 4H) 1.95-2.15 (m, 2H) 2.35 (s, 2H) 2.64 (t, J=6.61 Hz, 1H) 3.11-3.33 (m, 2H) 7.15-7.37 (m, 1H) 7.37-7.50 (m, 2H) 7.50-7.64 (m, 2H) 7.91 (s, 1H) 8.41 (t, J=5.59 Hz, 1H) 12.54 (s, 1H). MS (ESI+) m/z 409.1 (M+H)$^+$

Example 147

2-[(hexahydro-2,5-methanopentalen-3a(1H)-ylcarbonyl)amino]-N-(3-hydroxypropyl)-5-phenylthiophene-3-carboxamide The title compound was prepared as described in Example 166C, substituting Example 146B for Example 166B, and 3-amino-propan-1-ol for propylamine. $^1$H NMR (300 MHz, dimethylsulfoxide-d$_6$) δ ppm 1.53-2.13 (m, 12H) 2.35 (s, 2H) 2.65 (t, J=6.78 Hz, 1H) 3.18-3.40 (m, 2H) 3.40-3.59 (m, 2H) 4.50 (t, J=5.09 Hz, 1H) 7.30 (t, J=7.29 Hz, 1H) 7.44 (t, J=7.63

Hz, 2H) 7.57 (d, J=7.12 Hz, 2H) 7.90 (s, 1H) 8.41 (t, J=5.59 Hz, 1H) 12.53 (s, 1H). MS (ESI+) m/z 425.2 (M+H)$^+$

Example 148

N-[3-(morpholin-4-ylcarbonyl)-5-phenylthien-2-yl] hexahydro-2,5-methanopentalene-3a(1H)-carboxamide The title compound was prepared as described in Example 166C, substituting Example 146B and morpholine for propylamine. $^1$H NMR (300 MHz, dimethylsulfoxide-d$_6$) δ ppm 1.54-2.12 (m, 10H) 2.34 (s, 2H) 2.58-2.74 (m, 1H) 3.66 (s, 8H) 7.31 (d, J=7.46 Hz, 1H) 7.34-7.48 (m, 3H) 7.64 (d, J=7.12 Hz, 2H) 11.02 (s, 1H). MS (ESI+) m/z 437.2 (M+H)$^+$

Example 149

2-[(hexahydro-2,5-methanopentalen-3a(1H)-ylcarbonyl)amino]-N-propyl-5-pyridin-4-ylthiophene-3-carboxamide

Example 149A

2-[(Hexahydro-2,5-methano-pentalene-3a-carbonyl)-amino]-5-pyridin-4-yl-thiophene-3-carboxylic acid ethyl ester The title compound was prepared as described in Example 167A, substituting 2-amino-5-pyridin-4-yl-thiophene-3-carboxylic acid ethyl ester (Journal of Heterocyclic Chemistry (1991), 28(8), 1953-5) for Example 10A. MS (ESI+) m/z 396.2 (M+H)$^+$

Example 149B

2-[(Hexahydro-2,5-methano-pentalene-3a-carbonyl)-amino]-5-pyridin-4-yl-thiophene-3-carboxylic acid The title compound was prepared as described in Example 166B, substituting Example 149A for Example 166A. The crude product was used for the next step without further purification. MS (ESI+) m/z 369 (M+H)$^+$

Example 149C

2-[(hexahydro-2,5-methanopentalen-3a(1H)-ylcarbonyl)amino]-N-propyl-5-pyridin-4-ylthiophene-3-carboxamide The title compound was prepared as described in Example 166C, substituting Example 149B for Example 166B. $^1$H NMR (300 MHz, dimethylsulfoxide-d$_6$) δ ppm 0.92 (t, J=7.29 Hz, 3H) 1.43-2.14 (m, 10H) 2.35 (s, 2H) 2.65 (t, J=6.78 Hz, 1H) 3.11-3.32 (m, 4H) 7.46-7.57 (m, 2H) 8.21 (s, 1H) 8.42-8.54 (m, 1H) 8.52-8.62 (m, 2H) 12.61 (s, 1H). MS (ESI+) m/z 410.2 (M+H)$^+$

Example 150 ethyl 4-(2-furyl)-2-[(hexahydro-2,5-methanopentalen-3a(1H)-ylcarbonyl)amino]thiophene-3-carboxylate The title compound was prepared as described in Example 167A, substituting 2-amino-4-furan-2-yl-thiophene-3-carboxylic acid ethyl ester (ACROS) for Example 10A. $^1$H NMR (300 MHz, dimethylsulfoxide-d$_6$) δ ppm 1.49-2.12 (m, 12H) 2.35 (s, 3H) 2.58-2.79 (m, 1H) 4.21 (q, J=7.12 Hz, 2H) 6.36-6.66 (m, 2H) 7.17 (s, 1H) 7.69 (d, J=1.36 Hz, 1H) 11.26 (s, 1H). MS (ESI+) m/z 386.1 (M+H)$^+$. Anal. calcd. for C21H22NO4S C, 65.60; H, 5.77; N, 3.64. Found: C, 66.10; H, 5.99; N, 3.41.

Example 151 ethyl 5'-[(hexahydro-2,5-methanopentalen-3a(1H)-ylcarbonyl)amino]-2,3'-bithiophene-4'-carboxylate The title compound was prepared as described in Example 167A, substituting 5'-amino-[2,3']bithiophenyl-4'-carboxylic acid ethyl ester (ACROS) for Example 10A. $^1$H NMR (300 MHz, dimethylsulfoxide-d$_6$) δ ppm 1.04 (t, J=7.12 Hz, 3H) 1.51-2.09 (m, 10H) 2.28 (s, 2H) 2.66 (s, 1H) 4.15 (d, J=7.12 Hz, 2H) 6.82-7.31 (m, 3H) 7.52 (dd, J=4.92, 1.53 Hz, 1H) 11.33 (s, 1H). MS (ESI+) m/z 402.1 (M+H)$^+$. Anal. calcd. for C21H22NO3S2; C, 62.97; H, 5.54; N, 3.50. Found: C, 62.96; H, 5.70; N, 3.32.

Example 152

4-(2-furyl)-2-[(hexahydro-2,5-methanopentalen-3a (1H)-ylcarbonyl)amino]-N-propylthiophene-3-carboxamide

Example 152A

4-Furan-2-yl-2-[(hexahydro-2,5-methano-pentalene-3a-carbonyl)-amino]-thiophene-3-carboxylic acid The title compound was prepared as described in Example 166B, substituting Example 150 for Example 166A. The crude product was used for the next step without further purification. MS (ESI+) m/z 358 (M+H)$^+$

Example 152B 4-(2-furyl)-2-[(hexahydro-2,5-methanopentalen-3a (1H)-ylcarbonyl)amino]-N-propylthiophene-3-carboxamide The title compound was prepared as described in Example 166C, substituting Example 152A for Example 166B. $^1$H NMR (300 MHz, dimethylsulfoxide-d$_6$) δ ppm 0.83 (t, J=7.29 Hz, 3H) 1.26-2.11 (m, 12H) 2.33 (s, 2H) 2.64 (t, J=6.78 Hz, 1H) 3.06-3.26 (m, 2H) 6.58 (d, J=1.36 Hz, 2H) 7.17 (s, 1H) 7.38 (t, J=5.43 Hz, 1H) 7.62-7.93 (m, 1H) 11.35 (s, 1H). MS (ESI+) m/z 399.2 (M+H)$^+$

Example 153

5'-[(hexahydro-2,5-methanopentalen-3a(1H)-ylcarbonyl)amino]-N-propyl-2,3'-bithiophene-4'-carboxamide Example 153A 5'-[(Hexahydro-2,5-methano-pentalene-3a-carbonyl)-amino]-[2,3']bithiophenyl-4'-carboxylic acid The title compound was prepared as described in Example 166B, substituting Example 151 for Example 166A. The crude product was used for the next step without further purification. MS (ESI+) m/z 374 (M+H)$^+$

Example 153B

5'-[(hexahydro-2,5-methanopentalen-3a(1H)-ylcarbonyl)amino]-N-propyl-2,3'-bithiophene-4'-carboxamide The title compound was prepared as described in Example 166C, substituting Example 153A for Example 166B. $^1$H NMR (300 MHz, dimethylsulfoxide-$d_6$) δ ppm 0.73 (t, J=7.29 Hz, 3H) 1.11-1.45 (m, 2H) 1.53-2.12 (m, 10H) 2.24-2.44 (m, 2H) 2.64 (t, J=6.61 Hz, 1H) 2.97-3.22 (m, 2H) 6.69-6.86 (m, 1H) 7.06 (s, 1H) 7.08-7.31 (m, 2H) 7.65 (dd, J=5.09, 1.36 Hz, 1H) 11.76 (s, 1H). MS (ESI+) m/z 415.2 (M+H)$^+$

Example 154 ethyl 2-[(hexahydro-2,5-methanopentalen-3a(1H)-ylcarbonyl)amino]-5,6,7,8-tetrahydro-4H-cyclohepta[b]thiophene-3-carboxylate

Example 154A

2-Amino-5,6,7,8-tetrahydro-4H-cyclohepta[b]thiophene-3-carboxylic acid ethyl ester The title compound was prepared as described in Example 10A, substituting cycloheptanone for tetrahydro-4H-pyran-4-one. MS (ESI+) m/z 240 (M+H)$^+$

Example 154B ethyl 2-[(hexahydro-2,5-methanopentalen-3a(1H)-ylcarbonyl)amino]-5,6,7,8-tetrahydro-4H-cyclohepta[b]thiophene-3-carboxylate The title compound was prepared as described in Example 167A, substituting Example 154A for Example 10A. $^1$H NMR (300 MHz, dimethylsulfoxide-$d_6$) δ ppm 1.31 (t, J=7.12 Hz, 3H) 1.45-2.09 (m, 16H) 2.20-2.42 (m, 2H) 2.58-2.77 (m, 3H) 2.92-3.10 (m, 2H) 4.31 (q, J=7.12 Hz, 2H) 11.14 (s, 1H). MS (ESI+) m/z 388.1 (M+H)$^+$

Example 155

2-[(hexahydro-2,5-methanopentalen-3a(1H)-ylcarbonyl)amino]-N-propyl-5,6,7,8-tetrahydro-4H-cyclohepta[b]thiophene-3-carboxamide

Example 155A

2-[(Hexahydro-2,5-methano-pentalene-3a-carbonyl)-amino]-5,6,7,8-tetrahydro-4H-cyclohepta[b]thiophene-3-carboxylic acid The title compound was prepared as described in Example 166B, substituting Example 154B for Example 166A. The crude product was used for the next step without further purification. MS (ESI+) m/z 360 (M+H)$^+$.

Example 155B

2-[(hexahydro-2,5-methanopentalen-3a(1H)-ylcarbonyl)amino]-N-propyl-5,6,7,8-tetrahydro-4H-cyclohepta[b]thiophene-3-carboxamide The title compound was prepared as described in Example 166C, substituting Example 155A for Example 166B. $^1$H NMR (300 MHz, dimethylsulfoxide-$d_6$) δ ppm 0.75-1.00 (m, 3H) 1.38-2.07 (m, 17H) 2.31 (s, 2H) 2.58 (s, 2H) 2.71 (dd, J=20.85, 10.68 Hz, 4H) 3.08-3.28 (m, 2H) 7.77 (s, 1H) 10.60 (s, 1H). MS (ESI+) m/z 399.4 (M+H)$^+$. Anal. calcd. for C23H32N2O2S; C, 68.96; H, 8.05; N, 6.99. Found: C, 68.97, H, 8.16; N, 6.88.

Example 156

4-cyclobutyl-2-[(hexahydro-2,5-methanopentalen-3a(1H)-ylcarbonyl)amino]-N-propylthiophene-3-carboxamide

Example 156A

2-Amino-4-cyclobutyl-thiophene-3-carboxylic acid ethyl ester

The title compound was prepared as described in Example 10A, substituting 1-cyclobutyl-ethanone for tetrahydro-4H-pyran-4-one. MS (ESI+) m/z 226 (M+H)$^+$

Example 156B

4-Cyclobutyl-2-[(hexahydro-2,5-methano-pentalene-3a-carbonyl)-amino]-thiophene-3-carboxylic acid ethyl ester The title compound was prepared as described in Example 167A, substituting Example 156A for Example 10A. MS (ESI+) m/z 375 (M+H)$^+$

Example 156C

4-Cyclobutyl-2-[(hexahydro-2,5-methano-pentalene-3a-carbonyl)-amino]-thiophene-3-carboxylic acid The title compound was prepared as described in Example 166B, substituting Example 156B for Example 166A. The crude product was used for the next step without further purification. MS (ESI+) m/z 346 (M+H)$^+$

Example 156D 4-cyclobutyl-2-[(hexahydro-2,5-methanopentalen-3a(1H)-ylcarbonyl)amino]-N-propylthiophene-3-carboxamide The title compound was prepared as described in Example 166C, substituting Example 156C for Example 166B. $^1$H NMR (300 MHz, dimethylsulfoxide-$d_6$) δ ppm 0.90 (t, J=7.29 Hz, 3H) 1.39-2.10 (m, 16H) 2.20-2.37 (m, 4H) 2.60 (t, J=6.78 Hz, 1H) 3.12-3.29 (m, 2H) 3.85 (d, J=7.46 Hz, 1H) 6.67 (s, 1H) 7.48 (s, 1H) 11.50 (s, 1H). MS (ESI+) m/z 387.2 (M+H)$^+$. Anal. calcd. for C22H30N2O2S; C, 68.36; H, 7.82; N, 7.25. Found: C, 68.45; H, 7.87; N, 7.11.

Example 157

2-[(hexahydro-2,5-methanopentalen-3a(1H)-ylcarbonyl)amino]-4-methyl-N-propylthiophene-3-carboxamide

Example 157A

2-[(Hexahydro-2,5-methano-pentalene-3a-carbonyl)-amino]-4-methyl-thiophene-3-carboxylic acid ethyl ester The title compound was prepared as described in Example 167A, substituting 2-amino-4-methyl-thiophene-3-carboxylic acid ethyl ester (ACROS) for Example 10A. MS (ESI+) m/z 310 (M+H)$^+$

Example 157B

2-[(Hexahydro-2,5-methano-pentalene-3a-carbonyl)-amino]-4-methyl-thiophene-3-carboxylic acid The title compound was prepared as described in Example 166B, substituting Example 157A for Example 166A. The crude product was used for the next step without further purification. MS (ESI+) m/z 306 (M+H)$^+$

Example 157C

[(hexahydro-2,5-methanopentalen-3a(1H)-ylcarbonyl)amino]-4-methyl-N-propylthiophene-3-carboxamide The title compound was prepared as described in Example 166C, substituting Example 157B for Example 166B. $^1$H NMR (300 MHz, dimethylsulfoxide-d$_6$) δ ppm 0.90 (t, J=7.29 Hz, 3H) 1.34-2.14 (m, 12H) 2.36 (s, 5H) 2.60 (s, 1H) 3.14-3.31 (m, 2H) 6.63 (s, 1H) 7.34-7.77 (m, 1H) 11.74 (s, 1H). MS (ESI+) m/z 347.2 (M+H)$^+$. Anal. calcd. for C19H25N2O2S; C, 66.05; H, 7.29; N, 8.11. Found: C, 66.12; H, 7.72; N, 7.88.

Example 158

N-{3-[(2,5-dimethylmorpholin-4-yl)carbonyl]-4,7-dihydro-5H-thieno[2,3-c]pyran-2-yl}hexahydro-2,5-methanopentalene-3a(1H)-carboxamide The title compound was prepared as described in Example 166C, substituting Example 167B for Example 166B and 2,5-dimethyl-morpholine for propylamine. $^1$H NMR (300 MHz, dimethylsulfoxide-d$_6$) δ ppm 0.79-1.28 (m, 6H) 1.44-2.05 (m, 12H) 2.29 (s, 2H) 2.37-2.78 (m, 2H) 3.39-3.60 (m, 3H) 3.83 (t, J=5.26 Hz, 3H) 4.65 (s, 2H) 9.70 (s, 1H). MS (ESI+) m/z 445.2 (M+H)$^+$

Example 159

2-[(hexahydro-2,5-methanopentalen-3a(1H)-ylcarbonyl)amino]-N-propyl-4,5,6,7,8,9-hexahydrocycloocta[b]thiophene-3-carboxamide

Example 159A

2-Amino-4,5,6,7,8,9-hexahydro-cycloocta[b]thiophene-3-carboxylic acid ethyl ester The title compound was prepared as described in Example 10A, substituting cyclooctanone for tetrahydro-4H-pyran-4-one. MS (ESI+) m/z 254 (M+H)$^+$

Example 159B

2-[(Hexahydro-2,5-methano-pentalene-3a-carbonyl)-amino]-4,5,6,7,8,9-hexahydro-cycloocta[b]thiophene-3-carboxylic acid ethyl ester The title compound was prepared as described in Example 167A, substituting Example 159A for Example 10A. MS (ESI+) m/z 403 (M+H)$^+$

Example 159C

2-[(Hexahydro-2,5-methano-pentalene-3a-carbonyl)-amino]-4,5,6,7,8,9-hexahydro-cycloocta[b]thiophene-3-carboxylic acid The title compound was prepared as described in Example 166B, substituting Example 159B for Example 166A. The crude product was used for the next step without further purification. MS (ESI+) m/z 375 (M+H)$^+$

Example 159D

2-[(hexahydro-2,5-methanopentalen-3a(1H)-ylcarbonyl)amino]-N-propyl-4,5,6,7,8,9-hexahydrocycloocta[b]thiophene-3-carboxamide The title compound was prepared as described in Example 166C, substituting Example 159C for Example 166B. $^1$H NMR (300 MHz, dimethylsulfoxide-d$_6$) δ ppm 0.88 (t, J=7.29 Hz, 3H) 1.07-1.70 (m, 14H) 1.85 (s, 4H) 1.90-2.04 (m, 2H) 2.31 (s, 2H) 2.60 (d, 1H) 2.73 (d, J=4.75 Hz, 2H) 2.78-2.90 (m, 2H) 3.21 (s, 2H) 7.76 (s, 1H) 11.10 (s, 1H). MS (ESI+) m/z 415.2 (M+H)$^+$

Example 160

N-{3-[(4-hydroxypiperidin-1-yl)carbonyl]-4,7-dihydro-5H-thieno[2,3-c]pyran-2-yl}hexahydro-2,5-methanopentalene-3a(1H)-carboxamide The title compound was prepared as described in Example 166C, substituting Example 167B for Example 166B, and piperidin-4-ol for propylamine. $^1$H NMR (300 MHz, dimethylsulfoxide-d$_6$) δ ppm 1.17-2.06 (m, 16H) 2.29 (s, 3H) 2.55-2.72 (m, 1H) 2.78-3.11 (m, 2H) 3.36-3.53 (m, 2H) 3.71-3.96 (m, 2H) 4.64 (s, 2H) 5.04 (s, 1H) 9.26-9.68 (m, 1H). MS (ESI+) m/z 431.2 (M+H)$^+$

Example 161 isobutyl 2-[(hexahydro-2,5-methanopentalen-3a(1H)-ylcarbonyl)amino]-4,5,6,7-tetrahydro-1-benzothiophene-3-carboxylate

Example 161A

2-Amino-4,5,6,7-tetrahydro-benzo[b]thiophene-3-carboxylic acid isobutyl ester

The title compound was prepared from cyclohexanone and cyano-acetic acid isobutyl ester by the procedure described for Example 10A. MS (ESI+) m/z 254 (M+H)$^+$.

Example 161B isobutyl 2-[(hexahydro-2,5-methanopentalen-3a (1H)-ylcarbonyl)amino]-4,5,6,7-tetrahydro-1-benzothiophene-3-carboxylate The title compound was prepared from Example 161A by the procedure described for Example 167A. $^1$H NMR (300 MHz, dimethylsulfoxide-$d_6$) δ ppm 0.97 (d, J=6.78 Hz, 6H) 1.47-2.10 (m, 12H) 2.22-2.44 (m, 4H) 2.56-2.82 (m, 6H) 4.06 (d, J=6.44 Hz, 2H) 11.47 (s, 1H). MS (ESI+) m/z 402.1 (M+H)$^+$. Anal. calcd. for C23H31NO3S; C, 68.79; H, 7.78; N, 3.49. Found: C, 68.79; H, 7.99; N, 2.96.

Example 162 isopropyl 2-[(hexahydro-2,5-methanopentalen-3a (1H)-ylcarbonyl)amino]-4,5,6,7-tetrahydro-1-benzothiophene-3-carboxylate

Example 162A

2-Amino-4,5,6,7-tetrahydro-benzo[b]thiophene-3-carboxylic acid isopropyl ester

The title compound was prepared as described in Example 10A, substituting cyclohexanone for tetrahydro-4H-pyran-4-one and cyano-acetic acid isopropyl ester for ethyl cyanoacetate. MS (ESI+) m/z 240 (M+H)$^+$

Example 162B isopropyl 2-[(hexahydro-2,5-methanopentalen-3a (1H)-ylcarbonyl)amino]-4,5,6,7-tetrahydro-1-benzothiophene-3-carboxylate The title compound was prepared as described in Example 167A, substituting Example 162A for Example 10A. $^1$H NMR (300 MHz, dimethylsulfoxide-$d_6$) δ ppm 1.31 (d, J=6.10 Hz, 6H) 1.48-2.09 (m, 12H) 2.18-2.42 (m, 3H) 2.53-2.79 (m, 6H) 4.82-5.52 (m, 1H) 11.39 (s, 1H). MS (ESI+) m/z 388.1 (M+H)$^+$. Anal. calcd. for C22H29NO3S; C, 69.18; H, 7.54; N, 3.61. Found: C, 68.75; H, 7.79; N, 2.96.

Example 163

2-methoxyethyl 2-[(hexahydro-2,5-methanopentalen-3a(1H)-ylcarbonyl)amino]-4,5,6,7-tetrahydro-1-benzothiophene-3-carboxylate

Example 163A

2-Amino-4,5,6,7-tetrahydro-benzo[b]thiophene-3-carboxylic acid 2-methoxy-ethyl ester The title compound was prepared as described in Example 10A, substituting cyclohexanone for tetrahydro-4H-pyran-4-one and cyano-acetic acid 2-methoxy-ethyl ester for ethyl cyanoacetate. MS (ESI+) m/z 256 (M+H)$^+$

Example 163B 2-methoxyethyl 2-[(hexahydro-2,5-methanopentalen-3a(1H)-ylcarbonyl)amino]-4,5,6,7-tetrahydro-1-benzothiophene-3-carboxylate The title compound was prepared as described in Example 167A, substituting Example 163A for Example 10A. $^1$H NMR (300 MHz, dimethylsulfoxide-$d_6$) δ ppm 1.48-2.14 (m, 14H) 2.33 (s, 2H) 2.54-2.80 (m, 5H) 3.29 (s, 3H) 3.63 (dd, J=5.43, 3.73 Hz, 2H) 4.13-4.56 (m, 2H) 11.25 (s, 1H). MS (ESI+) m/z 404.1 (M+H)$^+$. Anal. calcd. for C22H29NO4S; C, 65.48; H, 7.24; N, 3.47. Found: C, 65.66; H, 7.07; N, 3.24

Example 164 ethyl 4-cyclopropyl-2-[(hexahydro-2,5-methanopentalen-3a(1H)-ylcarbonyl)amino]thiophene-3-carboxylate

Example 164A 2-amino-4-cyclopropyl-thiophene-3-carboxylic acid ethyl ester

The title compound was prepared as described in Example 10A, substituting 1-cyclopropyl-ethanone for tetrahydro-4H-pyran-4-one. MS (ESI+) m/z 212 (M+H)$^+$

Example 164B ethyl 4-cyclopropyl-2-[(hexahydro-2,5-methanopentalen-3a(1H)-ylcarbonyl)amino]thiophene-3-carboxylate The title compound was prepared as described in Example 167A, substituting Example 164A for Example 10A. $^1$H NMR (300 MHz, dimethylsulfoxide-$d_6$) δ ppm 0.45-0.68 (m, 2H) 0.69-0.95 (m, 2H) 1.33 (t, J=7.12 Hz, 3H) 1.54-2.10 (m, 10H) 2.24-2.42 (m, 2H) 2.65 (t, J=5.76 Hz, 2H) 4.34 (q, J=7.12 Hz, 2H) 6.55 (s, 1H) 11.41 (s, 1H). MS (ESI+) m/z 360.1 (M+H)$^+$

Example 165

4-cyclopropyl-2-[(hexahydro-2,5-methanopentalen-3a(1H)-ylcarbonyl)amino]-N-propylthiophene-3-carboxamide

Example 165A 4-cyclopropyl-2-[(hexahydro-2,5-methano-pentalene-3a-carbonyl)-amino]-thiophene-3-carboxylic acid The title compound was prepared as described in Example 166B, substituting Example 164B for Example 166A. The crude product was used for the next step without further purification. MS (ESI+) m/z 332 (M+H)$^+$

Example 165B 4-cyclopropyl-2-[(hexahydro-2,5-methanopentalen-3a(1H)-ylcarbonyl)amino]-N-propylthiophene-3-carboxamide The title compound was prepared as described in Example 166C, substituting Example 165A for Example 166B. $^1$H NMR (300 MHz, dimethylsulfoxide-$d_6$) δ ppm 0.55-0.78 (m, 2H) 0.80-1.06 (m, 5H) 1.42-1.73 (m, 6H) 1.71-1.96 (m, 4H) 1.94-2.15 (m, 3H) 2.33 (s, 2H) 2.61 (t, J=6.78 Hz, 1H) 6.65 (s, 1H) 7.63 (t, J=5.59 Hz, 1H) 12.38 (s, 1H). MS (ESI+) m/z 373.1 (M+H)$^+$. Anal. calcd. for C21H28N2O2S; C, 67.71; H, 7.58; N, 7.52. Found: C, 67.85; H, 7.60; N, 7.46

Example 166

2-[(1-adamantylcarbonyl)amino]-N-propyl-4,7-dihydro-5H-thieno[2,3-c]pyran-3-carboxamide

Example 166A

2-[(Adamantane-1-carbonyl)-amino]-4,7-dihydro-5H-thieno[2,3-c]pyran-3-carboxylic acid ethyl ester To a solution of Example 10A (568 mg, 2.50 mmol) and triethylamine (1.05 mL, 7.50 mmol) in anhydrous tetrahydrofuran (20 mL) was added 546 mg (2.75 mmol) adamantane-1-carbonyl chloride (J. Am. Chem. Soc., 124 (9), 2056-2064, 2002). The mixture was stirred under $N_2$ atmosphere at room temperature overnight. Water (20 mL) was added and the mixture was extracted with dichloromethane (3×20 mL). The combined organic extracts were dried over magnesium sulfate, filtered, and concentrated by rotary evaporator to afford a crude solid. Recrystallization from ethyl acetate/hexanes afforded the title compound. Additional product was obtained by concentration of the liquor and subsequent recrystallization. $^1$H NMR (dimethylsulfoxide-$d_6$) δ 1.32 (t, J=7.1 Hz, 3H), 1.67-1.77 (m, 6H), 1.89-1.90 (m, 6H), 2.05 (br s, 3H), 2.78 (t, J=5.6 Hz, 2H), 3.84 (t, J=5.8 Hz, 2H), 4.32 (q, J=7.1 Hz, 2H), 4.62 (br s, 2H), 11.37 (br s, 1H). MS (ESI+) m/z 390.4 (M+H)$^+$.

Example 166B

2-[(Adamantane-1-carbonyl)-amino]-4,7-dihydro-5H-thieno[2,3-c]pyran-3-carboxylic acid A mixture of Example 166A (779 mg, 2.00 mmol) and solid potassium hydroxide (841 mg. 15.0 mmol) in ethanol (10 mL) and water (2 mL) was heated to reflux for 1 hour. After cooling to room temperature, 1N HCl was added to adjust the pH to 1. The mixture was extracted with ethyl acetate (4×20 mL). The combined organic extracts were dried over magnesium sulfate, filtered, and concentrated by rotary evaporator to afford a crude powder. The product was recrystallized from ethyl acetate/hexanes to afford the title compound. MS (ESI+) m/z 362.1 (M+H)$^+$.

Example 166C

2-[(1-adamantylcarbonyl)amino]-N-propyl-4,7-dihydro-5H-thieno[2,3-c]pyran-3-carboxamide A solution of Example 166B (195 mg, 0.500 mmol), hydroxybenzotriazole (135 mg, 1.00 mmol), triethylamine (278 μL, 2.00 mmol), and propylamine (82 μL, 1.0 mmol) was prepared in anhydrous dimethylformamide (5 mL). 1-[3-(dimethylamino)propyl]-3-ethylcarbodiimide hydrochloride (143 mg, 0.750 mmol) was added. The mixture was stirred at room temperature for 24 hours. The reaction was monitored by LC-MS. Water (10 mL) was added, and the mixture was extracted with dichloromethane (4×10 mL). The combined organic extracts were dried over magnesium sulfate, filtered, and concentrated by rotary evaporator to afford a crude oil. The product was purified by flash chromatography (silica gel: 25% ethyl acetate in hexanes, product $R_f$=0.3) to afford a semisolid. The product was recrystallized from ethyl acetate/hexanes to afford the title compound. $^1$H NMR (dimethylsulfoxide-$d_6$) δ 0.89 (t, J=7.5 Hz, 3H), 1.54 (q, J=7.0 Hz, 2H), 1.71-1.72 (m, 6H), 1.85-1.86 (m, 6H), 2.04 (br s, 3H), 2.81-2.85 (m, 2H), 3.23 (q, J=6.8 Hz, 2H), 3.84 (t, J=5.3 Hz, 2H), 4.64 (s, 2H), 7.34 (br s, 1H), 11.91 (br s, 1H). MS (ESI+) m/z 403.2 (M+H)$^+$. Anal. calcd. for C22H30N2O3S: C, 65.64; H, 7.51; N, 6.96. Found: C, 65.19; H, 7.61; N, 5.13.

Example 167

2-[(hexahydro-2,5-methanopentalen-3a(1H)-ylcarbonyl)amino]-N-propyl-4,7-dihydro-5H-thieno[2,3-c]pyran-3-carboxamide

Example 167A

2-[(Hexahydro-2,5-methano-pentalene-3a-carbonyl)-amino]-4,7-dihydro-5H-thieno[2,3-c]pyran-3-carboxylic acid ethyl ester Step One To an oven-dried, $N_2$-purged 250-mL, round-bottomed flask containing a magnetic stir bar were added the 3-noradamantanecarboxylic acid (4.99 g, 30.0 mmol) and anhydrous toluene (100 mL). Thionyl chloride (3.28 mL, 45.0 mmol) was added and a reflux condenser with $N_2$ inlet was attached. The solution was heated to reflux and stirred for 6 hours. After cooling, the solution was concentrated by rotary evaporator to afford 5.5 g of an oil that was used for the next step without further purification.

Step Two

The title compound was prepared as described in Example 166A, substituting the product of step one for adamantane-1-carbonyl chloride (J. Am. Chem. Soc., 124 (9), 2056-2064, 2002). $^1$H NMR (dimethylsulfoxide-$d_6$) δ 1.31 (t, J=7.1 Hz, 3H), 1.62-1.68 (m, 3H), 1.77-1.84 (m, 2H), 1.87-1.91 (m, 2H), 2.00-2.04 (m 2H), 2.34 (br s, 2H), 2.64 (t, J=6.6 Hz, 1H), 2.79 (t, J=5.6 Hz, 2H), 3.29 (br s, 1H), 3.84 (t, J=5.6 Hz, 2H), 4.30 (q, J=7.1 Hz, 2H), 4.62 (br s, 2H), 11.32 (br s, 1H). MS (ESI+) m/z 376.1 (M+H)$^+$. Anal. calcd. for $C_{20}H_{25}NO_4S$: C, 63.97; H, 6.71; N, 3.73. Found: C, 63.74; H, 6.75; N, 3.68.

Example 167B

2-[(Hexahydro-2,5-methano-pentalene-3a-carbonyl)-amino]-4,7-dihydro-5H-thieno[2,3-c]pyran-3-carboxylic acid The title compound was prepared as described in Example 166B, substituting Example 167A for Example 166A. The crude product was used for the next step without further purification.

Example 167C

2-[(hexahydro-2,5-methanopentalen-3a(1H)-ylcarbonyl)amino]-N-propyl-4,7-dihydro-5H-thieno[2,3-c]pyran-3-carboxamide The title compound was prepared as described in Example 166C, substituting Example 167B for Example 166B. $^1$H NMR (dimethylsulfoxide-$d_6$) δ 0.89 (t, J=7.3 Hz, 3H), 1.53 (q, J=7.1 Hz, 2H), 1.61-1.67 (m, 4H), 1.75-1.87 (m, 4H), 1.97-2.01 (m, 2H), 2.33 (br s, 2H), 2.60 (t, J=6.8 Hz, 1H), 2.83 (t, J=5.3 Hz, 1H), 3.22 (q, J=6.7 Hz, 2H), 3.84 (t, J=5.4 Hz, 2H), 4.65 (br s, 2H), 7.34 (t, J=5.2 Hz, 2H), 11.88 (br s, 1H). MS (ESI+) m/z 389.2 (M+H)$^+$. Anal. calcd. for $C_{21}H_{28}N_2O_3S$: C, 64.92; H, 7.26; N, 7.21. Found: C, 64.99; H, 7.39; N, 7.21.

Example 168

N-[3-(morpholin-4-ylcarbonyl)-4,7-dihydro-5H-thieno[2,3-c]pyran-2-yl]adamantane-1-carboxamide The title compound was prepared as described in Example 166C, substituting morpholine for propylamine. $^1$H NMR (dimethylsulfoxide-$d_6$) δ 1.69 (br s, 6H), 1.87-1.88 (m, 6H), 2.02 (br s, 3H), 3.29-3.31 (m, 2H), 3.37-3.57 (m, 8H), 3.82 (t, J=5.4 Hz, 2H), 4.63 (br s, 2H), 9.78 (br s, 1H). MS (ESI+) m/z 431.1 (M+H)$^+$. Anal. calcd. for $C_{23}H_{30}N_2O_4S$: C, 64.16; H, 7.02; N, 6.51. Found: C, 64.33; H, 7.10; N, 6.52.

Example 169

N-[3-(morpholin-4-ylcarbonyl)-4,7-dihydro-5H-thieno[2,3-c]pyran-2-yl]hexahydro-2,5-methanopentalene-3a(1H)-carboxamide The title compound was prepared from 2-[(hexahydro-2,5-methano-pentalene-3a-carbonyl)-amino]-4,7-dihydro-5H-thieno[2,3-c]pyran-3-carboxylic acid (Example 167B) and morpholine according to the procedure described for Example 166C. $^1$H NMR (dimethylsulfoxide-$d_6$) δ 1.58-1.62 (m, 4H), 1.75-1.81 (m, 2H), 1.88-1.97 (m, 4H), 2.29 (br s, 2H), 2.66 (t, J=7.0 Hz, 1H), 3.29-3.31 (m, 2H), 3.41 (br s, 4H), 3.71 (br s, 4H), 3.83 (t, J=5.6 Hz, 2H), 4.64 (br s, 2H), 9.74 (br s, 1H). MS (ESI+) m/z 417.2 (M+H)$^+$. Anal. calcd. for $C_{22}H_{28}N_2O_4S$: C, 63.44; H, 6.78; N, 7.21. Found: C, 63.29; H, 6.77; N, 6.65.

Example 170

2-{[(1-phenylcyclopentyl)carbonyl]amino}-N-propyl-4,7-dihydro-5H-thieno[2,3-c]pyran-3-carboxamide

Example 170A

2-[(1-Phenyl-cyclopentanecarbonyl)-amino]-4,7-dihydro-5H-thieno[2,3-c]pyran-3-carboxylic acid ethyl ester The title compound was prepared as described in Example 167A, substituting 1-phenyl-cyclopentanecarboxylic acid for 3-noradamantanecarboxylic acid. $^1$H NMR (dimethylsulfoxide-$d_6$) δ 1.23 (t, J=7.1 Hz, 3H), 1.67-1.72 (m, 4H), 2.02-2.11 (m, 2H), 2.47-2.56 (m, 2H), 2.72 (t, J=5.6 Hz, 2H), 3.80 (t, J=5.6 Hz, 2H), 4.20 (q, J=7.1 Hz, 2H), 4.58-4.60 (m, 2H), 7.27-7.33 (m, 1H), 7.39-7.41 (m, 4H), 11.01 (br s, 1H). MS (ESI+) m/z 400.2 (M+H)$^+$

Example 170B

2-[(1-Phenyl-cyclopentanecarbonyl)-amino]-4,7-dihydro-5H-thieno[2,3-c]pyran-3-carboxylic acid The title compound was prepared as described in Example 166B, substituting Example 170A for Example 166A. The crude product was used for the next step without further purification. LCMS (ESI+) m/z 372.2 (M+H)$^+$

Example 170C

2-{[(1-phenylcyclopentyl)carbonyl]amino}-N-propyl-4,7-dihydro-5H-thieno[2,3-c]pyran-3-carboxamide The title compound was prepared as described in Example 166C, substituting Example 170B for Example 166B. $^1$H NMR (dimethylsulfoxide-$d_6$) δ 0.86 (t, J=7.5 Hz, 3H), 1.48 (q, J=7.3 Hz, 2H) 1.64-1.72 (m, 4H), 1.98-2.04 (m, 2H), 2.49-2.52 (m, 2H), 2.77 (t, J=5.4 Hz, 2H), 3.16 (q, J=6.6 Hz, 2H) 3.80 (t, J=5.4 Hz, 2H), 4.61 (br s, 2H), 7.23-7.33 (m, 2H), 7.35-7.37 (m, 4H), 11.69 (br s, 1H). MS (ESI+) m/z 413.1 (M+H)$^+$. Anal. calcd. for $C_{23}H_{28}N_2O_3S$: C, 66.96; H, 6.84; N, 6.79. Found: C, 66.94; H, 6.89; N, 6.73

Example 171

N-propyl-2-({[(1R,3S)-1,2,2,3-tetramethylcyclopentyl]carbonyl}amino)-4,7-dihydro-5H-thieno[2,3-c]pyran-3-carboxamide

Example 171A

2-[(1,2,2,3-Tetramethyl-cyclopentanecarbonyl)-amino]-4,7-dihydro-5H-thieno[2,3-c]pyran-3-carboxylic acid ethyl ester The title compound was prepared as described in Example 167A, substituting D-campholic acid for 3-noradamantanecarboxylic acid. LCMS (ESI+) m/z 380.3 (M+H)$^+$

Example 171B

2-[(1,2,2,3-Tetramethyl-cyclopentanecarbonyl)-amino]-4,7-dihydro-5H-thieno[2,3-c]pyran-3-carboxylic acid The title compound was prepared as described in Example 166B, substituting Example 171A for Example 166A. The crude product was used for the next step without further purification. LCMS (ESI+) m/z 352.2 (M+H)$^+$

Example 171C

N-propyl-2-({[(1R,3S)-1,2,2,3-tetramethylcyclopentyl]carbonyl}amino)-4,7-dihydro-5H-thieno[2,3-c]pyran-3-carboxamide The title compound was prepared as described in Example 166C, substituting Example 171B for Example 166B. $^1$H NMR (dimethylsulfoxide-$d_6$) δ 0.55 (s, 3H), 0.83 (d, J=6.4 Hz, 3H), 0.89 (t, J=7.3 Hz, 3H), 1.02 (s, 3H), 1.20 (s, 3H), 1.24-1.31 (m, 1H), 1.42-1.59 (m, 3H), 1.84-1.99 (m, 2H), 2.39-2.47 (m, 1H), 2.83 (t, J=5.4 Hz, 2H), 3.20-3.27 (m, 2H), 3.84 (t, J=5.4 Hz, 2H), 4.65 (br s, 2H), 7.34 (t, J=5.6 Hz, 1H), 11.88 (br s, 1H). MS (ESI+) m/z 393.4 (M+H)$^+$. Anal. calcd. for $C_{21}H_{32}N_2O_3S$: C, 64.25; H, 8.22; N, 7.14. Found: C, 64.24; H, 8.38; N, 6.93.

Example 172

(1R,3S)-1,2,2,3-tetramethyl-N-[3-(morpholin-4-ylcarbonyl)-4,7-dihydro-5H-thieno[2,3-c]pyran-2-yl]cyclopentanecarboxamide The title compound was prepared as described in Example 166C, substituting Example 171B for Example 166B and morpholine for propylamine. $^1$H NMR (dimethylsulfoxide-$d_6$) δ 0.60 (s, 3H), 0.83 (d, J=6.4 Hz, 3H), 1.01 (s, 3H), 1.18 (s, 3H), 1.24-1.32 (m, 1H), 1.40-1.48 (m, 1H), 1.78-1.98 (m, 2H), 2.34-2.44 (m, 1H), 2.50-2.53 M, 2H), 3.38-3.46 (m, 4H), 3.58 (br s, 4H), 3.83 (t, J=5.3 Hz, 2H), 4.65 (br s, 2H), 9.51 (br s, 1H). MS (ESI+) m/z 421.2 (M+H)+. Anal. calcd. for C$_{22}$H$_{32}$N$_2$O$_4$S: C, 62.83; H, 7.67; N, 6.66. Found: C, 62.97; H, 7.67; N, 6.65.

Example 173

(1R,3aS,4R,6aR)-3a,6a-dimethyl-N-{3-[(propylamino)carbonyl]-4,7-dihydro-5H-thieno[2,3-c]pyran-2-yl}hexahydro-1H-1,4-methanocyclopenta[c]furan-1-carboxamide Example 173A ethyl 2-({[(1R,3aS,4R,6aR)-3a,6a-dimethylhexahydro-1H-1,4-methanocyclopenta[c]furan-1-yl]carbonyl}amino)-4,7-dihydro-5H-thieno[2,3-c]pyran-3-carboxylate The title compound was prepared as described in Example 167A, substituting 6,7-dimethyl-4-oxa-tricyclo[4.3.0.0$^{3,7}$]nonane-3-carboxylic acid for 3-noradamantanecarboxylic acid. $^1$H NMR (dimethylsulfoxide-d$_6$, 300 MHz) δ 0.78 (s, 3H), 0.89 (s, 3H), 1.30 (t, J=7.1 Hz, 3H), 1.34-1.38 (m, 2H), 1.67-1.79 (m, 3H), 1.94-1.99 (m, 2H), 2.78 (t, J=5.2 Hz, 2H), 3.63 (d, J=8.0 Hz, 1H), 3.82-3.85 (m, 3H), 4.24-4.32 (m, 2H), 4.62 (br s, 2H), 11.54 (br s, 1H), MS (ESI+) m/z 406.1 (M+H)+

Example 173B 2-({[(1R,3aS,4R,6aR)-3a,6a-dimethylhexahydro-1H-1,4-methanocyclopenta[c]furan-1-yl]carbonyl}amino)-4,7-dihydro-5H-thieno[2,3-c]pyran-3-carboxylic acid The title compound was prepared as described in Example 166B, substituting Example 173A for Example 166A. The crude product was used for the next step without further purification. LCMS (ESI+) m/z 378.3 (M+H)+

Example 173C (1R,3aS,4R,6aR)-3a,6a-dimethyl-N-{3-[(propylamino)carbonyl]-4,7-dihydro-5H-thieno[2,3-c]pyran-2-yl}hexahydro-1H-1,4-methanocyclopenta[c]furan-1-carboxamide The title compound was prepared as described in Example 166C, substituting Example 173B for Example 166B. $^1$H NMR (dimethylsulfoxide-d$_6$, 300 MHz) δ 0.77 (s, 3H), 0.89 (t, J=7.3 Hz, 3H), 0.89 (s, 3H), 1.27-1.38 (m, 2H), 1.45-1.58 (m, 2H), 1.69-1.71 (m, 2H), 1.96-1.99 M, 2H), 2.71-2.84 (m, 2H), 3.13-3.25 M, 2H), 3.61 (d, J=8.1 Hz, 2H), 3.79-3.89 (m, 3H), 4.65 (br s, 2H), 7.40 (t, J=5.6, 1H), 11.73 (br s, 1H). MS (ESI+) m/z 419.2 (M+H)+. Anal. calcd. for C$_{22}$H$_{30}$N$_2$O$_4$S: C, 63.13; H, 7.22; N, 6.69. Found: C, 62.99; H, 7.21; N, 6.60.

Example 174

(1R,3aS,4R,6aR)-3a,6a-dimethyl-N-[3-(morpholin-4-ylcarbonyl)-4,7-dihydro-5H-thieno[2,3-c]pyran-2-yl]hexahydro-1H-1,4-methanocyclopenta[c]furan-1-carboxamide The title compound was prepared as described in Example 166C, substituting Example 173B for Example 166B and morpholine for propylamine. $^1$H NMR (dimethylsulfoxide-d$_6$, 300 MHz) δ 0.79 (s, 3H), 0.88 (s, 3H), 1.27-1.38 (m, 2H), 1.64-1.76 (m, 3H), 1.91-1.98 (m, 2H), 3.42-3.86 (m, 14H), 4.68 (br s, 2H), 9.75 (br s, 1H). MS (ESI+) m/z 447.2 (M+H)+. Anal. calcd. for C$_{23}$H$_{30}$N$_2$O$_5$S: C, 61.86; H, 6.77; N, 6.27. Found: C, 61.93; H, 6.89; N, 6.25.

Example 175

2-{[(1-methylcyclohexyl)carbonyl]amino}-N-propyl-4,7-dihydro-5H-thieno[2,3-c]pyran-3-carboxamide Example 175A 2-[(1-Methyl-cyclohexanecarbonyl)-amino]-4,7-dihydro-5H-thieno[2,3-c]pyran-3-carboxylic acid ethyl ester The title compound was prepared as described in Example 167A, substituting 1-methylcyclohexanecarboxylic acid for 3-noradamantanecarboxylic acid. $^1$H NMR (dimethylsulfoxide-d$_6$, 300 MHz) δ 1.19 (s, 3H), 1.31 (t, J=7.1 Hz, 3H), 1.33-1.58 (m, 8H), 1.91-1.98 (m, 2H), 2.79 (t, J=5.6 Hz, 2H), 3.84 (t, J=5.6 Hz, 2H), 4.31 (q, J=7.1 Hz, 2H), 4.62 (br s, 2H), 11.44 (br s, 1H). MS (ESI+) m/z 352.3 (M+H)+

Example 175B

2-[(1-Methyl-cyclohexanecarbonyl)-amino]-4,7-dihydro-5H-thieno[2,3-c]pyran-3-carboxylic acid The title compound was prepared as described in Example 166B, substituting Example 175A for Example 166A. The crude product was used for the next step without further purification. LCMS (ESI+) m/z 323.2 (M+H)+

Example 175C

2-{[(1-methylcyclohexyl)carbonyl]amino}-N-propyl-4,7-dihydro-5H-thieno[2,3-c]pyran-3-carboxamide The title compound was prepared as described in Example 166C, substituting Example 175B for Example 166B. $^1$H NMR (dimethylsulfoxide-d$_6$, 300 MHz) δ 0.89 (t, J=7.5 HZ, 3H), 1.15 (s, 3H), 1.32-1.59 (m, 10H), 1.89-1.95 (m, 2H), 2.83 (t, J=5.4 Hz, 2H), 3.20-3.29 (m, 2H), 4.65 (br s, 2H), 3.84 (t, J=5.4 Hz, 2H), 7.35 (t, J=5.6 Hz, 2H), 11.99 (br s, 1H). MS (ESI+) m/z 365.1 (M+H)+. Anal. calcd. for C$_{19}$H$_{28}$N$_2$O$_3$S: C, 62.61; H, 7.74; N, 7.69. Found: C, 62.64; H, 7.88; N, 7.78.

Example 176

1-methyl-N-[3-(morpholin-4-ylcarbonyl)-4,7-dihydro-5H-thieno[2,3-c]pyran-2-yl]cyclohexanecarboxamide The title compound was prepared as described in Example 166C, substituting Example 175B for Example 166B, and morpholine for propylamine. $^1$H NMR (dimethylsulfoxide-d$_6$, 300 MHz) δ 1.15 (s, 3H), 1.24-1.53 (m, 8H), 1.96-2.02 (m, 2H), 2.47-2.51 (m, 2H), 3.38-3.44 (m, 4H), 3.55 (br s, 4H), 3.83 (t, J=5.4 Hz, 2H), 4.64 (br s, 2H), 9.77 (br s, 1H). MS (ESI+) m/z 393.1 (M+H)+. Anal. calcd. for C$_{20}$H$_{28}$N$_2$O$_4$S: C, 61.20; H, 7.19; N, 7.14. Found: C, 61.33; H, 7.27; N, 7.15.

Example 177

2-[(cycloheptylcarbonyl)amino]-N-propyl-4,7-dihydro-5H-thieno[2,3-c]pyran-3-carboxamide

Example 177A 2-(Cycloheptanecarbonyl-amino)-4,7-dihydro-5H-thieno[2,3-c]pyran-3-carboxylic acid ethyl ester The title compound was prepared as described in Example 167A, substituting cycloheptanecarboxylic acid for 3-noradamantanecarboxylic acid. $^1$H NMR (dimethylsulfoxide-$d_6$, 300 MHz) δ 1.32 (t, J=7.1 Hz, 3H), 1.48-1.74 (m, 10H), 1.87-1.96 (m, 2H), 2.67-2.75 (m, 1H), 2.78 (t, J=5.8 Hz, 2H), 3.84 (t, J=5.6 Hz, 2H), 4.29 (q, J=7.1 Hz, 2H), 4.61 (br s, 2H), 11.03 (br s, 1H). MS (ESI+) m/z 352.1 (M+H)$^+$.

Example 177B 2-(Cycloheptanecarbonyl-amino)-4,7-dihydro-5H-thieno[2,3-c]pyran-3-carboxylic acid The title compound was prepared as described in Example 166B, substituting Example 177A for Example 166A. The crude product was used for the next step without further purification. LCMS (ESI+) m/z 324.2 (M+H)$^+$.

Example 177C

2-[(cycloheptylcarbonyl)amino]-N-propyl-4,7-dihydro-5H-thieno[2,3-c]pyran-3-carboxamide The title compound was prepared as described in Example 166C, substituting Example 177B for Example 166B. $^1$H NMR (dimethylsulfoxide-$d_6$, 300 MHz) δ 0.88 (t, J=7.5 Hz, 3H), 1.45-1.74 (m, 12H), 1.83-1.91 (m, 2H), 2.56-2.65 (m, 1H), 2.77 (t, J=5.4 Hz, 2H), 3.22 (q, J=6.5 Hz, 2H), 3.83 (t, J=5.4 Hz, 2H), 4.63 (br s, 2H), 7.46 (t, J=5.3 Hz, 1H), 11.33 (Br s, 1H). MS (ESI+) m/z 365.1 (M+H)$^+$. Anal. calcd. for $C_{19}H_{28}N_2O_3S$: C, 62.61; H, 7.74; N, 7.69. Found: C, 61.79; H, 7.54; N, 7.54.

Example 178

N-[3-(morpholin-4-ylcarbonyl)-4,7-dihydro-5H-thieno[2,3-c]pyran-2-yl]cycloheptanecarboxamide The title compound was prepared as described in Example 166C, substituting Example 177B for Example 166B and morpholine for propylamine. $^1$H NMR (dimethylsulfoxide-$d_6$, 300 MHz) δ 1.43-1.83 (m, 12H), 2.41-2.46 (m, 2H), 2.62-2.73 (m, 1H), 3.29-3.53 (m, 8H), 3.64-3.68 (m, 2H), 3.82 (t, J=5.4 Hz, 2H), 4.61 (s, 2H), 10.43 (br s, 1H). MS (ESI+) m/z 393.1 (M+H)$^+$. Anal. calcd. for $C_{20}H_{28}N_2O_4S$: C, 61.20; H, 7.19; N, 7.14. Found: C, 60.40; H, 7.08; N, 7.04.

Example 179 ethyl 2-{[(7,7-dimethyl-2-oxobicyclo[2.2.1]hept-1-yl)carbonyl]amino}-4,7-dihydro-5H-thieno[2,3-c]pyran-3-carboxylate The title compound was prepared as described in Example 167A, substituting ketopinic acid for 3-noradamantanecarboxylic acid. $^1$H NMR (dimethylsulfoxide-$d_6$, 300 MHz) δ 1.00 (s, 3H), 1.12 (s, 3H), 1.31 (t, J=7.1 Hz, 3H), 1.47-1.56 (m, 1H), 1.66-1.75 (m, 1H), 2.03-2.18 (m, 3H), 2.41-2.46 (m, 1H), 2.61-2.67 (m, 1H), 2.80 (t, J=5.6 Hz, 2H), 3.84 (t, J=5.8 Hz, 2H), 4.32 (q, J=7.1 Hz, 2H), 4.63 (s, 2H), 11.73 (br s, 1H). MS (ESI+) m/z 391.9 (M+H)$^+$. Anal. calcd. for $C_{20}H_{25}NO_5S$: C, 61.36; H, 6.44; N, 3.58. Found: C, 61.24; H, 6.31; N, 3.68.

Example 180

2-[(hexahydro-2,5-methanopentalen-3a(1H)-ylcarbonyl)amino]-N-(2-methoxyethyl)-4,7-dihydro-5H-thieno[2,3-c]pyran-3-carboxamide The title compound was prepared as described in Example 166C, substituting Example 167B for Example 166B and 2-methoxyethylamine for propylamine. $^1$H NMR (dimethylsulfoxide-$d_6$, 300 MHz) δ 1.61-1.67 (m, 4H), 1.75-1.87 (m, 4H), 1.97-2.01 (m, 2H), 2.32 (br s, 2H), 2.58-2.63 (m, 1H), 2.81 (t, J=5.3 Hz, 2H), 3.27 (s, 3H), 3.42-3.45 (m, 4H), 3.84 (t, J=5.4 Hz, 2H), 4.65 (br s, 2H), 7.30 (br s, 1H), 11.87 (br s, 1H). MS (ESI+) m/z 405.2 (M+H)$^+$. Anal. calcd. for $C_{21}H_{28}N_2O_4S$: C, 62.35; H, 6.98; N, 6.93. Found: C, 62.38; H, 6.91; N, 6.99.

Example 181

2-[(hexahydro-2,5-methanopentalen-3a(1H)-ylcarbonyl)amino]-N-(tetrahydro-2H-pyran-4-ylmethyl)-4,7-dihydro-5H-thieno[2,3-c]pyran-3-carboxamide The title compound was prepared as described in Example 166C, substituting Example 167B for Example 166B and C-(tetrahydropyran-4-yl)-methylamine for propylamine. $^1$H NMR (dimethylsulfoxide-$d_6$, 300 MHz) δ 1.15-1.26 (m, 2H), 1.56-1.67 (m, 4H), 1.75-1.87 (m, 5H), 1.97-2.01 (m, 2H), 2.33 (br s, 2H), 2.57-2.61 (m, 1H), 2.83 (t, J=5.4 Hz, 2H), 3.15-3.30 (m, 5H), 3.83-3.86 (m, 4H), 4.65 (br s, 2H), 7.38 (t, J=5.6 Hz, 1H), 11.82 (s, 1H). MS (ESI+) m/z 445.1 (M+H)$^+$. Anal. calcd. for $C_{24}H_{32}N_2O_4S$: C, 64.84; H, 7.25; N, 6.30. Found: C, 64.63; H, 7.41; N, 6.12.

Example 182

2-[(hexahydro-2,5-methanopentalen-3a(1H)-ylcarbonyl)amino]-N-(3-hydroxypropyl)-4,7-dihydro-5H-thieno[2,3-c]pyran-3-carboxamide The title compound was prepared as described in Example 166C, substituting Example 167B for Example 166B, and 3-aminopropan-1-ol for propylamine. $^1$H NMR (dimethylsulfoxide-$d_6$, 300 MHz) δ 1.61-1.72 (m, 6H), 1.76-1.87 (m, 4H), 1.97-2.01 (m, 2H), 2.33 (br s, 2H), 2.58-2.62 (m, 1H), 2.82 (t, J=5.4 Hz, 2H), 3.32-3.37 (m, 2H), 3.49 (q, J=5.5 Hz, 2H), 3.84 (t, J=5.3 Hz, 2H), 4.59 (t, J=5.1 Hz, 1H), 4.65 (br s, 2H), 7.37 (t, J=5.4 Hz, 1H), 2.00 (br s, 1H). MS (ESI+) m/z 405.2 (M+H)$^+$. Anal. calcd. for $C_{21}H_{28}N_2O_4S$: C, 62.35; H, 6.98; N, 6.93. Found: C, 62.22; H, 6.90; N, 6.99.

Example 183

N-ethyl-2-[(hexahydro-2,5-methanopentalen-3a(1H)-ylcarbonyl)amino]-4,7-dihydro-5H-thieno[2,3-c]pyran-3-carboxamide The title compound was prepared as described in Example 166C, substituting Example 167B for Example 166B, and ethylamine for propylamine. $^1$H NMR (dimethylsulfoxide-$d_6$, 300 MHz) δ 1.12 (t, J=7.1 Hz, 3H), 1.61-1.67 (m, 4H), 1.76-1.87 (m, 4H), 1.98-2.01 (m, 2H), 2.33 (br s, 2H), 2.60 (t, J=6.8 Hz, 1H), 2.84 (t, J=5.4 Hz, 2H), 3.22-3.32 (m, 2H), 3.84 (t, J=5.4 Hz, 2H), 4.65 (br s, 2H), 7.34 (t, J=5.4 Hz, 1H), 11.94 (br s, 1H). MS (ESI+) m/z 375.1 (M+H)$^+$.

Example 184

2-[(hexahydro-2,5-methanopentalen-3a(1H)-ylcarbonyl)amino]-N-(2-phenylethyl)-4,7-dihydro-5H-thieno[2,3-c]pyran-3-carboxamide The title compound was prepared as described in Example 166C, substituting Example 167B for Example 166B, and phenethylamine for propylamine. $^1$H NMR (dimethylsulfoxide-d$_6$, 300 MHz), 1.62-1.67 (m, 4H), 1.76-1.87 (m, 4H), 1.97-2.00 (m, 2H), 2.33 (br s, 2H), 2.57-2.66 (m, 3H), 2.85 (t, J=7.3 Hz, 2H), 3.49-3.58 (m, 2H), 3.78 (t, J=5.4 Hz, 2H), 4.63 (br s, 2H), 7.17-7.34 (m, 6H), 11.86 (br s, 1H). MS (ESI+) m/z 451.1 (M+H)$^+$. Anal. calcd. for C$_{26}$H$_{30}$N$_2$O$_3$S: C, 69.30; H, 6.71; N, 6.22. Found: C, 69.09; H, 6.68; N, 6.18.

Example 185

2-[(hexahydro-2,5-methanopentalen-3a(1H)-ylcarbonyl)amino]-N-(2-thien-2-ylethyl)-4,7-dihydro-5H-thieno[2,3-c]pyran-3-carboxamide The title compound was prepared as described in Example 166C, substituting Example 167B for Example 166B, and 2-thiophen-2-yl-ethylamine for propylamine. $^1$H NMR (dimethylsulfoxide-d$_6$, 300 MHz) δ 1.61-1.67 (m, 4H), 1.76-1.87 (m, 4H), 1.97-2.01 (m, 2H), 2.33 (br s, 2H), 2.58-2.62 (m, 1H), 2.72 (t, J=5.1 Hz, 2H), 3.07 (t, J=7.0 Hz, 2H), 3.50-3.57 (m, 2H), 3.81 (t, J=5.4 Hz, 2H), 4.64 (br s, 2H), 6.92 (dd, J=1.9, 3.9 Hz, 1H), 6.94-6.97 (m, 1H), 7.34 (dd, J=5.1, 1.4 Hz, 1H), 7.41 (t, J=5.6 Hz, 1H), 11.87 (br s, 1H). MS (ESI+) m/z 457.1 (M+H)$^+$. Anal. calcd. for C$_{24}$H$_{28}$N$_2$O$_3$S$_2$: C, 63.13; H, 6.18; N, 6.13. Found: C, 62.93; H, 6.12; N, 6.11.

Example 186

N-[2-(2-fluorophenyl)ethyl]-2-[(hexahydro-2,5-methanopentalen-3a(1H)-ylcarbonyl)amino]-4,7-dihydro-5H-thieno[2,3-c]pyran-3-carboxamide The title compound was prepared as described in Example 166C, substituting Example 167B for Example 166B, and 2-(2-fluorophenyl)ethylamine for propylamine. $^1$H NMR (dimethylsulfoxide-d$_6$, 300 MHz) δ 1.62-1.67 (m, 4H), 1.75-1.86 (m, 4H), 1.96-2.00 (m, 2H), 2.33 (br s, 2H), 2.57-2.61 (m, 1H), 2.67 (t, J=5.3 Hz, 2H), 2.89 (t, J=7.0 Hz, 2H), 3.53 (q, J=6.8 Hz, 2H), 3.79 (t, J=5.3 Hz, 2H), 4.63 (br s, 2H), 7.10-7.18 (m, 2H), 7.23-7.33 (m, 2H), 7.39 (dd, J=5.8 Hz, 1H), 11.81 (br s, 1H). MS (ESI+) m/z 469.2 (M+H)$^+$. Anal. calcd. for C$_{26}$H$_{29}$FN$_2$O$_3$S: C, 66.64; H, 6.24; N, 6.30. Found: C, 66.69; H, 6.03; N, 5.96.

Example 187

2-[(hexahydro-2,5-methanopentalen-3a(1H)-ylcarbonyl)amino]-N-[2-(2-methoxyphenyl)ethyl]-4,7-dihydro-5H-thieno[2,3-c]pyran-3-carboxamide The title compound was prepared as described in Example 166C, substituting Example 167B for Example 166B, and 2-(2-methoxyphenyl)ethylamine for propylamine. $^1$H NMR (dimethylsulfoxide-d$_6$, 300 MHz) δ 1.62-1.67 (m, 4H), 1.76-1.87 (m, 4H), 1.97-2.00 (m, 2H), 2.33 (br s, 2H), 2.57-2.61 (m, 1H), 2.66 (t, J=4.9 Hz, 2H), 2.83 (t, J=7.0 Hz, 2H), 3.50 (q, J=6.5 Hz, 2H), 3.78-3.81 (m, 5H), 4.63 (br s, 2H), 6.86 (ddd, J=7.4, 7.4, 1.2 Hz, 1H), 6.96 (dd, J=8.1, 1.0 Hz, 1H), 1.7.14 (dd, J=7.4, 1.7 Hz, 1H), 7.17-7.23 (m, 1H), 7.26 (t, J=5.4 Hz, 1H), 11.88 (br s, 1H). MS (ESI+) m/z 481.2 (M+H)$^+$. Anal. calcd. for C$_{27}$H$_{32}$N$_2$O$_4$S: C, 67.47; H, 6.71; N, 5.83. Found: C, 66.65; H, 6.76; N, 5.74.

Example 188

2-[(hexahydro-2,5-methanopentalen-3a(1H)-ylcarbonyl)amino]-N-(2-pyridin-2-ylethyl)-4,7-dihydro-5H-thieno[2,3-c]pyran-3-carboxamide The title compound was prepared as described in Example 166C, substituting Example 167B for Example 166B, and 2-(2-pyridyl)ethylamine for propylamine. $^1$H NMR (dimethylsulfoxide-d$_6$, 300 MHz) δ 1.62-1.67 (m, 4H), 1.76-1.87 (m, 4H), 1.97-2.01 (m, 2H), 2.33 (Br s, 2H), 2.58-2.60 (m, 1H), 2.70 (t, J=5.3 Hz, 2H), 3.00 (t, J=6.8 Hz, 2H), 3.65 (q, J=5.8 Hz, 2H), 3.81 (t, J=5.4 Hz, 2H), 4.64 (s, 2H), 7.23 (ddd, J=7.5, 4.9, 1.2 Hz, 1H), 7.30 (d, J=7.8 Hz, 1H), 7.52 (dd, J=5.4 Hz, 1H), 7.72 (ddd, J=7.6, 7.6, 1.7 Hz, 1H), 8.49-8.52 (m, 1H), 11.99 (br s, 1H). MS (ESI+) m/z 452.1 (M+H)$^+$. Anal. calcd. for C$_{25}$H$_{29}$N$_3$O$_3$S: C, 66.49; H, 6.47; N, 9.31. Found: C, 66.14; H, 6.44; N, 9.21.

Example 189

N-(2-cyanoethyl)-2-[(hexahydro-2,5-methanopentalen-3a(1H)-ylcarbonyl)amino]-4,7-dihydro-5H-thieno[2,3-c]pyran-3-carboxamide The title compound was prepared as described in Example 166C, substituting Example 167B for Example 166B and 3-aminopropionitrile for propylamine. $^1$H NMR (dimethylsulfoxide-d$_6$, 300 MHz) δ 1.60-1.67 (m, 4H), 1.76-1.87 (m, 4H), 1.98-2.01 (m, 2H), 2.33 (br s, 2H), 2.58-2.63 (m, 1H), 2.77 (t, J=6.6 Hz, 2H), 2.85 (t, J=5.4 Hz, 2H), 3.52 (q, J=6.4 Hz, 2H), 3.86 (t, J=5.4 Hz, 2H), 4.66 (Br s, 2H), 7.65 (t, J=5.9 Hz, 1H), 11.75 (br s, 1H). MS (ESI+) m/z 399.9 (M+H)$^+$. Anal. calcd. for C$_{21}$H$_{25}$N$_3$O$_3$S: C, 63.13; H, 6.31; N, 10.52. Found: C, 62.19; H, 5.92; N, 10.29.

Example 190

N-{3-[(propylamino)carbonyl]-4,7-dihydro-5H-thieno[2,3-c]pyran-2-yl}-2-oxatricyclo[3.3.1.1$^{3,7}$]decane-1-carboxamide

Example 190A 2-oxatricyclo-[3.3.1.1$^{3,7}$]decane-1-carboxylic acid

To a solution of 2-oxatricyclo-[3.3.1.1$^{3,7}$]decane-1-carboxylic acid methyl ester (Richard, Partch; William, Brewster; Bruce, Stokes; *Croatia Chemical Acta* (1969), 58(4), 661-669) (2.5 g, 12.6 mmol) in methanol/water (1:1, 100 mL) was added aqueous 5N NaOH solution (3.8 mL, 19 mmol). The mixture was stirred at room temperature for three hours and then extracted with methylene chloride to remove unreacted starting material. The aqueous layer was acidified (pH~2) with 6N HCl and then extracted with methylene chloride. The combined organic extracts were dried (Na$_2$SO$_4$), filtered, and concentrated to provide the title compound. MS (ESI$^+$) m/z 183 (M+H)$^+$ . . . .

Example 190B

2-[(2-Oxa-tricyclo[3.3.1.1³,⁷]decane-1-carbonyl)-amino]-4,7-dihydro-5H-thieno[2,3-c]pyran-3-carboxylic acid ethyl ester The title compound was prepared as described in Example 167A, substituting 2-oxatricyclo-[3.3.1.1³,⁷]decane-1-carboxylic acid (Example 190A) for 3-noradamantanecarboxylic acid. $^1$H NMR (dimethylsulfoxide-$d_6$, 300 MHz) δ 1.32 (t, J=7.1 Hz, 3H), 1.67-1.80 (m, 4H), 1.89-2.03 (m, 6H), 2.18 (br s, 2H), 2.80 (t, J=5.6 Hz, 2H), 3.84 (t, J=5.6 Hz, 2H), 4.29 (q, J=7.1 Hz, 2H), 4.62 (br s, 2H), 11.58 (br s, 1H). MS (ESI+) m/z 392.1 (M+H)⁺.

Example 190C

2-[(2-Oxa-tricyclo[3.3.1.1³,⁷]decane-1-carbonyl)-amino]-4,7-dihydro-5H-thieno[2,3-c]pyran-3-carboxylic acid The title compound was prepared as described in Example 166B, substituting Example 190B for Example 166A. MS (ESI+) m/z 364.1 (M+H)⁺.

Example 190D

N-{3-[(propylamino)carbonyl]-4,7-dihydro-5H-thieno[2,3-c]pyran-2-yl}-2-oxatricyclo[3.3.1.1³,⁷]decane-1-carboxamide The title compound was prepared as described in Example 166C, substituting Example 190C for Example 166B. $^1$H NMR (dimethylsulfoxide-$d_6$, 300 MHz) δ 0.90 (t, J=7.5 Hz, 3H), 1.53 (q, J=7.1 Hz, 2H), 1.66-1.76 (m, 4H), 1.87-2.01 (m, 6H), 2.17 (br s, 2H), 2.81 (t, J=5.4 Hz, 2H), 3.21 (q, J=6.1 Hz, 2H), 3.84 (t, J=5.4 Hz, 2H), 4.26 (br s, 1H), 4.65 (br s, 2H), 7.40 (t, J=5.8 Hz, 1H), 11.87 (br s, 1H). MS (ESI+) m/z 405.1 (M+H)⁺. Anal. calcd. for $C_{21}H_{28}N_2O_4S$: C, 62.35; H, 6.98; N, 6.93. Found: C, 62.27; H, 6.98; N, 6.92.

Example 191

N-(2-ethoxyethyl)-2-[(hexahydro-2,5-methanopentalen-3a(1H)-ylcarbonyl)amino]-4,7-dihydro-5H-thieno[2,3-c]pyran-3-carboxamide The title compound was prepared as described in Example 166C, substituting Example 167B for Example 166B, and 2-ethoxyethylamine for propylamine. $^1$H NMR (dimethylsulfoxide-$d_6$, 300 MHz) δ 1.11 (t, J=7.0 Hz, 3H), 1.61-1.67 (m, 4H), 1.76-1.87 (m, 4H), 1.98-2.01 (m, 2H), 2.33 (br s, 2H), 2.58-2.61 (m, 1H), 2.81 (t, J=5.4 Hz, 2H), 3.40-3.51 (m, 6H), 3.85 (t, J=5.4 Hz, 2), 4.65 (s, 2H), 7.28 (t, J=5.3 Hz, 1H), 11.89 (br s, 1H). MS (ESI+) m/z 419.1 (M+H)⁺. Anal. calcd. for $C_{22}H_{30}N_2O_4S$: C, 63.13; H, 7.22; N, 6.69. Found: C, 62.67; H, 6.90; N, 6.60.

Example 192

2-[(hexahydro-2,5-methanopentalen-3a(1H)-ylcarbonyl)amino]-N-(3-hydroxybutyl)-4,7-dihydro-5H-thieno[2,3-c]pyran-3-carboxamide The title compound was prepared as described in Example 166C, substituting Example 167B for Example 166B, and 4-amino-butan-2-ol for propylamine. $^1$H NMR (dimethylsulfoxide-$d_6$, 300 MHz) δ 1.09 (d, J=6.1 Hz, 3H), 1.50-1.67 m, 6H), 1.76-1.87 (m, 4H), 1.98-2.01 (m, 2H), 2.33 (br s, 2H), 2.58-2.62 (m, 1H), 2.81 (t, J=5.3 Hz, 2H), 3.32-3.39 (m, 2H), 3.68-3.75 (m, 1H), 3.84 (t, J=5.4 Hz, 2H), 4.65-4.67 (m, 3H), 7.41 (t, J=5.4 Hz, 1H), 12.05 (br s, 1H). MS (ESI+) m/z 419.1 (M+H)⁺. Anal. calcd. for $C_{22}H_{30}N_2O_4S$: C, 63.13; H, 7.22; N, 6.69. Found: C, 62.96; H, 7.20; N, 6.66.

Example 193

2-[(hexahydro-2,5-methanopentalen-3a(1H)-ylcarbonyl)amino]-N-[(1R)-1-(hydroxymethyl)-2-methylpropyl]-4,7-dihydro-5H-thieno[2,3-c]pyran-3-carboxamide The title compound was prepared as described in Example 166C, substituting Example 167B for Example 166B, and (R)-2-amino-3-methyl-butan-1-ol for propylamine. $^1$H NMR (dimethylsulfoxide-$d_6$, 300 MHz) δ 0.90 (dd, J=9.8, 6.8 Hz, 7H), 1.61-1.67 (m, 4H), 1.76-2.01 (m, 6H), 2.32 (br s, 2H), 2.58-2.62 (m, 1H), 2.68-2.77 (m, 1H), 2.91-3.00 (m, 1H), 3.48-3.51 (m, 2H), 3.77-3.96 (m, 3H), 4.66-4.71 (m, 3H), 6.82 (d, J=9.2 Hz, 1H), 11.79 (br s, 1H). MS (ESI+) m/z 433.2 (M+H)⁺. Anal. calcd. for $C_{23}H_{32}N_2O_4S$: C, 63.86; H, 7.46; N, 6.48. Found: C, 63.06; H, 7.52; N, 6.37.

Example 194

2-[(hexahydro-2,5-methanopentalen-3a(1H)-ylcarbonyl)amino]-N-(1-methyl-3-phenylpropyl)-4,7-dihydro-5H-thieno[2,3-c]pyran-3-carboxamide The title compound was prepared as described in Example 166C, substituting Example 167B for Example 166B, and 1-methyl-3-phenyl-propylamine for propylamine. $^1$H NMR (dimethylsulfoxide-$d_6$, 300 MHz) δ 1.60-1.66 (m, 4H), 1.75-1.87 (m, 6H), 1.97-2.01 (m, 2H), 2.32 (br s, 2H), 2.57-2.65 (m, 3H), 2.73-2.95 (m, 2H), 3.80-3.91 (m, 2H), 3.96-4.03 (m, 1H), 4.68 (Br s, 2H), 7.15-7.29 (m, 6H), 11.58 (br s, 1H). MS (ESI+) m/z 479.2 (M+H)⁺. Anal. calcd. for $C_{28}H_{34}N_2O_3S$: C, 70.26; H, 7.16; N, 5.85. Found: C, 69.64; H, 6.92; N, 5.56.

Example 195

2-[(hexahydro-2,5-methanopentalen-3a(1H)-ylcarbonyl)amino]-N-isobutyl-4,7-dihydro-5H-thieno[2,3-c]pyran-3-carboxamide The title compound was prepared as described in Example 166C, substituting Example 167B for Example 166B, and isobutylamine for propylamine. $^1$H NMR (dimethylsulfoxide-$d_6$, 300 MHz) δ 0.89 (d, J=6.8 Hz, 6H), 1.61-1.67 (m, 4H), 1.76-1.86 (m, 5H), 1.97-2.00 (m, 2H), 2.33 (br s, 2H), 2.57-2.61 (m, 1H), 2.85 (t, J=5.3 Hz, 2H), 3.10 (t, J=6.4 Hz, 2H), 3.85 (t, J=5.4 Hz, 2H), 4.65 (br s, 2H), 7.35 (t, J=5.8 Hz, 1H), 11.81 (br s, 1H). MS (ESI+) m/z 403.2 (M+H)⁺. Anal. calcd. for $C_{22}H_{30}N_2O_3S$: C, 65.64; H, 7.51; N; 6.96. Found: C, 65.17; H, 7.07; N, 6.72.

Example 196

2-[(hexahydro-2,5-methanopentalen-3a(1H)-ylcarbonyl)amino]-N-(2-methoxy-1-methylethyl)-4,7-dihydro-5H-thieno[2,3-c]pyran-3-carboxamide The title compound was prepared as described in Example 166C, substituting Example 167B for Example 166B, and 2-methoxy-1-methyl-ethylamine for propylamine. ¹H NMR (dimethylsulfoxide-$d_6$, 300 MHz) δ 1.14 (d, J=6.8 Hz, 3H), 1.61-1.67 (m, 4H), 1.76-1.87 (m, 4H), 1.97-2.01 (m, 2H), 2.33 (br s, 2H), 2.58-2.63 (m, 1H), 2.73-2.88 (m, 2H), 3.38-3.44 (m, 1H), 3.78-3.89 (m, 2H), 4.14-4.23 (m, 1H), 4.65 (br s, 2H), 7.08 (d, J=8.5 Hz, 1H), 11.64 (br s, 1H). MS (ESI+) m/z 419.2 (M+H)⁺. Anal. calcd. for $C_{22}H_{30}N_2O_4S$: C, 63.13; H, 7.22; N, 6.69. Found: C, 63.01; H, 6.67; N, 6.72.

Example 197

2-[(hexahydro-2,5-methanopentalen-3a(1H)-ylcarbonyl)amino]-N-[(2R)-tetrahydrofuran-2-ylmethyl]-4,7-dihydro-5H-thieno[2,3-c]pyran-3-carboxamide The title compound was prepared as described in Example 166C, substituting Example 167B for Example 166B, and (R)—C-(tetrahydrofuran-2-yl)-methylamine for propylamine. ¹H NMR (dimethylsulfoxide-$d_6$, 300 MHz) δ 1.54-1.87 (m, 5H), 1.75-2.01 (m, 9H), 2.32 (br s, 2H), 2.58-2.62 (m, 1H), 2.81 (br s, 2H), 3.30-3.37 (m, 2H), 3.60-3.67 (m, 1H), 3.74-3.81 (m, 1H), 3.85 (t, J=5.4 Hz, 2H), 3.93-4.01 (m, 1H), 4.65 (br s, 2H), 7.30 (t, J=5.8 Hz, 1H), 11.87 (br s, 1H). MS (ESI+) m/z 431.2 (M+H)⁺. Anal. calcd. for $C_{23}H_{30}N_2O_4S$: C, 64.16; H, 7.02; N, 6.51. Found: C, 64.00; H, 6.91; N, 6.48.

Example 198

2-[(hexahydro-2,5-methanopentalen-3a(1H)-ylcarbonyl)amino]-N-[(2S)-tetrahydrofuran-2-ylmethyl]-4,7-dihydro-5H-thieno[2,3-c]pyran-3-carboxamide The title compound was prepared as described in Example 166C, substituting Example 167B for Example 166B, and (S)—C-(tetrahydro-furan-2-yl)-methylamine for propylamine. ¹H NMR (dimethylsulfoxide-$d_6$, 300 MHz) δ 1.54-1.87 (m, 5H), 1.75-2.01 (m, 9H), 2.32 (br s, 2H), 2.58-2.62 (m, 1H), 2.81 (br s, 2H), 3.30-3.37 (m, 2H), 3.60-3.67 (m, 1H), 3.74-3.81 (m, 1H), 3.85 (t, J=5.4 Hz, 2H), 3.93-4.01 (m, 1H), 4.65 (br s, 2H), 7.30 (t, J=5.8 Hz, 1H), 11.87 (br s, 1H). MS (ESI+) m/z 431.2 (M+H)⁺. Anal. calcd. for $C_{23}H_{30}N_2O_4S$: C, 64.16; H, 7.02; N, 6.51. Found: C, 63.95; H, 6.99; N, 6.49.

Example 199

2-[(hexahydro-2,5-methanopentalen-3a(1H)-ylcarbonyl)amino]-N-(2-hydroxypropyl)-4,7-dihydro-5H-thieno[2,3-c]pyran-3-carboxamide The title compound was prepared as described in Example 166C, substituting Example 167B for Example 166B, and 1-amino-propan-2-ol for propylamine. ¹H NMR (dimethylsulfoxide-$d_6$, 300 MHz) δ 1.07 (d, J=6.1 Hz, 3H), 1.61-1.67 (m, 4H), 1.76-1.86 (m, 4H), 1.96-2.01 (m, 2H), 2.32 (br s, 2H), 2.58-2.62 (m, 1H), 2.84 (br s, 2H), 3.13-3.30 (m, 2H), 3.74-3.82 (m, 1H), 3.85 (t, J=5.4 Hz, 2H), 4.65 (br s, 2H), 4.80 (d, J=4.7 Hz, 1H), 7.17 (t, J=4.9 Hz, 1H), 12.00 (br s, 1H). MS (ESI+) m/z 405.2 (M+H)⁺.

Example 200

2-[(hexahydro-2,5-methanopentalen-3a(1H)-ylcarbonyl)amino]-N-(2-hydroxybutyl)-4,7-dihydro-5H-thieno[2,3-c]pyran-3-carboxamide The title compound was prepared as described in Example 166C, substituting Example 167B for Example 166B, and 1-aminobutan-2-ol for propylamine. ¹H NMR (dimethylsulfoxide-$d_6$, 300 MHz) δ 0.88 (t, J=7.5 Hz, 3H), 1.26-1.50 (m, 2H), 1.60-1.66 (m, 4H), 1.75-1.86 (m, 4H), 1.98-2.00 (m, 2H), 2.31 (br s, 2H), 2.57-2.61 (m, 1H), 2.83 (br s, 2H), 3.11-3.20 (m, 1H), 3.30-3.37 (m, 1H), 3.48-3.54 (m, 1H), 3.85 (t, J=5.4 Hz, 2H), 4.64 (br s, 2H), 4.78 (d, J=5.1 Hz, 1H), 7.13 (t, J=5.4 Hz, 1H), 12.00 (br s, 1H). MS (ESI+) m/z 419.2 (M+H)⁺. Anal. calcd. for $C_{22}H_{30}N_2O_4S$: C, 63.13; H, 7.22; N, 6.69. Found: C, 62.90; H, 7.22; N, 6.77.

Example 201

2-[(hexahydro-2,5-methanopentalen-3a(1H)-ylcarbonyl)amino]-N-[2-(methylthio)ethyl]-4,7-dihydro-5H-thieno[2,3-c]pyran-3-carboxamide The title compound was prepared as described in Example 166C, substituting Example 167B for Example 166B, and 2-methylsulfanylethylamine for propylamine. ¹H NMR (dimethylsulfoxide-$d_6$, 300 MHz) δ 1.61-1.67 (m, 4H), 1.76-1.87 (m, 4H), 1.97-2.01 (m, 2H), 2.09 (s, 3H), 2.33 (br s, 2H), 2.58-2.68 (m, 3H), 2.85 (t, J=5.3 Hz, 2H), 3.44-3.50 (m, 2H), 3.85 (t, J=5.4 Hz, 2H), 4.65 (br s, 2H), 7.42 (t, J=5.6 Hz, 1H), 11.88 (br s, 1H). MS (ESI+) m/z 421.1 (M+H)⁺. Anal. calcd. for $C_{21}H_{28}N_2O_3S_2$: C, 59.97; H, 6.71; N, 6.66. Found: C, 59.80; H, 6.68; N, 6.74.

Example 202

2-{[(1-phenylcyclohexyl)carbonyl]amino}-N-propyl-4,7-dihydro-5H-thieno[2,3-c]pyran-3-carboxamide Example 202A 2-[(1-Phenyl-cyclohexanecarbonyl)-amino]-4,7-dihydro-5H-thieno[2,3-c]pyran-3-carboxylic acid ethyl ester The title compound was prepared as described in Example 167A, substituting 1-phenyl-cyclohexanecarboxylic acid for 3-noradamantanecarboxylic acid. ¹H NMR (dimethylsulfoxide-$d_6$, 300 MHz) δ 1.25 (t, J=7.1 Hz, 3H), 1.33-1.62 (m, 4H), 1.95-2.03 (m, 2H), 2.30-2.36 (m, 2H), 2.73 (t, J=5.6 Hz, 2H), 3.04-3.13 (m, 2H), 3.81 (t, J=5.8 Hz, 2H), 4.23 (q, J=7.1 Hz, 2H), 4.60 (br s, 2H), 7.24-7.30 (m, 1H), 7.36-7.44 (m, 4H), 11.21 (br s, 1H). MS (ESI+) m/z 413.8 (M+H)⁺.

Example 202B

2-[(1-Phenyl-cyclohexanecarbonyl)-amino]-4,7-dihydro-5H-thieno[2,3-c]pyran-3-carboxylic acid The title compound was prepared as described in Example 166B, substituting Example 202A for Example 166A. The crude product was used for the next step without further purification. LCMS (ESI+) m/z 386.2 (M+H)⁺.

Example 202C

2-{[(1-phenylcyclohexyl)carbonyl]amino}-N-propyl-4,7-dihydro-5H-thieno[2,3-c]pyran-3-carboxamide The title compound was prepared as described in Example 166C, substituting Example 202B for Example 166B. ¹H NMR (dimethylsulfoxide-$d_6$, 300 MHz) δ 0.86 (t, J=7.5 Hz, 3H), 1.42-1.63 (m, 8H), 1.88-1.99 (m, 2H), 2.32-2.36 (m, 2H), 2.78 (t, J=5.1 Hz, 2H), 3.14-3.21 (m, 2H), 3.81 (t, J=5.4

Hz, 2H), 4.63 (br s, 2H), 7.22-7.41 (m, 6H), 11.87 (br s, 1H). MS (ESI+) m/z 427.2 (M+H)⁺. Anal. calcd. for $C_{24}H_{30}N_2O_3S$: C, 67.58; H, 7.09; N, 6.57. Found: C, 67.70; H, 7.16; N, 6.51.

Example 203

2-[(hexahydro-2,5-methanopentalen-3a(1H)-ylcarbonyl)amino]-N-propyl-4,5,6,7-tetrahydro-1-benzothiophene-3-carboxamide

Example 203A

2-[(Hexahydro-2,5-methano-pentalene-3a-carbonyl)-amino]-4,5,6,7-tetrahydro-benzo[b]thiophene-3-carboxylic acid ethyl ester The title compound was prepared as described in Example 167A, substituting 2-amino-4,5,6,7-tetrahydro-benzo[b]thiophene-3-carboxylic acid ethyl ester (Aldrich) for Example 10A.

Example 203B

2-[(Hexahydro-2,5-methano-pentalene-3a-carbonyl)-amino]-4,5,6,7-tetrahydro-benzo[b]thiophene-3-carboxylic acid The title compound was prepared as described in Example 166B, substituting Example 203A for Example 166A. MS (ESI+) m/z 346.2 (M+H)⁺.

Example 203C

2-[(hexahydro-2,5-methanopentalen-3a(1H)-ylcarbonyl)amino]-N-propyl-4,5,6,7-tetrahydro-1-benzothiophene-3-carboxamide The title compound was prepared as described in Example 166C, substituting Example 203B for Example 166B. ¹H NMR (dimethylsulfoxide-d₆, 300 MHz) δ 0.89 (t, J=7.5 Hz, 3H), 1.52 (q, J=7.2 Hz, 2H), 1.59-1.66 (m, 4H), 1.72-1.79 (m, 6H), 1.81-1.85 (m, 2H), 1.96-2.00 (m, 2H), 2.32 (br s, 2H), 2.56-2.63 (m, 3H), 2.70-2.73 (m, 2H), 3.22 (q, J=6.8 Hz, 2H), 7.30 (t, J=5.8 Hz, 1H), 11.81 (br s, 1H). MS (ESI+) m/z 387.2 (M+H)⁺. Anal. calcd. for $C_{22}H_{30}N_2O_2S$: C, 68.36; H, 7.82; N, 7.25. Found: C, 68.04; H, 7.93; N, 7.14.

Example 204

2-[(hexahydro-2,5-methanopentalen-3a(1H)-ylcarbonyl)amino]-N-(3-hydroxypropyl)-4,5,6,7-tetrahydro-1-benzothiophene-3-carboxamide The title compound was prepared as described in Example 166C, substituting Example 203B for Example 166B, and 3-aminopropan-1-ol for propylamine. ¹H NMR (dimethylsulfoxide-d₆, 300 MHz) δ 1.60-1.86 (m, 14H), 1.96-2.00 (m, 2H), 2.32 (br s, 2H), 2.56-2.62 (m, 3H), 2.70 (t, J=4.1 Hz, 2H), 3.30-3.38 (m, 2H), 3.46-3.51 (m, 2H), 4.58 (t, J=5.1 Hz, 1H), 7.34 (t, J=5.4 Hz, 1H), 11.94 (br s, 1H). MS (ESI+) m/z 401.2 (M+H)⁺. Anal. calcd. for $C_{22}H_{30}N_2O_3S$: C, 65.64; H, 7.51; N, 6.96. Found: C, 65.67; H, 7.59; N, 7.00.

Example 205

2-[(bicyclo[2.2.1]hept-2-ylcarbonyl)amino]-N-propyl-4,7-dihydro-5H-thieno[2,3-c]pyran-3-carboxamide

Example 205A 2 2-[(Bicyclo[2.2.1]heptane-2-carbonyl)-amino]-4,7-dihydro-5H-thieno[2,3-c]pyran-3-carboxylic acid ethyl ester The title compound was prepared as described in Example 167A, substituting endo-bicyclo[2.2.1]heptane-2-carboxylic acid for 3-noradamantanecarboxylic acid. ¹H NMR (dimethylsulfoxide-d₆, 300 MHz) δ 1.14-1.19 (m, 2H), 1.32 (t, J=7.1 Hz, 3H), 1.37-1.73 (m, 5H), 2.25-2.28 (m, 1H), 2.51-2.55 (m, 1H), 2.78 (t, J=5.6 Hz, 2H), 3.06-3.13 (m, 1H), 3.84 (t, J=5.8 Hz, 2H), 4.30 (q, J=7.1 Hz, 2H), 4.62 (br s, 2H), 11.05 (br s, 1H). MS (ESI+) m/z 350.0 (M+H)⁺.

Example 205B

2-[(Bicyclo[2.2.1]heptane-2-carbonyl)-amino]-4,7-dihydro-5H-thieno[2,3-c]pyran-3-carboxylic acid The title compound was prepared as described in Example 166B, substituting Example 205A for Example 166A. The crude product was used for the next step without further purification. LCMS (ESI+) m/z 322.2 (M+H)⁺.

Example 205C

2-[(bicyclo[2.2.1]hept-2-ylcarbonyl)amino]-N-propyl-4,7-dihydro-5H-thieno[2,3-c]pyran-3-carboxamide The title compound was prepared as described in Example 166C, substituting Example 205B for Example 166B. ¹H NMR (dimethylsulfoxide-d₆, 300 MHz) δ 0.89 (t, J=7.3 Hz, 3H), 1.11-1.80 (m, 11H), 2.25-2.40 (m, 2H), 2.76-2.80 (m, 2H), 3.18-3.26 (m, 2H), 3.81-3.86 (m, 2H), 4.63-4.64 (m, 2H), 7.40-7.48 (m, 1H), 11.42 (br s, 1H). MS (ESI+) m/z 363.1 (M+H)⁺.

Example 206

N-[3-(morpholin-4-ylcarbonyl)-4,5,6,7-tetrahydro-1-benzothien-2-yl]hexahydro-2,5-methanopentalene-3a(1H)-carboxamide The title compound was prepared as described in Example 166C, substituting Example 203B for Example 166B, and morpholine for propylamine. ¹H NMR (dimethylsulfoxide-d₆, 300 MHz) δ 1.57-1.62 (m, 4H), 1.67-1.80 (m, 6H), 1.86-1.96 (m, 4H), 2.28 (br s, 2H), 2.37-2.40 (m, 2H), 2.60-2.67 (m, 3H), 3.40 (br s, 4H), 3.52-3.55 (m, 4H), 9.51 (br s, 1H). MS (ESI+) m/z 415.1 (M+H)⁺.

Example 207

2-[(hexahydro-2,5-methanopentalen-3a(1H)-ylcarbonyl)amino]-N-prop-2-ynyl-4,7-dihydro-5H-thieno[2,3-c]pyran-3-carboxamide The title compound was prepared as described in Example 166C, substituting Example 167B for Example 166B, and prop-2-ynylamine for propylamine. $^1$H NMR (dimethylsulfoxide-d$_6$, 300 MHz) δ 1.61-1.62 (m, 4H), 1.75-1.87 (m, 4H), 1.97-2.01 (m, 2H), 2.32 (br s, 2H), 2.58-2.62 (m, 1H), 2.81 (t, J=5.3 Hz, 2H), 3.12 (t, J=2.4 Hz, 1H), 3.83 (t, J=5.4 Hz, 2H), 4.03 (dd, J=5.4, 2.4 Hz, 2H), 4.64 (br s, 2H), 7.73 (t, J=5.6 Hz, 1H), 11.79 (br s, 1H). MS (ESI+) m/z 385.1 (M+H)$^+$. Anal. calcd. for C$_{21}$H$_{24}$N$_2$O$_3$S: C, 65.60; H, 6.29; N, 7.29. Found: C, 65.56; H, 6.18; N, 7.24.

Example 208

N-(cyanomethyl)-2-[(hexahydro-2,5-methanopentalen-3a(1H)-ylcarbonyl)amino]-4,7-dihydro-5H-thieno[2,3-c]pyran-3-carboxamide The title compound was prepared as described in Example 166C, substituting Example 167B for Example 166B, and aminoacetonitrile for propylamine. $^1$H NMR (dimethylsulfoxide-d$_6$, 300 MHz) δ 1.61-1.67 (m, 4H), 1.76-1.88 (m, 4H), 1.98-2.02 (m, 2H), 2.33 (br s, 2H), 2.59-2.63 (m, 1H), 2.80 (t, J=5.3 Hz, 2H), 3.84 (t, J=5.4 Hz, 2H), 4.28 (d, J=5.4 Hz, 2H), 4.64 (br s, 2H), 7.89 (t, J=5.6 Hz, 1H), 11.76 (br s, 1H). MS (ESI+) m/z 386.1 (M+H)$^+$.

Example 209

Trans-2-[(hexahydro-2,5-methanopentalen-3a(1H)-ylcarbonyl)amino]-N-(2-hydroxycyclopentyl)-4,7-dihydro-5H-thieno[2,3-c]pyran-3-carboxamide The title compound was prepared as described in Example 166C, substituting Example 167B for Example 166B, and trans-2-aminocyclopentanol for propylamine. $^1$H NMR (dimethylsulfoxide-d$_6$, 300 MHz) δ 1.41-1.57 (m, 2H), 1.61-1.67 (m, 6H), 1.76-1.87 (m, 5H), 1.98-2.01 (m, 3H), 2.33 (br s, 2H), 2.58-2.62 (m, 1H), 2.73-2.91 (m, 2H), 3.76-3.91 (m, 2H), 3.93-4.03 (m, 2H), 4.65 (Br s, 2H), 4.78 (d, J=4.1 Hz, 1H), 7.08 (d, J=6.8 Hz, 1H), 11.63 (br s, 1H). MS (ESI+) m/z 431.1 (M+H)$^+$. Anal. calcd. for C$_{23}$H$_{30}$N$_2$O$_4$S: C, 64.16; H, 7.02; N, 6.51. Found: C, 63.89; H, 6.74; N, 6.35.

Example 210

N-hexahydro-2,5-methanopentalen-3a(1H)-yl-2-[(hexahydro-2,5-methanopentalen-3a(1H)-ylcarbonyl)amino]-4,7-dihydro-5H-thieno[2,3-c]pyran-3-carboxamide The title compound was prepared as described in Example 166C, substituting Example 167B for Example 166B, and 3-aminonoradamantane for propylamine. $^1$H NMR (dimethylsulfoxide-d$_6$, 300 MHz) δ 1.51-1.55 (m, 4H), 1.61-1.67 (m, 4H), 1.76-1.87 (m, 4H), 1.93-2.00 (m, 6H), 2.07-2.11 (m, 2H), 2.24 (br s, 2H), 2.33 (br s, 2H), 2.40-2.47 (m, 1H), 2.58-2.62 (m, 1H), 2.81 (t, J=4.7 Hz, 2H), 3.84 (t, J=5.4 Hz, 2H), 4.65 (s, 2H), 7.36 (br s, 1H), 11.53 (br s, 1H). MS (ESI+) m/z 467.2 (M+H)$^+$.

Example 211

2-[(hexahydro-2,5-methanopentalen-3a(1H)-ylcarbonyl)amino]-N-(3-hydroxy-2,2-dimethylpropyl)-4,7-dihydro-5H-thieno[2,3-c]pyran-3-carboxamide The title compound was prepared as described in Example 166C, substituting Example 167B for Example 166B, and 3-amino-2,2-dimethyl-propan-1-ol for propylamine. $^1$H NMR (dimethylsulfoxide-d$_6$, 300 MHz) δ 0.85 (s, 6H), 1.61-1.67 (m, 4H), 1.75-1.87 (m, 4H), 1.97-2.01 (m, 2H), 2.33 (br s, 2H), 2.57-2.62 (m, 1H), 2.83 (t, J=5.1 Hz, 2H), 3.19-3.22 (m, 4H), 3.86 (t, J=5.3 Hz, 2H), 4.65 (br s, 2H), 4.84 (t, J=5.1 Hz, 1H), 7.41 (t, J=5.9 Hz, 1H), 12.00 (br s, 1H). MS (ESI+) m/z 433.1 (M+H)$^+$. Anal. calcd. for C$_{23}$H$_{32}$N$_2$O$_4$S: C, 63.86; H, 7.46; N, 6.48. Found: C, 63.36; H, 7.47; N, 6.36.

Example 212

N-{3-[(2-phenylhydrazino)carbonyl]-4,7-dihydro-5H-thieno[2,3-c]pyran-2-yl}hexahydro-2,5-methanopentalene-3a(1H)-carboxamide The title compound was prepared as described in Example 166C, substituting Example 167B for Example 166B, and phenylhydrazine for propylamine. $^1$H NMR (dimethylsulfoxide-d$_6$, 300 MHz) δ 1.58-1.65 (m, 4H), 1.73-1.84 (m, 4H), 1.95-1.99 (m, 2H), 2.30 (br s, 2H), 2.57-2.61 (m, 1H), 3.01 (br s, 2H), 3.89 (t, J=5.4 Hz, 2H), 4.68 (br s, 2H), 6.73 (t, J=7.3 Hz, 1H), 6.81 (d, J=7.8 Hz, 2H), 7.16 (dd, J=7.8, 7.8 Hz, 2H), 7.95 (d, J=1.7 Hz, 1H), 9.35 (d, J=2.0 Hz, 1H), 11.54 (br s, 1H). MS (ESI+) m/z 438.2 (M+H)$^+$. Anal. calcd. for C$_{24}$H$_{27}$N$_3$O$_3$S: C, 65.88; H, 6.22; N, 9.60. Found: C, 65.77; H, 5.98; N, 9.58.

Example 213

2-[(hexahydro-2,5-methanopentalen-3a(1H)-ylcarbonyl)amino]-N-[2-(methylsulfonyl)ethyl]-4,7-dihydro-5H-thieno[2,3-c]pyran-3-carboxamide To a 50-mL round-bottomed flask containing a magnetic stir bar were added water (2 mL) and OXONE® (155 mg, 0.252 mmol). The flask was cooled in an ice bath. A solution of Example 201 in methanol (11 mL) was added and the resulting slurry was stirred at 0° C. for 30 minutes. The mixture was allowed to warm to room temperature over 3 hours. The mixture was extracted with dichloromethane (3×5 mL). The combined organic extracts were dried over magnesium sulfate, filtered, and concentrated by rotary evaporator. The crude material was recrystallized from ethyl acetate/hexanes to afford the title compound. $^1$H NMR (dimethylsulfoxide-d$_6$, 300 MHz) δ 1.62-1.67 (m, 4H), 1.76-1.88 (m, 4H), 1.98-2.02 (m, 2H), 2.33 (br s, 2H), 2.59-2.63 (m, 1H), 2.84 (t, J=4.8 Hz, 2H), 3.05 (s, 3H), 3.39 (t, J=6.6 Hz, 2H), 3.69-3.75 (m, 2H), 3.84 (t, J=5.4 Hz, 2H), 4.65 (br s, 2H), 7.48 (t, J=5.8 Hz, 1H), 11.94 (br s, 1H). MS (ESI+) m/z 453.1 (M+H)$^+$. Anal. calcd. for C$_{21}$H$_{28}$N$_2$O$_5$S$_2$: C, 55.73; H, 6.24; N, 6.19. Found: C, 55.76; H, 6.25; N, 6.10.

Example 214 ethyl 2-{[(1-phenylcyclohexyl)carbonyl]amino}-4,7-dihydro-5H-thieno[2,3-c]pyran-3-carboxylate The title compound was prepared as described in Example 167A, substituting 1-phenyl-cyclohexanecarboxylic acid for 3-noradamantanecarboxylic acid. $^1$H NMR (dimethylsulfoxide-d$_6$, 300 MHz) δ 1.25 (t, J=7.1 Hz, 3H), 1.33-1.62 (m, 4H), 1.95-2.03 (m, 2H), 2.30-2.36 (m, 2H), 2.73 (t, J=5.6 Hz, 2H), 3.04-3.13 (m, 2H), 3.81 (t, J=5.8 Hz, 2H), 4.23 (q, J=7.1 Hz, 2H), 4.60 (br s, 2H), 7.24-7.30 (m, 1H), 7.36-7.44 (m, 4H), 11.21 (br s, 1H). MS (ESI+) m/z 413.8 (M+H)$^+$.

Example 215 ethyl 2-({[1-(2-fluorophenyl)cyclohexyl]
carbonyl}amino)-4,7-dihydro-5H-thieno[2,3-c]pyran-3-carboxylate The title compound was prepared as described in Example 167A, substituting 1-(2-fluorophenyl)-cyclohexanecarboxylic acid for 3-noradamantanecarboxylic acid. $^1$H NMR (dimethylsulfoxide-$d_6$, 300 MHz) δ 1.20 (t, J=7.4 Hz, 3H), 1.36-1.64 (m, 6H), 2.00-2.08 (m, 2H), 2.24-2.29 (m, 2H), 2.73 (t, J=5.4 Hz, 2H), 3.81 (t, J=5.6 Hz, 2H), 4.15 (q, J=7.1 Hz, 2H), 4.61 (br s, 2H), 7.17 (ddd, J=12.6, 8.0, 1.4 Hz, 1H), 7.31 (ddd, J=7.6, 7.5, 1.4 Hz, 1H), 7.36-7.43 (m, 1H), 7.61 (ddd, J=8.1, 8.0, 1.9 Hz, 1H), 10.99 (br s, 1H). MS (ESI+) m/z 432.2 (M+H)$^+$. Anal. calcd. for $C_{23}H_{26}FNO_4S$: C, 64.02; H, 6.07; N, 3.25. Found: C, 64.17; H, 5.60; N, 3.41.

Example 216 ethyl 2-({[1-(3-fluorophenyl)cyclohexyl]
carbonyl}amino)-4,7-dihydro-5H-thieno[2,3-c]pyran-3-carboxylate The title compound was prepared as described in Example 167A, substituting 1-(3-fluorophenyl)-cyclohexanecarboxylic acid for 3-noradamantanecarboxylic acid. $^1$H NMR (dimethylsulfoxide-$d_6$, 300 MHz) δ 1.26 (t, J=7.1 Hz, 3H), 1.35-1.62 (m, 6H), 1.97-2.05 (m, 2H), 2.28-2.34 (m, 2H), 2.74 (t, J=5.6 Hz, 2H), 3.81 (t, J=5.6 Hz, 2H), 4.24 (q, J=7.2 Hz, 2H), 4.61 (br s, 2H), 7.10-7.16 (m, 1H), 7.22-7.27 (m, 2H), 7.40-7.48 (m, 1H), 11.22 (br s, 1H). MS (ESI+) m/z 432.2 (M+H)$^+$.

Example 217 ethyl 2-({[1-(4-methoxyphenyl)cyclohexyl]
carbonyl}amino)-4,7-dihydro-5H-thieno[2,3-c]pyran-3-carboxylate The title compound was prepared as described in Example 167A, substituting 1-(4-methoxyphenyl)-cyclohexanecarboxylic acid for 3-noradamantanecarboxylic acid. $^1$H NMR (dimethylsulfoxide-$d_6$, 300 MHz) δ 1.25 (t, J=7.1 Hz, 3H), 1.33-1.61 (m, 6H), 1.93-1.99 (m, 2H), 2.26-2.33 (m, 2H), 2.73-2.76 (m, 2H), 3.73 (s, 3H), 3.81 (t, J=5.6 Hz, 2H), 4.23 (q, J=7.1 Hz, 2H), 4.60 (br s, 2H), 6.94 (d, J=9.0 Hz, 2H), 7.33 (d, J=8.8 Hz, 2H), 11.16 (br s, 1H). MS (ESI+) m/z 444.2 (M+H)$^+$. Anal. calcd. for $C_{24}H_{29}NO_5S$: C, 64.99; H, 6.59; N, 3.16. Found: C, 64.66; H, 6.63; N, 3.06.

Example 218

Trans-2-[(hexahydro-2,5-methanopentalen-3a(1H)-ylcarbonyl)amino]-N-(2-hydroxycyclohexyl)-4,7-dihydro-5H-thieno[2,3-c]pyran-3-carboxamide The title compound was prepared as described in Example 166C, substituting Example 10A for Example 166B, and trans-2-aminocyclohexanol for propylamine. $^1$H NMR (dimethylsulfoxide-$d_6$, 300 MHz) δ 1.20-1.28 (m, 4H), 1.62-1.67 (m, 6H), 1.75-1.91 (m, 2H), 1.97-2.01 (m, 2H), 2.33 (br s, 2H), 2.58-2.63 (m, 1H), 2.86 (br s, 2H), 3.35-3.41 (m, 1H), 3.58-3.66 (m, 1H), 3.80-3.89 (m, 2H), 4.66 (br s, 2H), 4.71 (d, J=5.1 Hz, 1H), 6.91 (d, J=7.5 Hz, 1H), 11.81 (br s, 1H). MS (ESI+) m/z 445.2 (M+H)$^+$. Anal. calcd. for $C_{24}H_{32}N_2O_4S$: C, 64.84; H, 7.25; N, 6.30. Found: C, 64.74; H, 7.11; N, 6.11.

Example 219

Cis-2-[(hexahydro-2,5-methanopentalen-3a(1H)-ylcarbonyl)amino]-N-(2-hydroxycyclohexyl)-4,7-dihydro-5H-thieno[2,3-c]pyran-3-carboxamide The title compound was prepared as described in Example 166C, substituting Example 10A for Example 166B, and cis-2-aminocyclohexanol for propylamine. $^1$H NMR (dimethylsulfoxide-$d_6$, 300 MHz) δ 1.25-1.34 (m, 2H), 1.43-1.72 (m, 10H), 1.75-1.87 (m, 4H), 1.98-2.02 (m, 2H), 2.33 (br s, 2H), 2.58-2.62 (m, 1H), 2.73-2.89 (m, 2H), 3.79-3.90 (m, 4H), 4.66 (br s, 2H), 4.92 (d, J=4.4 Hz, 1H), 6.72 (d, J=7.8 Hz, 1H), 12.21 (br s, 1H). MS (ESI+) m/z 445.2 (M+H)$^+$. Anal. calcd. for $C_{24}H_{32}N_2O_4S$: C, 64.84; H, 7.25; N, 6.30. Found: C, 64.81; H, 6.95; N, 6.14.

Example 220

2-[(hexahydro-2,5-methanopentalen-3a(1H)-ylcarbonyl)amino]-N-(3,3,3-trifluoropropyl)-4,7-dihydro-5H-thieno[2,3-c]pyran-3-carboxamide The title compound was prepared from 2-[(hexahydro-2,5-methano-pentalene-3a-carbonyl)-amino]-4,7-dihydro-5H-thieno[2,3-c]pyran-3-carboxylic acid. (Example 10A) and 3,3,3-trifluoropropylamine according to the procedure described for Example 166C. $^1$H NMR (DMSO-$d_6$, 300 MHz) δ 1.62-1.67 (m, 4H), 1.76-1.88 (m, 4H), 1.98-2.02 (m, 2H), 2.33 (br s, 2H), 2.51-2.63 (m, 3H), 2.81 (t, J=5.3 Hz, 2H), 3.52 (q, J=6.8 Hz, 2H), 3.85 (t, J=5.4 Hz, 2H), 4.65 (br s, 2H), 7.50 (t, J=5.6 Hz, 1H), 11.83 (br s, 1H). MS (ESI+) m/z 443.1 (M+H)$^+$. Anal. calcd. for $C_{21}H_{25}F_3N_2O_3S$: C, 57.00; H, 5.69; N, 6.33. Found: C, 57.24; H, 5.56; N, 6.27.

Example 221

Trans-2-[(hexahydro-2,5-methanopentalen-3a(1H)-ylcarbonyl)amino]-N-(2-(hydroxymethyl)cyclohexyl)-4,7-dihydro-5H-thieno[2,3-c]pyran-3-carboxamide The title compound was prepared as described in Example 166C, substituting Example 167B for Example 166B, and (trans-2-aminocyclohexyl)methanol for propylamine. $^1$H NMR (dimethylsulfoxide-$d_6$, 300 MHz) δ 1.19-1.32 (m, 4H), 1.44-1.54 (m, 2H), 1.61-1.67 (m, 6H), 1.76-2.01 (m, 8H), 2.33 (br s, 2H), 2.57-2.62 (m, 1H), 2.82-2.83 (m, 2H), 3.37-3.46 (m, 1H), 3.57-3.66 (m, 1H), 3.84 (t, J=5.4 Hz, 2H), 4.44 (t, J=5.3 Hz, 1H), 4.65 (br s, 2H), 7.25 (d, J=8.1 Hz, 1H), 11.69 (br s, 1H). MS (ESI+) m/z 459.3 (M+H)$^+$. Anal. calcd. for $C_{25}H_{34}N_2O_4S$: C, 65.47; H, 7.47; N, 6.11. Found: C, 65.04; H, 7.46; N, 6.02.

Example 222 ethyl 2-[(hexahydro-2,5-methanopentalen-3a(1H)-ylcarbonyl)amino]-4,7-dihydro-5H-thieno[2,3-c]pyran-3-carboxylate Step One To an oven-dried, $N_2$-purged 250-mL, round-bottomed flask containing a magnetic stir bar were added the 3-noradamantanecarboxylic acid (4.99 g, 30.0 mmol) and anhydrous toluene (100 mL). Thionyl chloride (3.28 mL, 45.0 mmol) was added and a reflux condenser with $N_2$ inlet was attached. The solution was heated to reflux and stirred for 6 hours. After cooling, the solution was concentrated by rotary evaporator to afford 5.5 g of an oil that was used for the next step without further purification.

Step Two

The title compound was prepared as described in Example 166A, substituting the product of step one for adamantane-1-carbonyl chloride (*J. Am. Chem. Soc.*, 124 (9), 2056-2064, 2002). $^1$H NMR (dimethylsulfoxide-$d_6$) δ 1.31 (t, J=7.1 Hz, 3H), 1.62-1.68 (m, 3H), 1.77-1.84 (m, 2H), 1.87-1.91 (m, 2H), 2.00-2.04 (m 2H), 2.34 (br s, 2H), 2.64 (t, J=6.6 Hz, 1H), 2.79 (t, J=5.6 Hz, 2H), 3.29 (br s, 1H), 3.84 (t, J=5.6 Hz, 2H), 4.30 (q, J=7.1 Hz, 2H), 4.62 (br s, 2H), 11.32 (br s, 1H). MS (ESI+) m/z 376.1 (M+H)$^+$. Anal. calcd. for $C_{20}H_{25}NO_4S$: C, 63.97; H, 6.71; N, 3.73. Found: C, 63.74; H, 6.75; N, 3.68.

Example 223

N-cyclobutyl-2-[(hexahydro-2,5-methanopentalen-3a (1H)-ylcarbonyl)amino]-4,7-dihydro-5H-thieno[2,3-c]pyran-3-carboxamide The title compound was prepared as described in Example 166C, substituting Example 167B for Example 166B, and cyclobutylamine for propylamine. $^1$H NMR (dimethylsulfoxide-$d_6$, 300 MHz) δ 1.61-1.72 (m, 6H), 1.76-1.87 (m, 4H), 1.97-2.12 (m, 4H), 2.17-2.26 (m, 2H), 2.32 (br s, 2H), 2.57-2.62 (m, 1H), 2.86 (t, J=5.4 Hz, 2H), 3.84 (t, J=5.6 Hz, 2H), 4.33-4.46 (m, 1H), 4.65 (br s, 2H), 7.47 (d, J=7.5 Hz, 1H), 11.68 (br s, 1H). MS (ESI+) m/z 401.2 (M+H)$^+$. Anal. calcd. for $C_{22}H_{28}N_2O_3S$: C, 65.97; H, 7.05; N, 6.99. Found: C, 65.36; H, 6.79; N, 6.75.

Example 224

N-cyclopentyl-2-[(hexahydro-2,5-methanopentalen-3a(1H)-ylcarbonyl)amino]-4,7-dihydro-5H-thieno[2,3-c]pyran-3-carboxamide The title compound was prepared as described in Example 166C, substituting Example 167B for Example 166B, and cyclopentylamine for propylamine. $^1$H NMR (dimethylsulfoxide-$d_6$, 300 MHz) δ 1.50-1.67 (m, 10H), 1.75-1.87 (m, 6H), 1.97-2.01 (m, 2H), 2.33 (br s, 2H), 2.58-2.62 (m, 1H), 2.81 (t, J=5.3 Hz, 2H), 3.83 (t, J=5.3 Hz, 2H), 4.17-4.23 (m, 1H), 4.65 (br s, 2H), 7.18 (d, J=6.8 Hz, 1H), 11.63 (br s, 1H). MS (ESI+) m/z 401.2 (M+H)$^+$. Anal. calcd. for $C_{23}H_{30}N_2O_3S$: C, 66.64; H, 7.29; N, 6.76. Found: C, 66.55; H, 7.20; N, 6.75.

Example 225

Cis-2-[(hexahydro-2,5-methanopentalen-3a(1H)-ylcarbonyl)amino]-N-(2-methylcyclohexyl)-4,7-dihydro-5H-thieno[2,3-c]pyran-3-carboxamide The title compound was prepared as described in Example 166C, substituting Example 167B for Example 166B, and cis-2-methylcyclohexylamine for propylamine. $^1$H NMR (dimethylsulfoxide-$d_6$, 300 MHz) δ 0.88 (d, J=6.4 Hz, 3H), 1.01-1.32 (m, 4H), 1.42-1.53 (m, 1H), 1.61-1.85 (m, 12H), 1.96-1.99 (m, 2H), 2.32 (br s, 2H), 2.56-2.61 (m, 1H), 2.69-2.78 (m, 1H), 2.88-2.96 (m, 1H), 3.45-3.56 (m, 1H), 3.76-3.93 (m, 2H), 4.65 (br s, 2H), 7.10 (d, J=9.1 Hz, 1H), 11.58 (br s, 1H). MS (ESI+) m/z 443.2 (M+H)$^+$.

Example 226

Trans-2-[(hexahydro-2,5-methanopentalen-3a(1H)-ylcarbonyl)amino]-N-(2-methylcyclohexyl)-4,7-dihydro-5H-thieno[2,3-c]pyran-3-carboxamide The title compound was prepared as described in Example 166C, substituting Example 167B for Example 166B, and trans-2-methylcyclohexylamine for propylamine. $^1$H NMR (dimethylsulfoxide-$d_6$, 300 MHz) δ 0.87 (d, J=6.8 Hz, 3H), 1.29-1.37 (m, 4H), 1.46-1.55 (m, 2H), 1.60-1.66 (m, 6H), 1.75-1.87 (m, 5H), 1.96-2.00 (m, 2H), 2.32 (br s, 2H), 2.57-2.61 (m, 1H), 2.73-2.94 (m, 2H), 3.81-3.93 (m, 2H), 4.08-4.14 (m, 1H), 4.66 (br s, 2H), 6.81 (d, J=8.8 Hz, 1H), 11.70 (br s, 1H). MS (ESI+) m/z 443.2 (M+H)$^+$.

Example 227

2-[(hexahydro-2,5-methanopentalen-3a(1H)-ylcarbonyl)amino]-N-(4-methylcyclohexyl)-4,7-dihydro-5H-thieno[2,3-c]pyran-3-carboxamide The title compound was prepared as described in Example 166C, substituting Example 167B for Example 166B, and 4-methylcyclohexylamine for propylamine. $^1$H NMR (dimethylsulfoxide-$d_6$, 300 MHz) δ 0.87-0.93 (m, 3H), 0.98-1.08 (m, 1H), 1.25-1.35 (m, 2H), 1.48-1.87 (m, 14H), 1.97-2.00 (m, 2H), 2.33 (br s, 2H), 2.58-2.62 (m, 1H), 2.79-2.87 (m, 2H), 3.67-3.98 (m, 3H), 4.64-4.66 (m, 2H), 7.01-7.07 (m, 1H), 11.64-11.71 (m, 1H), MS (ESI+) m/z 443.2 (M+H)$^+$. Anal. calcd. for $C_{25}H_{34}N_2O_3S$: C, 67.84; H, 7.74; N, 6.33. Found: C, 67.68; H, 7.67; N, 6.21.

Example 228

2-[(hexahydro-2,5-methanopentalen-3a(1H)-ylcarbonyl)amino]-N-[(1R,2S,3S,5S)-2,6,6-trimethylbicyclo[3.1.1]hept-3-yl]-4,7-dihydro-5H-thieno[2,3-c]pyran-3-carboxamide The title compound was prepared as described in Example 166C, substituting Example 167B for Example 166B, and (+)-isopinocampheylamine for propylamine. $^1$H NMR (dimethylsulfoxide-$d_6$, 300 MHz) δ 1.05 (s, 3H), 1.07 (d, J=7.5 Hz, 3H), 1.15 (d, J=9.8 Hz, 1H), 1.22 (s, 3H), 1.61-2.01 (m, 14H), 2.27-2.32 (m, 1H), 2.32 (br s, 2H), 2.41-2.45 (m, 1H), 2.58-2.62 (m, 1H), 2.72-2.80 (m, 1H), 2.88-2.96 (m, 1H), 3.76-3.92 (m, 2H), 4.25-4.36 (m, 1H), 4.66 (br s, 2H), 7.36 (d, J=8.1 Hz, 1H), 11.42 (br s, 1H). MS (ESI+) m/z 483.3 (M+H)$^+$.

Example 229

2-[(hexahydro-2,5-methanopentalen-3a(1H)-ylcarbonyl)amino]-N-[(1S,2R,3R,5R)-2,6,6-trimethylbicyclo[3.1.1]hept-3-yl]-4,7-dihydro-5H-thieno[2,3-c]pyran-3-carboxamide The title compound was prepared as described in Example 166C, substituting Example 167B for Example 166B, and (−)-isopinocampheylamine for propylamine. $^1$H NMR (dimethylsulfoxide-$d_6$, 300 MHz) δ 1.05 (s, 3H), 1.07 (d, J=7.5 Hz, 3H), 1.15 (d, J=9.8 Hz, 1H), 1.22 (s, 3H), 1.61-2.01 (m, 14H), 2.27-2.32 (m, 1H), 2.32 (br s, 2H), 2.41-2.45 (m, 1H), 2.58-2.62 (m, 1H), 2.72-2.80 (m, 1H), 2.88-2.96 (m, 1H), 3.76-3.92 (m, 2H), 4.25-4.36 (m, 1H), 4.66 (br s, 2H), 7.36 (d, J=8.1 Hz, 1H), 11.42 (br s, 1H). MS (ESI+) m/z 483.3

(M+H)⁺. Anal. calcd. for $C_{28}H_{38}N_2O_3S$: C, 69.67; H, 7.94; N, 5.80. Found: C, 69.36; H, 8.10; N, 5.73.

Example 230

N-{[3-(dimethylamino)tetrahydrothien-3-yl]methyl}-2-[(hexahydro-2,5-methanopentalen-3a(1H)-ylcarbonyl)amino]-4,7-dihydro-5H-thieno[2,3-c]pyran-3-carboxamide The title compound was prepared as described in Example 166C, substituting Example 167B for Example 166B, and (3-aminomethyl-tetrahydro-thiophen-3-yl)-dimethyl-amine for propylamine. $^1$H NMR (dimethylsulfoxide-$d_6$, 300 MHz) δ 1.61-1.67 (m, 4H), 1.76-1.92 (m, 4H), 1.98-2.10 (m, 2H), 2.31 (br s, 6H), 2.33 (br s, 2H), 2.57-2.63 (m, 2H), 2.77-2.82 (m, 4H), 2.89 9d, J=11.2 Hz, 1H), 3.43-3.61 (m, 2H), 3.88 (t, J=5.6 Hz, 3H), 4.68 (br s, 2H), 7.17 (t, J=5.4 Hz, 1H), 12.09 (br s, 1H). MS (ESI+) m/z 490.3 (M+H)⁺. Anal. calcd. for $C_{25}H_{35}N_3O_3S_2$: C, 61.32; H, 7.20; N, 8.58. Found: C, 60.65; H, 6.79; N, 8.46.

Example 231

N-benzyl-2-[(hexahydro-2,5-methanopentalen-3a (1H)-ylcarbonyl)amino]-4,7-dihydro-5H-thieno[2,3-c]pyran-3-carboxamide The title compound was prepared as described in Example 166C, substituting Example 167B for Example 166B, and benzylamine for propylamine. $^1$H NMR (dimethylsulfoxide-$d_6$, 300 MHz) δ 1.60-1.66 (m, 4H), 1.74-1.85 (m, 4H), 1.96-1.99 (m, 2H), 2.31 (br s, 2H), 2.56-2.61 (m, 1H)__, 2.87 (t, J=5.1 Hz, 2H), 3.85 (t, J=5.4 Hz, 2H), 4.49 (d, J=6.1 Hz, 2H), 4.66 (br s, 2H), 7.21-7.36 (m, 5H), 7.90 (t, J=5.9 Hz, 1H), 11.82 (br s, 1H). MS (ESI+) m/z 437.2 (M+H)⁺. Anal. calcd. for $C_{25}H_{28}N_2O_3S$: C, 68.78; H, 6.46; N, 6.42. Found: C, 68.54; H, 6.48; N, 6.35.

Example 232

2-[(hexahydro-2,5-methanopentalen-3a(1H)-ylcarbonyl)amino]-N-[3-(methylthio)propyl]-4,7-dihydro-5H-thieno[2,3-c]pyran-3-carboxamide The title compound was prepared as described in Example 166C, substituting Example 167B for Example 166B, and 3-methylsulfanylpropylamine for propylamine. $^1$H NMR (dimethylsulfoxide-$d_6$, 300 MHz) δ 1.62-1.67 (m, 4H), 1.74-1.87 (m, 6H), 1.97-2.01 (m, 2H), 2.05 (s, 3H), 2.33 (br s, 2H), 2.51-2.53 (m, 2H), 2.58-2.62 (m, 1H), 2.83 (t, J=5.3 Hz, 2H), 3.31-3.37 (m, 2H), 3.84 (t, J=5.4 Hz, 2H), 4.65 (br s, 2H), 7.38 (t, J=5.8 Hz, 1H), 11.85 (br s, 1H). MS (ESI+) m/z 435.2 (M+H)⁺. Anal. calcd. for $C_{22}H_{30}N_2O_3S_2$: C, 60.80; H, 6.96; N, 6.45. Found: C, 60.67; H, 6.90; N, 6.41.

Example 233 ethyl 2-({[1-(4-fluorophenyl)cyclohexyl]carbonyl}amino)-4,7-dihydro-5H-thieno[2,3-c]pyran-3-carboxylate The title compound was prepared as described in Example 167A, substituting 1-(4-fluorophenyl)-cyclohexanecarboxylic acid for 3-noradamantanecarboxylic acid. $^1$H NMR (dimethylsulfoxide-$d_6$, 300 MHz) δ 1.26 (t, J=7.1 Hz, 3H), 1.34-1.59 (m, 6H), 1.95-2.03 (m, 2H), 2.28-2.34 (m, 2H), 2.74 (t, J=5.6 Hz, 2H), 3.81 (t, J=5.6 Hz, 2H), 4.23 (q, J=7.1 Hz, 2H), 4.60 (br s, 2H), 7.18-7.24 (m, 2H), 7.42-7.49 (m, 2H), 11.20 (br s, 1H). MS (ESI+) m/z 432.1 (M+H)⁺.

Example 234

N-phenyl-2-{[(2,2,3,3-tetramethylcyclopropyl)carbonyl]amino}-4,7-dihydro-5H-thieno[2,3-c]pyran-3-carboxamide Example 234A 2-Amino-4,7-dihydro-5H-thieno[2,3-c]pyran-3-carboxylic acid phenylamide The title compound was prepared as described in Example 10A, substituting 2-cyano-N-phenylacetamide for ethyl cyanoacetate. $^1$H NMR (dimethylsulfoxide-$d_6$, 300 MHz), 2.78 (t, J=5.4 Hz, 2H), 3.81 (t, J=5.4 Hz, 2H), 4.51 (br s, 2H), 6.73 (br s, 2H), 6.99-7.04 (m, 1H), 7.28 (dd, J=8.1, 8.1 Hz, 2H), 7.61 (dd, J=8.6, 1.2 Hz, 2H), 8.93 (br s, 1H). MS (ESI+) m/z 275 (M+H)⁺.

Example 234B

N-phenyl-2-{[(2,2,3,3-tetramethylcyclopropyl)carbonyl]amino}-4,7-dihydro-5H-thieno[2,3-c]pyran-3-carboxamide The title compound was prepared as described in Example 167A, substituting Example 234A for Example 10A and tetramethylcyclopropanecarboxlic acid for 3-noradamantanecarboxylic acid. $^1$H NMR (dimethylsulfoxide-$d_6$, 300 MHz) δ 1.17 (s, 6H), 1.22 (s, 6H), 1.51 (s, 1H), 2.78 (t, J=5.4 Hz, 2H), 3.84 (t, J=5.4 Hz, 2H), 4.65 (br s, 2H), 7.08 (t, J=7.3 Hz, 1H), 7.33 (dd, J=7.5 Hz, 2H), 7.69 (d, J=7.5 Hz, 2H), 9.68 (br s, 1H), 10.72 (br s, 1H). MS (ESI+) m/z 399.1 (M+H)⁺. Anal. calcd. for $C_{22}H_{26}N_2O_3S$: C, 66.30; H, 6.58; N, 7.03. Found: C, 66.23; H, 6.64; N, 6.97.

Example 235

Trans-ethyl 2-({[2-(4-fluorophenyl)cyclopentyl]carbonyl}amino)-4,7-dihydro-5H-thieno[2,3-c]pyran-3-carboxylate The title compound was prepared as described in Example 167A, substituting 2-(4-fluorophenyl)-cyclopentanecarboxylic acid for 3-noradamantanecarboxylic acid. $^1$H NMR (dimethylsulfoxide-$d_6$, 300 MHz) δ 1.26 (t, J=7.1 Hz, 3H), 1.69-1.98 (m, 4H), 2.07-2.21 (m, 2H), 2.73 (t, J=5.4 Hz, 2H), 3.05-3.14 (m, 1H), 3.19-3.28 (m, 1H), 3.81 (t, J=5.6 Hz, 2H), 4.22 (q, J=7.1 Hz, 2H), 4.59 (br s, 2H), 7.09 (dd, J=9.0, 9.0 Hz, 2H), 7.31 (dd, J=8.8, 5.8 Hz, 2H), 10.75 (br s, 1H). MS (ESI+) m/z 418.1 (M+H)⁺. Anal. calcd. for $C_{22}H_{24}FNO_4S$: C, 63.29; H, 5.79; N, 3.35. Found: C, 63.27; H, 5.47; N, 3.24.

Example 236

N-{3-[(3,3-difluoroazetidin-1-yl)carbonyl]-4,7-dihydro-5H-thieno[2,3-c]pyran-2-yl}hexahydro-2,5-methanopentalene-3a(1H)-carboxamide The title compound was prepared as described in Example 166C, substituting Example 167B for Example 166B, and 3,3-difluoroazetidine for propylamine. $^1$H NMR (dimethylsulfoxide-$d_6$, 300 MHz) δ 1.60-1.65 (m, 4H), 1.77-1.82 (m, 2H), 1.87-2.01 (m, 4H), 2.31 (br s, 2H), 2.61-2.68 (m, 3H), 3.80 (t, J=5.3 Hz, 2H), 4.44 (t, J=12.6 Hz, 4H), 0.65 (br s, 2H), 10.31 (br s, 1H). MS (ESI+) m/z 423.1 (M+H)⁺. Anal. calcd. for C₂₁H₂₄F₂N₂O₃S: C, 59.70; H, 5.73; N, 6.63. Found: C, 59.64; H, 5.74; N, 6.59.

Example 237

2-[(hexahydro-2,5-methanopentalen-3a(1H)-ylcarbonyl)amino]-N-phenyl-4,7-dihydro-5H-thieno[2,3-c]pyran-3-carboxamide The title compound was prepared as described in Example 167A, substituting Example 234A for Example 10A. ¹H NMR (dimethylsulfoxide-d₆, 300 MHz) δ 1.59-1.65 (m, 4H), 1.74-1.81 (m, 2H), 1.84-1.88 (m, 2H), 1.97-2.01 (m, 2H), 2.31 (br s, 2H), 2.61-2.65 (m, 1H), 2.92 (t, J=5.1 Hz, 2H), 3.86 (t, J=5.4 Hz, 2H), 4.69 (br s, 2H), 7.08-7.14 (m, 1H), 7.35 (dd, J=7.5 Hz, 2H), 7.64 (d, J=6.5 Hz, 2H), 9.40 (br s, 1H), 11.09 (br s, 1H). MS (ESI+) m/z 423.2 (M+H)⁺. Anal. calcd. for C₂₁H₂₆N₂O₃S: C, 68.22; H, 6.20; N, 6.63. Found: C, 67.68; H, 6.03; N, 6.55.

Example 238

Trans-ethyl 2-({[3-phenylbicyclo[2.2.1]hept-2-yl]carbonyl}amino)-4,7-dihydro-5H-thieno[2,3-c]pyran-3-carboxylate The title compound was prepared as described in Example 167A, substituting trans-3-phenyl-bicyclo[2.2.1]heptane-2-carboxylic acid for 3-noradamantanecarboxylic acid. ¹H NMR (dimethylsulfoxide-d₆, 300 MHz) δ 1.17-1.27 (m, 1H), 1.30 (t, J=7.0 Hz, 3H), 1.38-1.51 (m, 3H), 1.57-1.67 (m, 1H), 1.79 (d, J=9.5 Hz, 1H), 2.39 (d, J=3.4 Hz, 1H), 2.68 (br s, 1H), 2.78 (t, J=5.4 Hz, 2H), 3.20-3.22 (m, 2H), 3.84 (t, J=5.8 Hz, 2H), 4.24-4.32 (m, 2H), 4.62 (br s, 2H), 7.14-7.20 (m, 1H), 7.25-7.32 (m, 4H), 11.06 (br s, 1H). MS (ESI+) m/z 426.2 (M+H)⁺. Anal. calcd. for C₂₄H₂₇NO₄S: C, 67.74; H, 6.40; N, 3.29. Found: C, 67.30; H, 6.38; N, 3.37.

Example 239 exo-N-[bicyclo[2.2.1]hept-2-yl]-2-[(hexahydro-2,5-methanopentalen-3a(1H)-ylcarbonyl)amino]-4,7-dihydro-5H-thieno[2,3-c]pyran-3-carboxamide The title compound was prepared as described in Example 166C, substituting Example 167B for Example 166B, and exo-bicyclo[2.2.1]hept-2-ylamine for propylamine. ¹H NMR (dimethylsulfoxide-d₆, 300 MHz) δ 1.10-1.23 (m, 4H), 1.40-1.51 (m, 4H), 1.61-1.67 (m, 4H), 1.75-1.87 (m, 4H), 1.97-2.01 (m, 2H), 2.23 (br s, 2H), 2.33 (br s, 2H), 2.58-2.64 (m, 1H), 2.79-2.84 (m, 2H), 3.67-3.74 (m, 1H), 3.81-3.86 (m, 2H), 4.64 (br s, 2H), 7.04 (d, J=6.4 Hz, 1H), 11.51 (br s, 1H). MS (ESI+) m/z 441.2 (M+H)⁺. Anal. calcd. for C₂₅H₃₂N₂O₃S: C, 68.15; H, 7.32; N, 6.36. Found: C, 67.95; H, 7.18; N, 6.30.

Example 240 ethyl 2-({[2-phenylbicyclo[2.2.1]hept-2-yl]carbonyl}amino)-4,7-dihydro-5H-thieno[2,3-c]pyran-3-carboxylate The title compound was prepared as described in Example 167A, substituting 2-phenyl-bicyclo[2.2.1]heptane-2-carboxylic acid for 3-noradamantanecarboxylic acid. ¹H NMR (dimethylsulfoxide-d₆, 300 MHz) δ 1.06-1.20 (m, 2H), 1.29 (t, J=7.1 Hz, 3H), 1.40 (br s, 2H), 1.48-1.58 (m, 2H), 1.88 (d, J=13.2 Hz, 1H), 2.35-2.38 (m, 1H), 2.61-2.67 (m, 1H), 2.72 (t, J=5.4 Hz, 2H), 3.22 (br s, 1H), 3.79 (t, J=5.6 Hz, 2H), 4.28 ((q, J=7.1 Hz, 2H), 4.57 (br s, 2H), 7.23-7.31 (m, 1H), 7.38-7.39 (m, 4H), 11.20 (br s, 1H). MS (ESI+) m/z 426.1 (M+H)⁺. Anal. calcd. for C₂₄H₂₇NO₄S: C, 67.74; H, 6.40; N, 3.29. Found: C, 67.60; H, 6.34; N, 3.26.

Example 241 ethyl 5,5,7,7-tetramethyl-2-{[(2,2,3,3-tetramethylcyclopropyl)carbonyl]amino}-4,5,6,7-tetrahydrothieno[2,3-c]pyridine-3-carboxylate

Example 241A

2-Amino-5,5,7,7-tetramethyl-4,5,6,7-tetrahydrothieno[2,3-c]pyridine-3-carboxylic acid ethyl ester The title compound was prepared as described in Example 10A, substituting 2,2,6,6-tetramethyl-piperidin-4-one for tetrahydro-4H-pyran-4-one. ¹H NMR (dimethylsulfoxide-d₆, 300 MHz) δ 1.07 (s, 6H), 1.24 (t, J=7.2 Hz, 3H), 1.25 (s, 6H), 1.66 (s, 1H), 2.47 (s, 2H), 4.15 (q, J=7.1 Hz, 2H), 7.19 (br s, 2H). MS (ESI+) m/z 283.1 (M+H)⁺.

Example 241B ethyl 5,5,7,7-tetramethyl-2-{[(2,2,3,3-tetramethylcyclopropyl)carbonyl]amino}-4,5,6,7-tetrahydrothieno[2,3-c]pyridine-3-carboxylate The title compound was prepared as described in Example 167A, substituting Example 241A for Example 10A, and tetramethylcyclopropanecarboxlic acid for 3-noradamantanecarboxylic acid. ¹H NMR (dimethylsulfoxide-d₆, 300 MHz) δ 1.09 (s, 6H), 1.20 (s, 6H), 1.23 (s, 6H), 1.31 (t, J=7.2 Hz, 3H), 1.36 (br s, 6H), 1.51 (br s, 1H), 2.23 (s, 1H), 2.67 (br s, 2H), 4.29 (q, J=7.1 Hz, 2H), 11.08 (br s, 1H). MS (ESI+) m/z 407.2 (M+H)⁺. Anal. calcd. for C₂₂H₃₄N₂O₃S: C, 64.99; H, 8.43; N, 6.89. Found: C, 63.66; H, 8.46; N, 6.53.

Example 242

4-[(2,2,3,3-Tetramethyl-cyclopropanecarbonyl)-amino]-3-thia-11-aza-tricyclo[6.2.1.0²,⁶]undeca-2(6),4-diene-5,11-dicarboxylic acid diethyl ester

Example 242A

4-Amino-3-thia-11-aza-tricyclo[6.2.1.0²,⁶]undeca-2(6),4-diene-5,11-dicarboxylic acid diethyl ester The title compound was prepared as described in Example 10A, substituting N-carbethoxytropinone for tetrahydro-4H-pyran-4-one. ¹H NMR (dimethylsulfoxide-d₆, 300 MHz) δ 1.14 (br s, 3H), 1.24 (t, J=7.2 Hz, 3H), 1.58-1.60 (m, 1H), 1.86 (t, dd, J=9.8, 9.8 Hz, 1H), 2.00 (br s, 1H), 2.14 (br s, 1H), 2.47-2.53 (m, 1H), 3.05 (br s, 1H), 3.99-4.05 (m, 2H), 4.13 (q, J=7.1 Hz, 2H), 4.35 (dd, J=7.6, 4.6 Hz, 1H), 4.70 (d, J=5.1 Hz, 1H), 7.24 (br s, 2H). MS (ESI+) m/z 325.0 (M+H)⁺.

Example 242B diethyl 2-{[(2,2,3,3-tetramethylcyclopropyl)carbonyl]amino}-5,6,7,8-tetrahydro-4H-58-epiminocyclohepta[b]thiophene-3,9-dicarboxylate The title compound was prepared as described in Example 167A, substituting Example 242A for Example 10A, and tetramethylcyclopropanecarboxylic acid for 3-noradamantanecarboxylic acid. $^1$H NMR (dimethylsulfoxide-d$_6$, 300 MHz) δ 1.12-1.17 (m, 3H), 1.28 (s, 6H), 1.22 (s, 3H), 1.23 (s, 3H), 1.31 (t, J=7.1 Hz, 3H), 1.36 (s, 1H), 1.54 (s, 1H), 1.64-1.80 (m, 1H), 2.00-2.22 (m, 2H), 2.60-2.73 (m, 2H), 3.13-3.19 (m, 1H), 3.97-4.04 (m, 2H), 4.27 (q, J=7.1 Hz, 2H), 4.40-4.44 (m, 1H), 4.91 (d, J=11.04 (br s, 1H). MS (ESI+) m/z 449.2 (M+H)$^+$. Anal. calcd. for C$_{22}$H$_{34}$N$_2$O$_3$S: C, 61.58; H, 7.19; N, 6.24. Found: C, 60.40; H, 7.17; N, 6.00.

Example 243 ethyl 4,4,6,6-tetramethyl-2-{[(2,2,3,3-tetramethylcyclopropyl)carbonyl]amino}-4,6-dihydrothieno[2,3-c]furan-3-carboxylate Example 243A 2-Amino-4,4,6,6-tetramethyl-4,6-dihydro-thieno[2,3-c]furan-3-carboxylic acid ethyl ester The title compound was prepared as described in Example 10A, substituting 2,2,5,5-tetramethyl-dihydro-furan-3-one for tetrahydro-4H-pyran-4-one. $^1$H NMR (dimethylsulfoxide-d$_6$, 300 MHz) δ 1.26 (t, J=7.1 Hz, 3H), 1.36 (s, 6H), 1.47 (s, 6H), 4.19 (q, J=7.1 Hz, 2H), 7.43 (br s, 2H). MS (ESI+) m/z 269.9 (M+H)$^+$.

Example 243B ethyl 4,4,6,6-tetramethyl-2-{[(2,2,3,3-tetramethylcyclopropyl)carbonyl]amino}-4,6-dihydrothieno[2,3-c]furan-3-carboxylate The title compound was prepared as described in Example 167A, substituting Example 243A for Example 10A, and tetramethylcyclopropanecarboxylic acid for 3-noradamantanecarboxylic acid. $^1$H NMR (dimethylsulfoxide-d$_6$, 300 MHz) δ 1.21 (s, 6H), 1.23 (s, 6H), 1.33 (t, J=7.1 Hz, 3H), 1.43 (s, 6H), 1.51 (s, 6H), 1.58 (s, 1H), 4.33 (q, J=7.1 Hz, 2H), 11.12 (br s, 1H). MS (ESI+) m/z 394.2 (M+H)$^+$. Anal. calcd. for C$_{21}$H$_{31}$NO$_4$S: C, 64.09; H, 7.94; N, 3.56. Found: C, 63.74; H, 8.04; N, 3.52.

Example 244

2-[(hexahydro-2,5-methanopentalen-3a(1H)-ylcarbonyl)amino]-N-(2,2,2-trifluoroethyl)-4,7-dihydro-5H-thieno[2,3-c]pyran-3-carboxamide The title compound was prepared as described in Example 166C, substituting Example 167B for Example 166B, and 2,2,2-trifluoroethylamine hydrochloride for propylamine. $^1$H NMR (dimethylsulfoxide-d$_6$, 300 MHz) δ 1.61-1.67 (m, 4H), 1.75-1.88 (m, 4H), 1.97-2.01 (m, 2H), 2.33 (br s, 1H), 2.59-2.63 (m, 1H), 2.81 (t, J=5.4 Hz, 2H), 3.85 (t, J=5.4 Hz, 2H), 4.03-4.15 (m, 2H), 4.66 (br s, 2H), 7.94 (t, J=6.4 Hz, 2H), 11.46 (br s, 1H). MS (ESI+) m/z 429.1 (M+H)$^+$.

Example 245 ethyl 2-[(hexahydro-2,5-methanopentalen-3a(1H)-ylcarbonyl)amino]-4,4,6,6-tetramethyl-4,6-dihydrothieno[2,3-c]furan-3-carboxylate The title compound was prepared as described in Example 167A, substituting Example 243A for Example 10A. $^1$H NMR (dimethylsulfoxide-d$_6$, 300 MHz) δ 1.33 (t, J=7.1 Hz, 3H), 1.45 (s, 6H), 1.52 (s, 6H), 1.62-1.82 (m, 8H), 1.87-1.90 (m, 2H), 1.97-2.04 (m, 2H), 2.28 (br s, 1H), 4.35 (q, J=7.1 Hz, 2H), 11.35 (br s, 1H). MS (ESI+) m/z 418.2 (M+H)$^+$. Anal. calcd. for C$_{23}$H$_{31}$NO$_4$S: C, 66.16; H, 7.48; N, 3.35. Found: C, 66.82; H, 7.70; N, 2.87.

Example 246 ethyl 2-({[2-methylbicyclo[2.2.1]hept-2-yl]carbonyl}amino)-4,7-dihydro-5H-thieno[2,3-c]pyran-3-carboxylate The title compound was prepared as described in Example 167A, substituting 2-methyl-bicyclo[2.2.1]heptane-2-carboxylic acid for 3-noradamantanecarboxylic acid. $^1$H NMR (dimethylsulfoxide-d$_6$, 300 MHz) δ 0.95 (dd, J=12.5, 2.2 Hz, 1H), 1.15-1.28 (m, 2H), 1.29 (s, 3H), 1.32 (t, J=7.2 Hz, 3H), 1.44-1.52 (m, 2H), 1.66-1.72 (m, 1H), 2.24 (br s, 1H), 2.33-2.41 (m, 2H), 2.79 (t, J=5.6 Hz, 2H), 3.07-3.11 (m, 1H), 3.84 (t, J=5.6 Hz, 2H), 4.31 (q, J=7.1 Hz, 2H), 4.62 (br s, 2H), 11.35 (br s, 1H). MS (ESI+) m/z 364.1 (M+H)$^+$.

Example 247 ethyl 2-{[(1-methoxybicyclo[2.2.2]oct-2-yl)carbonyl]amino}-4,7-dihydro-5H-thieno[2,3-c]pyran-3-carboxylate The title compound was prepared as described in Example 167A, substituting 1-methoxy-bicyclo[2.2.2]octane-2-carboxylic acid for 3-noradamantanecarboxylic acid. $^1$H NMR (dimethylsulfoxide-d$_6$, 300 MHz) δ 1.30 (t, J=7.2 Hz, 3H), 1.34-1.44 (m, 1H), 1.51-1.75 (m, 8H), 1.80-1.87 (m, 1H), 2.27-2.35 (m, 1H), 2.78 (t, J=5.6 Hz, 2H), 2.89-2.94 (m, 1H), 3.19 (s, 3H), 3.83 (t, J=5.6 Hz, 2H), 4.28 (q, J=7.1 Hz, 2H), 4.61 (s, 2H), 11.57 (br s, 1H). MS (ESI+) m/z 394.1 (M+H)$^+$.

Example 248

2-[(cyclohexylcarbonyl)amino]-N-propyl-4,5,6,7-tetrahydro-1-benzothiophene-3-carboxamide Example 248A 2-Amino-4,5,6,7-tetrahydro-benzo[b]thiophene-3-carboxylic acid The title compound was prepared as described in Example 166B, substituting 2-amino-4,5,6,7-tetrahydro-benzo[b]thiophene-3-carboxylic acid ethyl ester (ALDRICH) for Example 166A. The crude product was used for the next step without further purification. MS (ESI+) m/z 198 (M+H)$^+$ Example 248B 2-Amino-4,5,6,7-tetrahydro-benzo[b]thiophene-3-carboxylic acid propylamide The title compound was prepared as described in Example 166C, substituting Example 248A for Example 166B. The resulting solid was used without further purification. MS (ESI+) m/z 239.1 (M+H)$^+$

Example 248C

2-[(cyclohexylcarbonyl)amino]-N-propyl-4,5,6,7-tetrahydro-1-benzothiophene-3-carboxamide To a 20 mL scintillation vial was added Example 248B (19.64 mg, 0.08 mmol) in tetrahydrofuran (0.688 mL), cyclohexanecarbonyl chloride (1.2 eq.) in tetrahydrofuran (0.494 mL) and diisopropylethylamine (2.0 eq, 0.16 mmol) in tetrahydrofuran (0.688 mL). The resulting mixture was heated to 50 degrees Celsius for three hours. MP-Carbonate resin (Macroporous triethylammonium methylpolystyrene carbonate resin-Argonaut Technologies) (3.0 eq, 93.7 mg, 2.64 mmol/g) was added to the crude reaction and the resulting mixture was shaken for 0.5 hours at ambient temperature. The crude mixture was filtered and concentrated. The residues were dissolved in 1:1 dimethylsulfoxide/methanol and purified by reverse phase preparative HPLC on a Waters Symmetry C8 column (25 mm×100 mm, 7 µm particle size) using a gradient of 10% to 100% acetonitrile:0.1% aqueous trifluoroacetic acid over 8 min (10 min run time) at a flow rate of 40 mL/min). $^1$H NMR (dimethylsulfoxide-d$_6$, 300 MHz) δ ppm 0.89 (t, J=7.48 Hz, 3H) 1.02-1.45 (m, 6H) 1.42-1.63 (m, 2H) 1.59-1.93 (m, 9H) 2.57-2.79 (m, 4H) 3.21 (t, J=7.02 Hz, 2H) MS (ESI+) m/z 373.1 (M+H)$^+$.

Example 249

N-benzyl-2-[(hexahydro-2,5-methanopentalen-3a (1H)-ylcarbonyl)amino]-4,5,6,7-tetrahydro-1-benzothiophene-3-carboxamide A solution of Example 203B (35 mg, 0.1 mmol) in 1:1 acetonitrile/dimethylacetamide (0.7 mL) was added to a suspension of 3 equivalents of SiliaBond dichlorotriazine (Si-DCT, commercially available from Silicycle) and N-methylmorpholine (41 mg, 0.4 mmol) in 1:1 acetonitrile/dimethylacetamide (0.7 mL). After stirring for 1 minute at room temperature, a solution of benzylamine (15 mg, 0.13 mmol) in dimethylacetamide (0.7 mL) was added and the mixture was shaken at room temperature overnight. The mixture was filtered through Si-Carbonate (6 mL-1 g cartridge from Silicycle) and concentrated to dryness. The residue was dissolved in 1:1 dimethylsulfoxide/methanol and purified by reverse phase preparative HPLC on a Waters Symmetry C8 column (25 mm×100 mm, 7 µm particle size) using a gradient of 10% to 100% acetonitrile:0.1% aqueous trifluoroacetic acid over 8 min (10 min run time) at a flow rate of 40 mL/min) to afford the title compound. $^1$H NMR (500 MHz, dimethylsulfoxide-d$_6$) δ ppm 1.54-1.68 (m, 4H) 1.68-1.87 (m, 8H) 1.90-2.01 (m, 2H) 2.26-2.37 (m, 2H) 2.55-2.58 (m, 1H) 2.60-2.66 (m, 2H) 2.69-2.77 (m, 2H) 4.43-4.56 (m, 2H) 7.08-7.46 (m, 5H).

Example 250

2-[(hexahydro-2,5-methanopentalen-3a(1H)-ylcarbonyl)amino]-N-(2-methoxybenzyl)-4,5,6,7-tetrahydro-1-benzothiophene-3-carboxamide A solution of 2-[(hexahydro-2,5-methano-pentalene-3a-carbonyl)-amino]-4,5,6,7-tetrahydro-benzo[b]thiophene-3-carboxylic acid (35 mg, 0.1 mmol) in 1:1 acetonitrile/dimethylacetamide (0.7 mL) was added to a suspension of 3 equivalents of SiliaBond dichlorotriazine (Si-DCT, commercially available from Silicycle) and N-methylmorpholine (41 mg, 0.4 mmol) in 1:1 acetonitrile/dimethylacetamide (0.7 mL). After stirring for 1 minute at room temperature, a solution of 2-methoxybenzylamine (17 mg, 0.125 mmol) in dimethylacetamide (0.7 mL) was added and the mixture was shaken at room temperature overnight. The mixture was filtered through Si-Carbonate (6 mL-1 g cartridge from Silicycle) and then concentrated to dryness. The residue was dissolved in 1:1 dimethylsulfoxide/methanol and purified by reverse phase HPLC on a Waters Symmetry C8 column (25 mm×100 mm, 7 µm particle size) using a gradient of 10% to 100% acetonitrile:0.1% aqueous trifluoroacetic acid over 8 min (10 min run time) at a flow rate of 40 mL/min) to afford the title compound. $^1$H NMR (500 MHz, dimethylsulfoxide-d$_6$) δ ppm 1.55-1.68 (m, 4H) 1.70-1.86 (m, 8H) 1.90-2.00 (m, 2H) 2.26-2.35 (m, 2H) 2.54-2.59 (m, 1H) 2.60-2.66 (m, 2H) 2.69-2.83 (m, 2H) 3.79-3.86 (m, 3H) 4.30-4.50 (m, 2H) 6.81-7.40 (m, 4H); MS (ESI) m/z 465 (M+H)$^+$.

Example 251

N-(2-fluorobenzyl)-2-[(hexahydro-2,5-methanopentalen-3a(1H)-ylcarbonyl)amino]-4,5,6,7-tetrahydro-1-benzothiophene-3-carboxamide A solution of 2-[(hexahydro-2,5-methano-pentalene-3a-carbonyl)-amino]-4,5,6,7-tetrahydro-benzo[b]thiophene-3-carboxylic acid (35 mg, 0.1 mmol) in 1:1 acetonitrile/dimethylacetamide (0.7 mL) was added to a suspension of 3 equivalents of SiliaBond dichlorotriazine (Si-DCT, commercially available from Silicycle) and N-methylmorpholine (41 mg, 0.4 mmol) in 1:1 acetonitrile/dimethylacetamide (0.7 mL). After stirring for 1 minute at room temperature, a solution of 2-fluorobenzylamine (16 mg, 0.125 mmol) in dimethylacetamide (0.7 mL) was added and the mixture was shaken at room temperature overnight. The mixture was filtered through Si-Carbonate (6 mL-1 g cartridge from Silicycle) and then concentrated to dryness. The residue was dissolved in 1:1 dimethylsulfoxide/methanol and purified by reverse phase HPLC on a Waters Symmetry C8 column (25 mm×100 mm, 7 µm particle size) using a gradient of 10% to 100% acetonitrile:0.1% aqueous trifluoroacetic acid over 8 min (10 min run time) at a flow rate of 40 mL/min) to afford the title compound. $^1$H NMR (500 MHz, dimethylsulfoxide-d$_6$) δ ppm 1.53-1.69 (m, 4H) 1.68-1.87 (m, 8H) 1.90-2.02 (m, 2H) 2.26-2.34 (m, 2H) 2.55-2.59 (m, 1H) 2.60-2.67 (m, 2H) 2.68-2.78 (m, 2H) 4.39-4.56 (m, 2H) 7.08-7.42 (m, 4H); MS (ESI) m/z 453 (M+H)$^+$.

Example 252

N-(3-chlorobenzyl)-2-[(hexahydro-2,5-methanopentalen-3a(1H)-ylcarbonyl)amino]-4,5,6,7-tetrahydro-1-benzothiophene-3-carboxamide A solution of 2-[(hexahydro-2,5-methano-pentalene-3a-carbonyl)-amino]-4,5,6,7-tetrahydro-benzo[b]thiophene-3-carboxylic acid commercial? (35 mg, 0.1 mmol) in 1:1 acetonitrile/dimethylacetamide (0.7 mL) was added to a suspension of 3 equivalents of SiliaBond dichlorotriazine (Si-DCT, commercially available from Silicycle) and N-methylmorpholine (41 mg, 0.4 mmol) in 1:1 acetonitrile/dimethylacetamide (0.7 mL). After stirring for 1 minute at room temperature, a solution of 3-chlorobenzylamine (18 mg, 0.125 mmol) in dimethylacetamide (0.7 mL) was added and the mixture was shaken at room temperature overnight. The mixture was filtered through Si-Carbonate (6 mL-1 g cartridge from Silicycle) and then concentrated to dryness. The residue was dissolved in 1:1 dimethylsulfoxide/methanol and purified by reverse phase HPLC on a Waters Symmetry C8 column (25 mm×100 mm, 7 μm particle size) using a gradient of 10% to 100% acetonitrile:0.1% aqueous trifluoroacetic acid over 8 min (10 min run time) at a flow rate of 40 mL/min) to afford the title compound. $^1$H NMR (500 MHz, dimethyl-sulfoxide-d$_6$) δ ppm 1.53-1.69 (m, 4H) 1.70-1.87 (m, 8H) 1.90-2.01 (m, 2H) 2.28-2.34 (m, 2H) 2.55-2.59 (m, 1H) 2.59-2.67 (m, 2H) 2.69-2.77 (m, 2H) 4.38-4.54 (m, 2H) 7.15-7.47 (m, 4H); MS (ESI) m/z 470 (M+H)$^+$.

Example 253

2-[(hexahydro-2,5-methanopentalen-3a(1H)-ylcarbonyl)amino]-6-methyl-N-propyl-4,5,6,7-tetrahydrothieno[2,3-c]pyridine-3-carboxamide Example 253A 2-Amino-4,7-dihydro-5H-thieno[2,3-c]pyridine-3,6-dicarboxylic acid 6-tert-butyl ester 3-ethyl ester To a solution of t-butyl-4-oxo-1-piperidinecarboxylate (25 g, 0.13 mol), ethyl cyanoacetate (15 mL, 0.14 mol) and sulfur (4.4 g, 0.14 mol) in 200 mL of ethanol was added morpholine (31 mL, 0.35 mol). The mixture was warmed to 50° C. and stirred for 3 hours. The reaction mixture was then cooled to ambient temperature, diluted with diethyl ether and filtered. The residue was washed with H$_2$O and diethyl ether and saved. The filtrate was concentrated under reduced pressure and purified via column chromatography (SiO$_2$, 70% hexanes:ethyl acetate). The resulting material was combined with the filtration residue to afford the title compound. MS (DCI/NH$_3$) m/z 327 (M+H)$^+$.

Example 253B

2-[(Hexahydro-2,5-methano-pentalene-3a-carbonyl)-amino]-4,7-dihydro-5H-thieno[2,3-c]pyridine-3,6-dicarboxylic acid 6-tert-butyl ester 3-ethyl ester Step One
A solution of 3-noradamantanecarboxylic acid (Aldrich, 12 g, 70 mmol) in 100 mL of thionyl chloride was warmed to reflux for 1 hour. The mixture was then cooled to ambient temperature and concentrated under reduced pressure. The residue was dissolved in 100 mL benzene and concentrated under reduced pressure (3x) to afford hexahydro-2,5-methano-pentalene-3a-carbonyl chloride.
Step Two
To a solution of Example 253A (16.4 g, 50 mmol) and pyridine (5.1 mL, 63 mmol) in 400 mL CH$_3$CN at 0° C. was added a solution of the product from step one in 50 mL CH$_3$CN via cannula. The ice-bath was removed and the reaction mixture was warmed to reflux for 3 hours. The mixture was cooled to ambient temperature, diluted with CH$_2$Cl$_2$ and washed with saturated aqueous NH$_4$Cl. The aqueous phase was extracted twice with CH$_2$Cl$_2$. The combined organic extracts were dried over Na$_2$SO$_4$, filtered, concentrated under reduced pressure and purified via column chromatography (SiO$_2$, 10% ethyl acetate/hexanes) to afford the title compound. MS (DCI/NH$_3$) m/z 475 (M+H)$^+$.

Example 253C

2-[(Hexahydro-2,5-methano-pentalene-3a-carbonyl)-amino]-4,7-dihydro-5H-thieno[2,3-c]pyridine-3,6-dicarboxylic acid 6-tert-butyl ester To a solution of the product of Example 253B (14.25 g, 30 mmol) in 250 mL of ethanol was added 80 mL of 10% aqueous KOH. This mixture was warmed to reflux and stirred for 4 hours. The mixture was then cooled to 0° C., quenched with 1 N aqueous HCl and diluted with CH$_2$Cl$_2$. The layers were separated and the aqueous phase was extracted twice with CH$_2$Cl$_2$. The combined organic extracts were dried over anhydrous Na$_2$SO$_4$, filtered, concentrated under reduced pressure to afford the title compound (9.5 g, 21 mmol, 71% yield). MS (DCI/NH$_3$) m/z 447 (M+H)$^+$.

Example 253D

2-[(Hexahydro-2,5-methano-pentalene-3a-carbonyl)-amino]-3-propylcarbamoyl-4,7-dihydro-5H-thieno[2,3-c]pyridine-6-carboxylic acid tert-butyl ester To a solution of Example 253C (8.9 g, 20 mmol), propylamine (1.3 g, 22 mmol) and N,N-diisopropylethylamine (12.7 g, 21 mmol) in 200 mL of tetrahydrofuran was added o-(7-azabenzotriazol-1-yl)-N,N,N',N'-tetramethyluronium hexafluorophosphate (HATU, 8.0 g, 21 mmol). This mixture stirred at ambient temperature for 18 hours and was quenched with H$_2$O and diluted with ethyl acetate. The layers were separated and the organic phase was washed with saturated aqueous NaHCO$_3$. The combined aqueous layers were extracted twice with ethyl acetate. The organic extracts were combined, dried over Na$_2$SO$_4$, filtered, concentrated under reduced pressure and purified via column chromatography (SiO$_2$, 70% hexanes:ethyl acetate) to afford the title compound. MS (DCI/NH$_3$) m/z 488 (M+H)$^+$.

Example 253E

2-[(Hexahydro-2,5-methano-pentalene-3a-carbonyl)-amino]-4,5,6,7-tetrahydro-thieno[2,3-c]pyridine-3-carboxylic acid propylamide To a solution of Example 253D (0.177 g, 3.0 mmol) in 4 mL CH$_2$Cl$_2$ at 0° C. was added trifluoroacetic acid (4 mL). The mixture was allowed to warm to ambient temperature and stir for 2 hours. The mixture was then concentrated under reduced pressure and purified via column chromatography (SiO$_2$, 9:1:0.1 CH$_2$Cl$_2$:CH$_3$OH:NH$_4$OH) to afford the title compound. MS (DCI/NH$_3$) m/z 388 (M+H)$^+$.

Example 253F

2-[(hexahydro-2,5-methanopentalen-3a(1H)-ylcarbonyl)amino]-6-methyl-N-propyl-4,5,6,7-tetrahydrothieno[2,3-c]pyridine-3-carboxamide To a solution of Example 253E (0.172 g, 0.5 mmol) in 5 mL formaldehyde (37% aqueous solution) was added sodium triacetoxyborohydride (0.16 g, 0.74 mmol). The mixture stirred at ambient temperature for 18 hours and was quenched with saturated, aqueous NaHCO$_3$ and diluted with CH$_2$Cl$_2$. The layers were separated and the organic layer was dried over Na$_2$SO$_4$, filtered, concentrated under reduced pressure and purified via column chromatography (SiO$_2$, 9:1:0.1 CH$_2$Cl$_2$:CH$_3$OH:NH$_4$OH) to afford the title compound. $^1$H NMR (500 MHz, dimethylsulfoxide-d$_6$) δ ppm 0.89 (t, J=7 Hz, 3H) 1.47-1.58 (m, 2H) 1.58-1.70 (m, 4H) 1.72-1.88 (m, 4H) 1.93-2.04 (m, 2H) 2.26-2.41 (m, 5H) 2.55-2.66 (m, 3H) 2.75-2.88 (m, 2H) 3.16-3.26 (m, 2H) 3.39-3.51 (m, 2H) 7.21-7.40 (m, 1H) 11.83-11.96 (m, 1H). MS (DCI/NH$_3$) m/z 402 (M+H)$^+$. anal. calculated for C$_{22}$H$_{31}$N$_3$O$_2$S.0.2C$_4$H$_8$O$_2$: C, 65.33; H, 7.84; N, 10.02. Found: C, 65.30; H, 7.71; N, 8.80.

Example 254

2-[(hexahydro-2,5-methanopentalen-3a(1H)-ylcarbonyl)amino]-6-(methylsulfonyl)-N-propyl-4,5,6,7-tetrahydrothieno[2,3-c]pyridine-3-carboxamide To a solution of Example 253E (0.17 g, 0.50 mmol) in 5 mL of tetrahydrofuran was added methanesulfonyl chloride (0.69 g, 0.55 mmol). This mixture stirred at ambient temperature for 18 hours and was quenched with saturated aqueous NaHCO$_3$ and diluted with CH$_2$Cl$_2$. The layers were separated and the organic extract was dried over Na$_2$SO$_4$, filtered, concentrated under reduced pressure and purified via column chromatography (SiO$_2$, 9:1: CH$_2$Cl$_2$:CH$_3$OH:) to afford the title compound. $^1$H NMR (500 MHz, dimethylsulfoxide-d$_6$) δ ppm 0.90 (t, 3H) 1.17 (t, 2H) 1.53 (dd, 2H) 1.64 (dd, 4H) 1.74-1.90 (m, 4H) 1.93-2.04 (m, 2H) 2.30-2.38 (m, 2H) 2.55-2.65 (m, 1H) 2.92-3.00 (m, 5H) 3.05-3.14 (m, 1H) 3.17-3.27 (m, 1H) 3.41-3.48 (m, 1H) 4.35-4.38 (m, 1H) 7.37-7.48 (m, 1H) 11.74-11.81 (m, 1H). MS (DCI/NH$_3$) m/z 462 (M+H)$^+$.

Example 255

5-tert-butyl 3-ethyl 2-[(hexahydro-2,5-methanopentalen-3a(1H)-ylcarbonyl)amino]-6,7-dihydrothieno[3,2-c]pyridine-3,5(4H)-dicarboxylate

Example 255A

2-Amino-6,7-dihydro-4H-thieno[3,2-c]pyridine-3,5-dicarboxylic acid 5-tert-butyl ester To a solution of 3-oxo-piperidine-1-carboxylic acid tert-butyl ester (25 g, 0.13 mol), ethyl cyanoacetate (15 mL, 0.14 mol) and sulfur (4.4 g, 0.14 mol) in 200 mL of ethanol was added morpholine (31 mL, 0.35 mol). This mixture was warmed to 50° C. and stirred for 3 hours. The reaction mixture was then cooled to ambient temperature, diluted with ethyl acetate and washed with H$_2$O. The organic extracts were dried over Na$_2$SO$_4$, filtered, concentrated under reduced pressure and purified via column chromatography (SiO$_2$, 70% hexanes:ethyl acetate) to afford the title compound. MS (DCI/NH$_3$) m/z 327 (M+H)$^+$.

Example 255B 5-tert-butyl 3-ethyl 2-[(hexahydro-2,5-methanopentalen-3a(1H)-ylcarbonyl)amino]-6,7-dihydrothieno[3,2-c]pyridine-3,5(4H)-dicarboxylate Step One
A solution of 3-noradamantanecarboxylic acid (Aldrich, 4.5 g, 26 mmol) in 40 mL of thionyl chloride was warmed to reflux for 1 hour. The mixture was then cooled to ambient temperature and concentrated under reduced pressure. The residue was dissolved in 40 mL benzene and concentrated under reduced pressure (3×) to afford hexahydro-2,5-methano-pentalene-3a-carbonyl chloride.

Step Two
To a solution of Example 255A (6.5 g, 20 mmol) and pyridine (1.9 mL, 26 mmol) in 150 mL CH$_3$CN at 0° C. was added a solution of the product from step one in 50 mL CH$_3$CN via cannula. The ice-bath was removed and the reaction mixture was warmed to reflux for 3 hours. The mixture was cooled to ambient temperature, diluted with CH$_2$Cl$_2$ and washed with saturated aqueous NH$_4$Cl. The layers were separated and the aqueous phase was extracted twice with CH$_2$Cl$_2$. The combined organic extracts were dried over Na$_2$SO$_4$, filtered, concentrated under reduced pressure and purified via column chromatography (SiO$_2$, 10% ethyl acetate/hexanes) to afford the title compound. $^1$H NMR (500 MHz, dimethylsulfoxide-d$_6$) δ ppm 1.29-1.37 (m, 3H) 1.40-1.44 (m, 9H) 1.51-2.05 (m, 20H) 2.31-2.39 (m, 2H) 3.56-3.64 (m, 2H) 4.51-4.57 (m, 2H) 11.29-11.32 (m, 1H) 11.93-12.04 (m, 1H). MS (DCI/NH$_3$) m/z 475 (M+H)$^+$. anal. calculated for C$_{25}$H$_{34}$N$_3$O$_8$S: C, 63.47; H, 7.22; N, 5.90. Found: C, 63.14; H, 6.70; N, 5.51

Example 256 ethyl 2-[(hexahydro-2,5-methanopentalen-3a(1H)-ylcarbonyl)amino]-5-(2-methoxyethyl)-4,5,6,7-tetrahydrothieno[3,2-c]pyridine-3-carboxylate

Example 256A

22-[(Hexahydro-2,5-methano-pentalene-3a-carbonyl)-amino]-4,5,6,7-tetrahydro-thieno[3,2-c]pyridine-3-carboxylic acid ethyl ester To a solution of Example 255B (1.77 g, 3.0 mmol) in 4 mL of CH$_2$Cl$_2$ at 0° C. was added trifluoroacetic acid (4 mL) The mixture was allowed to warm to ambient temperature and stir for 2 hours. The mixture was then concentrated under reduced pressure and purified via column chromatography (SiO$_2$, 9:1: 0.1 CH$_2$Cl$_2$:CH$_3$OH:NH$_4$OH) to afford the title compound. MS (DCI/NH$_3$) m/z 388 (M+H)$^+$.

Example 256B ethyl 2-[(hexahydro-2,5-methanopentalen-3a(1H)-ylcarbonyl)amino]-5-(2-methoxyethyl)-4,5,6,7-tetrahydrothieno[3,2-c]pyridine-3-carboxylate To a solution of Example 256A (0.194 g, 0.5 mmol) in 1.5 mL DMF was added 2-bromoethyl methyl diethyl ether (80 mg, 0.60 mmol). The mixture was warmed to 120° C. and stirred for 1 hours. The reaction mixture was then cooled to ambient temperature, diluted with diethyl ether and washed with H$_2$O. The organic extracts were dried over Na$_2$SO$_4$, filtered, concentrated under reduced pressure and purified via column chromatography (SiO$_2$, 0-50% ethyl acetate/hexanes gradient) to afford the title compound. $^1$H NMR (500 MHz, CDCl$_3$) δ ppm 1.37 (t, 3H) 1.44-2.21 (m, 14H) 2.34-2.42 (m, 2H) 2.69-2.82 (m, 2H) 3.26-3.42 (m, 6H) 3.60-3.75 (m, 2H) 4.27-4.41 (m, 2H) MS (DCI/NH$_3$)m/z 433 (M+H)$^+$.

Example 257

2-({[1-(4-fluorophenyl)cyclohexyl]carbonyl}amino)-N-propyl-4,7-dihydro-5H-thieno[2,3-c]pyran-3-carboxamide

Example 257A

2-{[1-(4-fluoro-phenyl)-cyclohexanecarbonyl]-amino)-4,7-dihydro-5H-thieno[2,3-c]pyran-3-carboxylic acid The title compound was prepared as described in Example 166B, substituting Example 233 for Example 166A. LCMS (ESI+) m/z 404 (M+H)$^+$.

Example 257B 2-({[1-(4-fluorophenyl)cyclohexyl]carbonyl}amino)-N-propyl-4,7-dihydro-5H-thieno[2,3-c]pyran-3-carboxamide The title compound was prepared as described in Example 166C, substituting Example 257A for Example 166B. $^1$H NMR (CDCl$_3$, 300 MHz) δ ppm 0.97 (t, J=7.29 Hz, 3H), 1.57-1.68 (m, 6H), 1.96-2.08 (m, 2H), 2.39-2.53 (m, 2H), 2.76 (t, J=5.26 Hz, 2H), 3.31-3.41 (m, 2H), 3.95 (t, J=5.43 Hz, 2H), 4.71 (t, J=1.53 Hz, 3H), 5.72 (s, 1H), 6.97-7.06 (m, 2H), 7.40-7.49 (m, 3H), 12.28 (s, 1H); MS (DCI/NH$_3$) m/z 445 (M+H)$^+$.

Example 258

N-{3-[2-azabicyclo[2.2.1]hept-2-ylcarbonyl]-4,5,6,7-tetrahydro-1-benzothien-2-yl}hexahydro-2,5-methanopentalene-3a(1H)-carboxamide The title compound was prepared as described in Example 166C, substituting Example 167B for Example 166B, and 2-aza-bicyclo[2.2.1]heptane for propylamine. $^1$H NMR (CDCl$_3$, 500 MHz) δ ppm 1.40-1.52 (m, 3H), 1.61-1.75 (m, 9H), 1.78-1.93 (m, 7H), 2.06 (d, J=10.37 Hz, 2H), 2.35 (s, 2H), 2.48 (s, 2H), 2.58-2.76 (m, 4H), 3.47 (br s, 1H), 4.09 (br s, 1H), 9.21 (br s, 1H); MS (DCI/NH$_3$) m/z 425 (M+H)$^+$.

Example 259

N-{3-[2-azabicyclo[2.2.1]hept-2-ylcarbonyl]-4,7-dihydro-5H-thieno[2,3-c]pyran-2-yl}hexahydro-2,5-methanopentalene-3a(1H)-carboxamide The title compound was prepared as described in Example 166C, substituting Example 167B for Example 166B, and 2-aza-bicyclo[2.2.1]heptane for propylamine. $^1$H NMR (CDCl$_3$, 300 MHz) δ ppm 1.58-1.67 (m, 6H), 1.67-1.76 (m, 4H), 1.81-1.92 (m, 5H), 2.02-2.11 (m, 3H), 2.37 (br s, 2H), 2.58-2.79 (m, 4H), 3.50 (d, J=2.37 Hz, 1H), 3.85 (s, 1H), 3.90-3.99 (m, 1H), 4.77 (s, 1H), 9.55 (br s, 1H); MS (DCI/NH$_3$) m/z 427 (M+H)$^+$.

Example 260

N-propyl-2-{[(2,2,3,3-tetramethylcyclopropyl)carbonyl]amino}-4,5-dihydrothieno[2,3-b]thiophene-3-carboxamide

Example 260A

2-Amino-4,5-dihydro-thieno[2,3-b]thiophene-3-carboxylic acid ethyl ester

The title compound was prepared as described in Example 10A, substituting dihydro-thiophen-3-one (Aldrich, 1003-04-9) for tetrahydro-4H-pyran-4-one. MS (ESI+) m/z 103.0 (M+H)$^+$

Example 260B

2-[(2,2,3,3-Tetramethyl-cyclopropanecarbonyl)-amino]-4,5-dihydro-thieno[2,3-b]thiophene-3-carboxylic acid ethyl ester The title compound was prepared as described in Example 10B, substituting Example 260A for Example 10A. MS (ESI+) m/z 354.1 (M+H)$^+$

Example 260C

2-[(2,2,3,3-Tetramethyl-cyclopropanecarbonyl)-amino]-4,5-dihydro-thieno[2,3-b]thiophene-3-carboxylic acid The title compound was prepared as described in Example 166B, substituting Example 260B for Example 166A. The crude product was used for the next step without further purification.
MS (ESI+) m/z 324.0 (M–H)$^−$

Example 260D

N-propyl-2-{[(2,2,3,3-tetramethylcyclopropyl)carbonyl]amino}-4,5-dihydrothieno[2,3-b]thiophene-3-carboxamide The title compound was prepared as described in Example 166C, substituting Example 260C for Example 166B. $^1$H NMR (500 MHz, dimethylsulfoxide-d$_6$) δ ppm 0.88 (t, J=7.46 Hz, 3H) 1.03-1.35 (m, 12H) 1.40 (s, 1H) 1.46-1.75 (m, 2H) 3.06-3.29 (m, 4H) 3.76 (t, J=7.80 Hz, 2H) 7.38 (t, J=5.43 Hz, 1H) 11.54 (s, 1H). MS (ESI+) m/z 367.3 (M+H)$^+$. Anal. calcd. for C$_{18}$H$_{26}$N$_2$O$_2$S$_2$: C, 58.98; H, 7.15; N, 7.64. Found: C, 59.21; H, 7.27; N, 7.64.

Example 261

N-{3-[(3-hydroxyazetidin-1-yl)carbonyl]-4,7-dihydro-5H-thieno[2,3-c]pyran-2-yl}hexahydro-2,5-methanopentalene-3a(1H)-carboxamide The title compound was prepared as described in Example 166C, substituting Example 167B for Example 166B, and 3-hydroxyazetidine hydrochloride (Matrix, 18621-18-6) for propylamine. $^1$H NMR (500 MHz, dimethylsulfoxide-d$_6$) δ ppm 1.45-1.77 (m, 4H) 1.72-2.10 (m, 4H) 2.32 (s, 2H) 2.53-2.83 (m, 4H) 3.59-3.89 (m, 4H) 4.21 (dd, J=10.34, 6.95 Hz, 2H) 4.47 (d, J=6.10 Hz, 1H) 4.65 (s, 2H) 5.41-5.95 (m, 2H) 10.47 (s, 1H). MS (ESI+) m/z 403.1 (M+H)$^+$ Anal. calcd. for C$_{21}$H$_{26}$N$_2$O$_4$S: C, 62.66; H, 6.51; N, 6.96. Found: C, 62.54; H, 6.49; N, 6.63.

Example 262

N-{3-[(3-methoxyazetidin-1-yl)carbonyl]-4,7-dihydro-5H-thieno[2,3-c]pyran-2-yl}hexahydro-2,5-methanopentalene-3a(1H)-carboxamide The title compound was prepared as described in Example 166C, substituting Example 167B for Example 166B, and 3-methoxyazetidine hydrochloride (J&W PharmLab LLC, 25-0002) for propylamine. $^1$H NMR (500 MHz, dimethylsulfoxide-d$_6$) δ ppm 1.42-1.77 (m, 4H) 1.74-2.18 (m, 6H) 2.32 (s, 2H) 2.52-2.84 (m, 3H) 3.20 (s, 3H) 3.63-3.94 (m, 4H) 4.10-4.35 (m, 3H) 4.65 (s, 2H) 10.40 (s, 1H). MS (ESI+) m/z 417.1 (M+H)$^+$. Anal. calcd. for C$_{22}$H$_{28}$N$_2$O$_4$S: C, 63.44; H, 6.78; N, 6.75. Found: C, 63.08; H, 6.83; N, 6.62.

Example 263

N-{3-[(3,3-difluoroazetidin-1-yl)carbonyl]-4,5,6,7-tetrahydro-1-benzothien-2-yl}hexahydro-2,5-methanopentalene-3a(1H)-carboxamide The title compound was prepared as described in Example 166C, substituting Example 203B for Example 166B, and 3,3-difluoroazetidine hydrochloride (Matrix, 288315-03-7) for propylamine. $^1$H NMR (500 MHz, dimethylsulfoxide-d$_6$) δ ppm 1.49-1.83 (m, 10H) 1.83-2.07 (m, 5H) 2.30 (s, 2H) 2.55-2.72 (m, 4H) 4.40 (t, J=12.54 Hz, 4H) 10.09 (s, 1H). MS (ESI+) m/z 421.2 (M+H)$^+$. Anal. calcd. for C22H26F2N2O2S: C, 62.84; H, 6.23; N, 6.66. Found: C, 63.17; H, 6.06; N, 6.44.

Example 264 isopropyl 2-[(hexahydro-2,5-methanopentalen-3a (1H)-ylcarbonyl)amino]-4,7-dihydro-5H-thieno[2,3-c]pyran-3-carboxylate

Example 264A

2-Amino-4,7-dihydro-5H-thieno[2,3-c]pyran-3-carboxylic acid isopropyl ester

The title compound was prepared as described in Example 10A, substituting cyano-acetic acid isopropyl ester for ethyl cyanoacetate. MS (ESI+) m/z 242.1 (M+H)$^+$

Example 264B isopropyl 2-[(hexahydro-2,5-methanopentalen-3a (1H)-ylcarbonyl)amino]-4,7-dihydro-5H-thieno[2,3-c]pyran-3-carboxylate The title compound was prepared as described in Example 167A, substituting Example 264A for Example 10A. $^1$H NMR (500 MHz, dimethylsulfoxide-d$_6$) δ ppm 1.31 (d, J=6.10 Hz, 6H) 1.47-1.95 (m, 6H) 1.92-2.09 (m, 4H) 2.31 (d, J=17.29 Hz, 4H) 2.65 (d, J=5.76 Hz, 2H) 2.79 (t, J=5.59 Hz, 2H) 3.84 (t, J=5.76 Hz, 1H) 4.88-5.43 (m, 1H) 11.35 (s, 1H). MS (ESI+) m/z 390.1 (M+H)$^+$

Example 265

N-{3-[(3,3-difluoroazetidin-1-yl)carbonyl]-5-phenylthien-2-yl}hexahydro-2,5-methanopentalene-3a (1H)-carboxamide The title compound was prepared as described in Example 166C, substituting Example 146B for Example 166B, and 3,3-difluoroazetidine hydrochloride (Matrix, 288315-03-7) for propylamine. $^1$H NMR (500 MHz, dimethylsulfoxide-d$_6$) δ ppm 1.53-1.72 (m, 8H) 1.80 (d, J=7.12 Hz, 2H) 1.84-1.95 (m, 2H) 1.95-2.14 (m, 2H) 2.35 (s, 2H) 2.65 (t, J=6.61 Hz, 1H) 4.13-5.21 (m, 4H) 7.30 (t, J=7.29 Hz, 1H) 7.37-7.51 (m, 2H). MS (ESI+) m/z 443.1 (M+H)$^+$

Example 266 isobutyl 2-[(hexahydro-2,5-methanopentalen-3a (1H)-ylcarbonyl)amino]-5,6-dihydro-4H-4,7-ethanothieno[2,3-b]pyridine-3-carboxylate

Example 266A

4-Amino-3-thia-1-aza-tricyclo[5.2.2.0$^{2,6}$]undeca-2 (6),4-diene-5-carboxylic acid isobutyl ester The title compound was prepared as described in Example 10A, substituting 3-quinuclidinone hydrochloride (Aldrich, 1193-65-3) for tetrahydro-4H-pyran-4-one and isobutyl cyanoacetate for ethyl cyanoacetate. MS (ESI+) m/z 281.1.0 (M+H)$^+$.

Example 266B isobutyl 2-[(hexahydro-2,5-methanopentalen-3a (1H)-ylcarbonyl)amino]-5,6-dihydro-4H-4,7-ethanothieno[2,3-b]pyridine-3-carboxylate The title compound was prepared as described in Example 167A, substituting Example 266A for Example 10A. $^1$H NMR (500 MHz, dimethylsulfoxide-d$_6$) δ ppm 0.97 (d, J=6.78 Hz, 6H) 1.19-1.46 (m, 2H) 1.55-2.01 (m, 8H) 1.87-2.18 (m, 4H) 2.34 (s, 3H) 2.64 (s, 1H) 2.64 (s, 1H) 3.10 (d, J=4.07 Hz, 3H) 3.79 (s, 1H) 4.11 (d, J=6.44 Hz, 2H) 11.35 (s, 1H). MS (ESI+) m/z 429.2 (M+H)$^+$.

Example 267 isobutyl 2-[(hexahydro-2,5-methanopentalen-3a (1H)-ylcarbonyl)amino]-4,7-dihydro-5H-thieno[2,3-c]pyran-3-carboxylate

Example 267A

2-Amino-4,7-dihydro-5H-thieno[2,3-c]pyran-3-carboxylic acid isobutyl ester

The title compound was prepared as described in Example 10A, substituting isobutyl cyanoacetate for ethyl cyanoacetate. MS (ESI+) m/z 256.1.0 (M+H)$^+$

Example 267B isobutyl 2-[(hexahydro-2,5-methanopentalen-3a (1H)-ylcarbonyl)amino]-4,7-dihydro-5H-thieno[2,3-c]pyran-3-carboxylate The title compound was prepared as described in Example 167A, substituting Example 267A for Example 10A. $^1$H NMR (500 MHz, dimethylsulfoxide-d$_6$) δ ppm 0.97 (d, J=6.78 Hz, 6H) 1.37-1.75 (m, 6H) 1.71-2.14 (m, 6H) 2.34 (s, 2H) 2.81 (t, J=5.43 Hz, 2H) 3.86 (t, J=5.59 Hz, 2H) 4.07 (d, J=6.44 Hz, 2H) 4.63 (s, 2H) 11.42 (s, 1H)

MS (ESI+) m/z 404.1 (M+H)$^+$

Example

2-[(hexahydro-2,5-methanopentalen-3a(1H)-ylcarbonyl)amino]-5-methyl-N-propylthiophene-3-carboxamide

Example 268A

2-[(Hexahydro-2,5-methano-pentalene-3a-carbonyl)-amino]-5-methyl-thiophene-3-carboxylic acid methyl ester The title compound was prepared as described in Example 167A, substituting 2-amino-5-methyl-thiophene-3-carboxylic acid methyl ester (Oakwood) for Example 10A. MS (ESI+) m/z 320.1.0 (M+H)$^+$

Example 268B

2-[(Hexahydro-2,5-methano-pentalene-3a-carbonyl)-amino]-5-methyl-thiophene-3-carboxylic acid The title compound was prepared as described in Example 166B, substituting Example 268A for Example 166A. The crude product was used for the next step without further purification. MS (ESI+) m/z 303.0 (M−H)⁻

Example 268C

2-[(hexahydro-2,5-methanopentalen-3a(1H)-ylcarbonyl)amino]-5-methyl-N-propylthiophene-3-carboxamide The title compound was prepared as described in Example 166C, substituting Example 268B for Example 166B. $^1$H NMR (500 MHz, dimethylsulfoxide-$d_6$) δ ppm 0.88 (t, J=7.29 Hz, 3H) 1.26-1.72 (m, 8H) 1.68-1.94 (m, 4H) 1.92-2.18 (m, 2H) 2.34 (s, 3H) 2.60 (t, J=6.78 Hz, 1H) 3.03-3.27 (m, 2H) 7.12 (s, 1H) 8.24 (t, J=5.76 Hz, 1H) 12.40 (s, 1H) MS (ESI+) m/z 347.0 (M+H)⁺

Example 269

5-tert-butyl-2-[(hexahydro-2,5-methanopentalen-3a(1H)-ylcarbonyl)amino]-N-propylthiophene-3-carboxamide

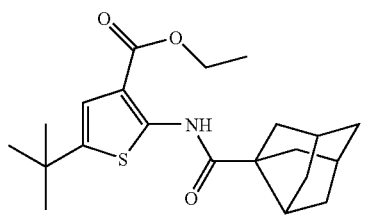

Example 269A 5-tert-Butyl-2-[(hexahydro-2,5-methano-pentalene-3a-carbonyl)-amino]-thiophene-3-carboxylic acid ethyl ester The title compound was prepared as described in Example 167A, substituting 2-amino-5-tert-butyl-thiophene-3-carboxylic acid ethyl ester (Fluorochem) for Example 10A. MS (ESI+) m/z 376.2 (M+H)⁺

Example 269B 5-tert-Butyl-2-[(hexahydro-2,5-methano-pentalene-3a-carbonyl)-amino]-thiophene-3-carboxylic acid The title compound was prepared as described in Example 166B, substituting Example 269A for Example 166A. The crude product was used for the next step without further purification.

Example 269C 5-tert-butyl-2-[(hexahydro-2,5-methanopentalen-3a(1H)-ylcarbonyl)amino]-N-propylthiophene-3-carboxamide The title compound was prepared as described in Example 166C, substituting Example 269B for Example 166B. $^1$H NMR (500 MHz, dimethylsulfoxide-$d_6$) δ ppm 0.89 (t, J=7.29 Hz, 3H) 1.32 (s, 9H) 1.41-1.73 (m, 6H) 1.71-1.93 (m, 4H) 1.92-2.09 (m, 2H) 2.33 (s, 2H) 2.60 (t, J=6.78 Hz, 1H) 3.01-3.27 (m, 2H) 7.22 (s, 1H) 8.28 (t, J=5.59 Hz, 1H) 12.42 (s, 1H). MS (ESI+) m/z 389.2 (M+H)⁺

Example 270

5-ethyl-2-[(hexahydro-2,5-methanopentalen-3a(1H)-ylcarbonyl)amino]-N-propylthiophene-3-carboxamide

Example 270A

5-Ethyl-2-[(hexahydro-2,5-methano-pentalene-3a-carbonyl)-amino]-thiophene-3-carboxylic acid ethyl ester The title compound was prepared as described in Example 167A, substituting ethyl 2-amino-5-ethylthiophene-3-carboxylate (Oakwood) for Example 10A. MS (ESI+) m/z 348.2 (M+H)⁺

Example 270B

5-Ethyl-2-[(hexahydro-2,5-methano-pentalene-3a-carbonyl)-amino]-thiophene-3-carboxylic acid The title compound was prepared as described in Example 166B, substituting Example 270A for Example 166A. The crude product was used for the next step without further purification. MS (ESI+) m/z 346 (M−H)⁻.

Example 270C 5-ethyl-2-[(hexahydro-2,5-methanopentalen-3a(1H)-ylcarbonyl)amino]-N-propylthiophene-3-carboxamide The title compound was prepared as described in Example 166C, substituting Example 270B for Example 166B. $^1$H NMR (500 MHz, dimethylsulfoxide-$d_6$) δ ppm 0.88 (t, J=7.46 Hz, 3H) 1.23 (t, J=7.46 Hz, 3H) 1.35-1.75 (m, 7H) 1.72-1.97 (m, 3H) 1.92-2.12 (m, 2H) 2.33 (s, 2H) 2.56-2.67 (m, 1H) 2.70 (q, J=7.69 Hz, 2H) 3.01-3.26 (m, 2H) 7.16 (s, 1H) 8.25 (t, J=5.59 Hz, 1H) 12.41 (s, 1H). MS (ESI+) m/z 361.1 (M+H)⁺

Example 271

2-[(hexahydro-2,5-methanopentalen-3a(1H)-ylcarbonyl)amino]-5-methoxy-4-methyl-N-propylthiophene-3-carboxamide

Example 271A

2-Amino-5-methoxy-4-methyl-thiophene-3-carboxylic acid ethyl ester

The title compound was prepared as described in Example 10A, substituting methoxyacetone for tetrahydro-4H-pyran-4-one. MS (ESI+) m/z 216.1 (M+H)⁺.

Example 271B

2-[(Hexahydro-2,5-methano-pentalene-3a-carbonyl)-amino]-5-methoxy-4-methyl-thiophene-3-carboxylic acid ethyl ester The title compound was prepared as described in Example 167A, substituting Example 271A for Example 10A. MS (ESI+) m/z 364.2 (M+H)+

Example 271C

2-[(Hexahydro-2,5-methano-pentalene-3a-carbonyl)-amino]-5-methoxy-4-methyl-thiophene-3-carboxylic acid The title compound was prepared as described in Example 166B, substituting Example 271B for Example 166A. The crude product was used for the next step without further purification. MS (ESI+) m/z 334 (M–H)−

Example 271D

2-[(hexahydro-2,5-methanopentalen-3a(1H)-ylcarbonyl)amino]-5-methoxy-4-methyl-N-propylthiophene-3-carboxamide The title compound was prepared as described in Example 166C, substituting Example 271C for Example 166B. $^1$H NMR (500 MHz, dimethylsulfoxide-$d_6$) δ ppm 0.89 (t, J=7.46 Hz, 3H) 1.24-1.71 (m, 6H) 1.68-1.87 (m, 4H) 1.97 (dd, J=11.36, 1.53 Hz, 2H) 2.15 (s, 3H) 2.32 (s, 2H) 2.58 (t, J=6.44 Hz, 1H) 3.04-3.28 (m, 2H) 3.62-3.90 (m, 3H) 7.46 (s, 1H) 11.55 (s, 1H). MS (ESI+) m/z 377.1 (M+H)+

Example 272

N-{5-tert-butyl-3-[(3,3-difluoroazetidin-1-yl)carbonyl]thien-2-yl}hexahydro-2,5-methanopentalene-3a(1H)-carboxamide The title compound was prepared as described in Example 166C, substituting Example 269B for Example 166B and 3,3-difluoroazetidine for propylamine. $^1$H NMR (500 MHz, dimethylsulfoxide-$d_6$) δ ppm 1.14-1.43 (m, 9H) 1.47-1.73 (m, 4H) 1.71-1.93 (m, 4H) 1.88-2.06 (m, 2H) 2.21-2.42 (m, 2H) 2.52-2.67 (m, 1H) 4.29-5.15 (m, 4H) 6.78 (s, 1H) 12.05 (s, 1H). MS (ESI+) m/z 423.2 (M+H)+

Example 273

N-{3-[(3,3-difluoroazetidin-1-yl)carbonyl]thien-2-yl}hexahydro-2,5-methanopentalene-3a(1H)-carboxamide

Example 273A

2-[(Hexahydro-2,5-methano-pentalene-3a-carbonyl)-amino]-thiophene-3-carboxylic acid methyl ester The title compound was prepared as described in Example 167A, substituting methyl 2-aminothiophene-3-carboxylate (Aldrich) for Example 10A. MS (ESI+) m/z 306.1 (M+H)+

Example 273B

2-[(Hexahydro-2,5-methano-pentalene-3a-carbonyl)-amino]-thiophene-3-carboxylic acid The title compound was prepared as described in Example 166B, substituting Example 273A for Example 166A. The crude product was used for the next step without further purification. MS (ESI+) m/z 290 (M–H)−

Example 273C

N-{3-[(3,3-difluoroazetidin-1-yl)carbonyl]thien-2-yl}hexahydro-2,5-methanopentalene-3a(1H)-carboxamide The title compound was prepared as described in Example 166C, substituting Example 273B for Example 166B. $^1$H NMR (500 MHz, dimethylsulfoxide-$d_6$) δ ppm 1.34-1.77 (m, 4H) 1.70-1.96 (m, 4H) 1.95-2.10 (m, 2H) 2.34 (s, 2H) 2.54-2.72 (m, 1H) 4.71 (s, 4H) 6.96-7.07 (m, 1H) 7.14 (d, J=5.76 Hz, 1H) 12.15 (s, 1H). MS (ESI+) m/z 365.1 (M+H)+. Anal. calcd. for C18H20N2O2S: C, 59.0; H, 5.50; N, 7.65. Found: C, 59.35; H, 5.38; N, 7.51.

Example 274

N-{5-bromo-3-[(3,3-difluoroazetidin-1-yl)carbonyl]thien-2-yl}hexahydro-2,5-methanopentalene-3a(1H)-carboxamide To a solution of 273C (0.12 g, 0.31 mmol) in 5 mL dichloromethane was added bromine (0.06 g, 0.37 mmol). The reaction was stirred at room temperature for 2 hours, diluted with ethyl acetate (20 mL) and washed with sodium bicarbonate solution, brine, dried over sodium sulfate, filtered, and concentrated. The residue purified by flash chromatography (gradient elution, 5% to 10% ethyl acetate/hexanes) to afford the title compound. $^1$H NMR (500 MHz, dimethylsulfoxide-$d_6$) δ ppm 1.42-1.72 (m, 4H) 1.70-1.93 (m, 4H) 1.93-2.09 (m, 2H) 2.33 (s, 2H) 2.62 (t, J=6.61 Hz, 1H) 4.74 (s, 4H) 7.30 (s, 1H) 12.22 (s, 1H). MS (ESI+) m/z 447.0 (M+H)+. Anal. calcd. for C18H19BrF2N2O2S: C, 48.55; H, 4.30; N, 6.29. Found: C, 48.75; H, 4.13; N, 6.18.

Example 275

N-[3-(azetidin-1-ylcarbonyl)-4,7-dihydro-5H-thieno[2,3-c]pyran-2-yl]hexahydro-2,5-methanopentalene-3a(1H)-carboxamide The title compound was prepared as described in Example 166C, substituting Example 167B for Example 166B and azetidine hydrochloride for propylamine. $^1$H NMR (300 MHz, CDCl$_3$) δ ppm 1.61-1.72 (m, 4H), 1.84-1.96 (m, 4H), 2.09-2.17 (m, 2H), 2.28-2.43 (m, 4H), 2.67-2.80 (m, 3H), 3.86 (t, J=5.3 Hz, 2H), 4.21 (t, J=7.8 Hz, 4H), 4.76 (t, J=1.7 Hz, 2H), 10.74 (s, 1H); MS (DCI/NH$_3$) m/z 387 (M+H)+; anal. calculated for C$_{21}$H$_{26}$N$_2$O$_3$S.0.1H$_2$O: C, 64.95; H, 6.80; N, 7.21. Found: C, 64.61; H, 6.61; N, 6.83.

Example 276

N-{3-[(3,3-difluoropyrrolidin-1-yl)carbonyl]-4,7-dihydro-5H-thieno[2,3-c]pyran-2-yl}hexahydro-2,5-methanopentalene-3a(1H)-carboxamide The title compound was prepared as described in Example 166C, substituting Example 167B for Example 166B and 3,3 difluoropyrrolidine for propylamine. $^1$H NMR (400 MHz, CDCl$_3$) δ ppm 1.26 (s, 2H), 1.62-1.71 (m, 4H), 1.83-1.91 (m, 4H), 2.04-2.11 (m, 2H), 2.32-2.44 (m, 4H), 2.63-2.68 (m, 2H), 2.74 (t, J=6.6 Hz, 1H), 3.79 (t, J=7.4 Hz, 2H), 3.88 (t, J=5.2 Hz, 4H), 4.77 (t, J=1.7 Hz, 2H), 9.68 (s, 1H); MS (DCI/NH$_3$) m/z 437 (M+H)$^+$;

Example 277 ethyl 2-{[(2,2,3,3-tetrafluoro-1-methyl cyclobutyl-carbonyl]amino}-4,7-dihydro-5H-thieno[2,3-c]pyran-3-carboxylate The product of Example 167B and 2,2,3,3-tetrafluoro-1-methylcyclobutanecarbonyl chloride were processed as described in Example 166C to give the title compound. $^1$H NMR (300 MHz, CDCl$_3$) δ ppm 1.40 (t, J=7.1 Hz, 5H), 1.68 (s, 3H), 2.30-2.47 (m, 1H), 2.90 (tt, J=5.6, 1.8 Hz, 4H), 3.28-3.48 (m, 1H), 3.95 (ddd, J=11.4, 7.3, 5.8 Hz, 4H), 4.38 (q, J=7.1 Hz, 2H), 4.71 (t, J=1.9 Hz, 2H), 11.72 (s, 1H); MS (DCI/NH$_3$) m/z 395 (M)$^+$; anal. calculated for C$_{16}$H$_{17}$F$_4$NO$_4$S: C, 48.61; H, 4.33; N, 3.54. Found: C, 48.53; H, 4.32; N, 3.48.

Example 278 ethyl 2-[(hexahydro-2,5-methanopentalen-3a(1H)-ylcarbonyl)amino]-4,5-dihydronaphtho[2,1-b]thiophene-1-carboxylate Example 278A Ethyl 2-amino-4,5-dihydronaphtho[2,1-b]thiophene-1-carboxylate The title compound was prepared as described in Example 10A, substituting 3,4-dihydronapthalen-1-(2H)-one for tetrahydro-4H-pyran-4-one. $^1$H NMR (300 MHz, CD$_3$OD) δ ppm 1.29 (t, J=7.1 Hz, 3H), 2.79-2.86 (m, 2H), 2.89-2.97 (m, 2H), 4.20 (t, J=7.1 Hz, 2H), 6.95 (dd, J=7.5, 2.4 Hz, 1H), 7.03 (td, J=7.3, 1.4 Hz, 1H), 7.10-7.17 (m, 2H), 7.61 (s, 2H). MS (DCI/NH$_3$) m/z 274 (M+H)$^+$;

Example 278B ethyl 2-[(hexahydro-2,5-methanopentalen-3a(1H)-ylcarbonyl)amino]-4,5-dihydronaphtho[2,1-b]thiophene-1-carboxylate The title compound was prepared as described in Example 12, substituting Example 278A for 2-amino-4,5,6,7-tetrahydro-benzo[b]thiophene-3-carboxylic acid ethyl ester and 2-hexahydro-2,5-methano-pentalene-3a-carboxylic acid for 2,2,3,3-tetramethylcyclopropanecarboxylic acid. $^1$H NMR (300 MHz, CD$_3$OD) δ ppm 1.35 (t, J=7.0 Hz, 3H) 1.60-1.73 (m, 4H) 1.77-1.87 (m, 2H) 1.92 (dd, J=10.2, 2.7 Hz, 2H) 2.00-2.10 (m, 2H) 2.68 (t, J=6.8 Hz, 1H) 2.85-2.94 (m, 2H) 2.99-3.08 (m, 2H) 4.36 (q, J=7.1 Hz, 2H) 7.09-7.31 (m, 4H) 11.44 (s, 1H).

Example 279

N-[3-(azetidin-1-ylcarbonyl)-5-tert-butylthien-2-yl] hexahydro-2,5-methanopentalene-3a(1H)-carboxamide The title compound was prepared as described in Example 166C from Example 269B and azetidine hydrochloride. $^1$H NMR (300 MHz, CDCl$_3$) δ ppm 1.35 (s, 9H), 1.66 (dd, J=10.9, 2.7 Hz, 4H), 1.84-1.98 (m, 4H), 2.30-2.45 (m, 4H), 2.77 (t, J=6.6 Hz, 1H), 4.36 (t, J=7.6 Hz, 4H), 6.65 (s, 1H), 12.31 (s, 1H); MS (DCI/NH$_3$) m/z 387 (M+H)$^+$.

Example 280 ethyl 2-{[(2,2,3,3-tetramethylcyclopropyl)carbonyl]amino}-5,6-dihydro-4H-4,7-ethanothieno[2,3-b]pyridine-3-carboxylate Example 280A 4-Amino-3-thia-1-aza-tricyclo[5.2.2.0$^{2,6}$]undeca-2(6),4-diene-5-carboxylic acid ethyl ester To a 250-mL round-bottomed flask containing a magnetic stir bar were added 3-quinuclidinone hydrochloride (4.82 g, 30.0 mmol) and sulfur (1.06 g, 33.0 mmol). Absolute ethanol (100 mL) was added to form a slurry. Ethyl cyanoacetate (3.52 mL, 33.0 mmol) and morpholine (5.23 mL, 60 mmol) were added. A reflux condenser was attached and a heating mantle was applied. The mixture was heated to reflux and stirred for 6 hours. After cooling to room temperature, the precipitate was removed by vacuum filtration. The liquor was concentrated by rotary evaporator to afford an oil. The crude product was recrystallized from ethanol/hexanes to afford the title compound. $^1$H NMR (dimethylsulfoxide-d$_6$, 300 MHz) δ 1.26 (t, J=7.1 Hz, 3H), 1.30-1.40 (m, 2H), 1.67-1.75 (m, 2H), 2.43-2.48 (m, 2H), 2.96-3.05 (m, 2H), 3.64-3.68 (m, 1H), 4.18 (q, J=7.1 Hz, 2H), 7.18 (br s, 2H); MS (ESI+) m/z 253 (M+H)$^+$.

Example 280B ethyl 2-{[(2,2,3,3-tetramethylcyclopropyl)carbonyl]amino}-5,6-dihydro-4H-4,7-ethanothieno[2,3-b]pyridine-3-carboxylate Step One
To an oven-dried, N$_2$-purged, 50-mL, round-bottomed flask containing a magnetic stir bar were added 2,2,3,3-tetramethyl-cyclopropanecarboxylic acid (711 mg, 5.00 mmol) and anhydrous toluene (10 mL). Thionyl chloride (547 µL, 7.50 mmol) was added. A reflux condenser with N$_2$-inlet was attached and a heating mantle was applied. The mixture was heated to reflux and stirred for 4 hours. After cooling to room temperature, the solution was concentrated by rotary evaporator to afford an oil.
Step Two
To an oven-dried, N$_2$-purged, 100-mL, round-bottomed flask containing a magnetic stir bar was added Example 280A (757 mg, 3.00 mmol), anhydrous tetrahydrofuran (25 mL), and triethylamine (1.67 mL, 12.0 mmol). A solution of the product from step one above in anhydrous tetrahydrofuran (5 mL) was added, and the resulting slurry was stirred at room temperature overnight. Water (25 mL) was added and the mixture was extracted with dichloromethane (3×20 mL). The combined organic extracts were dried over magnesium sulfate, filtered, and concentrated by rotary evaporator to afford an oil. The product was recrystallized from ethyl acetate/hexanes to afford the title compound. $^1$H NMR (dimethylsulfoxide-d$_6$, 300 MHz) δ 1.20 (s, 6H), 1.22 (s, 6H), 1.30-1.40 (m, 2H), 1.33 (t, J=7.1 Hz, 3H), 1.52 (s, 1H), 1.74-1.82 (m, 2H), 2.43-2.48 (m, 2H), 3.04-3.12 (m, 2H), 3.75-3.79 (m, 1H), 4.32 (q, J=7.1 Hz, 2H), 11.05 (br s, 1H); MS (ESI+) m/z 377 (M+H)+. Anal. calcd. for $C_{20}H_{28}N_2O_3S$: C, 63.80; H, 7.50; N, 7.44. Found: C, 63.92; H, 7.53; N, 7.44.

Example 281 ethyl 2-[(hexahydro-2,5-methanopentalen-3a(1H)-ylcarbonyl)amino]-5,6-dihydro-4H-4,7-ethanothieno[2,3-b]pyridine-3-carboxylate The title compound was prepared as described in Example 280B, from Example 280A and 3-noradamantanecarboxylic acid. $^1$H NMR (dimethylsulfoxide-$d_6$, 300 MHz) δ 1.33 (t, J=7.1 Hz, 3H), 1.35-1.39 (m, 2H), 1.62-1.65 (m, 3H), 1.68-1.69 (m, 1H), 1.76-1.83 (m, 4H), 1.86-1.91 (m, 2H), 1.99-2.04 (m, 2H), 2.34 (br s, 2H), 2.44-2.48 (m, 2H), 2.62-2.67 (m, 1H), 3.05-3.14 (m, 2H), 3.77-3.79 (m, 1H), 4.34 (q, J=7.1 Hz, 2H), 11.28 (br s, 1H); MS (ESI+) m/z 400 (M+H)+. Anal. calcd. for $C_{22}H_{28}N_2O_3S$: C, 65.97; H, 7.05; N, 6.99. Found: C, 65.88; H, 7.05; N, 6.95.

Example 282

2-[(hexahydro-2,5-methanopentalen-3a(1H)-ylcarbonyl)amino]-N-propyl-5,6-dihydro-4H-4,7-ethanothieno[2,3-b]pyridine-3-carboxamide Example 282A 4-[(Hexahydro-2,5-methano-pentalene-3a-carbonyl)-amino]-3-thia-1-aza-tricyclo[5.2.2.0$^{2,6}$]undeca-2(6),4-diene-5-carboxylic acid To a 25-mL, round-bottomed flask containing a magnetic stir bar were added Example 281 (300 mg, 0.750 mmol) and absolute ethanol (4 mL). Solid potassium hydroxide (280 mg, 5.00 mmol) was added. A reflux condenser was attached and a heating mantle was applied. The mixture was heated to reflux for 1 hour. After cooling to room temperature, a solution of HCl in diethyl ether was added to form a precipitate. The solid was collected by vacuum filtration on a glass frit and dried under vacuum. LCMS (ESI+) m/z 373 (M+H)+.

Example 282B

2-[(hexahydro-2,5-methanopentalen-3a(1H)-ylcarbonyl)amino]-N-propyl-5,6-dihydro-4H-4,7-ethanothieno[2,3-b]pyridine-3-carboxamide To a 20-mL, scintillation vial containing a magnetic stir bar were added Example 282A (242 mg, 0.650 mmol), hydroxybenzotriazole (132 mg, 0.975 mmol), and anhydrous N,N-dimethylformamide (5 mL). Diisopropylethylamine (453 µL, 2.60 mmol) and propylamine (107 µL, 1.30 mmol) were added followed by the addition of solid N-3-dimethylaminopropyl)-N'ethylcarbodiimide hydrochloride (187 mg, 0.975 mmol). The resulting slurry was stirred overnight. The mixture was concentrated by rotary evaporator to afford an oil. Water (10 mL) was added and the mixture was extracted with dichloromethane (3×8 mL). The combined organic extracts were dried over magnesium sulfate, filtered, and concentrated by rotary evaporator to afford an oil. The crude product was purified by flash chromatography (silica gel: 35% ethyl acetate, 65% hexanes–product $R_f$=0.2) to afford an oil that was recrystallized from ethyl acetate/hexanes to afford the title compound. $^1$H NMR (dimethylsulfoxide-$d_6$, 300 MHz) δ 0.89 (t, J=7.5 Hz, 3H), 1.40-1.49 (m, 2H), 1.51-1.59 (m, 2H), (q, J=7.3 Hz, 2H), 1.60-1.67 (m, 4H), 1.74-1.86 (m, 5H), 1.97-2.01 (m, 1H), 2.32 (br s, 2H), 2.43-2.49 (m, 2H), 2.57-2.62 (m, 1H), 3.04-3.12 (m, 2H), 3.22-3.28 (m, 2H), 3.58-3.66 (m, 1H), (m, 7.55 (t, J=5.4 Hz, 1H), 12.16 (br s, 1H), MS (ESI+) m/z 412 (M+H)+. Anal. calcd. for $C_{23}H_{31}N_3O_2S$: C, 66.79; H, 7.56; N, 10.16. Found: C, 66.69; H, 7.58; N, 10.10.

Example 283

N-propyl-2-{[(2,2,3,3-tetramethylcyclopropyl)carbonyl]amino}-5,6-dihydro-4H-4,7-ethanothieno[2,3-b]pyridine-3-carboxamide Example 283A 4-[(2,2,3,3-Tetramethyl-cyclopropanecarbonyl)-amino]-3-thia-1-aza-tricyclo[5.2.2.02,6]undeca-2(6),4-diene-5-carboxylic acid The title compound was prepared from Example 281 using the method described in Example 282A. The unpurified product was used for the next step without further purification. LCMS (ESI+) m/z 348 (M+H)+.

Example 283B

N-propyl-2-{[(2,2,3,3-tetramethylcyclopropyl)carbonyl]amino}-5,6-dihydro-4H-4,7-ethanothieno[2,3-b]pyridine-3-carboxamide The title compound was prepared as described in Example 282B, substituting Example 283A for Example 282A. $^1$H NMR (dimethylsulfoxide-$d_6$, 300 MHz) 0.89 (t, J=7.5 Hz, 3H), 1.19 (s, 6H), 1.21 (s, 6H), 1.36 (s, 1H), 1.39-1.49 (m, 2H), 1.55 (q, J=7.1 Hz, 2H), 1.71-1.81 (m, 2H), 2.42-2.51 (m, 2H), 3.02-3.11 (m, 2H), 3.21-3.31 (m, 2H), 3.55-3.57 (m, 1H), 7.58 (t, J=5.4 Hz, 1H), 11.68 (br s, 1H); MS (ESI+) m/z 390 (M+H)+. Anal. calcd. for $C_{21}H_{31}N_3O_2S$: C, 64.75; H, 8.02; N, 10.79. Found: C, 64.49; H, 7.86; N, 10.58.

Example 284 ethyl 2-({[1-(2-fluorophenyl)cyclohexyl]carbonyl}amino)-5,6-dihydro-4H-4,7-ethanothieno[2,3-b]pyridine-3-carboxylate The title compound was prepared as described in Example 280B, substituting 1-(2-fluorophenyl)cyclohexanecarboxylic acid for 2,2,3,3-tetramethyl-cyclopropanecarboxylic acid. $^1$H NMR (dimethylsulfoxide-$d_6$, 300 MHz) δ 1.22 (t, J=7.1 Hz, 3H), 1.29-1.43 (m, 3H), 1.53-1.65 (m, 5H), 1.72-1.79 (m, 2H), 1.99-2.07 (m, 2H), 2.23-2.31 (m, 2H), 2.43-2.48 (m, 2H), 3.03-3.12 (m, 2H), 3.70-3.74 (m, 1H), 4.18 (q, J=7.1 Hz, 2H), 7.17 (ddd, J=12.5, 8.0, 1.5 Hz, 1H), 7.32 (ddd, J=7.5, 7.5, 1.5 Hz, 1H), 7.36-7.44 (m, 1H), 7.62 (ddd, J=8.1, 8.0, 1.9 Hz, 1H), 10.97 (br s, 1H); MS (ESI+) m/z 457 (M+H)+. Anal. calcd. for $C_{25}H_{29}N_2O_3S$: C, 65.77; H, 6.40; N, 6.14. Found: C, 65.66; H, 6.09; N, 5.99.

Example 285 ethyl 2-[(hexahydro-2,5-methanopentalen-3a(1H)-ylcarbonyl)amino]-6-methyl-4,5,6,7-tetrahydrothieno[2,3-b]pyridine-3-carboxylate The title compound was prepared as described in Example 280B, substituting 2-amino-6-methyl-4,5,6,7-tetrahydrothieno[2,3-b]pyridine-3-carboxylic acid ethyl ester for Example 280A and 3-noradamantanecarboxylic acid for 2,2,3,3-tetramethyl-cyclopropanecarboxylic acid. $^1$H NMR (dimethylsulfoxide-$d_6$, 300 MHz) δ 1.31 (t, J=7.1 Hz, 3H), 1.52-1.56 (m, 2H), 1.59-1.64 (m, 2H), 1.67-1.73 (m, 2H), 1.77-1.84 (m, 2H), 1.87-1.93 (m, 2H), 1.95-2.00 (m, 2H), 2.23 (br s, 2H), 2.33 (s, 3H), 2.53-2.66 (m, 2H), 2.79 (t, J=5.8 Hz, 2H), 3.41 (br s, 2H), 4.30 (q, J=7.1 Hz, 2H), 11.32 (br s, 1H), 11.98 (br s, 1H). MS (ESI+) m/z 389 (M+H)$^+$. Anal. calcd. for $C_{21}H_{28}N_2O_3S$: C, 64.92; H, 7.26; N, 7.21. Found: C, 64.44; H, 7.55; N, 7.04.

Example 286

N-{3-[(3,3-difluoroazetidin-1-yl)carbonyl]-5,6-dihydro-4H-4,7-ethanothieno[2,3-b]pyridin-2-yl}-2,2,3,3-tetramethylcyclopropanecarboxamide The title compound was prepared as described in Example 282B, substituting Example 283A for Example 282A and 3,3-difluoroazetidine hydrochloride for propylamine. $^1$H NMR (dimethylsulfoxide-$d_6$, 300 MHz) δ 1.19 (s, 6H), 1.22 (s, 6H), 1.32-1.38 (m, 2H), 1.41 (s, 1H), 1.75-1.81 (m, 2H), 2.43-2.48 (m, 1H), 3.04-3.11 (m, 2H), 3.29-3.33 (m, 2H), 4.46 (t, J=12.6 Hz, 4H), 10.54 (br s, 1H); MS (ESI+) m/z 424 (M+H)$^+$. Anal. calcd. for $C_{21}H_{27}F_2N_3O_3S$: C, 59.55; H, 6.43; N, 9.92. Found: C, 59.56; H, 6.52; N, 9.88.

Example 287 propyl 2-[(hexahydro-2,5-methanopentalen-3a(1H)-ylcarbonyl)amino]-4,7-dihydro-5H-thieno[2,3-c]pyran-3-carboxylate

Example 287A 2-amino-4,7-dihydro-5H-thieno[2,3-c]pyran-3-carboxylic acid propyl ester The title compound was prepared as described in Example 10A, substituting propyl cyanoacetate for ethyl cyanoacetate. MS (ESI+) m/z 242 (M+H)$^+$.

Example 287B propyl 2-[(hexahydro-2,5-methanopentalen-3a(1H)-ylcarbonyl)amino]-4,7-dihydro-5H-thieno[2,3-c]pyran-3-carboxylate The title compound was prepared as described in Example 167A, substituting Example 287A for Example 10A. $^1$H NMR (dimethylsulfoxide-$d_6$, 300 MHz) δ 0.96 (t, J=7.3 Hz, 3H), 1.57-1.83 (m, 8H), 1.87-1.91 (m, 2H), 2.00-2.04 (m, 2H), 2.34 (br s, 2H), 2.62-2.66 (m, 1H), 2.79 (t, J=5.6 Hz, 2H), 3.85 (t, J=5.8 Hz, 2H), 4.22 (t, J=6.4 Hz, 2H), 4.83 (br s, 2H), 11.38 (br s, 1H). MS (ESI+) m/z 390 (M+H)$^+$. Anal. calcd. for $C_{21}H_{27}NO_4S$: C, 64.75; H, 6.99; N, 3.60. Found: C, 63.95; H, 6.99; N, 3.55.

Example 288 ethyl 2-[(hexahydro-2,5-methanopentalen-3a(1H)-ylcarbonyl)amino]-4,4-dimethyl-5,6-dihydro-4H-cyclopenta[b]thiophene-3-carboxylate

Example 288A ethyl 2-amino-4,4-dimethyl-5,6-dihydro-4H-cyclopenta[b]thiophene-3-carboxylate The title compound was prepared as described in Example 10A, substituting 2,2-dimethylcyclopentanone for tetrahydro-4H-pyran-4-one. MS (ESI+) m/z 240 (M+H)$^+$.

Example 288B ethyl 2-[(hexahydro-2,5-methanopentalen-3a(1H)-ylcarbonyl)amino]-4,4-dimethyl-5,6-dihydro-4H-cyclopenta[b]thiophene-3-carboxylate The title compound was prepared as described in Example 167A, substituting Example 288A for Example 10A. $^1$H NMR (dimethylsulfoxide-$d_6$, 300 MHz) δ 1.31 (s, 6H), 1.34 (t, J=7.3 Hz, 3H), 1.62-1.82 (m, 8H), 1.87-1.90 (m, 2H), 1.97-2.04 (m, 2H), 2.16-2.21 (m, 2H), 2.28 (br s, 1H), 2.74-2.78 (m, 2H), 4.35 (q, J=7.2 Hz, 2H), 11.41 (br s, 1H); MS (ESI+) m/z 388 (M+H)$^+$.

Example 289 ethyl-2-{[(2,2,3,3-tetramethylcyclopropyl)carbonyl]amino}-4,5,6,7-tetrahydro-4,7-methano-1-benzothiophene-3-carboxylate

Example 289A

4-Amino-3-thia-tricyclo[5.2.1.0$^{2,6}$]deca-2(6),4-diene-5-carboxylic acid ethyl ester The title compound was prepared as described in Example 10A, substituting norcamphor for tetrahydro-4H-pyran-4-one. MS (ESI+) m/z 238 (M+H)$^+$.

Example 289B ethyl-2-{[(2,2,3,3-tetramethylcyclopropyl)carbonyl]amino}-4,5,6,7-tetrahydro-4,7-methano-1-benzothiophene-3-carboxylate The title compound was prepared as described in Example 280B, substituting Example 289A for Example 280A. $^1$H NMR (CDCl$_3$, 300 MHz), 1.22 (s, 6H), 1.26-1.28 (m, 3H), 1.28 (s, 6H), 1.42 (t, J=7.1 Hz, 3H), 1.47-1.51 (m, 2H), 1.74-1.82 (m, 2H), 3.42 (br s, 1H), 3.70 (br s, 1H), 4.35 (q, J=7.1 Hz, 2H), 10.96 (br s, 1H).
LC-MS (ESI+) m/z 362 (M+H)$^+$.

Example 290

2-[(hexahydro-2,5-methanopentalen-3a(1H)-ylcarbonyl)amino]-N-[(3R)-tetrahydrofuran-3-yl]-4,7-dihydro-5H-thieno[2,3-c]pyran-3-carboxamide The title compound was prepared as described in Example 166C, substituting Example 167B for Example 166B, and (R)-tetrahydrofuran-3-amine for propylamine. $^1$H NMR (dimethylsulfoxide-$d_6$, 300 MHz) δ 1.61-1.67 (m, 4H), 1.75-2.01 (m, 7H), 2.08-2.20 (m, 1H), 2.33 (br s, 2H), 2.58-2.63 (m, 1H), 2.80-2.83 (m, 2H), 3.60 (dd, J=8.8, 4.1 Hz, 1H), 3.67-3.80 (m, 2H), 3.80-3.86 (m, 3H), δ 4.40-4.49 (m, 1H), 4.65 (br s, 2H), 7.44 (d, J=6.1 Hz, 1H), 11.48 (s, 1H); MS (ESI+) m/z 417 (M+H)$^+$. Anal. calcd. for $C_{22}H_{28}N_2O_4S$: C, 63.44; H, 6.78; N, 6.73. Found: C, 63.45; H, 6.72; N, 6.65.

Example 291

N-{3-[(3,3-difluoroazetidin-1-yl)carbonyl]-4,7-dihydro-5H-thieno[2,3-c]pyran-2-yl}-1-phenylcyclohexanecarboxamide The title compound was prepared as described in Example 166C, substituting Example 202B for Example 166B, and 3,3-difluoroazetdine hydrochloride for propylamine. $^1$H NMR (dimethylsulfoxide-$d_6$, 300 MHz) δ 1.30-1.37 (m, 1H), 1.43-1.62 (m, 5H), 1.84-1.91 (m, 2H), 2.37-2.41 (m, 2H), 2.54-2.58 (m, 2H), 3.78 (t, J=5.4 Hz, 2H), 4.26-4.35 (m, 4H), 4.63 (br s, 2H), 7.23-7.30 (m, 1H), 7.34-7.38 (m, 4H), 10.21 (br s, 1H); MS (ESI+) m/z 461 (M+H)$^+$. Anal. calcd. for $C_{24}H_{26}F_2N_2O_3S$: C, 62.59; H, 5.69; N, 6.08. Found: C, 62.40; H, 5.70; N, 5.98.

Example 292 ethyl 2-[(hexahydro-2,5-methanopentalen-3a(1H)-ylcarbonyl)amino]-4,5,6,7-tetrahydro-4,7-methano-1-benzothiophene-3-carboxylate The title compound was prepared as described in Example 280B, substituting Example 289A for Example 280A, and 3-noradamantane carboxylic acid for 2,2,3,3-tetramethyl-cyclopropanecarboxylic acid. $^1$H NMR (dimethylsulfoxide-$d_6$, 300 MHz) d 0.79-0.88 (m, 2H), 1.33 (t, J=7.1 Hz, 2H), 1.48-1.90 (m, 6H), 1.97-2.02 (m, 4H), 2.28-2.34 (m, 4H), 2.61-2.68 (m, 4H), 3.49 (br s, 1H), 3.66 (br s, 1H), 4.31 (q, J=7.1 Hz, 2H), 11.05 (br s, 1H) MS (ESI+) m/z 386 (M+H)$^+$.

Example 293 ethyl 2-[(hexahydro-2,5-methanopentalen-3a(1H)-ylcarbonyl)amino]-4-methyl-4,6-dihydrothieno[2,3-c]furan-3-carboxylate

Example 293A

2-Amino-4-methyl-4,6-dihydrothieno[2,3-c]furan-3-carboxylic acid ethyl ester

The title compound was prepared as described in Example 10A, substituting 2-methyldihydrofuran-3(2H)-one for tetrahydro-4H-pyran-4-one. $^1$H NMR (dimethylsulfoxide-$d_6$, 300 MHz) δ 1.24 (t, J=7.1 Hz, 3H), 1.33 (d, J=6.1 Hz, 3H), 4.06-4.25 (m, 2H), 4.68 (dd, J=10.8, 2.0 Hz, 1H), 4.82 (dd, J=10.8, 4.6 Hz, 1H), 5.05-5.15 (m, 1H), 7.34 (br s, 2H); MS (ESI+) m/z 228 (M+H)$^+$.

Example 293B ethyl 2-[(hexahydro-2,5-methanopentalen-3a(1H)-ylcarbonyl)amino]-4-methyl-4,6-dihydrothieno[2,3-c]furan-3-carboxylate The title compound was prepared as described in Example 280B, substituting Example 293A for Example 280A, and 3-noradamantane carboxylic acid for 2,2,3,3-tetramethyl-cyclopropanecarboxylic acid. $^1$H NMR (dimethylsulfoxide-$d_6$, 300 MHz) δ 1.30 (t, J=7.1 Hz, 3H), 1.38 (d, J=6.1 Hz, 3H), 1.61-1.69 (m, 4H), 1.78-1.84 (m, 2H), 1.88-1.92 (m, 2H), 2.01-2.05 (m, 2H), 2.34 (br s, 2H), 2.64-2.66 (m, 1H), 4.21-4.40 (m, 2H), 4.85 (dd, J=11.9, 2.0 Hz, 1H), 4.98 (dd, J=11.5, 4.4 Hz, 1H), 5.22-6.31 (m, 1H), 11.11 (br s, 1H); MS (ESI+) m/z 376 (M+H)$^+$. Anal. calcd. for $C_{20}H_{25}NO_4S$: C, 63.97; H, 6.71; N, 3.73. Found: C, 63.57; H, 6.74; N, 3.58.

Example 294 ethyl 7-hydroxy-4-methyl-2-{[(2,2,3,3-tetramethyl-cyclopropyl)carbonyl]amino}-4,5,6,7-tetrahydro-4,7-ethano-1-benzothiophene-3-carboxylate

Example 294A

4-Amino-1-hydroxy-7-methyl-3-thia-tricyclo[5.2.2.0$^{2,6}$]undeca-2(6),4-diene-5-carboxylic acid ethyl ester The title compound was prepared as described in Example 10A, substituting 4-hydroxy-1-methylbicyclo[2.2.2]octan-2-one for tetrahydro-4H-pyran-4-one. MS (ESI+) m/z 282 (M+H)$^+$.

Example 294B ethyl 7-hydroxy-4-methyl-2-{[(2,2,3,3-tetramethyl-cyclopropyl)carbonyl]amino}-4,5,6,7-tetrahydro-4,7-ethano-1-benzothiophene-3-carboxylate The title compound was prepared as described in Example 280B, substituting Example 294A for Example 280A. $^1$H NMR (CDCl$_3$, 300 MHz) δ 1.20 (s, 3H), 1.22 (s, 6H), 1.23-1.30 (m, 4H), 1.32 (s, 6H), 1.38 (t, J=7.1 Hz, 3H), 1.67-1.77 (m, 1H), 2.04-2.09 (m, 1H), 2.48-2.53 (m, 1H), 2.78-2.82 (m, 2H), 3.03-3.08 (m, 1H), 4.32 (q, J=7.1 Hz, 2H), 11.29 (br s, 1H); MS (ESI+) m/z 406 (M+H)$^+$.

Example 295 ethyl 2-[(2-oxatricyclo[3.3.1.1$^{3,7}$]dec-1-ylcarbonyl)amino]-4,7-dihydro-5H-thieno[2,3-c]pyran-3-carboxylate The title compound was prepared as described in Example 280B, substituting Example 10A for Example 280A, and 2-oxaadamantane 1-carboxylic acid (Example 190A) for 2,2,3,3-tetramethyl-cyclopropanecarboxylic acid. $^1$H NMR (dimethylsulfoxide-$d_6$, 300 MHz) δ 1.32 (t, J=7.1 Hz, 3H), 1.66-2.03 (m, 10H), 2.18 (br s, 2H), 2.80 (t, J=5.6 Hz, 2H), 3.84 (t, J=5.6 Hz, 2H), 4.26-4.33 (m, 3H), 4.62 (br s, 2H), 11.58 (br s, 1H); MS (ESI+) m/z 392 (M+H)$^+$.

Example 296

N-{3-[(3,3-difluoroazetidin-1-yl)carbonyl]-4,7-dihydro-5H-thieno[2,3-c]pyran-2-yl}-2-oxatricyclo[3.3.1.1$^{3,7}$]decane-1-carboxamide

Example 296A

2-[(2-Oxa-tricyclo[3.3.1.1$^{3,7}$]decane-1-carbonyl)-amino]-4,7-dihydro-5H-thieno[2,3-c]pyran-3-carboxylic acid The title compound was prepared as described in Example 166B using Example 295. The crude product was used for the next step without further purification. LCMS (ESI+) m/z 364 (M+H)$^+$.

Example 296B

N-{3-[(3,3-difluoroazetidin-1-yl)carbonyl]-4,7-dihydro-5H-thieno[2,3-c]pyran-2-yl}-2-oxatricyclo[3.3.1.1$^{3,7}$]decane-1-carboxamide The title compound was prepared as described in Example 166C, substituting Example 296A for Example 166B, and 3,3-difluoroazetidine hydrochloride for propylamine. $^1$H NMR (CDCl$_3$, 300 MHz) δ 1.67-2.02 (m, 10H), 2.18 (br s, 2H), 2.63-2.67 (m, 2H), 3.78-3.82 (m, 2H), 4.27 (br s, 1H), 4.45-4.54 (m, 4H), 4.65 (br s, 2H), 10.49 (br s, 1H); MS (ESI+) m/z 439 (M+H)$^+$. Anal. calcd. for C$_{21}$H$_{24}$F$_2$N$_2$O$_4$S: C, 57.52; H, 5.52; N, 6.39. Found: C, 57.00; H, 5.46; N, 6.24.

Example 297

N-cyclopropyl-2-[(hexahydro-2,5-methanopentalen-3a(1H)-ylcarbonyl)amino]-4,7-dihydro-5H-thieno[2,3-c]pyran-3-carboxamide The title compound was prepared as described in Example 166C, substituting Example 167B for Example 166B, and cyclopropylamine for propylamine. $^1$H NMR (CDCl$_3$, 300 MHz) δ 0.55-0.58 (m, 2H), 0.68-0.74 (m, 2H), 1.62-1.67 (m, 4H), 1.76-1.86 (m, 4H), 1.98-2.02 (m, 2H), 2.33 (br s, 2H), 2.59-2.63 (m, 1H), 2.73-2.83 (m, 3H), 3.80 (t, J=5.4 Hz, 2H), 4.63 (br s, 2H), 7.41 (d, J=3.0 Hz, 1H), 11.73 (br s, 1H); MS (ESI+) m/z 387 (M+H)$^+$. Anal. calcd. for C$_{21}$H$_{26}$N$_2$O$_3$S: C, 65.26; H, 7.70; N, 3.45. Found: C, 64.74; H, 7.46; N, 3.24.

Example 298

4,4,6,6-tetramethyl-N-propyl-2-{[(2,2,3,3-tetramethylcyclopropyl)carbonyl]amino}-4,6-dihydrothieno[2,3-c]furan-3-carboxamide

Example 298A 2-amino-4,4,6,6-tetramethyl-4,6-dihydrothieno[2,3-c]furan-3-carboxylic acid ethyl ester The title compound was prepared as described in Example 10A, substituting 2,2,5,5-tetramethyldihydro-furan-3-one for tetrahydro-4H-pyran-4-one. $^1$H NMR (dimethylsulfoxide-d$_6$, 300 MHz) δ 1.26 (t, J=7.1 Hz, 3H), 1.36 (s, 6H), 1.47 (s, 6H), 4.19 (q, J=7.1 Hz, 2H), 7.43 (br s, 2H); LC-MS (ESI+) m/z 270 (M+H)$^+$.

Example 298B ethyl 4,4,6,6-tetramethyl-2-{[(2,2,3,3-tetramethylcyclopropyl)carbonyl]amino}-4,6-dihydrothieno[2,3-c]furan-3-carboxylate The title compound was prepared as described in Example 280B, substituting Example 298A for Example 280A. $^1$H NMR (dimethylsulfoxide-d$_6$, 300 MHz) δ 1.21 (s, 6H), 1.23 (s, 6H), 1.33 (t, J=7.1 Hz, 3H), 1.43 (s, 6H), 1.51 (s, 6H), 1.58 (s, 1H), 4.33 (q, J=7.1 Hz, 2H), 11.12 (br s, 1H); MS (ESI+) m/z 394 (M+H)$^+$. Anal. calcd. for C$_{21}$H$_{31}$NO$_4$S: C, 64.09; H, 7.94; N, 3.56. Found: C, 63.74; H, 8.04; N, 3.52.

Example 298C 4,4,6,6-tetramethyl-2-(2,23-tetramethylcyclopropanecarboxamido)-4,6-dihydrothieno[3,2-c]furan-3-carboxylic acid The title compound was prepared as described in Example 166B, substituting Example 298B for Example 166A. The crude product was used for the next step without further purification. LCMS (ESI+) m/z 366 (M+H)$^+$.

Example 298D 4,4,6,6-tetramethyl-N-propyl-2-{[(2,2,3,3-tetramethylcyclopropyl)carbonyl]amino}-4,6-dihydrothieno[2,3-c]furan-3-carboxamide The title compound was prepared as described in Example 166C, substituting Example 167B for Example 166B. $^1$H NMR (dimethylsulfoxide-d$_6$, 300 MHz) δ 0.88 (t, J=7.5 Hz, 3H), 1.22 (s, 6H), 1.16 (s, 6H), 1.43 (s, 6H), 1.42 (s, 6H), 1.45-1.53 (m, 3H), 3.14-3.21 (m, 2H), 10.80 (br s, 1H); MS (ESI+) m/z 407 (M+H)$^+$.

Example 299

N-{3-[(3,3-difluoroazetidin-1-yl)carbonyl]-4,5,6,7-tetrahydro-4,7-methano-1-benzothien-2-yl}hexahydro-2,5-methanopentalene-3a(1H)-carboxamide

Example 299A

4-[(Hexahydro-2,5-methano-pentalene-3a-carbonyl)-amino]-3-thia-tricyclo[5.2.1.0$^{2,6}$]deca-2(6),4-diene-5-carboxylic acid The title compound was prepared as described in Example 166B, substituting Example 292 for Example 166A. The crude product was used for the next step without further purification. LCMS (ESI+) m/z 358 (M+H)$^+$.

Example 299B

N-{3-[(3,3-difluoroazetidin-1-yl)carbonyl]-4,5,6,7-tetrahydro-4,7-methano-1-benzothien-2-yl}hexahydro-2,5-methanopentalene-3a(1H)-carboxamide The title compound was prepared as described in Example 166C, substituting Example 299A for Example 166B. $^1$H NMR (CDCl$_3$, 300 MHz) δ 0.72-0.82 (m, 2H), 1.49-1.52 (m, 1H), 1.60-1.66 (m, 4H), 1.73-1.86 (m, 7H), 1.97-2.01 (m, 2H), 2.32 (br s, 2H), 2.59-2.63 (m, 1H), 3.48 (br s, 2H), 4.44-4.71 (m, 4H), 11.01 (br s, 1H); MS (ESI+) m/z 433 (M+H)$^+$. Anal. calcd. for C$_{23}$H$_{26}$F$_2$N$_2$O$_2$S: C, 63.87; H, 6.06; N, 6.48. Found: C, 63.89; H, 5.95; N, 6.26.

Example 300 ethyl 2-[(2-oxatricyclo[3.3.1.1$^{3,7}$]dec-1-ylcarbonyl)amino]-4,5,6,7-tetrahydro-1-benzothiophene-3-carboxylate The title compound was prepared as described in Example 280B, substituting ethyl 2-amino-4,5,6,7-tetrahydrobenzo[b]thiophene-3-carboxylate for Example 280A, and 2-oxaadamantane 1-carboxylic acid for 2,2,3,3-tetramethyl-cyclopropanecarboxylic acid. $^1$H NMR (CDCl$_3$, 300 MHz) δ 1.32 (t, J=7.1 Hz, 3H), 1.67-1.78 (m, 8H), 1.88-2.03 (m, 6H), 2.18 (br s, 2H), 2.58-2.62 (m, 2H), 2.72 (br s, 2H), 4.24-4.20 (m, 3H), 11.57 (br s, 1H); MS (ESI+) m/z 390 (M+H)$^+$. Anal. calcd. for C$_{21}$H$_{27}$NO$_4$S: C, 64.75; H, 6.99; N, 3.60. Found: C, 64.52; H, 6.96; N, 3.39.

Example 301 ethyl 2-[(2-oxatricyclo[3.3.1.1$^{3,7}$]dec-1-ylcarbonyl)amino]-5,6-dihydro-4H-cyclopenta[b]thiophene-3-carboxylate The title compound was prepared as described in Example 280B, substituting ethyl 2-amino-5,6-dihydro-4H-cyclopenta[b]thiophene-3-carboxylate for Example 280A, and 2-oxaadamantane-1-carboxylic acid (Example 190A) for 2,2,3,3-tetramethyl-cyclopropanecarboxylic acid. $^1$H NMR (CDCl$_3$, 300 MHz) δ 1.31 (t, J=7.1 Hz, 3H), 1.67-1.80 (m, 4H), 1.88-1.94 (m, 4H), 1.99-2.03 (m, 2H), 2.18 (br s, 2H), 2.27-2.37 (m, 2H), 2.77-2.86 (m, 4H), 4.23-4.30 (m, 3H), 11.44 (br s, 1H); MS (ESI+) m/z 390 (M+H)$^+$. Anal. calcd. for C$_{20}$H$_{25}$NO$_4$S: C, 63.97; H, 6.71; N, 3.73. Found: C, 63.59; H, 6.45; N, 3.64.

Example 302 ethyl-2-[(2-oxatricyclo[3.3.1.1$^{3,7}$]dec-1-ylcarbonyl)amino]-4,5,6,7-tetrahydro-4,7-methano-1-benzothiophene-3-carboxylate The title compound was prepared as described in Example 280B, substituting Example 289A for Example 280A, and 2-oxaadamantane-1-carboxylic acid (Example 190A) for 2,2,3,3-tetramethyl-cyclopropanecarboxylic acid. $^1$H NMR (CDCl$_3$, 300 MHz) δ 1.34 (t, J=7.1 Hz, 3H), 1.46-1.51 (m, 2H), 1.60-2.02 (m, 12H), 2.17-2.19 (m, 2H), 2.61-2.64 (m, 1H), 3.25-3.28 (m, 1H), 3.48 (br s, 1H), 3.67 (br s, 1H), 4.27-4.34 (m, 3H), 11.40 (br s, 1H); MS (ESI+) m/z 402 (M+H)$^+$. Anal. calcd. for C$_{20}$H$_{25}$NO$_4$S: C, 65.81; H, 6.78; N, 3.49. Found: C, 65.01; H, 6.46; N, 3.34.

Example 303

N-{3-[(3,3-difluoroazetidin-1-yl)carbonyl]-4,5,6,7-tetrahydro-1-benzothien-2-yl}-2-oxatricyclo[3.3.1.1$^{3,7}$]decane-1-carboxamide

Example 303A

2-[(2-Oxa-tricyclo[3.3.1.1$^{3,7}$]decane-1-carbonyl)amino]-4,5,6,7-tetrahydro-benzo[b]thiophene-3-carboxylic acid The title compound was prepared as described in Example 166B, substituting Example 300 for Example 166A. The crude product was used for the next step without further purification. LCMS (ESI+) m/z 362 (M+H)$^+$.

Example 303B

N-{3-[(3,3-difluoroazetidin-1-yl)carbonyl]-4,5,6,7-tetrahydro-1-benzothien-2-yl}-2-oxatricyclo[3.3.1.1$^{3,7}$]decane-1-carboxamide The title compound was prepared as described in Example 166C, substituting Example 303A for Example 166B, and 3,3-difluoroazetidine hydrochloride for propylamine. $^1$H NMR (CDCl$_3$, 300 MHz) δ 1.66-1.80 (m, 7H), 1.86-2.01 (m, 6H), 2.17 (br s, 2H), 2.51-2.55 (m, 2H), 2.60-2.64 (m, 2H), 4.26 (br s, 1H), 4.42-4.50 (m, 4H), 10.28 (br s, 1H); MS (ESI+) m/z 437 (M+H)$^+$; Anal. calcd. for C$_{20}$H$_{25}$NO$_4$S: C, 60.53; H, 6.00; N, 6.42. Found: C, 60.78; H, 6.22; N, 6.27.

Example 304 tert-butyl [2-[(hexahydro-2,5-methanopentalen-3a(1H)-ylcarbonyl)amino]-3-[(propylamino)carbonyl]-4,7-dihydrothieno[2,3-c]pyridin-6(5H)-yl]acetate

Example 304A

2-[(Hexahydro-2,5-methano-pentalene-3a-carbonyl)amino]-4,7-dihydro-5H-thieno[2,3-c]pyridine-3,6-dicarboxylic acid 6-tert-butyl ester 3-ethyl ester The title compound was prepared as described in Example 12, substituting Example 306A for 2-amino-4,5,6,7-tetrahydro-benzo[b]thiophene-3-carboxylic acid ethyl ester and 3-noradamantanecarboxylic acid for 2,2,3,3-tetramethyl-cyclopropanecarboxylic acid. MS (DCI/NH$_3$) m/z 475 (M+H)$^+$.

Example 304B

2-[(Hexahydro-2,5-methano-pentalene-3a-carbonyl)amino]-3-propylcarbamoyl-4,7-dihydro-5H-thieno[2,3-c]pyridine-6-carboxylic acid tert-butyl ester The product of Example 304A was processed according to the procedure described in Example 29A to afford the corresponding carboxylic acid, which was coupled with propylamine according to the procedure described in Example 29B to give the title compound (58%). MS (DCI/NH$_3$) m/z 488 (M+H)$^+$.

Example 304C

2-[(Hexahydro-2,5-methano-pentalene-3a-carbonyl)amino]-4,5,6,7-tetrahydro-thieno[2,3-c]pyridine-3-carboxylic acid propylamide The title compound was prepared as described in Example 5A, substituting Example 304B for Example 4B. MS (DCI/NH$_3$) m/z 388 (M+H)$^+$.

Example 304D tert-butyl [2-[(hexahydro-2,5-methanopentalen-3a(1H)-ylcarbonyl)amino]-3-[(propylamino)carbonyl]-4,7-dihydrothieno[2,3-c]pyridin-6(5H)-yl]acetate Example 304C (200 mg, 0.500 mmol) and tert-butyl 2-bromoacetate (Aldrich, 120 mg, 0.623 mmol) were combined 2 mL of N,N-dimethylformamide and heated to 100° C. for 30 minutes. After cooling to ambient temperature, the mixture was partitioned between diethyl ether and brine and the layers were separated. The organic extract was washed three times with brine, dried over Na$_2$SO$_4$, filtered, and concentrated under reduced pressure. Purification via column chromatography (SiO$_2$, 0-70% ethyl acetate/hexanes gradient) afforded the title compound. $^1$H NMR (300 MHz, dimethylsulfoxide-d$_6$) δ ppm 0.82-0.94 (m, 3H) 1.33-1.38 (m, 1H) 1.43 (s, 9H) 1.44-1.58 (m, 2H) 1.57-1.69 (m, 4H) 1.71-1.90 (m, 4H) 1.93-2.03 (m, 2H) 2.32 (s, 2H) 2.54-2.65 (m, 1H) 2.76-2.85 (m, 3H) 3.11-3.27 (m, 3H) 3.64 (s, 2H) 7.28-7.36 (m, 2H) 11.86 (s, 1H); MS (DCI/NH$_3$) m/z 502 (M+H)$^+$; anal. calculated for C$_{22}$H$_{29}$N$_3$O$_4$S: C, 61.23; H, 6.77; N, 9.74. Found: C, 61.17; H, 6.42; N, 9.39.

Example 305 ethyl 7-(2-amino-2-oxoethyl)-2-[(hexahydro-2,5-methanopentalen-3a(1H)-ylcarbonyl)amino]-4,5,6,7-tetrahydrothieno[2,3-b]pyridine-3-carboxylate The title compound was prepared as described in Example 304D, using Example 306C. $^1$H NMR (300 MHz, dimethylsulfoxide-d$_6$) δ ppm 1.29 (t, J=7.1 Hz, 3H) 1.57-1.92 (m, 11H) 1.97 (s, 2H) 2.32 (s, 2H) 2.67 (s, 2H) 3.18 (s, 2H) 3.63 (s, 2H) 4.27 (q, J=6.9 Hz, 2H) 7.11 (s, 1H) 7.38 (s, 1H) 11.13 (s, 1H); MS (DCI/NH$_3$) m/z 432 (M+H)$^+$.

Example 306 ethyl 2-[(hexahydro-2,5-methanopentalen-3a(1H)-ylcarbonyl)amino]-4,5,6,7-tetrahydrothieno[2,3-b]pyridine-3-carboxylate Example 306A 2-Amino-5,6-dihydro-4H-thieno[2,3-b]pyridine-3,7-dicarboxylic acid 7-tert-butyl ester 3-ethyl ester The title compound was prepared as described in Example 4A, substituting t-butyl-3-oxo-1-piperidinecarboxylate for t-butyl-4-oxo-1-piperidinecarboxylate. MS (DCI/NH$_3$) m/z 327 (M+H)$^+$.

Example 306B

2-[(Hexahydro-2,5-methano-pentalene-3a-carbonyl)-amino]-5,6-dihydro-4H-thieno[2,3-b]pyridine-3,7-dicarboxylic acid 7-tert-butyl ester 3-ethyl ester The title compound was prepared as described in Example 12, substituting Example 306A for 2-amino-4,5,6,7-tetrahydro-benzo[b]thiophene-3-carboxylic acid ethyl ester and 3-noradamantanecarboxylic acid for 2,2,3,3-tetramethyl-cyclopropanecarboxylic acid. MS (DCI/NH$_3$) m/z 474 (M+H)$^+$.

Example 306C ethyl 2-[(hexahydro-2,5-methanopentalen-3a(1H)-ylcarbonyl)amino]-4,5,6,7-tetrahydrothieno[2,3-b]pyridine-3-carboxylate The title compound was prepared as described in Example 5A, substituting Example 306B for Example 4B. $^1$H NMR (300 MHz, dimethylsulfoxide-d$_6$) δ ppm 1.29 (t, J=7.1 Hz, 3H) 1.52-1.91 (m, 5H) 1.92-2.09 (m, 3H) 2.33 (s, 3H) 2.55-2.78 (m, 4H) 2.97-3.15 (m, 3H) 4.26 (q, J=7.1 Hz, 3H) 5.36-5.57 (m, 1H) 11.16 (s, 1H); MS (DCI/NH$_3$) m/z 374 (M+H)$^+$; anal. calculated for C$_{20}$H$_{26}$N$_2$O$_3$S.0.1 CH$_3$OH: C, 63.92; H, 7.05; N, 7.02. Found: C, 63.82; H, 7.15; N, 7.08.

Example 307 ethyl 7-[(6-chloropyridin-2-yl)carbonyl]-2-[(hexahydro-2,5-methanopentalen-3a(1H)-ylcarbonyl)amino]-4,5,67-tetrahydrothieno[2,3-b]pyridine-3-carboxylate The title compound was prepared as described in Example 12, substituting Example 306C for 2-amino-4,5,6,7-tetrahydro-benzo[b]thiophene-3-carboxylic acid ethyl ester and 6-chloropicolinic acid for 2,2,3,3-tetramethyl-cyclopropanecarboxylic acid. $^1$H NMR (300 MHz, dimethylsulfoxide-d$_6$) δ ppm 1.33 (t, J=7.0 Hz, 3H) 1.57-1.97 (m, 10H) 1.98-2.10 (m, 2H) 2.35 (s, 2H) 2.66 (t, J=6.4 Hz, 1H) 2.88 (t, J=6.3 Hz, 2H) 3.66-3.80 (m, 2H) 4.33 (q, J=7.1 Hz, 2H) 7.70 (d, J=7.8 Hz, 1H) 7.76 (d, J=7.5 Hz, 1H) 8.07 (t, J=8.0 Hz, 1H) 11.34 (s, 1H); MS (DCI/NH$_3$) m/z 515 (M+H)$^+$.

Example 308 ethyl 7-[(6-chloropyridin-3-yl)carbonyl]-2-[(hexahydro-2,5-methanopentalen-3a(1H)-ylcarbonyl)amino]-4,5,6,7-tetrahydrothieno[2,3-b]pyridine-3-carboxylate The title compound was prepared as described in Example 12, substituting Example 306 and for 2-amino-4,5,6,7-tetrahydro-benzo[b]thiophene-3-carboxylic acid ethyl ester and 6-chloronicotinic acid for 2,2,3,3-tetramethyl-cyclopropanecarboxylic acid. $^1$H NMR (300 MHz, dimethylsulfoxide-d$_6$) δ ppm 1.33 (t, J=7.1 Hz, 3H) 1.56-2.13 (m, 12H) 2.35 (s, 2H) 2.65 (t, J=6.6 Hz, 1H) 2.86 (t, J=6.3 Hz, 2H) 3.68-3.80 (m, 2H) 4.33 (q, J=6.9 Hz, 2H) 7.67 (d, J=8.5 Hz, 1H) 8.08 (dd, J=8.3, 2.5 Hz, 1H) 8.62 (d, J=2.4 Hz, 1H) 11.32 (s, 1H); MS (DCI/NH$_3$) m/z 515 (M+H)$^+$; anal. calculated for C$_{26}$H$_{28}$ClN$_3$O$_4$S.0.4CH$_2$Cl$_2$: C, 57.86; H, 5.30; N, 7.67. Found: C, 57.65; H, 5.45; N, 7.29.

Example 309

N-{3-[(3,3-difluoroazetidin-1-yl)carbonyl]-2-naphthyl}hexahydro-2,5-methanopentalene-3a(1H)-carboxamide In a 20 mL vial containing 3 equivalents of PS-DCC (polymer bound dicyclohexylcarbodidiimide, 1.2 mmol/g) and 1.05 equivalent of 3-amino-2-naphthoic acid, 0.5 ml acetonitrile was added followed by HOBT (1-hydroxybenzotriazole, 12.6 mg, 1 equivalent) dissolved in 0.7 mL dimethylacetamide. Then a solution of 3,3-difluoro-azetidine (12 mg, 1 equivalent) and diisopropylethylamine (49 μL, 3 equivalent) dissolved in 0.7 mL acetonitrile was added to the vial. The reaction was placed on a heater/shaker for 5 hours at 60° C. Then the reaction was filtered through a Si-Carbonate catridge (6 mL-1 g supplied by Silicycle chemical Division) and concentrated. The crude material was again dissolved in 1.4 mL CH$_2$Cl$_2$ and 24 μL diisopropylethylamine (1.5 equivalent). To this, noradamantane carboxylic acid chloride (17 mg, 1 equivalent) was added and the resulting solution was shaken at room temperature for 2 hours. The reaction was checked by LC/MS and concentrated to dryness. The residues were dissolved in 1:1 dimethylsulfoxide/methanol and purified by reverse phase preparative HPLC on a Waters Symmetry C8 column (25 mm×100 mm, 7 μm particle size) using a gradient of 10% to 100% acetonitrile:0.1% aqueous trifluoroacetic acid over 8 min (10 min run time) at a flow rate of 40 mL/min). $^1$H NMR (500 MHz, dimethylsulfoxide-D$_2$O) δ ppm 1.52-1.72 (m, 4H) 1.74-1.94 (m, 4H) 2.01-2.14 (m, 2H) 2.27-2.40 (m, 2H) 2.65-2.76 (m, 1H) 4.36-4.59 (m, 2H) 4.72-4.90 (m, 2H) 7.47-7.57 (m, 1H) 7.56-7.68 (m, 1H) 7.82-7.90 (m, 1H) 7.95-8.05 (m, 1H) 8.12-8.19 (m, 1H) 8.47-8.54 (m, 1H); MS (ESI) positive ion 411 (M+H).

Examples 310-327 were prepared in analogous fashion to Example 309 using an appropriate anthranilic acid derivative:

Example 310

N-{4-bromo-2-[(3,3-difluoroazetidin-1-yl)carbonyl]phenyl}hexahydro-2,5-methanopentalene-3a(1H)-carboxamide $^1$H NMR (500 MHz, dimethylsulfoxide-D$_2$O) δ ppm 1.52-1.68 (m, 4H) 1.73-1.90 (m, 4H) 1.94-2.07 (m, 2H) 2.24-2.37 (m, 2H) 2.58-2.73 (m, 1H) 4.28-4.85 (m, 4H) 7.62-7.74 (m, 2H) 7.84-8.00 (m, 1H); MS (ESI) positive ion 440 (M+H).

Example 311

N-{2-[(3,3-difluoroazetidin-1-yl)carbonyl]-4-iodophenyl}hexahydro-2,5-methanopentalene-3a(1H)-carboxamide $^1$H NMR (500 MHz, dimethylsulfoxide-D$_2$O) δ ppm 1.47-1.70 (m, 4H) 1.72-1.91 (m, 4H) 1.91-2.07 (m, 2H) 2.17-2.39 (m, 2H) 2.60-2.70 (m, 1H) 4.13-5.07 (m, 4H) 7.60-8.01 (m, 3H) 9.86-10.21 (m, 1H); MS (ESI) positive ion 487 (M+H).

Example 312

N-{2-[(3,3-difluoroazetidin-1-yl)carbonyl]-5-methylphenyl}hexahydro-2,5-methanopentalene-3a(1H)-carboxamide $^1$H NMR (500 MHz, dimethylsulfoxide-D$_2$O) δ ppm 1.53-1.71 (m, 4H) 1.73-1.91 (m, 4H) 1.92-2.13 (m, 2H) 2.26-2.41 (m, 5H) 2.60-2.71 (m, 1H) 4.26-4.92 (m, 4H) 6.86-7.02 (m, 1H) 7.36-7.49 (m, 1H) 8.01-8.12 (m, 1H); MS (ESI) positive ion 375 (M+H).

Example 313

N-{2-[(3,3-difluoroazetidin-1-yl)carbonyl]-4,6-diiodophenyl}hexahydro-2,5-methanopentalene-3a(1H)-carboxamide $^1$H NMR (500 MHz, dimethylsulfoxide-D$_2$O) δ ppm 1.50-1.67 (m, 4H) 1.71-1.91 (m, 4H) 1.98-2.09 (m, 2H) 2.19-2.36 (m, 2H) 2.69-2.77 (m, 1H) 4.16-4.59 (m, 4H) 7.71-7.81 (m, 1H) 8.28-8.39 (m, 1H); MS (ESI) positive ion 613 (M+H).

Example 314

N-{4-chloro-2-[(3 3-difluoroazetidin-1-yl)carbonyl]phenyl}hexahydro-2,5-methanopentalene-3a(1H)-carboxamide $^1$H NMR (500 MHz, dimethylsulfoxide-D$_2$O) δ ppm 1.47-1.69 (m, 4H) 1.72-1.87 (m, 4H) 1.93-2.08 (m, 2H) 2.17-2.36 (m, 2H) 2.61-2.76 (m, 1H) 4.21-5.08 (m, 4H) 7.40-7.71 (m, 2H) 7.91-8.03 (m, 1H); MS (ESI) positive ion 395 (M+H).

Example 315

N-{2-[(3,3-difluoroazetidin-1-yl)carbonyl]-4,5-dimethoxyphenyl}hexahydro-2,5-methanopentalene-3a(1H)-carboxamide $^1$H NMR (500 MHz, dimethylsulfoxide-D$_2$O) δ ppm 1.53-1.67 (m, 4H) 1.74-1.91 (m, 4H) 1.95-2.08 (m, 2H) 2.25-2.37 (m, 2H) 2.59-2.74 (m, 1H) 3.76-3.83 (m, 6H) 4.19-5.01 (m, 4H) 6.83-7.09 (m, 1H) 7.92-8.08 (m, 1H) 10.52-10.73 (m, 1H); MS (ESI) positive ion 421 (M+H).

Example 316

N-{5-chloro-2-[(3 3-difluoroazetidin-1-yl)carbonyl]phenyl}hexahydro-2,5-methanopentalene-3a(1H)-carboxamide $^1$H NMR (500 MHz, dimethylsulfoxide-D$_2$O) δ ppm 1.54-1.66 (m, 4H) 1.74-1.88 (m, 4H) 1.94-2.09 (m, 2H) 2.24-2.38 (m, 2H) 2.59-2.75 (m, 1H) 4.24-4.95 (m, 4H) 7.12-7.30 (m, 1H) 7.43-7.71 (m, 1H) 8.19-8.41 (m, 1H) 10.48-10.63 (m, 1H); MS (ESI) positive ion 395 (M+H).

Example 317

N-{2-[(3,3-difluoroazetidin-1-yl)carbonyl]-5-(trifluoromethyl)phenyl}hexahydro-2,5-methanopentalene-3a(1H)-carboxamide $^1$H NMR (500 MHz, dimethylsulfoxide-D$_2$O) δ ppm 1.52-1.68 (m, 4H) 1.75-1.87 (m, 4H) 1.95-2.17 (m, 2H) 2.23-2.43 (m, 2H) 2.61-2.82 (m, 1H) 4.21-5.01 (m, 4H) 7.36-7.60 (m, 1H) 7.64-7.85 (m, 1H) 8.21-8.59 (m, 1H); MS (ESI) positive ion 429 (M+H).

Example 318

N-{2-[(3,3-difluoroazetidin-1-yl)carbonyl]-5-fluorophenyl}hexahydro-2,5-methanopentalene-3a(1H)-carboxamide $^1$H NMR (500 MHz, dimethylsulfoxide-D$_2$O) δ ppm 1.52-1.69 (m, 4H) 1.74-1.89 (m, 4H) 1.95-2.06 (m, 2H) 2.25-2.42 (m, 2H) 2.60-2.70 (m, 1H) 4.22-4.98 (m, 4H) 6.93-7.07 (m, 1H) 7.50-7.73 (m, 1H) 8.02-8.29 (m, 1H) 10.52-10.90 (m, 1H); MS (ESI) positive ion 379 (M+H).

Example 319

N-{2-[(3,3-difluoroazetidin-1-yl)carbonyl]-4-fluorophenyl}hexahydro-2,5-methanopentalene-3a(1H)-carboxamide $^1$H NMR (500 MHz, dimethylsulfoxide-D$_2$O) δ ppm 1.56-1.66 (m, 4H) 1.75-1.88 (m, 4H) 1.91-2.07 (m, 2H) 2.26-2.35 (m, 2H) 2.61-2.72 (m, 1H) 4.19-4.83 (m, 4H) 7.17-7.55 (m, 2H) 7.74-8.02 (m, 1H) 9.84-10.18 (m, 1H); MS (ESI) positive ion 379 (M+H).

Example 320

N-{2-[(3 3-difluoroazetidin-1-yl)carbonyl]phenyl}hexahydro-2,5-methanopentalene-3a(1H)-carboxamide $^1$H NMR (500 MHz, dimethylsulfoxide-D$_2$O) δ ppm 1.55-1.71 (m, 4H) 1.75-1.88 (m, 4H) 1.91-2.11 (m, 2H) 2.24-2.34 (m, 2H) 2.63-2.76 (m, 1H) 4.14-4.96 (m, 4H) 7.00-7.30 (m, 1H) 7.36-7.64 (m, 2H) 7.94-8.34 (m, 1H); MS (ESI) positive ion 361 (M+H).

Example 321

N-{2-[(3,3-difluoroazetidin-1-yl)carbonyl]-3-fluorophenyl}hexahydro-2,5-methanopentalene-3a(1H)-carboxamide $^1$H NMR (500 MHz, dimethylsulfoxide-D$_2$O) δ ppm 1.52-1.69 (m, 4H) 1.73-1.89 (m, 4H) 1.93-2.02 (m, 2H) 2.25-2.33 (m, 2H) 2.63-2.73 (m, 1H) 4.19-4.70 (m, 4H) 7.04-7.18 (m, 1H) 7.33-7.44 (m, 1H) 7.46-7.58 (m, 1H) 9.51-9.69 (m, 1H); MS (ESI) positive ion 379 (M+H).

Example 322

N-{2-[(3 3-difluoroazetidin-1-yl)carbonyl]-5-nitrophenyl}hexahydro-2,5-methanopentalene-3a(1H)-carboxamide $^1$H NMR (500 MHz, dimethylsulfoxide-D$_2$O) δ ppm 1.57-1.71 (m, 4H) 1.78-1.91 (m, 4H) 1.99-2.11 (m, 2H) 2.28-2.36 (m, 2H) 2.62-2.74 (m, 1H) 4.26-4.88 (m, 4H) 7.72-7.86 (m, 1H) 7.89-8.06 (m, 1H) 8.77-9.03 (m, 1H); MS (ESI) positive ion 406 (M+H).

Example 323

N-{2-[(3,3-difluoroazetidin-1-yl)carbonyl]-3-methylphenyl}hexahydro-2,5-methanopentalene-3a(1H)-carboxamide $^1$H NMR (500 MHz, dimethylsulfoxide-D$_2$O) δ ppm 1.51-1.67 (m, 4H) 1.71-1.88 (m, 4H) 1.90-2.05 (m, 2H) 2.20-2.35 (m, 5H) 2.61-2.70 (m, 1H) 4.10-4.66 (m, 4H) 7.05-7.25 (m, 2H) 7.28-7.41 (m, 1H); MS (ESI) positive ion 375 (M+H).

Example 324

N-{3-chloro-2-[(3,3-difluoroazetidin-1-yl)carbonyl]phenyl}hexahydro-2,5-methanopentalene-3a(1H)-carboxamide $^1$H NMR (500 MHz, dimethylsulfoxide-D$_2$O) δ ppm 1.49-1.69 (m, 4H) 1.71-1.88 (m, 4H) 1.90-2.01 (m, 2H) 2.22-2.35 (m, 2H) 2.61-2.83 (m, 1H) 4.21-4.62 (m, 4H) 7.26-7.32 (m, 1H) 7.38-7.45 (m, 1H) 7.45-7.56 (m, 1H); MS (ESI) positive ion 395 (M+H).

Example 325

N-[2-[(3 3-difluoroazetidin-1-yl)carbonyl]-5-(methylsulfonyl)phenyl]hexahydro-2,5-methanopentalene-3a(1H)-carboxamide $^1$H NMR (500 MHz, dimethylsulfoxide-D$_2$O) δ ppm 1.49-1.70 (m, 4H) 1.73-1.91 (m, 4H) 1.95-2.11 (m, 2H) 2.26-2.37 (m, 2H) 2.62-2.73 (m, 1H) 3.11-3.32 (m, 3H) 4.15-5.09 (m, 4H) 7.62-7.73 (m, 1H) 7.74-7.86 (m, 1H) 8.47-8.69 (m, 1H); MS (ESI) positive ion 439 (M+H).

Example 326

N-{4,6-dibromo-3-chloro-2-[(3 3-difluoroazetidin-1-yl)carbonyl]phenyl}hexahydro-2,5-methanopentalene-3a(1H)-carboxamide $^1$H NMR (500 MHz, dimethylsulfoxide-D$_2$O) δ ppm 1.54-1.66 (m, 4H) 1.70-1.89 (m, 4H) 1.94-2.04 (m, 2H) 2.26-2.32 (m, 2H) 2.62-2.71 (m, 1H) 4.21-4.61 (m, 4H) 8.27-8.32 (m, 1H); MS (ESI) positive ion 553 (M+H).

Example 327

N-{2-[(3,3-difluoroazetidin-1-yl)carbonyl]-4,5-difluorophenyl}hexahydro-2,5-methanopentalene-3a(1H)-carboxamide $^1$H NMR (500 MHz, dimethylsulfoxide-D$_2$O) δ ppm 1.51-1.89 (m, 8H) 1.94-2.09 (m, 2H) 2.25-2.35 (m, 2H) 2.60-2.73 (m, 1H) 4.25-5.06 (m, 4H) 7.50-7.80 (m, 1H) 8.06-8.43 (m, 1H); MS (ESI) positive ion 397 (M+H).

Example 328

N-[2-[(3,3-difluoroazetidin-1-yl)carbonyl]-5-(methylsulfonyl)phenyl]-2-oxatricyclo[3.3.1.1$^{3,7}$]decane-1-carboxamide 2-Amino-4-(methylsulfonyl)benzoic acid (0.25 g) and 3,3-difluoro-azetidine hydrochloride (0.19 g) were reacted according to the method described in Example 332C. The resultant intermediate (0.14 g) was then reacted with 2-oxaadamantane-1-carbonylchloride (1.25 equiv) (prepared from 2-oxaadamantane-1-carboxylic acid and thionyl chloride as in Example 12) and triethylamine (2 equiv) in acetonitrile (10 mL). Evaporation of solvents and flash chromotography over silica gel (10% ethyl acetate/hexane) provided 110 mg of the title compound. $^1$H NMR (dimethylsulfoxide-d$_6$, 300 MHz) δ 1.66-2.03 (m, 10H), 2.19 (br s, 2H), 3.25 (s, 3H), 4.43-4.57 (br, 2H), 4.63-4.70 (br, 2H), 7.66 (dd, 1H), 7.82 (d, 1H), 8.79 (d, 1H), 10.76 (s, 1H); MS (ESI+) m/z 455 (M+H)$^+$.

Example 329

N-{2-[(3 3-difluoroazetidin-1-yl)carbonyl]-4,5-difluorophenyl}-2-oxatricyclo[3.3.1.1$^{3,7}$]decane-1-carboxamide 2-Amino-4-(methylsulfonyl)benzoic acid (0.25 g) and 3,3-difluoro-azetidine hydrochloride (0.19 g) were reacted according to the method of Example 333C. The resultant intermediate (0.14 g) was then reacted with 2-oxaadamantane 1-carbonylchloride (1.25 equiv) (prepared from 2-oxaadamantane 1-carboxylic acid and thionyl chloride as in Example 12) and triethylamine (2 equiv) in acetonitrile (10 mL). Evaporation of solvents and flash chromotography over silica gel (10% ethyl acetate/hexane) provided 110 mg of the title compound. $^1$H NMR (DMSO-d$_6$, 300 MHz) δ 1.66-2.03 (m, 10H), 2.19 (br s, 2H), 3.25 (s, 3H), 4.43-4.57 (br, 2H), 4.63-4.70 (br, 2H), 7.66 (dd, 1H), 7.82 (d, 1H), 8.79 (d, 1H), 10.76 (s, 1H); MS (ESI+) m/z 455 (M+H)$^+$.

Example 330

N-{4-chloro-2-[(3,3-difluoroazetidin-1-yl)carbonyl]phenyl}-2-oxatricyclo[3.3.1.1$^{3,7}$]decane-1-carboxamide 2-Amino-5-chlorobenzoic acid (0.25 g) and 3,3-difluoro-azetidine hydrochloride (0.24 g) were reacted according to the method of Example 332C. The resultant intermediate (0.16 g) was then reacted with 2-oxaadamantane 1-carbonylchloride (1.25 equiv) (prepared from 2-oxaadamantane 1-carboxylic acid and thionyl chloride as in Example 12) and triethylamine (2 equiv) in acetonitrile (10 mL). Evaporation of solvents and flash chromatography over silica gel (20% ethyl acetate/hexane) provided 190 mg of the title compound. $^1$H NMR (dimethylsulfoxide-$d_6$, 300 MHz) δ 1.66-2.03 (m, 10H), 2.19 (br s, 2H), 4.36-4.81 (br, 4H), 7.54 (dd, 1H), 7.59 (d, 1H), 8.18 (d, 1H), 10.52 (s, 1H); MS (ESI+) m/z 411 (M+H)$^+$.

Example 331

N-{2-[(3 3-difluoroazetidin-1-yl)carbonyl]-3-fluorophenyl}-2-oxatricyclo[3.3.1.1$^{3,7}$]decane-1-carboxamide 2-Amino-6-fluorobenzoic acid (0.25 g) and 3,3-difluoroazetidine hydrochloride (0.25 g) were reacted according to the method of Example 332C. The resultant intermediate (0.15 g) was then reacted with 2-oxaadamantane 1-carbonyl-chloride (1.25 equiv) (prepared from 2-oxaadamantane 1-carboxylic acid and thionyl chloride as in Example 12) and triethylamine (2 equiv) in acetonitrile (10 mL). Evaporation of solvents and flash chromotography over silica gel (20% ethyl acetate/hexane) provided 80 mg of the title compound. $^1$H NMR (dimethylsulfoxide-$d_6$, 300 MHz) δ 1.66-2.03 (m, 10H), 2.17 (br s, 2H), 4.36-4.53 (m, 4H), 7.09 (m, 1H), 7.49 (m, 1H), 7.63 (d, 1H), 9.85 (s, 1H); MS (ESI+) m/z 395 (M+H)$^+$.

Example 332

N-{2-[(3,3-difluoroazetidin-1-yl)carbonyl]pyridin-3-yl}hexahydro-2,5-methanopentalene-3a(1H)-carboxamide Example 332A 3-[(Hexahydro-2,5-methano-pentalene-3a-carbonyl)-amino]-pyridine-2-carboxylic acid ethyl ester To a solution of 0.166 g (1 mmol.) 3-amino-pyridine-2-carboxylic acid ethyl ester (Journal of Organic Chemistry, 69(1), 54-61; 2004) in acetonitrile (10 mL) was added triethylamine (0.2 g, 2 mmol) followed by noradamantane carboxylic acid chloride. The solution was heated to reflux for 3 hours, cooled and diluted with ethyl acetate (50 mL). The organics were washed with sodium bicarbonate solution, brine, dried over MgSO$_4$ and concentrated. Flash chromatography (gradient elution: 20% ethyl acetate/hexane to 40%) afforded the title compound as a white solid. MS (ESI) m/z 315 (M+H)$^+$.

Example 332B

3-[(Hexahydro-2,5-methano-pentalene-3a-carbonyl)-amino]-pyridine-2-carboxylic acid To a solution of Example 332A (0.23 g, 0.73 mmol) in ethanol/water (10/2) was added potassium hydroxide (0.2 g, 3.66 mmol). The solution was warmed to 65 degrees for 12 hours, cooled and diluted with ethyl acetate (50 mL). The solution was acidified with 0.5M HCl (10 mL), then washed with brine, dried over MgSO$_4$, filtered, and concentrated to afford the title compound. MS (ESI) m/z 286 (M+H)$^+$.

Example 332C

N-{2-[(3,3-difluoroazetidin-1-yl)carbonyl]pyridin-3-yl}hexahydro-2,5-methanopentalene-3a(1H)-carboxamide To a solution of Example 332B (0.1 g, 0.35 mmol) in dimethylformamide (5 mL) was added N-(3-dimethylaminopropyl)-N'-ethylcarbodiimide (0.1 g, 0.52 mmol), 1-hydroxybenzotriazole hydrate (0.07 g, 0.52 mmol), triethylamine (0.11 g, 1.05 mmol) and 3,3-difluoro-azetidine hydrochloride (0.07 g, 0.52 mmol). The reaction was stirred at room temperature for 16 hours, diluted with ethyl acetate (50 mL) and the organics were washed with sodium bicarbonate solution, brine, dried over MgSO$_4$, filtered, and concentrated. Flash chromatography (20% ethyl acetate in hexane) afforded the title compound. $^1$H NMR (dimethylsulfoxide-$d_6$, 300 MHz) δ ppm 1.50-1.73 (m, 4H) 1.73-1.93 (m, 4H) 1.95-2.19 (m, 2H) 2.33 (s, 2H) 2.67 (t, J=6.61 Hz, 1H) 4.53 (t, J=12.37 Hz, 2H) 5.03 (t, J=12.54 Hz, 2H) 7.57 (dd, J=8.65, 4.58 Hz, 1H) 8.30 (dd, J=4.41, 1.36 Hz, 1H) 8.98 (dd, J=8.65, 1.53 Hz, 1H) 11.82 (s, 1H). MS (ESI+) m/z 362.1 (M+H)$^+$ Example 333

N-{3-[(3,3-difluoroazetidin-1-yl)carbonyl]pyridin-4-yl}hexahydro-2,5-methanopentalene-3a(1H)-carboxamide Example 333A (4-Amino-pyridin-3-yl)-(3,3-difluoro-azetidin-1-yl)-methanone The title compound was prepared from 4-aminonicotinic acid (0.25 g, 1.8 mmol) (CAS: 7418-65-7) by the procedure described for Example 332C. MS (ESI+) m/z 214 (M+H)$^+$ Example 333B N-{3-[(3,3-difluoroazetidin-1-yl)carbonyl]pyridin-4-yl}hexahydro-2,5-methanopentalene-3a(1H)-carboxamide The title compound was prepared from 333A and hexahydro-2,5-methanopentalene-3a(1H)-carboxylic acid by the procedure described for Example 12. $^1$H NMR (dimethylsulfoxide-$d_6$, 300 MHz) δ ppm 1.44-1.76 (m, 4H) 1.86 (d, J=2.71 Hz, 4H) 1.92-2.21 (m, 2H) 2.21-2.45 (m, 2H) 2.61-2.86 (m, 1H) 4.32-4.75 (m, 2H) 4.73-5.15 (m, 2H) 8.33 (d, J=5.76 Hz, 1H) 8.56 (d, J=5.76 Hz, 1H) 8.69 (s, 1H) 10.88 (s, 1H). MS (ESI+) m/z 362.1 (M+H)$^+$.

Many variations in the invention will suggest themselves to those skilled in the art in light of the foregoing detailed description. All such obvious variations are within the full intended scope of the appended claims.

The invention claimed is:
1. A compound of formula (I),

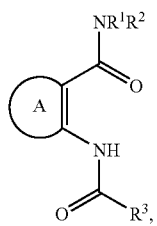

or a pharmaceutically acceptable salt thereof, wherein A is formula (v)

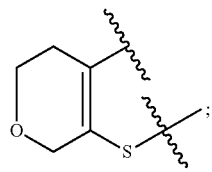

wherein formula (v) is independently unsubstituted or further substituted with 1 or 2 substituents independently selected from the group consisting of alkyl or halogen;
$R^1$ is hydrogen, alkyl, or haloalkyl;
$R^2$ is alkyl, alkenyl, alkynyl, $G^1$, —N($R^b$)($R^f$), —($CR^dR^e$)$_m$—CN, —($CR^dR^e$)$_n$—$OR^f$, —($CR^dR^e$)$_n$—$S(R^c)$, —($CR^dR^e$)$_m$—$S(O)_2R^c$, —($CR^dR^e$)$_n$—N($R^b$)($R^f$), —($CR^dR^e$)$_m$—C(O)$R^b$, —($CR^dR^e$)$_m$—C(O)O($R^b$), —($CR^dR^e$)$_m$-$G^1$, or haloalkyl; or
$R^1$ and $R^2$, together with the nitrogen atom to which they are attached, form a 4- to 6-membered monocyclic heterocycle containing zero or one additional heteroatom selected from the group consisting of O, or S, and two non-adjacent atoms of said monocyclic heterocycle are optionally linked by an alkylene bridge of 1-4 carbon atoms, said monocyclic heterocycle is optionally substituted with 1, or 2 substituents independently selected from the group consisting of alkyl, halogen, oxo, —$OR^a$, haloalkyl;
$G^1$, at each occurrence, is independently aryl, heteroaryl, heterocycle, cycloalkyl, or cycloalkenyl; wherein each $G^1$ is independently unsubstituted or further substituted with 1, 2, or 3 substituents independently selected from the group consisting of alkyl, alkenyl, alkynyl, halogen, oxo, —CN, —$NO_2$, $OR^a$, —$S(R^c)$, —$S(O)(R^c)$, —$S(O)_2R^c$, —$S(O)_2N(R^b)_2$, $C(O)R^b$, —$C(O)O(R^b)$, —$C(O)N(R^b)_2$, —$N(R^b)_2$, —$N(R^b)C(O)R^b$, —$N(R^b)C(O)O(R^b)$, —$N(R^b)S(O)_2R^c$, haloalkyl, —($CR^dR^e$)$_m$—$OR^a$, —($CR^dR^e$)$_m$—$S(R^c)$, and —($CR^dR^e$)$_m$—$S(O)(R^c)$;
$R^a$, at each occurrence, is independently hydrogen, alkyl, haloalkyl, or —($CR^dR^e$)$_m$—O(alkyl),
$R^b$, at each occurrence, is independently hydrogen, alkyl, or haloalkyl;
$R^c$, at each occurrence, is independently alkyl or haloalkyl;
$R^f$, at each occurrence, is independently hydrogen, alkyl, $G^1$, —($CR^dR^e$)$_m$-$G^1$, or haloalkyl;
$R^d$ and $R^e$, at each occurrence, are each independently hydrogen, halogen, alkyl, or haloalkyl;
m, at each occurrence, is independently 1, 2, 3, 4, 5, or 6;
n, at each occurrence, is independently 2, 3, 4, 5, or 6;
$R^3$ is formula (a) or (b),

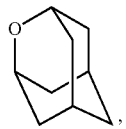

wherein formula (a) and (b) are each independently unsubstituted or further substituted with 1 or 2 substituents independently selected from the group consisting of alkyl, halogen, oxo, —CN, —O(alkyl), and haloalkyl.

2. The compound according to claim 1 having formula (II), or a pharmaceutically acceptable salt thereof

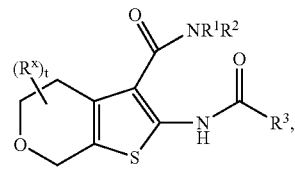

wherein $R^x$ is an optional substituent, and each $R^x$ is independently alkyl or halogen; and
t is 0, 1, or 2.

3. The compound according to claim 2, wherein $R^3$ is formula (a)

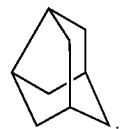

4. The compound according to claim 3 or a pharmaceutically acceptable salt thereof, wherein $R^1$ and $R^2$ together with the nitrogen atom to which they are attached form a 4- to 8-membered monocyclic heterocycle.

5. The compound according to claim 3 or a pharmaceutically acceptable salt thereof, wherein $R^1$ is hydrogen and $R^2$ is alkyl, alkynyl, or haloalkyl.

6. The compound according to claim 3 or a pharmaceutically acceptable salt thereof, wherein $R^1$ is hydrogen and $R^2$ is —($CR^dR^e$)$_n$—$OR^f$, —($CR^dR^e$)$_m$—CN, —($CR^dR^e$)$_n$—$S(R^c)$, —($CR^dR^e$)$_m$—$S(O)_2R^c$, or —N($R^b$)($R^f$).

7. The compound according to claim 3 or a pharmaceutically acceptable salt thereof, wherein $R^1$ is hydrogen, $R^2$ is —($CR^dR^e$)$_m$-$G^1$, and $G^1$ is aryl, heteroaryl, heterocycle, or cycloalkyl.

8. The compound according to claim 3 or a pharmaceutically acceptable salt thereof, wherein $R^1$ is hydrogen, $R^2$ is $G^1$, and $G^1$ is aryl, cycloalkyl, or heterocycle.

9. The compound according to claim 2 or a pharmaceutically acceptable salt thereof wherein R³ is formula (b)

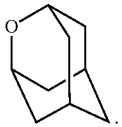
(b)

10. The compound according to claim 9 or a pharmaceutically acceptable salt thereof, wherein R¹ is hydrogen and R² is alkyl.

11. The compound according to claim 9 or a pharmaceutically acceptable salt thereof, wherein R¹ and R², together with the nitrogen atom to which they are attached form a 4- to 6-membered monocyclic heterocycle.

12. The compound according to claim 1 or a pharmaceutically acceptable salt thereof, selected from the group consisting of:
- N-{3-[(2,5-dimethylmorpholin-4-yl)carbonyl]-4,7-dihydro-5H-thieno[2,3-c]pyran-2-yl}hexahydro-2,5-methanopentalene-3a(1H)-carboxamide;
- N-{3-[(4-hydroxypiperidin-1-yl)carbonyl]-4,7-dihydro-5H-thieno[2,3-c]pyran-2-yl}hexahydro-2,5-methanopentalene-3a(1H)-carboxamide;
- 2-[(hexahydro-2,5-methanopentalen-3a(1H)-ylcarbonyl)amino]-N-propyl-4,7-dihydro-5H-thieno[2,3-c]pyran-3-carboxamide;
- N-[3-(morpholin-4-ylcarbonyl)-4,7-dihydro-5H-thieno[2,3-c]pyran-2-yl]hexahydro-2,5-methanopentalene-3a(1H)-carboxamide;
- 2-[(hexahydro-2,5-methanopentalen-3a(1H)-ylcarbonyl)amino]-N-(2-methoxyethyl)-4,7-dihydro-5H-thieno[2,3-c]pyran-3-carboxamide;
- 2-[(hexahydro-2,5-methanopentalen-3a(1H)-ylcarbonyl)amino]-N-(tetrahydro-2H-pyran-4-ylmethyl)-4,7-dihydro-5H-thieno[2,3-c]pyran-3-carboxamide;
- 2-[(hexahydro-2,5-methanopentalen-3a(1H)-ylcarbonyl)amino]-N-(3-hydroxypropyl)-4,7-dihydro-5H-thieno[2,3-c]pyran-3-carboxamide;
- N-ethyl-2-[(hexahydro-2,5-methanopentalen-3a(1H)-ylcarbonyl)amino]-4,7-dihydro-5H-thieno[2,3-c]pyran-3-carboxamide;
- 2-[(hexahydro-2,5-methanopentalen-3a(1H)-ylcarbonyl)amino]-N-(2-phenylethyl)-4,7-dihydro-5H-thieno[2,3-c]pyran-3-carboxamide;
- 2-[(hexahydro-2,5-methanopentalen-3a(1H)-ylcarbonyl)amino]-N-(2-thien-2-ylethyl)-4,7-dihydro-5H-thieno[2,3-c]pyran-3-carboxamide;
- N-[2-(2-fluorophenyl)ethyl]-2-[(hexahydro-2,5-methanopentalen-3a(1H)-ylcarbonyl)amino]-4,7-dihydro-5H-thieno[2,3-c]pyran-3-carboxamide;
- 2-[(hexahydro-2,5-methanopentalen-3a(1H)-ylcarbonyl)amino]-N-[2-(2-methoxyphenyl)ethyl]-4,7-dihydro-5H-thieno[2,3-c]pyran-3-carboxamide;
- 2-[(hexahydro-2,5-methanopentalen-3a(1H)-ylcarbonyl)amino]-N-(2-pyridin-2-ylethyl)-4,7-dihydro-5H-thieno[2,3-c]pyran-3-carboxamide;
- N-(2-cyanoethyl)-2-[(hexahydro-2,5-methanopentalen-3a(1H)-ylcarbonyl)amino]-4,7-dihydro-5H-thieno[2,3-c]pyran-3-carboxamide;
- N-{3-[(propylamino)carbonyl]-4,7-dihydro-5H-thieno[2,3-c]pyran-2-yl}-2-oxatricyclo[3.3.1.1³,⁷]decane-1-carboxamide;
- N-(2-ethoxyethyl)-2-[(hexahydro-2,5-methanopentalen-3a(1H)-ylcarbonyl)amino]-4,7-dihydro-5H-thieno[2,3-c]pyran-3-carboxamide;
- 2-[(hexahydro-2,5-methanopentalen-3a(1H)-ylcarbonyl)amino]-N-(3-hydroxybutyl)-4,7-dihydro-5H-thieno[2,3-c]pyran-3-carboxamide;
- 2-[(hexahydro-2,5-methanopentalen-3a(1H)-ylcarbonyl)amino]-N-[(1R)-1-(hydroxymethyl)-2-methylpropyl]-4,7-dihydro-5H-thieno[2,3-c]pyran-3-carboxamide;
- 2-[(hexahydro-2,5-methanopentalen-3a(1H)-ylcarbonyl)amino]-N-(1-methyl-3-phenylpropyl)-4,7-dihydro-5H-thieno[2,3-c]pyran-3-carboxamide;
- 2-[(hexahydro-2,5-methanopentalen-3a(1H)-ylcarbonyl)amino]-N-isobutyl-4,7-dihydro-5H-thieno[2,3-c]pyran-3-carboxamide;
- 2-[(hexahydro-2,5-methanopentalen-3a(1H)-ylcarbonyl)amino]-N-(2-methoxy-1-methylethyl)-4,7-dihydro-5H-thieno[2,3-c]pyran-3-carboxamide;
- 2-[(hexahydro-2,5-methanopentalen-3a(1H)-ylcarbonyl)amino]-N-[(2R)-tetrahydrofuran-2-ylmethyl]-4,7-dihydro-5H-thieno[2,3-c]pyran-3-carboxamide;
- 2-[(hexahydro-2,5-methanopentalen-3a(1H)-ylcarbonyl)amino]-N-[(2S)-tetrahydrofuran-2-ylmethyl]-4,7-dihydro-5H-thieno[2,3-c]pyran-3-carboxamide;
- 2-[(hexahydro-2,5-methanopentalen-3a(1H)-ylcarbonyl)amino]-N-(2-hydroxypropyl)-4,7-dihydro-5H-thieno[2,3-c]pyran-3-carboxamide;
- 2-[(hexahydro-2,5-methanopentalen-3a(1H)-ylcarbonyl)amino]-N-(2-hydroxybutyl)-4,7-dihydro-5H-thieno[2,3-c]pyran-3-carboxamide;
- 2-[(hexahydro-2,5-methanopentalen-3a(1H)-ylcarbonyl)amino]-N-[2-(methylthio)ethyl]-4,7-dihydro-5H-thieno[2,3-c]pyran-3-carboxamide;
- 2-[(hexahydro-2,5-methanopentalen-3a(1H)-ylcarbonyl)amino]-N-prop-2-ynyl-4,7-dihydro-5H-thieno[2,3-c]pyran-3-carboxamide;
- N-(cyanomethyl)-2-[(hexahydro-2,5-methanopentalen-3a(1H)-ylcarbonyl)amino]-4,7-dihydro-5H-thieno[2,3-c]pyran-3-carboxamide;
- Trans-2-[(hexahydro-2,5-methanopentalen-3a(1H)-ylcarbonyl)amino]-N-(2-hydroxycyclopentyl)-4,7-dihydro-5H-thieno[2,3-c]pyran-3-carboxamide;
- N-hexahydro-2,5-methanopentalen-3a(1H)-yl-2-[(hexahydro-2,5-methanopentalen-3a(1H)-ylcarbonyl)amino]-4,7-dihydro-5H-thieno[2,3-c]pyran-3-carboxamide;
- 2-[(hexahydro-2,5-methanopentalen-3a(1H)-ylcarbonyl)amino]-N-(3-hydroxy-2,2-dimethylpropyl)-4,7-dihydro-5H-thieno[2,3-c]pyran-3-carboxamide;
- N-{3-[(2-phenylhydrazino)carbonyl]-4,7-dihydro-5H-thieno[2,3-c]pyran-2-yl}hexahydro-2,5-methanopentalene-3 all H)-carboxamide;
- 2-[(hexahydro-2,5-methanopentalen-3a(1H)-ylcarbonyl)amino]-N-[2-(methylsulfonyl)ethyl]-4,7-dihydro-5H-thieno[2,3-c]pyran-3-carboxamide;
- Trans-2-[(hexahydro-2,5-methanopentalen-3a(1H)-ylcarbonyl)amino]-N-(2-hydroxycyclohexyl)-4,7-dihydro-5H-thieno[2,3-c]pyran-3-carboxamide;
- Cis-2-[(hexahydro-2,5-methanopentalen-3a(1H)-ylcarbonyl)amino]-N-(2-hydroxycyclohexyl)-4,7-dihydro-5H-thieno[2,3-c]pyran-3-carboxamide;
- 2-[(hexahydro-2,5-methanopentalen-3a(1H)-ylcarbonyl)amino]-N-(3,3,3-trifluoropropyl)-4,7-dihydro-5H-thieno[2,3-c]pyran-3-carboxamide;
- Trans-2-[(hexahydro-2,5-methanopentalen-3a(1H)-ylcarbonyl)amino]-N-(2-(hydroxymethyl)cyclohexyl)-4,7-dihydro-5H-thieno[2,3-c]pyran-3-carboxamide;

N-cyclobutyl-2-[(hexahydro-2,5-methanopentalen-3a (1H)-ylcarbonyl)amino]-4,7-dihydro-5H-thieno[2,3-c]pyran-3-carboxamide;

N-cyclopentyl-2-[(hexahydro-2,5-methanopentalen-3a (1H)-ylcarbonyl)amino]-4,7-dihydro-5H-thieno[2,3-c]pyran-3-carboxamide;

Cis-2-[(hexahydro-2,5-methanopentalen-3a(1H)-ylcarbonyl)amino]-N-(2-methylcyclohexyl)-4,7-dihydro-5H-thieno[2,3-c]pyran-3-carboxamide;

Trans-2-[(hexahydro-2,5-methanopentalen-3a(1H)-ylcarbonyl)amino]-N-(2-methylcyclohexyl)-4,7-dihydro-5H-thieno[2,3-c]pyran-3-carboxamide;

2-[(hexahydro-2,5-methanopentalen-3a(1H)-ylcarbonyl)amino]-N-(4-methylcyclohexyl)-4,7-dihydro-5H-thieno[2,3-c]pyran-3-carboxamide;

2-[(hexahydro-2,5-methanopentalen-3a(1H)-ylcarbonyl)amino]-N-[(1R,2S,3S,5S)-2,6,6-trimethylbicyclo[3.1.1]hept-3-yl]-4,7-dihydro-5H-thieno[2,3-c]pyran-3-carboxamide;

2-[(hexahydro-2,5-methanopentalen-3a(1H)-ylcarbonyl)amino]-N-[(1S,2R,3R,5R)-2,6,6-trimethylbicyclo[3.1.1]hept-3-yl]-4,7-dihydro-5H-thieno[2,3-c]pyran-3-carboxamide;

N-{[3-(dimethylamino)tetrahydrothien-3-yl]methyl}-2-[(hexahydro-2,5-methanopentalen-3a(1H)-ylcarbonyl)amino]-4,7-dihydro-5H-thieno[2,3-c]pyran-3-carboxamide;

N-benzyl-2-[(hexahydro-2,5-methanopentalen-3a(1H)-ylcarbonyl)amino]-4,7-dihydro-5H-thieno[2,3-c]pyran-3-carboxamide;

2-[(hexahydro-2,5-methanopentalen-3a(1H)-ylcarbonyl)amino]-N-[3-(methylthio)propyl]-4,7-dihydro-5H-thieno[2,3-c]pyran-3-carboxamide;

N-{3-[(3,3-difluoroazetidin-1-yl)carbonyl]-4,7-dihydro-5H-thieno[2,3-c]pyran-2-yl}hexahydro-2,5-methanopentalene-3a(1H)-carboxamide;

2-[(hexahydro-2,5-methanopentalen-3a(1H)-ylcarbonyl)amino]-N-phenyl-4,7-dihydro-5H-thieno[2,3-c]pyran-3-carboxamide;

exo-N-[bicyclo[2.2.1]hept-2-yl]-2-[(hexahydro-2,5-methanopentalen-3a(1H)-ylcarbonyl)amino]-4,7-dihydro-5H-thieno[2,3-c]pyran-3-carboxamide;

2-[(hexahydro-2,5-methanopentalen-3a(1H)-ylcarbonyl)amino]-N-(2,2,2-trifluoroethyl)-4,7-dihydro-5H-thieno[2,3-c]pyran-3-carboxamide;

N-{3-[2-azabicyclo[2.2.1]hept-2-ylcarbonyl]-4,7-dihydro-5H-thieno[2,3-c]pyran-2-yl}hexahydro-2,5-methanopentalene-3a(1H)-carboxamide;

N-{3-[(3-hydroxyazetidin-1-yl)carbonyl]-4,7-dihydro-5H-thieno[2,3-c]pyran-2-yl}hexahydro-2,5-methanopentalene-3a(1H)-carboxamide;

N-{3-[(3-methoxyazetidin-1-yl)carbonyl]-4,7-dihydro-5H-thieno[2,3-c]pyran-2-yl}hexahydro-2,5-methanopentalene-3a(1H)-carboxamide;

N-[3-(azetidin-1-ylcarbonyl)-4,7-dihydro-5H-thieno[2,3-c]pyran-2-yl]hexahydro-2,5-methanopentalene-3a(1H)-carboxamide;

N-{3-[(3,3-difluoropyrrolidin-1-yl)carbonyl]-4,7-dihydro-5H-thieno[2,3-c]pyran-2-yl}hexahydro-2,5-methanopentalene-3a(1H)-carboxamide;

2-[(hexahydro-2,5-methanopentalen-3a(1H)-ylcarbonyl)amino]-N-[(3R)-tetrahydrofuran-3-yl]-4,7-dihydro-5H-thieno[2,3-c]pyran-3-carboxamide;

N-{3-[(3,3-difluoroazetidin-1-yl)carbonyl]-4,7-dihydro-5H-thieno[2,3-c]pyran-2-yl}-2-oxatricyclo[3.3.1.1$^{3,7}$]decane-1-carboxamide; and N-cyclopropyl-2-[(hexahydro-2,5-methanopentalen-3a (1H)-ylcarbonyl)amino]-4,7-dihydro-5H-thieno[2,3-c]pyran-3-carboxamide.

13. A pharmaceutical composition comprising a therapeutically effective amount of a compound of formula (I) according to claim 1 or a pharmaceutically acceptable salt thereof, in combination with a pharmaceutically acceptable carrier.

* * * * *